US006406704B1

(12) United States Patent
Tan et al.

(10) Patent No.: US 6,406,704 B1
(45) Date of Patent: Jun. 18, 2002

(54) COMPOUNDS AND METHODS FOR TREATMENT AND DIAGNOSIS OF MYCOBACTERIAL INFECTIONS

(75) Inventors: Paul Tan; Elizabeth Visser; Ross Prestidge; James D. Watson, all of Auckland (NZ)

(73) Assignee: Genesis Research and Development Corporation Limited (NZ)

(*) Notice: Subject to any disclaimer, the term of this patent is extended or adjusted under 35 U.S.C. 154(b) by 0 days.

(21) Appl. No.: 09/205,426

(22) Filed: Dec. 4, 1998

Related U.S. Application Data

(63) Continuation-in-part of application No. 09/095,855, filed on Jun. 11, 1998, which is a continuation-in-part of application No. 08/997,362, filed on Dec. 23, 1997, now Pat. No. 5,985,287, which is a continuation-in-part of application No. 08/873,970, filed on Jun. 12, 1997, now Pat. No. 6,001,361, which is a continuation-in-part of application No. 08/705, 347, filed on Aug. 29, 1996.

(51) Int. Cl.$^{7}$ ........................ A61K 39/04; A61K 32/02; G12N 1/12

(52) U.S. Cl. ................................ 424/248.1; 424/185.1; 424/190.1; 424/192.1; 424/234.1; 424/282.1; 435/253.1; 530/300; 530/350; 536/23.1; 536/23.7

(58) Field of Search ........................... 424/185.1, 190.1, 424/192.1, 234.1, 248.1, 282.1; 435/253.1; 530/300, 350; 536/23.1, 23.7

(56) References Cited

U.S. PATENT DOCUMENTS

| | | | |
|---|---|---|---|
| 3,956,481 | A | 5/1976 | Jolles et al. |
| 4,036,953 | A | 7/1977 | Adam et al. |
| 4,716,038 | A | 12/1987 | Stanford et al. |
| 4,724,144 | A | 2/1988 | Rook et al. |
| 5,599,545 | A | 2/1997 | Stanford et al. |

FOREIGN PATENT DOCUMENTS

| | | | |
|---|---|---|---|
| EP | 0763361 | 3/1997 | .......... A61K/39/04 |
| WO | 9007935 | 7/1990 | .......... A61K/39/02 |
| WO | 9101751 | 2/1991 | .......... A61K/39/04 |
| WO | 9102542 | 3/1991 | .......... A61K/39/04 |
| WO | 9208484 | 3/1992 | .......... A61K/39/04 |
| WO | 9208488 | 5/1992 | .......... A61K/39/39 |
| WO | 9316727 | 9/1993 | .......... A61K/39/04 |
| WO | 9406466 | 3/1994 | .......... A61K/39/04 |
| WO | 9526742 | 10/1995 | .......... A61K/35/74 |

OTHER PUBLICATIONS

R.G. White et al., "Correlation of Adjuvant Activity and Chemical Structure of Wax D Fractions of Mycobacteria," Immunology 7, pp. 158–171, 1964.

R.G. White, "Characterization of Micobacterial Components of Adjuvant Mixtures," Symposium Series Immunobiol. Standard 6, pp. 49–58, 1967.

R.G. White et al., The Influence of Components of M. Tuberculosis and other Mycobacteria upon Antibody Production to Ovalbumin, Immunology I. pp. 54–66, 1958.

Skinner, Immunization with Heat–Killed Mycobacterium vaccae Stimulates CD8$^{+}$ Cytotoxic T Cells Specific for Macrophages Infected with *Mycobacterium tuberculosis, Infection and Immunity* 65:11, 4525–4530, 1997.

*Primary Examiner*—Rodney P Swartz

(74) *Attorney, Agent, or Firm*—Janet Sleath; Ann W. Speckman

(57) ABSTRACT

The present invention provides polypeptides comprising an immunogenic portion of a *M. vaccae* protein and DNA molecules encoding such polypeptides, together with methods for their use in the diagnosis and treatment of mycobacterial infection. Methods for enhancing the immune response to an antigen including administration of *M. vaccae* culture filtrate, delipidated *M. vaccae* cells or delipidated and deglycolipidated *M. vaccae* cells are also provided.

21 Claims, 26 Drawing Sheets

```
M.vaccae         MRLLDRIRGPW---ARRFGVVAVATAMMPALVGLAGGSATAGAFSRPGLPVEYLMVPSP
M.bovis          MQLVDRVRGAVTGMSRRLVVGAVGAALVSGLVGAVGGTATAGAFSRPGLPVEYLQVPSP
M.tuberculosis   MQLVDRVRGAVTGMSRRLVVGAVGAALVSGLVGAVGGTATAGAFSRPGLPVEYLQVPSP
M.leprae         MKFVDRFRGAVAGMLRRLVVEAMGVALLSALIGVVG-SAPAEAFSRPGLPVEYLQVPSP
CONSENSUS        M   DR RG      RR VV A         L G   G  A A AFSRPGLPVEYL VPSP

M.vaccae         SMGRDIKIQFQSGGENSPALYLLDGLRAQEDFNGWDINTQAFEWFLDSGISVVMPVGGQS
M.bovis          SMGRDIKVQFQSGGANSPALYLLDGLRAQDDFSGWDINTPAFEWYDQSGLSVVMPVGGQS
M.tuberculosis   SMGRDIKVQFQSGGANSPALYLLDGLRAQDDFSGWDINTPAFEWYDQSGLSVVMPVGGQS
M.leprae         SMGRDIKVQFQNGGANSPALYLLDGLRAQDDFSGWDINTTAFEWYYQSGISVVMPVGGQS
CONSENSUS        SMGRDIK QFQ GG NSPALYLLDGLRAQ DF GWDINT AFEW    SG SVVMPVGGQS

M.vaccae         SFYTDWYAPARNKGPTVTYKWETFLTQELPGWLQANRAVKPTGSGPVGLSMAGSAALNLA
M.bovis          SFYSDWYQPACGKAGCQTYKWETFLTSELPGWLQANRHVKPTGSAVVGLSMAASSALTLA
M.tuberculosis   SFYSDWYQPACGKAGCQTYKWETFLTSELPGWLQANRHVKPTGSAVVGLSMAASSALTLA
M.leprae         SFYSDWYSPACGKAGCQTYKWETFLTSELPEYLQSNKQIKPTGSAAVGLSMAGLSALTLA
CONSENSUS        SFY DWY PA  K     TYKWETFLT ELP  LQ N    KPTGS  VGLSMA   AL LA

M.vaccae         TWHPEQFIYAGSMSGFLNPSEGWWPFLINISMGDAGGFKADDMWGKTEGIPTAVGQRNDP
M.bovis          IYHPQQFVYAGAMSGLLDPSQAMGPTLIGLAMGDAGGYKASDMWGPKEDPAW---QRNDP
M.tuberculosis   IYHPQQFVYAGAMSGLLDPSQAMGPTLIGLAMGDAGGYKASDMWGPKEDPAW---QRNDP
M.leprae         IYHPDQFIYVGSMSGLLDPSNAMGPSLIGLAMGDAGGYKAADMWGPSTDPAW---KRNDP
CONSENSUS          HP QF YAG MSG L PS     P LI   MGDAGG KA DMWG              RNDP

M.vaccae         MLNIPTLVANNTRIWVYCGNGQPTELGGGDLPATFLEGLTIRT-NETFRDNYIAAGGHNG
M.bovis          LLNVGKLIANNTRVWVYCGNGKPSDLGGNNLPAKFLEGF-VRTSNIKFQDAYNAGGGHNG
M.tuberculosis   LLNVGKLIANNTRVWVYCGNGKPSDLGGNNLPAKFLEGF-VRTSNIKFQDAYNAGGGHNG
M.leprae         TVNVGTLIANNTRIWMYCGNGKPTELGGNNLPAKLLEGL-VRTSNIKFQDGYNAGGGHNA
CONSENSUS          N   L ANNTR W YCGNG P   LGG  LPA  LEG   RT N   F D Y A GGHN

M.vaccae         VFNFPANGTHNWAYWGRELQAMKPDLQAHLL*
M.bovis          VFDFPDSGTHSWEYWGAQLNAMKPDLQRALGATPNTGPAPQGA*
M.tuberculosis   VFDFPDSGTHSWEYWGAQLNAMKPDLQRALGATPNTGPAPQGA*
M.leprae         VFNFPDSGTHSWEYWGEQLNDMKPDLQQYLGAT-PGA*
CONSENSUS        VF FP  GTH W YWG  L  MKPDLQ  L
```

Fig. 3

COMPOUNDS AND METHODS FOR TREATMENT AND DIAGNOSIS OF MYCOBACTERIAL INFECTIONS

REFERENCE TO RELATED APPLICATIONS

This application is a continuation-in-part of U.S. application Ser. No. 09/095,855, filed Jun. 11, 1998, which is a continuation-in-part of U.S. patent application Ser. No. 08/997,362, filed Dec. 23, 1997, now U.S. Pat. No. 5,985, 287 which is a continuation-in-part of U.S. patent application Ser. No. 08/873,970, filed Jun. 12, 1997, now U.S. Pat. No. 6,001,361 which is a continuation-in-part of U.S. patent application Ser. No. 08/705,347, filed Aug. 29, 1996.

TECHNICAL FIELD

The present invention relates generally to the detection, treatment and prevention of infectious diseases. In particular, the invention is related to compounds and methods for the treatment of mycobacterial infections including *Mycobacterium tuberculosis* and *Mycobacterium avium*. The invention is further related to compounds that function as non-specific immune response amplifiers, and the use of such non-specific immune response amplifiers as adjuvants in vaccination or immunotherapy against infectious disease, and in certain treatments for immune disorders and cancer.

BACKGROUND OF THE INVENTION

Tuberculosis is a chronic, infectious disease, that is caused by infection with *Mycobacterium tuberculosis* (*M. tuberculosis*). It is a major disease in developing countries, as well as an increasing problem in developed areas of the world, with about 8 million new cases and 3 million deaths each year. Although the infection may be asymptomatic for a considerable period of time, the disease is most commonly manifested as a chronic inflammation of the lungs, resulting in fever and respiratory symptoms. If left untreated, significant morbidity and death may result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistant mycobacteria.

Inhibiting the spread of tuberculosis requires effective vaccination and accurate, early diagnosis of the disease. Currently, vaccination with live bacteria is the most efficient method for inducing protective immunity. The most common mycobacterium employed for this purpose is Bacillus Calmette-Guerin (BCG), an avirulent strain of *Mycobacterium bovis*. However, the safety and efficacy of BCG is a source of controversy and some countries, such as the United States, do not vaccinate the general public. Diagnosis of *M. tuberculosis* infection is commonly achieved using a skin test, which involves intradermal exposure to tuberculin PPD (protein-purified derivative). Antigen-specific T cell responses result in measurable induration at the injection site by 48–72 hours after injection, thereby indicating exposure to mycobacterial antigens. Sensitivity and specificity have, however, been a problem with this test, and individuals vaccinated with BCG cannot be distinguished from infected individuals.

A less well-known mycobacterium that has been used for immunotherapy for tuberculosis, and also leprosy, is *Mycobacterium vaccae*, which is non-pathogenic in humans. However, there is less information on the efficacy of *M. vaccae* compared with BCG, and it has not been used widely to vaccinate the general public. *M. bovis* BCG and *M. vaccae* are believed to contain antigenic compounds that are recognised by the immune system of individuals exposed to infection with *M. tuberculosis.*

Several patents and other publications disclose treatment of various conditions by administering mycobacteria, including *M. vaccae*, or certain mycobacterial fractions. International Patent Publication WO 91/02542 discloses treatment of chronic inflammatory disorders in which a patient demonstrates an abnormally high release of IL-6 and/or TNF or in which the patient's IgG shows an abnormally high proportion of agalactosyl IgG. Among the disorders mentioned in this publication are psoriasis, rheumatoid arthritis, mycobacterial disease, Crohn's disease, primary biliary cirrhosis, sarcoidosis, ulcerative colitis, systemic lupus erythematosus, multiple sclerosis, Guillain-Barre syndrome, primary diabetes mellitus, and some aspects of graft rejection. The therapeutic agent preferably comprises autoclaved *M. vaccae* administered by injection in a single dose.

U.S. Pat. No. 4,716,038 discloses diagnosis of, vaccination against and treatment of autoimmune diseases of various types, including arthritic diseases, by administering mycobacteria, including *M. vaccae*. U.S. Pat. No. 4,724,144 discloses an immunotherapeutic agent comprising antigenic material derived from *M. vaccae* for treatment of mycobacterial diseases, especially tuberculosis and leprosy, and as an adjuvant to chemotherapy. International Patent Publication WO 91/01751 discloses the use of antigenic and/or immunoregulatory material from *M. vaccae* as an immunoprophylactic to delay and/or prevent the onset of AIDS. International Patent Publication WO 94/06466 discloses the use of antigenic and/or immunoregulatory material derived from *M. vaccae* for therapy of HIV infection, with or without AIDS and with or without associated tuberculosis.

U.S. Pat. No. 5,599,545 discloses the use of mycobacteria, especially whole, inactivated *M. vaccae*, as an adjuvant for administration with antigens which are not endogenous to *M. vaccae*. This publication theorises that the beneficial effect as an adjuvant may be due to heat shock protein 65 (hsp 65). International Patent Publication WO 92/08484 discloses the use of antigenic and/or immunoregulatory material derived from *M. vaccae* for the treatment of uveitis. International Patent Publication WO 93/16727 discloses the use of antigenic and/or immunoregulatory material derived from *M. vaccae* for the treatment of mental diseases associated with an autoimmune reaction initiated by an infection. International Patent Publication WO 95/26742 discloses the use of antigenic and/or immunoregulatory material derived from *M. vaccae* for delaying or preventing the growth or spread of tumors.

There remains a need in the art for effective compounds and methods for preventing, treating and detecting tuberculosis.

SUMMARY OF THE INVENTION

Briefly stated, the present invention provides compounds and methods for the prevention, treatment and diagnosis of mycobacterial infection, together with adjuvants for use in vaccines or immunotherapy of infectious diseases and cancers.

In a first aspect, polypeptides derived from *Mycobacterium vaccae* are provided comprising an immunogenic portion of an antigen, or a variant of such an antigen. In one embodiment, the antigen includes an amino acid sequence selected from the group consisting of: (a) sequences recited in SEQ ID NO: 89 and 201; (b) sequences having at least about 50% identical residues to a sequence recited in SEQ ID NO: 89 and 201; (c) sequences having at least about 75% identical residues to a sequence recited in SEQ ID NO: 89 and 201; and (d) sequences having at least about 90% identical residues to a sequence recited in SEQ ID NO: 89 and 201, as measured using alignments produced by the computer algorithm BLASTP.

DNA sequences encoding the inventive polypeptides, expression vectors comprising these DNA sequences, and host cells transformed or transfected with such expression vectors are also provided. In another aspect, the present invention provides fusion proteins comprising at least one polypeptide of the present invention.

Within other aspects, the present invention provides pharmaceutical compositions that comprise at least one of the inventive polypeptides, or a DNA molecule encoding such a polypeptide, and a physiologically acceptable carrier. The invention also provides vaccines comprising at least one of the above polypeptides and a non-specific immune response amplifier, together with vaccines comprising at least one DNA sequence encoding such polypeptides and a non-specific immune response amplifier.

In yet another aspect, methods are provided for enhancing an immune response in a patient, comprising administering to a patient an effective amount of one or more of the above pharmaceutical compositions and/or vaccines. In one embodiment, the immune response is a Th1 response.

In further aspects of this invention, methods are provided for the treatment of a disorder in a patient, comprising administering to the patient a pharmaceutical composition or vaccine of the present invention. In certain embodiments, the disorder is selected from the group consisting of allergic diseases, autoimmune disorders, infectious diseases, HIV and cancer.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 3 is a comparison of the Antigen 85A protein sequence obtained from *M. vaccae* (SEQ ID NO: 43) with those from *M. bovis* (SEQ ID NO: 34), *M. tuberculosis* (SEQ ID NO: 30) and *M. leprae* (SEQ ID NO: 32).

FIG. 4C(ii) illustrates the non-specific immune amplifying effects of soluble *M. vaccae* proteins extracted with SDS from delipidated and deglycolipidated *M. vaccae*. FIG. 4C(iii) illustrates that the non-specific amplifying effects of the preparation of FIG. 4C(ii) are destroyed by treatment with the proteolytic enzyme Pronase.

DETAILED DESCRIPTION OF THE INVENTION

Figure 1A:
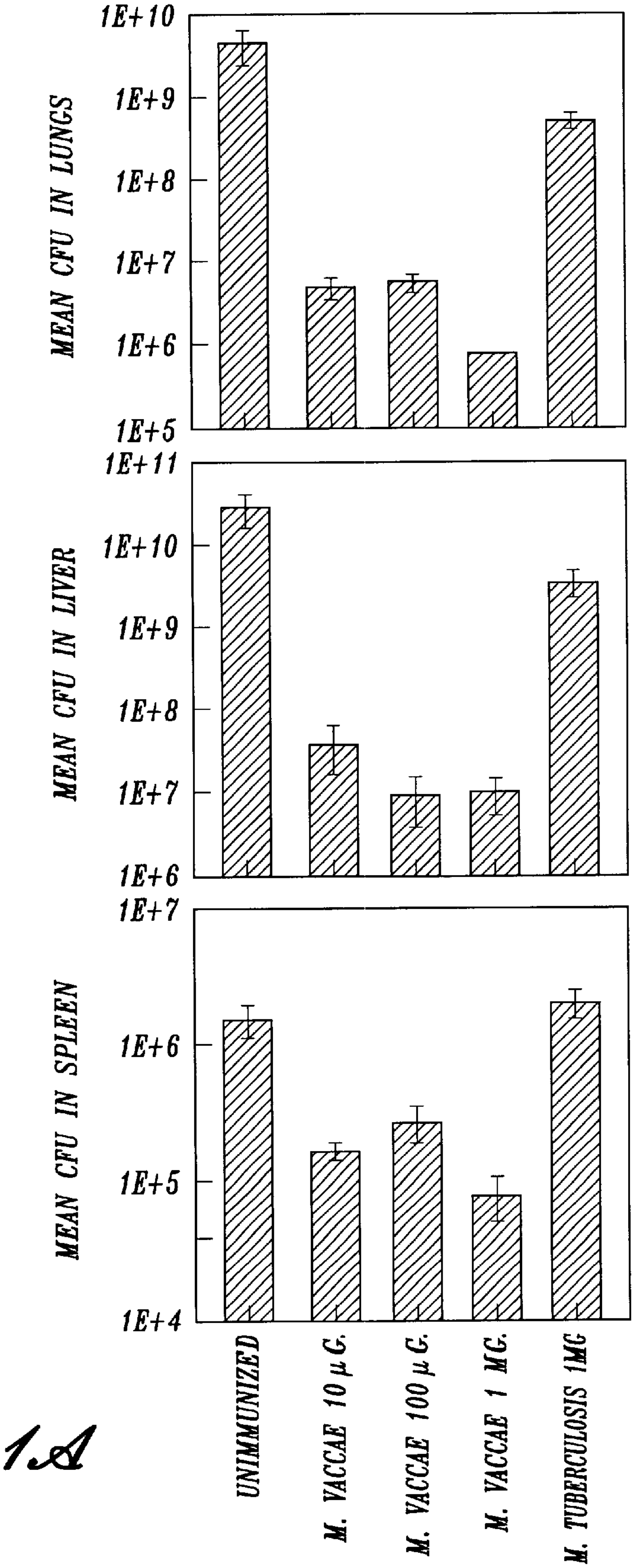
FIGS. 1A and 1B illustrate the protective effects of immunizing mice with autoclaved *M. vaccae* or unfractionated *M. vaccae* culture filtrates, respectively, prior to infection with live *M. tuberculosis* H37Rv.

As noted above, the present invention is generally directed to compositions and methods for preventing, treating and diagnosing mycobacterial infections, including *M. tuberculosis* and *M. avium* infections.

Considerable research efforts have been directed towards elucidating the mechanism of immune response to mycobacterial infection, in particular *M. tuberculosis* infection. While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in AIDS patients, due to the depletion of CD4 T cells associated with human immunodeficiency virus (HIV) infection. Mycobacterium-reactive CD4 T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, IL-12 has been shown to play a role in stimulating resistance to *M. tuberculosis* infection. Another property of $CD4^+$ T cells and macrophages is their ability to activate $CD8^+$ cytotoxic T cells which are capable of killing pathogen-infected cells. $CD8^+$ T cells have been shown to kill macrophages and other cells that harbour *M. tuberculosis*. For a review of the immunology of *M. tuberculosis* infection see Chan and Kaufmann in *Tuberculosis: Pathogenesis, Protection and Control*, Bloom (ed.), ASM Press, Washington, D.C., 1994.

The compositions of the present invention include polypeptides that comprise at least one immunogenic portion of a *M. vaccae* antigen, or a variant thereof. Such polypeptides stimulate T cell proliferation, and/or interferon gamma secretion from T cells of individuals exposed to *M. tuberculosis*. In certain embodiments, the inventive polypeptides comprise at least an immunogenic portion of a soluble *M. vaccae* antigen. A "soluble *M. vaccae* antigen" is a protein of *M. vaccae* origin that is present in *M. vaccae* culture filtrate. As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native *M. vaccae* antigen or may be heterologous, and such sequences may (but need not) be immunogenic.

"Immunogenic," as used herein, refers to the ability to elicit an immune response in a patient, such as a human, or in a biological sample. In particular, immunogenic antigens are capable of stimulating cell proliferation, interleukin-12 production or interferon-γ production in biological samples comprising one or more cells selected from the group of T cells, NK cells, B cells and macrophages, where the cells are derived from an *M. tuberculosis*-immune individual. Polypeptides comprising at least an immunogenic portion of one or more *M. vaccae* antigens may generally be used to detect tuberculosis or to induce protective immunity against tuberculosis in a patient.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

The compositions and methods of this invention also encompass variants of the above polypeptides and polynucleotides. As used herein, the term "variant" covers any sequence which has at least about 40%, more preferably at least about 60%, more preferably yet at least about 75% and most preferably at least about 90% identical residues (either nucleotides or amino acids) to a sequence of the present invention. The percentage of identical residues is determined by aligning the two sequences to be compared, determining the number of identical residues in the aligned portion, dividing that number by the total length of the inventive, or queried, sequence and multiplying the result by 100.

Polynucleotide or polypeptide sequences may be aligned, and percentage of identical nucleotides in a specified region may be determined against another polynucleotide, using computer algorithms that are publicly available. Two exemplary algorithms for aligning and identifying the similarity of polynucleotide sequences are the BLASTN and FASTA algorithms. The similarity of polypeptide sequences may be examined using the BLASTP algorithm. Both the BLASTN and BLASTP software are available on the NCBI anonymous FTP server (ftp://ncbi.nhn.nih.gov) under /blast/executables/. The BLASTN algorithm version 2.0.4 [Feb. 24, 1998], set to the default parameters described in the documentation and distributed with the algorithm, is preferred for use in the determination of variants according to the present invention. The use of the BLAST family of algorithms, including BLASTN and BLASTP, is described at NCBI's website at URL http://www.ncbi.nlm.nih.gov/BLAST/newblast.html and in the publication of Altschul, Stephen F., et al. (1997), "Gapped BLAST and PSI-BLAST: a new generation of protein database search programs", *Nucleic Acids Res.* 25:3389–3402. The computer algorithm FASTA is available on the Internet at the ftp site ftp://ftp.virginia.edu/pub/fasta/. Version 2.0u4, February 1996, set to the default parameters described in the documentation and distributed with the algorithm, is preferred for use in the determination of variants according to the present invention.

The use of the FASTA algorithm is described in W. R. Pearson and D. J. Lipman, "Improved Tools for Biological Sequence Analysis," *Proc. Natl. Acad. Sci. USA* 85:2444–2448 (1988) and W. R. Pearson, "Rapid and Sensitive Sequence Comparison with FASTP and FASTA," *Methods in Enzymology* 183:63–98 (1990).

The following running parameters are preferred for determination of alignments and similarities using BLASTN that contribute to the E values and percentage identity: Unix running command: blastall -p blastn -d embldb -e 10 -G 1 -E 1 -r 2 -v 50 -b 50 -i queryseq -o results; and parameter default values:

-p Program Name [String]
-d Database [String]
-e Expectation value (E) [Real]
-G Cost to open a gap (zero invokes default behavior) [Integer]
-E Cost to extend a gap (zero invokes default behavior) [Integer]
-r Reward for a nucleotide match (blastn only) [Integer]
-v Number of one-line descriptions (V) [Integer]
-b Number of alignments to show (B) [Integer]
-i Query File [File In]
-o BLAST report Output File [File Out] Optional For BLASTP the following running parameters are preferred: blastall -p blastp -d swissprotdb -e 10 -G 1 -E 1 -v 50 -b 50 -i queryseq -o results -p Program Name [String]
-d Database [String]
-e Expectation value (E) [Real]
-G Cost to open a gap (zero invokes default behavior) [Integer]
-E Cost to extend a gap (zero invokes default behavior) [Integer]
-v Number of one-line descriptions (v) [Integer]
-b Number of alignments to show (b) [Integer]
-I Query File [File In]
-o BLAST report Output File [File Out] Optional The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN and FASTA algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a hit is interpreted as meaning that in a database of the size of the EMBL database, one might expect to see 0.1 matches over the aligned portion of the sequence with a similar score simply by chance. By this criterion, the aligned and matched portions of the sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides, with reference to each of the polynucleotides of the present invention, preferably comprise sequences having the same number or fewer nucleic acids than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN or FASTA algorithms set at the default parameters. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at the default parameters.

Variant polynucleotide sequences will generally hybridize to the recited polynucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

A polypeptide of the present invention may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In general, *M. vaccae* antigens, and DNA sequences encoding such antigens, may be prepared using any of a variety of procedures. For example, soluble antigens may be isolated from *M. vaccae* culture filtrate as described below. Antigens may also be produced recombinantly by inserting a DNA sequence that encodes the antigen into an expression vector and expressing the antigen in an appropriate host. Any of a variety of expression vectors known to those of ordinary skill in the art may be employed. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, mycobacteria, insect, yeast or a mammalian cell line such as COS or CHO. The DNA sequences expressed in this manner may encode naturally occurring antigens, portions of naturally occurring antigens, or other variants thereof.

DNA sequences encoding *M. vaccae* antigens may be obtained by screening an appropriate *M. vaccae* cDNA or genomic DNA library for DNA sequences that hybridize to degenerate oligonucleotides derived from partial amino acid sequences of isolated soluble antigens. Suitable degenerate oligonucleotides may be designed and synthesized, and the screen may be performed as described, for example in Sambrook et al., *Molecular Cloning: A Laboratory Manual*, Cold Spring Harbor Laboratories, Cold Spring Harbor, N.Y., 1989. As described below, polymerase chain reaction (PCR) may be employed to isolate a nucleic acid probe from genomic DNA, or a cDNA or genomic DNA library. The library screen may then be performed using the isolated probe.

DNA molecules encoding *M. vaccae* antigens may also be isolated by screening an appropriate *M. vaccae* expression library with anti-sera (e.g., rabbit or monkey) raised specifically against *M. vaccae* antigens.

Regardless of the method of preparation, the antigens described herein have the ability to induce an immunogenic response. More specifically, the antigens have the ability to induce cell proliferation and/or cytokine production (for example, interferon-γ and/or interleukin-12 production) in T cells, NK cells, B cells or macrophages derived from an *M. tuberculosis*-immune individual. An *M. tuberculosis*-immune individual is one who is considered to be resistant to the development of tuberculosis by virtue of having mounted an effective T cell response to *M. tuberculosis*. Such individuals may be identified based on a strongly positive (i.e., greater than about 10 mm diameter induration) intradermal skin test response to tuberculosis proteins (PPD), and an absence of any symptoms of tuberculosis infection.

The selection of cell type for use in evaluating an immunogenic response to an antigen will depend on the desired response. For example, interleukin-12 production is most readily evaluated using preparations containing T cells, NK cells, B cells and macrophages derived from *M. tuberculosis*-immune individuals may be prepared using methods well known in the art. For example, a preparation of peripheral blood mononuclear cells (PBMCs) may be employed without further separation of component cells. PBMCs may be prepared, for example, using density centrifugation through Ficoll™ (Winthrop Laboratories, N.Y.). T cells for use in the assays described herein may be purified directly from PBMCs. Alternatively, an enriched T cell line reactive against mycobacterial proteins, or T cell clones reactive to individual mycobacterial proteins, may be employed. Such T cell clones may be generated by, for example, culturing PBMCs from *M. tuberculosis*-immune individuals with mycobacterial proteins for a period of 2–4 weeks. This allows expansion of only the mycobacterial protein-specific T cells, resulting in a line composed solely of such cells. These cells may then be cloned and tested with individual proteins, using methods well known in the art, to more accurately define individual T cell specificity. Assays for cell proliferation or cytokine production in T cells, NK cells, B cells or macrophages may be performed, for example, using the procedures described below.

In general, immunogenic antigens are those antigens that stimulate proliferation or cytokine production (i.e., interferon-γ and/or interleukin-12 production) in T cells, NK cells, B cells or macrophages derived from at least about 25% of *M. tuberculosis*-immune individuals. Among these immunogenic antigens, polypeptides having superior therapeutic properties may be distinguished based on the magnitude of the responses in the above assays and based on the percentage of individuals for which a response is observed. In addition, antigens having superior therapeutic properties will not stimulate cell proliferation or cytokine production in vitro in cells derived from more than about 25% of individuals that are not *M. tuberculosis*-immune, thereby eliminating responses that are not specifically due to *M. tuberculosis*-responsive cells. Thus, those antigens that induce a response in a high percentage of T cell, NK cell, B cell or macrophage preparations from *M. tuberculosis*-immune individuals (with a low incidence of responses in cell preparations from other individuals) have superior therapeutic properties.

Antigens with superior therapeutic properties may also be identified based on their ability to diminish the severity of *M. tuberculosis* infection, or other mycobacterial infection, in experimental animals, when administered as a vaccine. Suitable vaccine preparations for use in experimental animals are described in detail below.

Antigens having superior diagnostic properties may generally be identified based on the ability to elicit a response in an intradermal skin test performed on an individual with active tuberculosis, but not in a test performed on an individual who is not infected with *M. tuberculosis*. Skin tests may generally be performed as described below, with a response of at least about 5 mm induration considered positive.

Immunogenic portions of the antigens described herein may be prepared and identified using well known techniques, such as those summarized in Paul, *Fundamental Immunology*, 3d ed., Raven Press, 1993, pp. 243–247. Such techniques include screening polypeptide portions of the native antigen for immunogenic properties. The representative proliferation and cytokine production assays described herein may be employed in these screens. An immunogenic portion of a polypeptide is a portion that, within such representative assays, generates an immune response (e.g., cell proliferation, interferon-γ production or interleukin-12 production) that is substantially similar to that generated by the full-length antigen. In other words, an immunogenic portion of an antigen may generate at least about 20%, preferably about 65%, and most preferably about 100%, of the proliferation induced by the full-length antigen in the model proliferation assay described herein. An immunogenic portion may also, or alternatively, stimulate the production of at least about 20%, preferably about 65% and most preferably about 100%, of the interferon-γ and/or interleukin-12 induced by the full length antigen in the model assay described herein.

Portions and other variants of *M. vaccae* antigens may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems, Inc. (Foster City, Calif.), and may be operated according to the manufacturer's instructions. Variants of a native antigen may be prepared using standard mutagenesis techniques, such as oligonucleotide-directed site-specific mutagenesis. Sections of the DNA sequence may also be removed using standard techniques to permit preparation of truncated polypeptides.

In general, regardless of the method of preparation, the polypeptides disclosed herein are prepared in an isolated, substantially pure, form. Preferably, the polypeptides are at least about 80% pure, more preferably at least about 90% pure and most preferably at least about 99% pure. In certain preferred embodiments, described in detail below, the substantially pure polypeptides are incorporated into pharmaceutical compositions or vaccines for use in one or more of the methods disclosed herein.

The present invention also provides fusion proteins comprising a first and a second inventive polypeptide or, alternatively, a polypeptide of the present invention and a known *M. tuberculosis* antigen, such as the 38 kDa antigen described in Andersen and Hansen, *Infect. Immun.* 57:2481–2488, 1989, together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. Peptide linker sequences are not required when the first and second polypeptides have non-essential N-terminal amino acid regions that can be used to separate the functional domains and prevent steric interference.

The ligated DNA sequences encoding the fusion proteins are cloned into suitable expression systems using techniques known to those of ordinary skill in the art.

In another aspect, the present invention provides methods for using one or more of the inventive polypeptides or fusion proteins (or DNA molecules encoding such polypeptides or fusion proteins) to induce protective immunity against tuberculosis in a patient. As used herein, a "patient" refers to any warm-blooded animal, preferably a human. A patient may be afflicted with a disease, or may be free of detectable disease or infection. In other words, protective immunity may be induced to prevent or treat tuberculosis.

As detailed below, the inventors have demonstrated that heat-killed *M. vaccae*, DD-*M. vaccae* and recombinant *M. vaccae* proteins of the present invention may be employed to activate T cells and NK cells; to stimulate the production of cytokines (in particular Th1 class of cytokines) in human PBMC; to enhance the expression of co-stimulatory molecules on dendritic cells and monocytes (thereby enhancing activation); and to enhance dendritic cell maturation and function. Furthermore, the inventors have demonstrated similarities between the immunological properties of the inventive *M. vaccae* protein GV-23 and those of two known Th1-inducing adjuvants. GV-23 may thus be employed in the treatment of diseases that involve enhancing a Th1 immune response. Examples of such diseases include allergic diseases (for example, asthma and eczema) autoimmune diseases (for example, systemic lupus erythematosus) and infectious diseases (for example, tuberculosis and leprosy). In addition, GV-23 may be employed as a dendritic cell or NK cell enhancer in the treatment of immune deficiency disorders, such as HIV, and to enhance immune responses and cytotoxic responses to, for example, malignant cells in cancer and following immunosuppressive anti-cancer therapies, such as chemotherapy.

For use in such therapeutic methods, the polypeptide, fusion protein or DNA molecule is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response amplifier, such as an adjuvant or a liposome, into which the polypeptide is incorporated. Such pharmaceutical compositions and vaccines may also contain other mycobacterial antigens, either, as discussed above, incorporated into a fusion protein or present within a separate polypeptide.

Alternatively, a vaccine of the present invention may contain DNA encoding one or more polypeptides as described above, such that the polypeptide is generated in situ. In such vaccines, the DNA may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminator signal). Bacterial delivery systems involve the administration of a bacterium (such as Bacillus-Calmette-Guerin) that expresses an immunogenic portion of the polypeptide on its cell surface. In a preferred embodiment, the DNA may be introduced using a viral expression system (e.g., vaccinia or other poxvirus, retrovirus, or adenovirus), which may involve the use of a non-pathogenic, or defective, replication competent virus. Techniques for incorporating DNA into such expression systems are well known in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

A DNA vaccine as described above may be administered simultaneously with or sequentially to either a polypeptide of the present invention or a known mycobacterial antigen, such as the 38 kDa antigen described above. For example, administration of DNA encoding a polypeptide of the present invention, may be followed by administration of an antigen in order to enhance the protective immune effect of the vaccine.

Routes and frequency of administration, as well as dosage, will vary from individual to individual and may parallel those currently being used in immunization using BCG. In general, the pharmaceutical compositions and vaccines may be administered by injection (e.g., intradermal, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in a patient sufficient to protect the patient from mycobacterial infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.1 ml to about 5 ml.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to non-specifically enhance the immune response. Most adjuvants contain a substance designed to protect the antigen from rapid catabolism, such as aluminum hydroxide or mineral oil, and a non-specific stimulator of immune responses, such as lipid A, *Bordetella pertussis, M. tuberculosis*, or, as discussed below, *M. vaccae*. Suitable adjuvants are commercially available as, for example, Freund's Incomplete Adjuvant and Freund's Complete Adjuvant (Difco Laboratories, Detroit, Mich.), and Merck Adjuvant 65 (Merck and Company, Inc., Rahway, N.J.). Other suitable adjuvants include alum, biodegradable microspheres, monophosphoryl lipid A and Quil A.

In another aspect, this invention provides methods for using one or more of the polypeptides described above to diagnose tuberculosis using a skin test. As used herein, a "skin test" is any assay performed directly on a patient in which a delayed-type hypersensitivity (DTH) reaction (such as swelling, reddening or dermatitis) is measured following intradermal injection of one or more polypeptides as described above. Preferably, the reaction is measured at least 48 hours after injection, more preferably 48–72 hours.

The DTH reaction is a cell-mediated immune response, which is greater in patients that have been exposed previously to the test antigen (i.e., the immunogenic portion of the polypeptide employed, or a variant thereof). The response may be measured visually, using a ruler. In general, a response that is greater than about 0.5 cm in diameter, preferably greater than about 1.0 cm in diameter, is a positive response, indicative of tuberculosis infection.

For use in a skin test, the polypeptides of the present invention are preferably formulated, as pharmaceutical compositions containing a polypeptide and a physiologically acceptable carrier, as described above. Such compositions typically contain one or more of the above polypeptides in an amount ranging from about 1 $\mu$g to about 100 $\mu$g, preferably from about 10 $\mu$g to about 50 $\mu$g in a volume of 0.1 ml. Preferably, the carrier employed in such pharmaceutical compositions is a saline solution with appropriate preservatives, such as phenol and/or Tween 80™.

In a preferred embodiment, a polypeptide employed in a skin test is of sufficient size such that it remains at the site of injection for the duration of the reaction period. In general, a polypeptide that is at least 9 amino acids in length is sufficient. The polypeptide is also preferably broken down by macrophages or dendritic cells within hours of injection to allow presentation to T-cells. Such polypeptides may contain repeats of one or more of the above sequences or other immunogenic or nonimmunogenic sequences.

In another aspect, methods are provided for detecting mycobacterial infection in a biological sample, using one or more of the above polypeptides, either alone or in combination. In embodiments in which multiple polypeptides are employed, polypeptides other than those specifically described herein, such as the 38 kDa antigen described above, may be included. As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient or a blood supply. The polypeptide(s) are used in an assay, as described below, to determine the presence or absence of antibodies to the polypeptide(s) in the sample, relative to a predetermined cut-off value. The presence of such antibodies indicates the presence of mycobacterial infection.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with a Mycobacterium. After determining which samples test positive (as described below) with each polypeptide, combinations of two or more polypeptides may be formulated that are capable of detecting infection in most, or all, of the samples tested. For example, approximately 25–30% of sera from tuberculosis-infected individuals are negative for antibodies to any single protein, such as the 38 kDa antigen mentioned above. Complementary polypeptides may, therefore, be used in combination with the 38 kDa antigen to improve sensitivity of a diagnostic test.

A variety of assay formats employing one or more polypeptides to detect antibodies in a sample are well known in the art. See, e.g., Harlow and Lane, *Antibodies: A Laboratory Manual*, Cold Spring Harbor Laboratory, 1988. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labelled with a reporter group (e.g., in a semi-competitive assay). Alternatively, a competitive assay may be utilized, in which an antibody that binds to the polypeptide is labelled with a reporter group and allowed to bind to the immobilized antigen after incubation of the antigen with the sample. The extent to which components of the sample inhibit the binding of the labelled antibody to the polypeptide is indicative of the reactivity of the sample with the immobilized polypeptide.

The solid support may be any solid material to which the antigen may be attached. Suitable materials are well known in the art. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques well known in the art. In the context of the present invention, the term "bound" refers to both noncovalent association, such as adsorption, and covalent attachment, which may be a direct linkage between the antigen and functional groups on the support or a linkage by way of a cross-linking agent. Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme-linked immunosorbent assay (ELISA). This assay may be performed by first contacting a polypeptide antigen that has been immobilized on a solid support, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time, or incubation time, is that period of time that is sufficient to detect the presence of antibody within a *M. tuberculosis*-infected sample. Preferably, the contact time is sufficient to achieve a level of binding that is at least 95% of that achieved at equilibrium between bound and unbound antibody. The time necessary to achieve equilibrium may be readily determined by assaying the level of binding that occurs over a period of time. At room temperature, an incubation time of about 30 minutes is generally sufficient.

Unbound sample may be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known in the art. Common binding agents may also be purchased conjugated to a variety of reporter groups from many commercial sources (e.g., Zymed Laboratories, San Francisco, Calif., and Pierce, Rockford, Ill.).

The detection reagent is incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may be detected by the addition of substrate (generally for a specific period of time), followed by spectroscopic or other analysis of the reaction products.

To determine the presence or absence of anti-mycobacterial antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, pp. 106–107. In general, signals higher than the predetermined cut-off value are considered to be positive for mycobacterial infection.

The assay may also be performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-mycobacterial antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 $\mu$g, and more preferably from about 50 ng to about 500 ng. Such tests can typically be performed with a very small amount (e.g., one drop) of patient serum or blood.

Numerous other assay protocols exist that are suitable for use with the polypeptides of the present invention. The above descriptions are intended to be exemplary only.

The present invention also provides antibodies to the inventive polypeptides. Antibodies may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells may then be immortalized by fusion with a myeloma cell fusion partner, preferably one that is syngeneic with the immunized animal, using one of a variety of techniques well known in the art.

Monoclonal antibodies may be isolated from the supernatants of the resulting hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood.

Antibodies may be used in diagnostic tests to detect the presence of mycobacterial antigens using assays similar to those detailed above and other techniques well known to those of skill in the art, thereby providing a method for detecting mycobacterial infection, such as *M. tuberculosis* infection, in a patient.

Diagnostic reagents of the present invention may also comprise DNA sequences encoding one or more of the above polypeptides, or one or more portions thereof. For example, primers comprising at least 10 contiguous oligonucleotides of the subject DNA sequences may be used in polymerase chain reaction (PCR) based tests. Similarly, probes comprising at least 18 contiguous oligonucleotides of the subject DNA sequences may be used for hybridizing to specific sequences. Techniques for both PCR based tests and hybridization tests are well known in the art. Primers or probes may thus be used to detect *M. tuberculosis* and other mycobacterial infections in biological samples, preferably sputum, blood, serum, saliva, cerebrospinal fluid or urine. DNA probes or primers comprising oligonucleotide sequences described above may be used alone, in combination with each other, or with previously identified sequences, such as the 38 kDa antigen discussed above.

As discussed above, effective vaccines contain at least two different components. The first is a polypeptide comprising an antigen, which is processed by macrophages and other antigen-presenting cells and displayed for $CD4^+$ T cells or for $CD8^+$ T cells. This antigen forms the "specific" target of an immune response. The second component of a vaccine is a non-specific immune response amplifier, such as an adjuvant or a liposome, into which the antigen is incorporated. An adjuvant amplifies immune responses to a structurally unrelated compound or polypeptide. Several adjuvants are prepared from microbes such as *Bordetella pertussis, M. tuberculosis* and *M. bovis* BCG. Adjuvants may also contain components designed to protect polypeptide antigens from degradation, such as aluminum hydroxide or mineral oil.

While the antigenic component of a vaccine contains polypeptides that direct the immune attack against a specific pathogen, such as *M. tuberculosis*, the adjuvant is often capable of broad use in many different vaccine formulations. Certain pathogens, such as *M. tuberculosis*, as well as certain cancers, are effectively contained by an immune attack directed by T cells, known as cell-mediated immunity. Other pathogens, such as poliovirus, also require antibodies produced by B cells for containment. These different classes of immune attack (T cell or B cell) are controlled by different subpopulations of $CD4^+$ T cells, commonly referred to as Th1 and Th2 cells. A desirable property of an adjuvant is the ability to selectively amplify the function of either Th1 or Th2 populations of $CD4^+$ T cells. As shown below in Example 6, *M. vaccae* and a modified form of autoclaved *M. vaccae* have been found to have adjuvant properties. As used herein, the term "modified *M. vaccae*" includes delipidated *M. vaccae* cells, deglycolipidated *M. vaccae* cells and *M. vaccae* cells that have been both delipidated and deglycolipidated (hereinafter referred to as DD-*M. vaccae*). Furthermore, it has been found that *M. vaccae* produces compounds which amplify the immune response to *M. vaccae* antigens, as well as to antigens from other sources. The present invention thus provides methods for enhancing immune responses to an antigen comprising administering killed *M. vaccae* cells, *M. vaccae* culture filtrate or modified *M. vaccae* cells. As detailed below, further studies have demonstrated that this non-specific immune amplifying effect is due, at least in part, to an *M. vaccae* polypeptide having homology to heat shock protein 65 (GroEL), previously identified in *M. tuberculosis.*

As described below in Example 10, it has also been found that heat-killed *M. vaccae* and *M. vaccae* constituents have cytokine stimulation properties. In particular, it has been found that heat-killed *M. vaccae*, lyophilised *M. vaccae* and DD-*M. vaccae* stimulate the production of interleukin 12 (IL-12) from macrophages. Production of IL-12 from macrophages is known to enhance stimulation of a Th1 immune response.

The word "about," when used in this application with reference to a percentage by weight composition, contemplates a variance of up to 10 percentage units from the stated percentage. When used in reference to percentage identity or percentage probability, the word "about" contemplates a variance of up to one percentage unit from the stated percentage.

The following examples are offered by way of illustration and not by way of limitation.

EXAMPLE 1

Effect of Immunization of Mice with *M. VACCAE* on Tuberculosis

This example illustrates the effect of immunization with *M. vaccae* or *M. vaccae* culture filtrate in mice prior to challenge with live *M. tuberculosis.*

*M. vaccae* (ATCC Number 15483) was cultured in sterile Medium 90 (yeast extract, 2.5 g/l; tryptone, 5 g/l; glucose, 1 g/l) at 37° C. The cells were harvested by centrifugation, and transferred into sterile Middlebrook 7H9 medium (Difco Laboratories, Detroit, Mich., USA) with glucose at 37° C.

for one day. The medium was then centrifuged to pellet the bacteria, and the culture filtrate removed. The bacterial pellet was resuspended in phosphate buffered saline at a concentration of 10 mg/ml, equivalent to $10^{10}$ *M. vaccae* organisms per ml. The cell suspension was then autoclaved for 15 min at 120° C. The culture filtrate was passaged through a 0.45 $\mu$m filter into sterile bottles.

As shown in FIG. 1A, when mice were immunized with 1 mg, 100 $\mu$g or 10 $\mu$g of *M. vaccae* and infected three weeks later with $5\times10^5$ colony forming units (CFU) of live *M. tuberculosis* H37Rv, significant protection from infection was seen. In this example, spleen, liver and lung tissue was harvested from mice three weeks after infection, and live bacilli determined (expressed as CFU). The reduction in bacilli numbers, when compared to tissue from non-immunized control mice, exceeded 2 logs in liver and lung tissue, and 1 log in spleen tissue. Immunization of mice with heat-killed *M. tuberculosis* H37Rv had no significant protective effects on mice subsequently infected with live *M. tuberculosis* H37Rv.

Figure 1B:
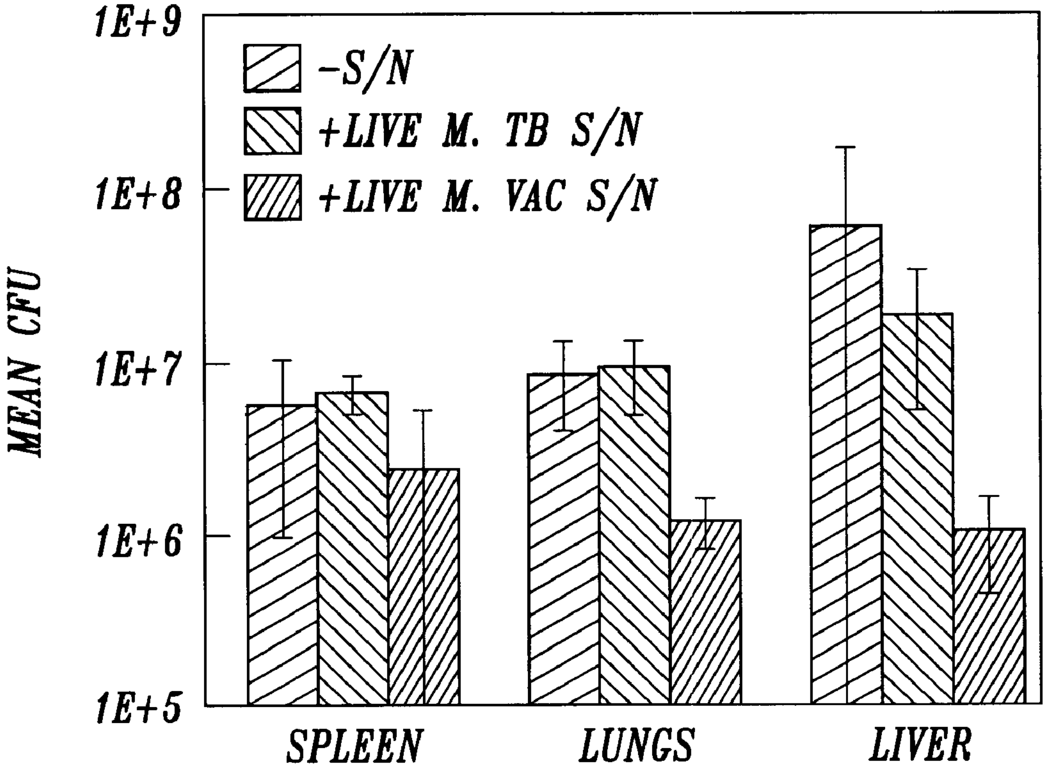

FIG. 1B shows that when mice were immunized with 100 $\mu$g of *M. vaccae* culture filtrate, and infected three weeks later with $5\times10^5$ CFU of *M. tuberculosis* H37Rv, significant protection was also seen. When spleen, liver and lung tissue was harvested from mice three weeks after infection, and live bacilli numbers (CFU) determined, a 1–2 log reduction in numbers, as compared to non-immunized control mice, was observed.

EXAMPLE 2

Purification and Characterization of Polypeptides from *M. vaccae* Culture Filtrate This example illustrates the preparation of *M. vaccae* soluble proteins from culture filtrate. Unless otherwise noted, all percentages in the following example are weight per volume.

*M. vaccae* (ATCC Number 15483) was cultured in sterile Medium 90 at 37° C. The cells were harvested by centrifugation, and transferred into sterile Middlebrook 7H9 medium with glucose at 37° C. for one day. The medium was then centrifuged (leaving the bulk of the cells) and filtered through a 0.45 $\mu$m filter into sterile bottles.

The culture filtrate was concentrated by lyophilization, and redissolved in MilliQ water. A small amount of insoluble material was removed by filtration through a 0.45 $\mu$m membrane. The culture filtrate was desalted by membrane filtration in a 400 ml Amicon stirred cell which contained a 3 kDa molecular weight cut-off (MWCO) membrane. The pressure was maintained at 50 psi using nitrogen gas. The culture filtrate was repeatedly concentrated by membrane filtration and diluted with water until the conductivity of the sample was less than 1.0 mS. This procedure reduced the 20 l volume to approximately 50 ml. Protein concentrations were determined by the Bradford protein assay (Bio-Rad, Hercules, Calif., USA).

The desalted culture filtrate was fractionated by ion exchange chromatography on a column of Q-Sepharose (Pharmacia Biotech, Uppsala, Sweden) (16×100 mm) equilibrated with 10 mM Tris HCl buffer pH 8.0. Polypeptides were eluted with a linear gradient of NaCl from 0 to 1.0 M in the above buffer system. The column eluent was monitored at a wavelength of 280 nm.

The pool of polypeptides eluting from the ion exchange column was concentrated in a 400 ml Amicon stirred cell which contained a 3 kDa MWCO membrane. The pressure was maintained at 50 psi using nitrogen gas. The polypeptides were repeatedly concentrated by membrane filtration and diluted with 1% glycine until the conductivity of the sample was less than 0.1 mS.

The purified polypeptides were then fractionated by preparative isoelectric focusing in a Rotofor device (Bio-Rad, Hercules, Calif., USA). The pH gradient was established with a mixture of Ampholytes (Pharmacia Biotech) comprising 1.6% pH 3.5–5.0 Ampholytes and 0.4% pH 5.0–7.0 Ampholytes. Acetic acid (0.5 M) was used as the anolyte, and 0.5 M ethanolamine as the catholyte. Isoelectric focusing was carried out at 12W constant power for 6 hours, following the manufacturer's instructions. Twenty fractions were obtained.

Fractions from isoelectric focusing were combined, and the polypeptides were purified on a Vydac C4 column (Separations Group, Hesperia, Calif., USA) 300 Angstrom pore size, 5 micron particle size (10×250 mm). The polypeptides were eluted from the column with a linear gradient of acetonitrile (0–80% v/v) in 0.05% (v/v) trifluoroacetic acid (TFA). The flow-rate was 2.0 ml/min and the HPLC eluent was monitored at 220 nm. Fractions containing polypeptides were collected to maximize the purity of the individual samples.

Relatively abundant polypeptide fractions were rechromatographed on a Vydac C4 column (Separations Group) 300 Angstrom pore size, 5 micron particle size (4.6×250 mm). The polypeptides were eluted from the column with a linear gradient from 20–60% (v/v) of acetonitrile in 0.05% (v/v) TFA at a flow-rate of 1.0 ml/min. The column eluent was monitored at 220 nm. Fractions containing the eluted polypeptides were collected to maximise the purity of the individual samples. Approximately 20 polypeptide samples were obtained and they were analysed for purity on a polyacrylamide gel according to the procedure of Laemmli (Laemmli, U. K., *Nature* 277:680–685, 1970).

The polypeptide fractions which were shown to contain significant contamination were further purified using a Mono Q column (Pharmacia Biotech) 10 micron particle size (5×50 mm) or a Vydac Diphenyl column (Separations Group) 300 Angstrom pore size, 5 micron particle size (4.6×250 mm). From a Mono Q column, polypeptides were eluted with a linear gradient from 0–0.5 M NaCl in 10 mM Tris HCl pH 8.0. From a Vydac Diphenyl column, polypeptides were eluted with a linear gradient of acetonitrile (20–60% v/v) in 0.1% TFA. The flow-rate was 1.0 ml/min and the column eluent was monitored at 220 nm for both columns. The polypeptide peak fractions were collected and analysed for purity on a 15% polyacrylamide gel as described above.

For sequencing, the polypeptides were individually dried onto Biobrene™ (Perkin Elmer/Applied BioSystems Division, Foster City, Calif.)-treated glass fiber filters. The filters with polypeptide were loaded onto a Perkin Elmer/Applied BioSystems Procise 492 protein sequencer and the polypeptides were sequenced from the amino terminal end using traditional Edman chemistry. The amino acid sequence was determined for each polypeptide by comparing the retention time of the PTH amino acid derivative to the appropriate PTH derivative standards.

Internal sequences were also determined on some antigens by digesting the antigen with the endoprotease Lys-C, or by chemically cleaving the antigen with cyanogen bromide. Peptides resulting from either of these procedures were separated by reversed-phase HPLC on a Vydac C18 column using a mobile phase of 0.05% (v/v) trifluoroacetic acid with a gradient of acetonitrile containing 0.05% (v/v) TFA (1%/min). The eluent was monitored at 214 mn. Major internal peptides were identified by their UV absorbance, and their N-terminal sequences were determined as described above.

Using the procedures described above, six soluble *M. vaccae* antigens, designated GVc-1, GVc-2, GVc-7, GVc-13, GVc-20 and GVc-22, were isolated. Determined N-terminal and internal sequences for GVc-1 are shown in SEQ ID NOS: 1, 2 and 3, respectively; the N-terminal sequence for GVc-2 is shown in SEQ ID NO: 4; internal sequences for GVc-7 are shown in SEQ ID NOS: 5–8; internal sequences for GVc-13 are shown in SEQ ID NOS: 9–11; internal sequence for GVc-20 is shown in SEQ ID NO: 12; and N-terminal and internal sequences for GVc-22 are shown in SEQ ID NO:56–59, respectively. Each of the internal peptide sequences provided herein begins with an amino acid residue which is assumed to exist in this position in the polypeptide, based on the known cleavage specificity of cyanogen bromide (Met) or Lys-C (Lys).

Three additional polypeptides, designated GVc-16, GVc-18 and GVc-21, were isolated employing a preparative sodium dodecyl sulfate-polyacrylamide gel electrophoresis (SDS-PAGE) purification step in addition to the preparative isoelectric focusing procedure described above. Specifically, fractions comprising mixtures of polypeptides from the preparative isoelectric focusing purification step previously described were purified by preparative SDS-PAGE on a 15% polyacrylamide gel. The samples were dissolved in reducing sample buffer and applied to the gel. The separated proteins were transferred to a polyvinylidene difluoride (PVDF) membrane by electroblotting in 10 mM 3-(cyclohexylamino)-1-propanesulfonic acid (CAPS) buffer pH 11 containing 10% (v/v) methanol. The transferred protein bands were identified by staining the PVDF membrane with Coomassie blue. Regions of the PVDF membrane containing the most abundant polypeptide species were cut out and directly introduced into the sample cartridge of the Perkin Elmer/Applied BioSystems Procise 492 protein sequencer. Protein sequences were determined as described above. The N-terminal sequences for GVc-16, GVc-18 and GVc-21 are provided in SEQ ID NOS: 13, 14 and 15, respectively.

Additional antigens, designated GVc-12, GVc-14, GVc-15, GVc-17 and GVc-19, were isolated employing a preparative SDS-PAGE purification step in addition to the chromatographic procedures described above. Specifically, fractions comprising a mixture of antigens from the Vydac C4 HPLC purification step previously described were fractionated by preparative SDS-PAGE on a polyacrylamide gel. The samples were dissolved in non-reducing sample buffer and applied to the gel. The separated proteins were transferred to a PVDF membrane by electroblotting in 10 mM CAPS buffer, pH 11 containing 10% (v/v) methanol. The transferred protein bands were identified by staining the PVDF membrane with Coomassie blue. Regions of the PVDF membrane containing the most abundant polypeptide species were cut out and directly introduced into the sample cartridge of the Perkin Elner/Applied BioSystems Procise 492 protein sequencer. Protein sequences were determined as described above. The determined N-terminal sequences for GVc-12, GVc-14, GVc-15, GVc-17 and GVc-19 are provided in SEQ ID NOS: 16–20, respectively.

All of the above amino acid sequences were compared to known amino acid sequences in the SwissProt data base (version R32) using the GeneAssist system. No significant homologies to the amino acid sequences GVc-2 to GVc-22 were obtained. The amino acid sequence for GVc-1 was found to bear some similarity to sequences previously identified from *M. bovis* and *M. tuberculosis*. In particular, GVc-1 was found to have some homology with *M. tuberculosis* MPT83, a cell surface protein, as well as MPT70. These proteins form part of a protein family (Harboe et al., *Scand. J. Immunol.* 42:46–51, 1995).

Subsequent studies led to the isolation of DNA sequences for GVc-13, GVc-14 and GVc-22 (SEQ ID NO: 142, 107 and 108, respectively). The corresponding predicted amino acid sequences for GVc-13, GVc-14 and GVc-22 are provided in SEQ ID NO: 143, 109 and 110, respectively. The determined DNA sequence for the full length gene encoding GVc-13 is provided in SEQ ID NO: 195, with the corresponding predicted amino acid sequence being provided in SEQ ID NO: 196.

Further studies with GVc-22 suggested that only a part of the gene encoding GVc-22 was cloned. When sub-cloned into the expression vector pET16, no protein expression was obtained. Subsequent screening of the *M. vaccae* BamHI genomic DNA library with the incomplete gene fragment led to the isolation of the complete gene encoding GVc-22. To distinguish between the full-length clone and the partial GVc-22, the antigen expressed by the full-length gene was called GV-22B. The determined nucleotide sequence of the gene encoding GV-22B and the predicted amino acid sequence are provided in SEQ ID NOS: 144 and 145 respectively.

Amplifications primers AD86 and AD112 (SEQ ID NO: 60 and 61, respectively) were designed from the amino acid sequence of GVc-1 (SEQ ID NO: 1) and the *M. tuberculosis* MPT70 gene sequence. Using these primers, a 310 bp fragment was amplified from *M. vaccae* genomic DNA and cloned into EcoRV-digested vector pBluescript II $SK^+$ (Stratagene). The sequence of the cloned insert is provided in SEQ ID NO: 62. The insert of this clone was used to screen a *M. vaccae* genomic DNA library constructed in lambda ZAP-Express (Stratagene, La Jolla, Calif.). The clone isolated contained an open reading frame with homology to the *M. tuberculosis* antigen MPT83 and was re-named GV-1/83. This gene also had homology to the *M. bovis* antigen MPB83. The determined nucleotide sequence and predicted amino acid sequences are provided in SEQ ID NOS: 146 and 147 respectively.

From the amino acid sequences provided in SEQ ID NOS: 1 and 2, degenerate oligonucleotides EV59 and EV61 (SEQ ID NOS: 148 and 149 respectively) were designed. Using PCR, a 100 bp fragment was amplified, cloned into plasmid pBluescript II $SK^+$ and sequenced (SEQ ID NO: 150) following standard procedures (Maniatis). The cloned insert was used to screen a *M. vaccae* genomic DNA library constructed in lambda ZAP-Express. The clone isolated had homology to *M. tuberculosis* antigen MPT70 and *M. bovis* antigen MPB70, and was named GV-1/70. The determined nucleotide sequence and predicted amino acid sequence for GV-1/70 are provided in SEQ ID NOS: 151 and 152 respectively.

For expression and purification, the genes encoding GV1/83, GV1/70, GVc-13, GVc-14 and GV-22B were sub-cloned into the expression vector pET16 (Novagen, Madison, Wisc.). Expression and purification were performed according to the manufacturer's protocol.

The purified polypeptides were screened for the ability to induce T-cell proliferation and IFN-γ in peripheral blood cells from immune human donors. These donors were known to be PPD (purified protein derivative from *M.*

*tuberculosis*) skin test positive and their T cells were shown to proliferate in response to PPD. Donor PBMCs and crude soluble proteins from *M. vaccae* culture filtrate were cultured in medium comprising RPMI 1640 supplemented with 10% (v/v) autologous serum, penicillin (60 μg/ml), streptomycin (100 μg/ml), and glutamine (2 mM).

After 3 days, 50 μl of medium was removed from each well for the determination of IFN-γ levels, as described below. The plates were cultured for a further 4 days and then pulsed with 1 μCi/well of tritiated thymidine for a further 18 hours, harvested and tritium uptake determined using a scintillation counter. Fractions that stimulated proliferation in both replicates two-fold greater than the proliferation observed in cells cultured in medium alone were considered positive.

IFN-γ was measured using an enzyme-linked immunosorbent assay (ELISA). ELISA plates were coated with a mouse monoclonal antibody directed to human IFN-γ (Endogen, Wobural, Mass.) 1 μg/ml phosphate-buffered saline (PBS) for 4 hours at 4° C. Wells were blocked with PBS containing 0.2% Tween 20 for 1 hour at room temperature. The plates were then washed four times in PBS/0.2% Tween 20, and samples diluted 1:2 in culture medium in the ELISA plates were incubated overnight at room temperature. The plates were again washed, and a biotinylated polyclonal rabbit anti-human IFN-γ serum (Endogen), diluted to 1 μg/ml in PBS, was added to each well. The plates were then incubated for 1 hour at room temperature, washed, and horseradish peroxidase-coupled avidin A (Vector Laboratories, Burlingame, Calif.) was added at a 1:4,000 dilution in PBS. After a further 1 hour incubation at room temperature, the plates were washed and orthophenylenediamine (OPD) substrate added. The reaction was stopped after 10 min with 10% (v/v) HCl. The optical density (OD) was determined at 490 nm. Fractions that resulted in both replicates giving an OD two-fold greater than the mean OD from cells cultured in medium alone were considered positive.

Examples of polypeptides containing sequences that stimulate peripheral blood mononuclear cells (PBMC) T cells to proliferate and produce IFN-γ are shown in Table 1, wherein (−) indicates a lack of activity, (+/−) indicates polypeptides having a result less than twice higher than background activity of control media, (+) indicates polypeptides having activity two to four times above background, and (++) indicates polypeptides having activity greater than four times above background.

TABLE 1

| Antigen | Proliferation | IFN-γ |
|---|---|---|
| GVc-1 | ++ | +/− |
| GVc-2 | + | ++ |
| GVc-7 | +/− | − |
| GVc-13 | + | ++ |
| GVc-14 | ++ | + |
| GVc-15 | + | + |
| GVc-20 | + | + |

EXAMPLE 3

Purification and Characterization of Polypeptides from *M. vaccae* Culture Filtrate by 2-DIMENSIONAL Polyacrylamide Gel Electrophoresis

*M. vaccae* soluble proteins were isolated from culture filtrate using 2-dimensional polyacrylamide gel electrophoresis as described below. Unless otherwise noted, all percentages in the following example are weight per volume.

*M. vaccae* (ATCC Number 15483) was cultured in sterile Medium 90 at 37° C. *M. tuberculosis* strain H37Rv (ATCC number 27294) was cultured in sterile Middlebrook 7H9 medium with Tween 80 and oleic acid/albumin/dextrose/catalase additive (Difco Laboratories, Detroit, Mich.). The cells were harvested by centrifugation, and transferred into sterile Middlebrook 7H9 medium with glucose at 37° C. for one day. The medium was then centrifuged (leaving the bulk of the cells) and filtered through a 0.45 μm filter into sterile bottles. The culture filtrate was concentrated by lyophilisation, and redissolved in MilliQ water. A small amount of insoluble material was removed by filtration through a 0.45 μm membrane filter.

The culture filtrate was desalted by membrane filtration in a 400 ml Amicon stirred cell which contained a 3 kDa MWCO membrane. The pressure was maintained at 60 psi using nitrogen gas. The culture filtrate was repeatedly concentrated by membrane filtration and diluted with water until the conductivity of the sample was less than 1.0 mS. This procedure reduced the 20 l volume to approximately 50 ml. Protein concentrations were determined by the Bradford protein assay (Bio-Rad, Hercules, Calif., USA).

The desalted culture filtrate was fractionated by ion exchange chromatography on a column of Q-Sepharose (Pharmacia Biotech) (16×100 mm) equilibrated with 10 mM TrisHCl buffer pH 8.0. Polypeptides were eluted with a linear gradient of NaCl from 0 to 1.0 M in the above buffer system. The column eluent was monitored at a wavelength of 280 nm.

Figure 2A:
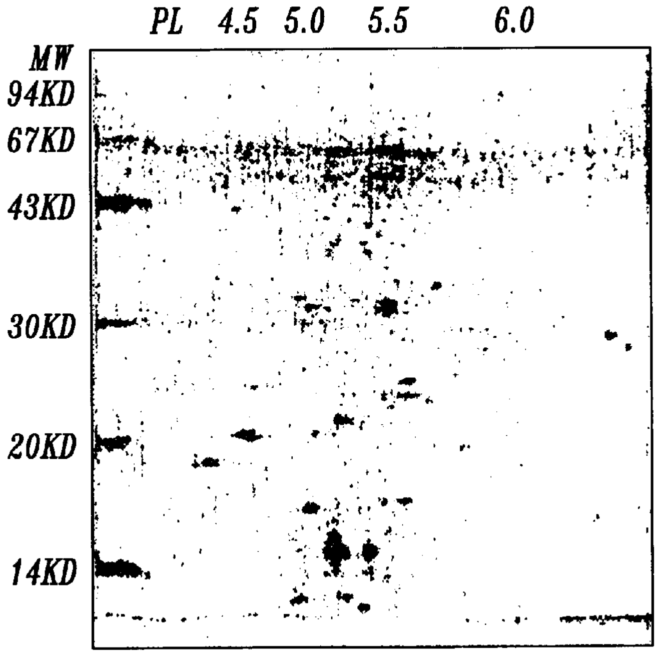
FIGS. 2A and B show components of *M. vaccae* and *M. tuberculosis* culture filtrates, respectively, as analysed by 2-dimensional polyacrylamide gel electrophoresis.
Figure 2B:
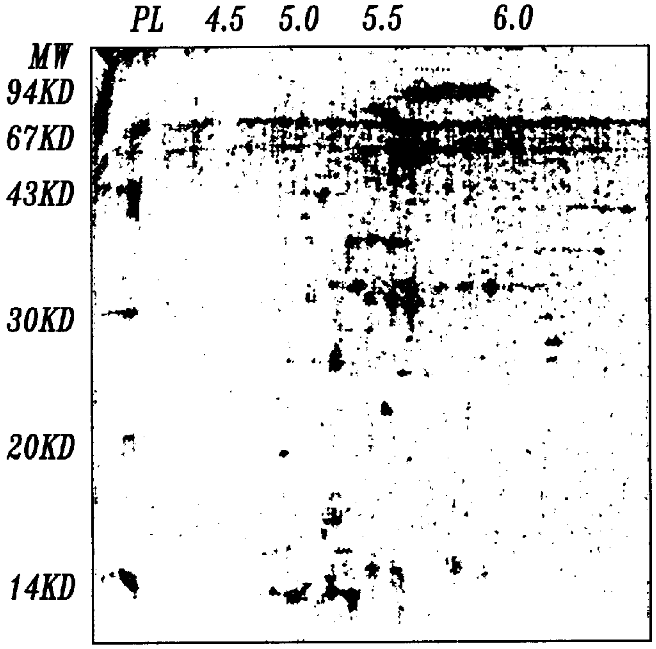

The pool of polypeptides eluting from the ion exchange column were fractionated by preparative 2D gel electrophoresis. Samples containing 200–500 μg of polypeptide were made 8M in urea and applied to polyacrylamide isoelectric focusing rod gels (diameter 2 mm, length 150 mm, pH 5-7). After the isoelectric focusing step, the first dimension gels were equilibrated with reducing buffer and applied to second dimension gels (16% polyacrylamide). FIGS. 2A and 2B are the 2-D gel patterns observed with *M. vaccae* culture filtrate and *M. tuberculosis* H37Rv culture filtrate, respectively. Polypeptides from the second dimension separation were transferred to PVDF membranes by electroblotting in 10 mM CAPS buffer pH 11 containing 10% (v/v) methanol. The PVDF membranes were stained for protein with Coomassie blue. Regions of PVDF containing polypeptides of interest were cut out and directly introduced into the sample cartridge of the Perkin Elmer/Applied BioSystems Procise 492 protein sequencer. The polypeptides were sequenced from the amino terminal end using traditional Edman chemistry. The amino acid sequence was determined for each polypeptide by comparing the retention time of the PTH amino acid derivative to the appropriate PTH derivative standards. Using these procedures, eleven polypeptides, designated GVs-1, GVs-3, GVs-4, GVs-5, GVs-6, GVs-8, GVs-9, GVs-10, GVs-11, GV-34 and GV-35 were isolated. The determined N-terminal sequences for these polypeptides are shown in SEQ ID NOS: 21–29, 63 and 64, respectively. Using the purification procedure described above, more protein was purified to extend the amino acid sequence previously obtained for GVs-9. The extended amino acid sequence for GVs-9 is provided in SEQ ID NO: 65. Further studies resulted in the isolation of DNA sequences for GVs-9 (SEQ ID NO: 111) and GV-35 (SEQ ID NO: 155). The corresponding predicted amino acid sequences are provided in SEQ ID NO: 112 and 156, respectively. An extended DNA sequence for GVs-9 is provided in SEQ ID NO: 153, with the corresponding predicted amino acid sequence being provided in SEQ ID NO: 154. The predicted amino acid sequence for GVs-9 has been amended in SEQ ID NO: 197.

All of these amino acid sequences were compared to known amino acid sequences in the SwissProt data base (version R35 plus update). No significant homologies were obtained, with the exceptions of GVs-3, GVs-4, GVs-5 and GVs-9. GVs-9 was found to bear some homology to two previously identified *M. tuberculosis* proteins, namely *M. tuberculosis* cutinase precursor and an *M. tuberculosis* hypothetical 22.6 kDa protein. GVs-3, GVs-4 and GVs-5 were found to bear some similarity to the antigen 85A and 85B proteins from *M. leprae* (SEQ ID NOS: 30 and 31, respectively), *M. tuberculosis* (SEQ ID NOS: 32 and 33, respectively) and *M. bovis* (SEQ ID NOS: 34 and 35, respectively), and the antigen 85C proteins from *M. leprae* (SEQ ID NO: 36) and *M. tuberculosis* (SEQ ID NO: 37). A comparison of the inventive antigen 85A protein from *M. vaccae* with those from *M. tuberculosis, M. bovis* and *M. leprae*, is presented in FIG. 3.

EXAMPLE 4

DNA Cloning Strategy for the *M. vaccae* Antigen 85 Series

Probes for antigens 85A, 85B, and 85C were prepared by the polymerase chain reaction (PCR) using degenerate oligonucleotides (SEQ ID NOS: 38 and 39) designed to regions of antigen 85 genomic sequence that are conserved between family members in a given mycobacterial species, and between mycobacterial species. These oligonucleotides were used under reduced stringency conditions to amplify target sequences from *M. vaccae* genomic DNA. An appropriately-sized 485 bp band was identified, purified, and cloned into T-tailed pBluescript II SK (Stratagene, La Jolla, Calif.). Twenty-four individual colonies were screened at random for the presence of the antigen 85 PCR product, then sequenced using the Perkin Elmer/Applied Biosystems Model 377 automated sequencer and the Ml 3-based primers, T3 and T7. Homology searches of the GenBank databases showed that twenty-three clones contained insert with significant homology to published antigen 85 genes from *M. tuberculosis* and *M. bovis*. Approximately half were most homologous to antigen 85C gene sequences, with the remainder being more similar to antigen 85B sequences. In addition, these two putative *M. vaccae* antigen 85 genomic sequences were 80% homologous to one another. Because of this high similarity, the antigen 85C PCR fragment was chosen to screen *M. vaccae* genomic libraries at low stringency for all three antigen 85 genes.

An *M. vaccae* genomic library was created in lambda Zap-Express (Stratagene, La Jolla, Calif.) by cloning BamHI partially-digested *M. vaccae* genomic DNA into similarly-digested $\lambda$ vector, with $3.4\times10^5$ independent plaque-forming units resulting. For screening purposes, twenty-seven thousand plaques from this non-amplified library were plated at low density onto eight 100 $cm^2$ plates. For each plate, duplicate plaque lifts were taken onto Hybond-$N^+$ nylon membrane (Amersham International, United Kingdom), and hybridised under reduced-stringency conditions (55° C.) to the radiolabelled antigen 85C PCR product. Autoradiography demonstrated that seventy-nine plaques consistently hybridised to the antigen 85C probe under these conditions. Thirteen positively-hybridising plaques were selected at random for further analysis and removed from the library plates, with each positive clone being used to generate secondary screening plates containing about two hundred plaques. Duplicate lifts of each plate were taken using Hybond-$N^+$ nylon membrane, and hybridised under the conditions used in primary screening. Multiple positively-hybridising plaques were identified on each of the thirteen plates screened. Two well-isolated positive phage from each secondary plate were picked for further analysis. Using in vitro excision, twenty-six plaques were converted into phagemid, and restriction-mapped. It was possible to group clones into four classes on the basis of this mapping. Sequence data from the 5' and 3' ends of inserts from several representatives of each group was obtained using the Perkin Elmer/Applied Biosystems Model 377 automated sequencer and the T3 and T7 primers. Sequence homologies were determined using BLASTN analysis of the EMBL database. Two of these sets of clones were found to be homologous to *M. bovis* and *M. tuberculosis* antigen 85A genes, each containing either the 5' or 3' ends of the *M. vaccae* gene (this gene was cleaved during library construction as it contains an internal BamHI site). The remaining clones were found to contain sequences homologous to antigens 85B and 85C from a number of mycobacterial species. To determine the remaining nucleotide sequence for each gene, appropriate subclones were constructed and sequenced. Overlapping sequences were aligned using the DNA Strider software. The determined DNA sequences for *M. vaccae* antigens 85A, 85B and 85C are shown in SEQ ID NOS: 40–42, respectively, with the predicted amino acid sequences being shown in SEQ ID NOS: 43–45, respectively.

The *M. vaccae* antigens GVs-3 and GVs-5 were expressed and purified as follows. Amplification primers were designed from the insert sequences of GVs-3 and GVs-5 (SEQ ID NO: 40 and 42, respectively) using sequence data downstream from the putative leader sequence and the 3' end of the clone. The sequences of the primers for GVs-3 are provided in SEQ ID NO: 66 and 67, and the sequences of the primers for GVs-5 are provided in SEQ ID NO: 68 and 69. A XhoI restriction site was added to the primers for GVs-3, and EcoRI and BamHI restriction sites were added to the primers for GVs-5 for cloning convenience. Following amplification from genomic *M. vaccae* DNA, fragments were cloned into the appropriate site of pProEX HT prokaryotic expression vector (Gibco BRL, Life Technologies, Gaithersburg, Md.) and submitted for sequencing to confirm the correct reading frame and orientation. Expression and purification of the recombinant protein was performed according to the manufacturer's protocol.

Expression of a fragment of the *M. vaccae* antigen GVs-4 (antigen 85B homolog) was performed as follows. The primers AD58 and AD59, described above, were used to amplify a 485 bp fragment from *M. vaccae* genomic DNA. This fragment was gel-purified using standard techniques and cloned into EcoRV-digested pBluescript containing added dTTP residues. The base sequences of inserts from five clones were determined and found to be identical to each other. These inserts had highest homology to Ag85B from *M. tuberculosis*. The insert from one of the clones was subcloned into the EcoRI/XhoI sites of pProEX HT prokaryotic expression vector (Gibco BRL), expressed and purified according to the manufacturer's protocol. This clone was renamed GV-4P because only a part of the gene was expressed. The amino acid and DNA sequences for the partial clone GV-4P are provided in SEQ ID NO: 70 and 106, respectively.

Similar to the cloning of GV-4P, the amplification primers AD58 and AD59 were used to amplify a 485 bp fragment from a clone containing GVs-5 (SEQ ID NO:42). This fragment was cloned into the expression vector pET16 and was called GV-5P. The determined nucleotide sequence and predicted amino acid sequence of GV-5P are provided in SEQ ID NOS: 157 and 158, respectively.

In subsequent studies, using procedures similar to those described above, GVs-3, GV-4P and GVs-5 were re-cloned into the alternative vector pET16 (Novagen, Madison, Wisc.).

The ability of purified recombinant GVs-3, GV-4P and GVs-5 to stimulate proliferation of T cells and interferon-γ production in human PBL from PPD-positive, healthy donors, was assayed as described above in Example 2. The results of this assay are shown in Table 2, wherein (−) indicates a lack of activity, (+/−) indicates polypeptides having a result less than twice higher than background activity of control media, (+) indicates polypeptides having activity two to four times above background, (++) indicates polypeptides having activity greater than four times above background, and ND indicates not determined.

TABLE 2

| | Donor G97005 | | Donor G97006 | | Donor G97007 | | Donor G97008 | | Donor G97009 | | Donor G97010 | |
|---|---|---|---|---|---|---|---|---|---|---|---|---|
| | Prolif | IFN-γ | Prolif | IFN-γ | Prolif | IFN-γ | Prolif | IFN-γ | Prolif | IFN-γ | Prolif | IFN-γ |
| GVs-3 | ++ | + | ND | ND | ++ | ++ | ++ | ++ | ++ | +/− | + | ++ |
| GV-4P | + | +/− | ND | ND | + | ++ | ++ | ++ | +/− | +/− | +/− | ++ |
| GVs-5 | ++ | ++ | ++ | ++ | ++ | ++ | + | ++ | ++ | + | + | ++ |

EXAMPLE 5

DNA Cloning Strategy for *M. vaccae* Antigens

An 84 bp probe for the *M. vaccae* antigen GVc-7 was amplified using degenerate oligonucleotides designed to the determined amino acid sequence of GVc-7 (SEQ ID NOS: 5–8). This probe was used to screen a *M. vaccae* genomic DNA library as described in Example 4. The determined nucleotide sequence for GVc-7 is shown in SEQ ID NO: 46 and predicted amino acid sequence in SEQ ID NO: 47. Comparison of these sequences with those in the databank revealed homology to a hypothetical 15.8 kDa membrane protein of *M. tuberculosis.*

The sequence of SEQ ID NO: 46 was used to design amplification primers (provided in SEQ ID NO: 71 and 72) for expression cloning of the GVc-7 gene using sequence data downstream from the putative leader sequence. A XhoI restriction site was added to the primers for cloning convenience. Following amplification from genomic *M. vaccae* DNA, fragments were cloned into the XhoI-site of pProEX HT prokaryotic expression vector (Gibco BRL) and submitted for sequencing to confirm the correct reading frame and orientation. Expression and purification of the fusion protein was performed according to the manufacturer's protocol. In subsequent studies, GVc-7 was re-cloned into the vector pET16 (Novagen).

The ability of purified recombinant GVc-7 to stimulate proliferation of T-cells and stimulation of interferon-y production in human PBL, from PPD-positive, healthy donors, was assayed as described previously in Example 2. The results are shown in Table 3, wherein (−) indicates a lack of activity, (+/−) indicates polypeptides having a result less than twice higher than background activity of control media, (+) indicates polypeptides having activity two to four times above background, and (++) indicates polypeptides having activity greater than four times above background.

TABLE 3

| Donor | Proliferation | Interferon-γ |
|---|---|---|
| G97005 | ++ | +/− |
| G97008 | ++ | + |
| G97009 | + | +/− |
| G97010 | +/− | ++ |

A redundant oligonucleotide probe (SEQ ID NO 73, referred to as MPG15) was designed to the GVs-8 peptide sequence shown in SEQ ID NO: 26 and used to screen a *M. vaccae* genomic DNA library using standard protocols. Two genomic clones containing genes encoding four different antigens was isolated. The determined DNA sequences for GVs-8A (re-named GV-30), GVs-8B (re-named GV-31), GVs-8C (re-named GV-32) and GVs-8D (re-named GV-33) are shown in SEQ ID NOS: 48–51, respectively, with the corresponding amino acid sequences being shown in SEQ ID NOS: 52–55, respectively. GV-30 contains regions showing some similarity to known prokaryotic valyl-tRNA synthetases; GV-31 shows some similarity to *M. smegmatis* aspartate semialdehyde dehydrogenase; and GV-32 shows some similarity to the *H. influenza* folylpolyglutamate synthase gene. GV-33 contains an open reading frame which shows some similarity to sequences previously identified in *M. tuberculosis* and *M. leprae*, but whose function has not been identified.

The determined partial DNA sequence for GV-33 is provided in SEQ ID NO: 74 with the corresponding predicted amino acid sequence being provided in SEQ ID NO: 75. Sequence data from the 3' end of the clone showed homology to a previously identified 40.6 kDa outer membrane protein of *M. tuberculosis*. Subsequent studies led to the isolation of a full-length DNA sequence for GV-33 (SEQ ID NO: 193). The corresponding predicted amino acid sequence is provided in SEQ ID NO: 194.

The gene encoding GV-33 was amplified from *M. vaccae* genomic DNA with primers based on the determined nucleotide sequence. This DNA fragment was cloned into EcoRv-digested pBluescript II $SK^+$ (Stratagene), and then transferred to pET16 expression vector. Recombinant protein was purified following the manufacturer's protocol.

The ability of purified recombinant GV-33 to stimulate proliferation of T-cells and stimulation of interferon-y production in human PBL was assayed as described previously in Example 2. The results are shown in Table 4, wherein (−) indicates a lack of activity, (+/−) indicates polypeptides having a result less than twice higher than background activity of control media, (+) indicates polypeptides having activity two to four times above background, and (++) indicates polypeptides having activity greater than four times above background.

TABLE 4

Stimulatory Activity of Polypeptides

| Donor | Proliferation | Interferon-γ |
|---|---|---|
| G97005 | ++ | + |
| G97006 | ++ | ++ |
| G97007 | – | +/– |
| G97008 | +/– | – |
| G97009 | +/– | – |
| G97010 | +/– | ++ |

EXAMPLE 6

Detection of Nonspecific Immune Amplifier from Whole *M. vaccae* and the Culture Filtrate of *M. vaccae*

This example illustrates the preparation of whole *M. vaccae* and *M. vaccae* culture filtrate and its non-specific immune amplifying or 'adjuvant' property.

*M. vaccae* bacteria was cultured, pelleted and autoclaved as described in Example 1. Culture filtrates of live *M. vaccae* refer to the supernatant from 24 hour cultures of *M. vaccae* in 7H9 medium with glucose. A delipidated form of *M. vaccae* was prepared by sonicating autoclaved *M. vaccae* for four bursts of 30 seconds on ice using the Virsonic sonicator (Virtis, Disa, USA). The material was then centrifuged (9000 rpm, 20 minutes, JA10 rotor, brake=5). The resulting pellet was suspended in 100 ml of chloroform/methanol (2:1), incubated at room temperature for 1 hour, re-centrifuged, and the chloroform/methanol extraction repeated. The pellet was obtained by centrifugation, dried in vacuo, weighed and resuspended in PBS at 50 mg (dry weight) per ml as delipidated *M. vaccae.*

Glycolipids were removed from the delipidated *M. vaccae* preparation by refluxing in 50% v/v ethanol for 2 hours. The insoluble material was collected by centrifugation (10,000 rpm, JA20 rotor, 15 mins, brake=5). The extraction with 50% v/v ethanol under reflux was repeated twice more. The insoluble material was collected by centrifugation and washed in PBS. Proteins were extracted by resuspending the pellet in 2% SDS in PBS at 56° C. for 2 hours. The insoluble material was collected by centrifugation and the extraction with 2% SDS/PBS at 56° C. was repeated twice more. The pooled SDS extracts were cooled to 4° C., and precipitated SDS was removed by centrifugation (10,000 rpm, JA20 rotor, 15 mins, brake=5). Proteins were precipitated from the supernatant by adding an equal volume of acetone and incubating at −20° C. for 2 hours. The precipitated proteins were collected by centrifugation, washed in 50% v/v acetone, dried in vacuo, and redissolved in PBS.

*M. vaccae* culture supernatant (S/N), killed *M. vaccae*, delipidated *M. vaccae* and delipidated and deglycolipidated *M. vaccae* (DD-*M. vaccae*) were tested for adjuvant activity in the generation of a cytotoxic T cell immune response to ovalbumin, a structurally unrelated protein, in the mouse. This anti-ovalbumin-specific cytotoxic response was detected as follows. C57BL/6 mice (2 per group) were immunized by the intraperitoneal injection of 100 μg of ovalbumin with the following test adjuvants: autoclaved *M. vaccae*; delipidated *M. vaccae*; delipidated *M. vaccae* with glycolipids also extracted (DD-*M. vaccae*) and proteins extracted with SDS; the SDS protein extract treated with Pronase (an enzyme which degrades protein); whole *M. vaccae* culture filtrate; and heat-killed *M. tuberculosis* or heat-killed *M. bovis* BCG, *M. phlei* or *M. smegmatis* or *M. vaccae* culture filtrate. After 10 days, spleen cells were stimulated in vitro for a further 6 days with E.G7 cells which are EL4 cells (a C57BL/6-derived T cell lymphoma) transfected with the ovalbumin gene and thus express ovalbumin. The spleen cells were then assayed for their ability to kill non-specifically EL4 target cells or to kill specifically the E.G7 ovalbumin expressing cells. Killing activity was detected by the release of $^{51}$ Chromium with which the EL4 and E.G7 cells have been labelled (100 μCi per $2\times10^6$), prior to the killing assay. Killing or cytolytic activity is expressed as % specific lysis using the formula:

$$\frac{cpm \text{ in test cultures} - cpm \text{ in control cultures}}{\text{total } cpm - cpm \text{ in control cultures}} \times 100\%$$

It is generally known that ovalbumin-specific cytotoxic cells are generated only in mice immunized with ovalbumin with an adjuvant but not in mice immunized with ovalbumin alone.

The diagrams that make up FIG. 4 show the effect of various *M. vaccae* derived adjuvant preparations on the generation of cytotoxic T cells to ovalbumin in C57BL/6 mice. As shown in FIG. 4A, cytotoxic cells were generated in mice immunized with (i) 10 μg, (ii) 100 μg or (iii) 1 mg of autoclaved *M. vaccae* or (iv) 75 μg of *M. vaccae* culture filtrate. FIG. 4B shows that cytotoxic cells were generated in mice immunized with (i) 1 mg whole autoclaved *M. vaccae* or (ii) 1 mg delipidated and deglycolipidated (DD-) *M. vaccae*. As shown in FIG. 4C(i), cytotoxic cells were generated in mice immunized with 1 mg whole autoclaved *M. vaccae*; FIG. 4C(ii) shows the active material in *M. vaccae* soluble proteins extracted with SDS from DD-*M. vaccae*. FIG. 4C(iii) shows that active material in the adjuvant preparation of FIG. 4C(ii) was destroyed by treatment with the proteolytic enzyme Pronase. By way of comparison, 100 μg of the SDS-extracted proteins had significantly stronger immune-enhancing ability (FIG. 4C(ii)) than did 1 mg whole autoclaved *M. vaccae* (FIG. 4C(i)).

Figure 4A:
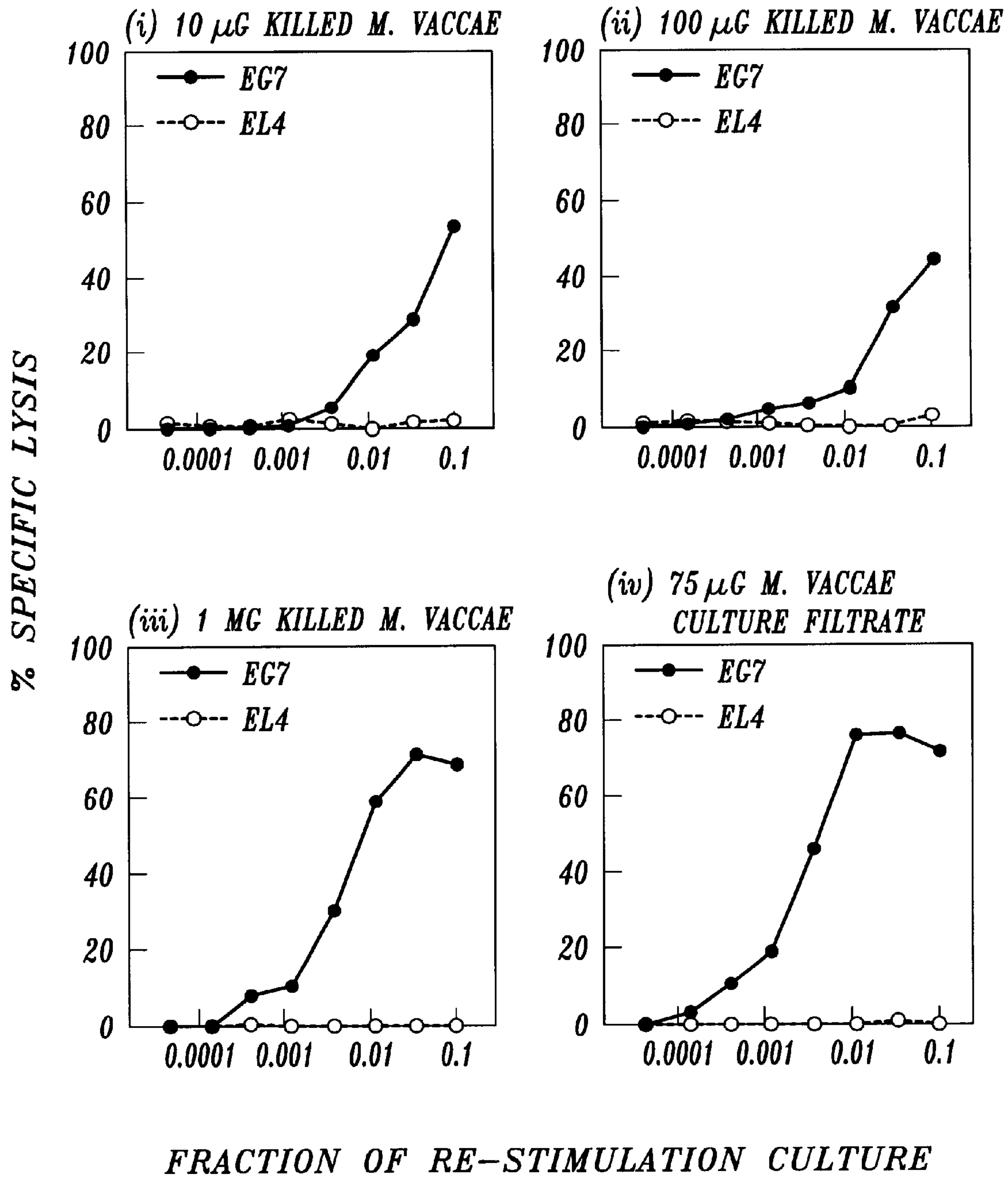
FIGS. 4A(i)–(iv) illustrate the non-specific immune amplifying effects of 10 $\mu$g, 100 $\mu$g and 1 mg autoclaved *M. vaccae* and 75 $\mu$g unfractionated culture filtrates of *M. vaccae*, respectively.
Figure 4B:
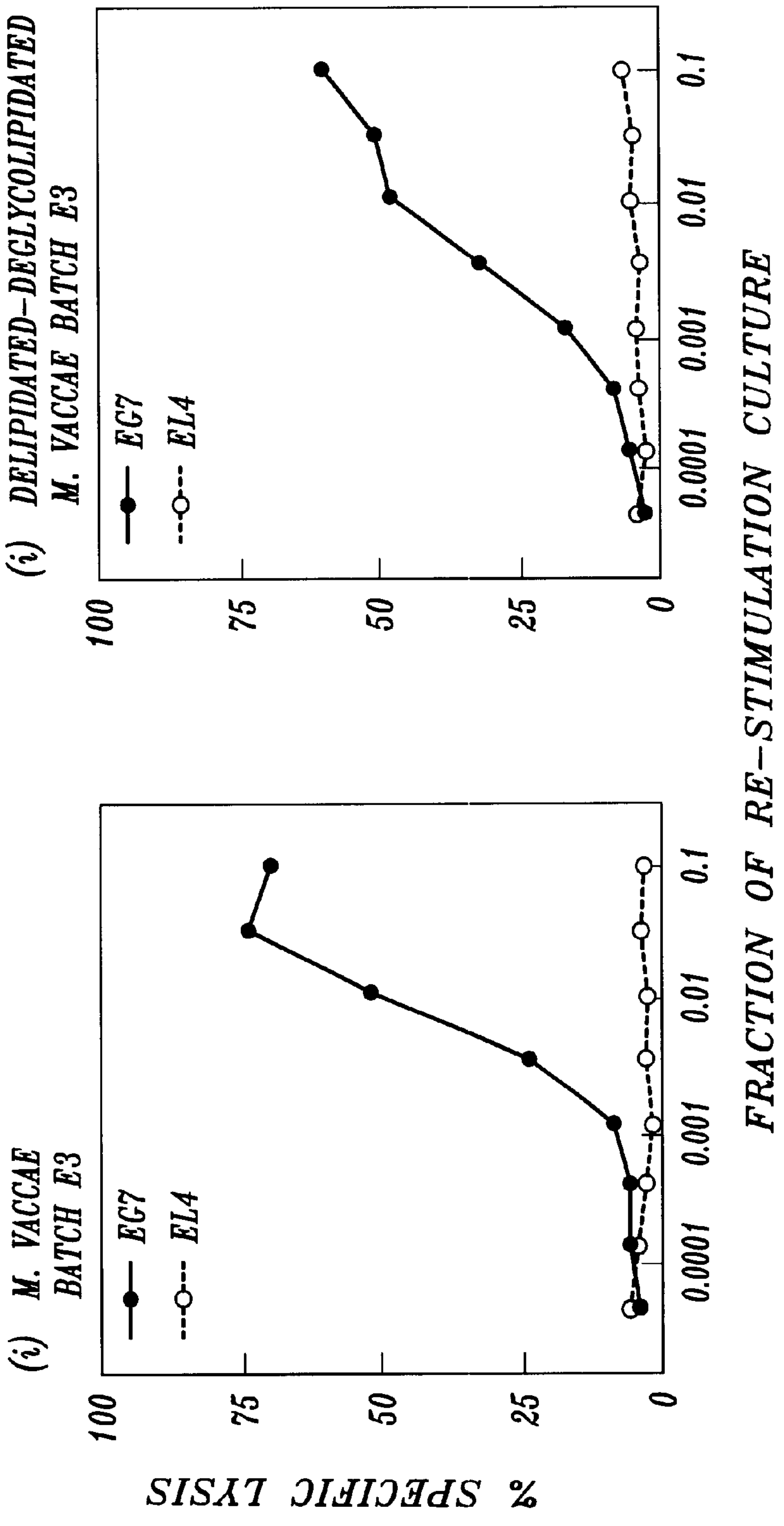
FIG. 4B(i) and (ii) illustrate the non-specific immune amplifying effects of autoclaved *M. vaccae*, and delipidated and deglycolipidated *M. vaccae*, respectively.
Figure 4C:
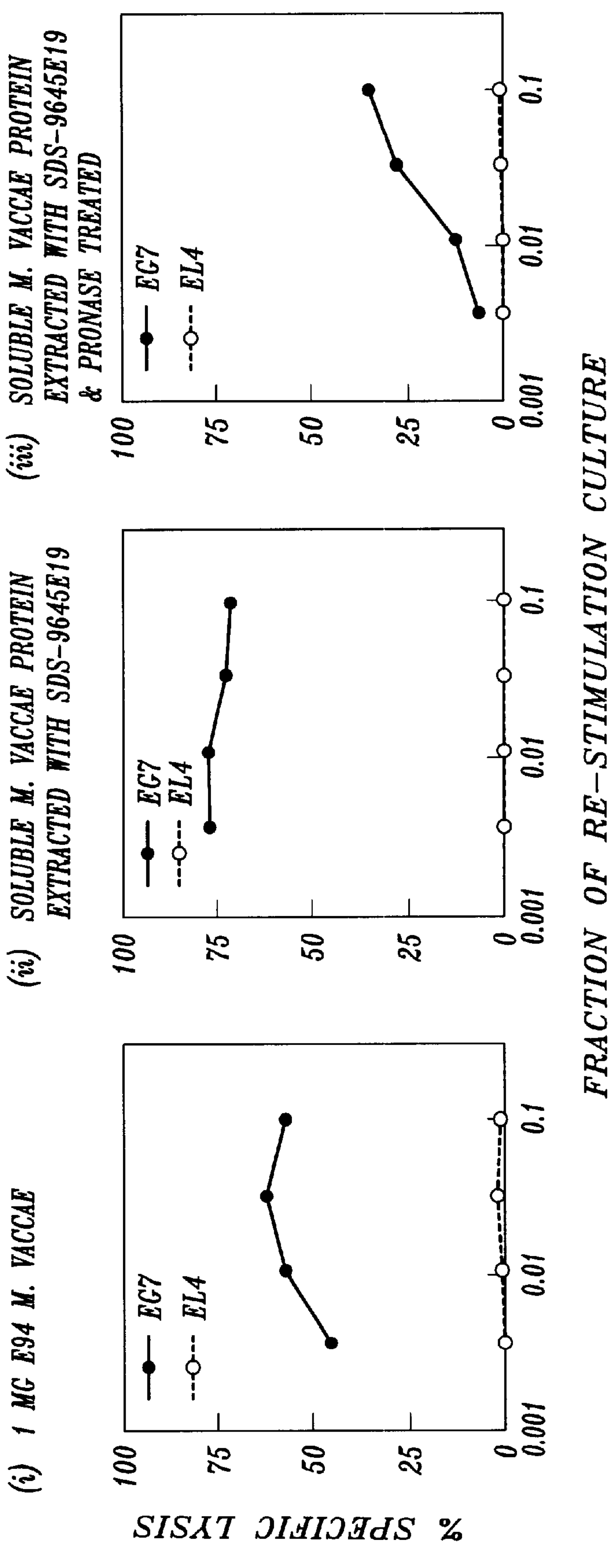
FIG. 4C(i) illustrates the non-specific immune amplifying effects of whole autoclaved *M. vaccae*.
Figure 4D:
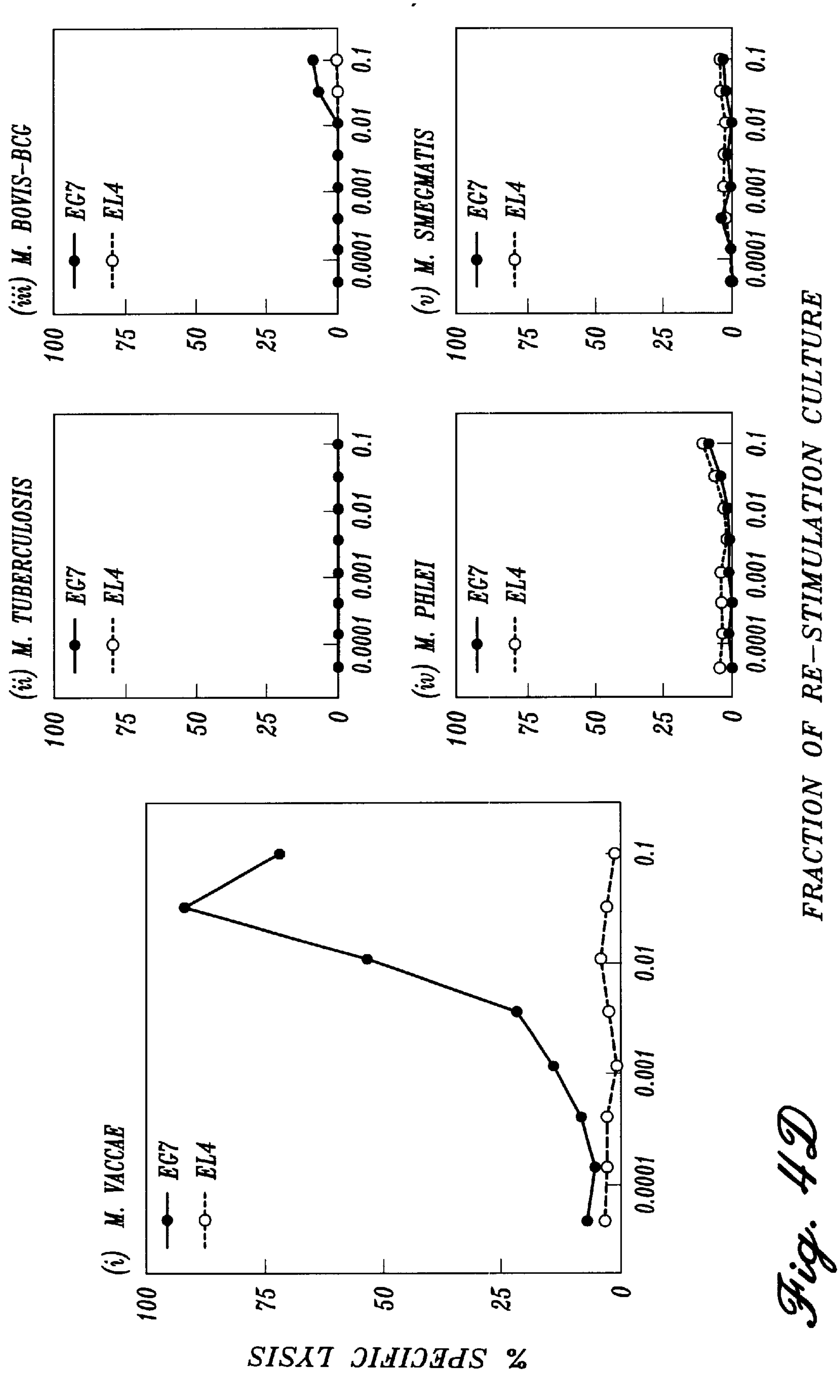
FIG. 4D illustrates the non-specific immune amplifying effects of heat-killed *M. vaccae* (FIG. 4D(i)), whereas a non-specific immune amplifying effect was not seen with heat-killed preparations of *M. tuberculosis* (FIG. 4D(ii)), *M. bovis* BCG (FIG. 4D(iii)), *M. phlei* (FIG. 4D(iv)) and *M. smegmatis* (FIG. 4D(v)).

Mice immunized with 1 mg heat-killed *M. vaccae* (FIG. 4D(i)) generated cytotoxic cells to ovalbumin, but mice immunized separately with 1 mg heat-killed *M. tuberculosis* (FIG. 4D(ii)), 1 mg *M. bovis* BCG (FIG. 4D(iii)), 1 mg *M. phlei* (FIG. 4D(iv)), or 1 mg *M. smegmatis* (FIG. 4D(v)) failed to generate cytotoxic cells.

These findings demonstrate that heat-killed *M. vaccae* and DD-*M. vaccae* have adjuvant properties not seen in other mycobacteria. Furthermore, delipidation and deglycolipidation of *M. vaccae* removes an NK cell-stimulating activity but does not result in a loss of T-cell stimulating activity.

Figure 5A:
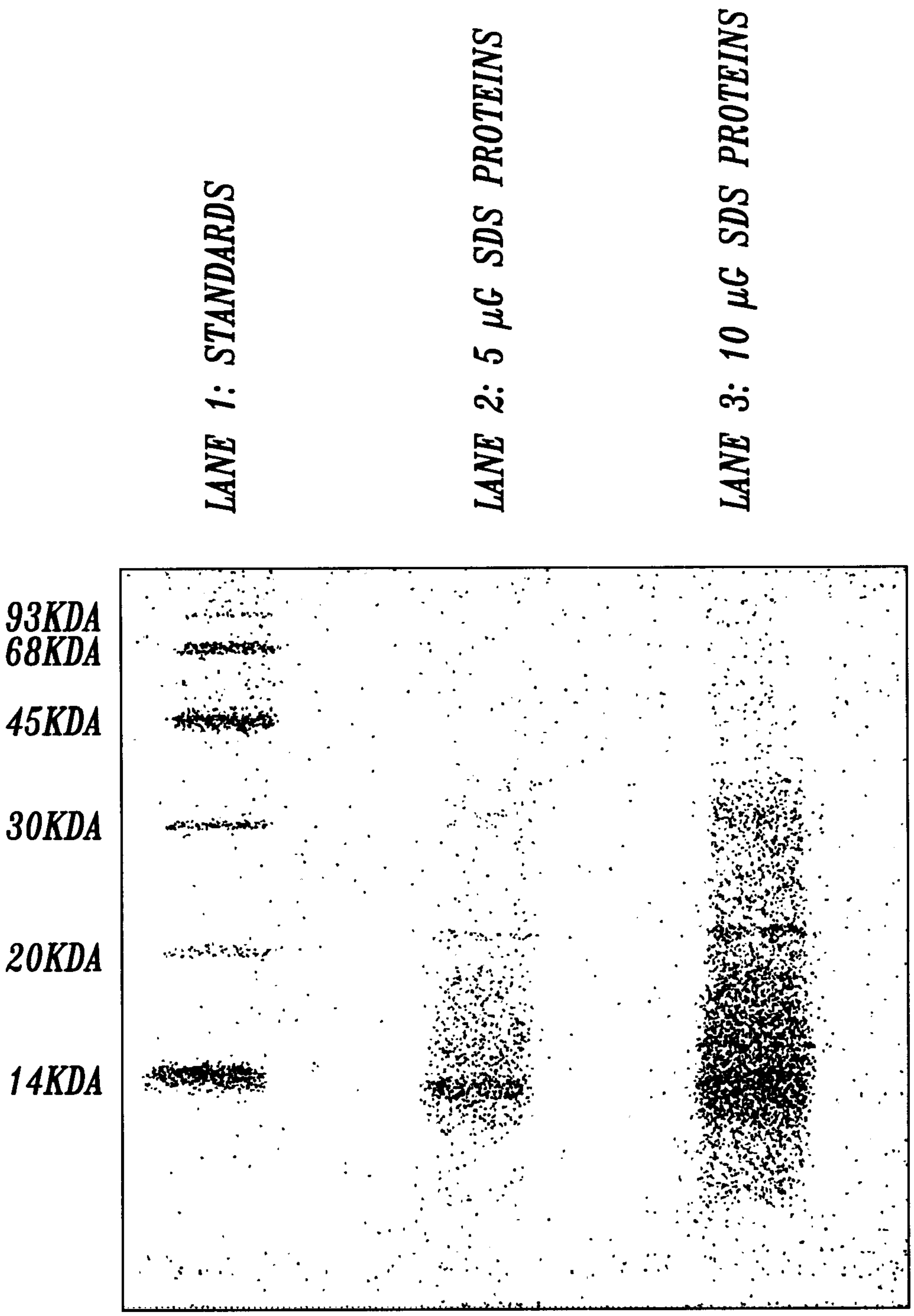
FIG. 5A shows the results of polyacrylamide gel electrophoresis analysis by silver staining of SDS-extracted proteins derived from delipidated and deglycolipidated *M. vaccae*.

The SDS-extracted proteins derived from delipidated and deglycolipidated *M. vaccae* were analysed by polyacrylamide gel electrophoresis. As shown in FIG. 5A, three major bands were observed after staining with silver.

Figure 5B:
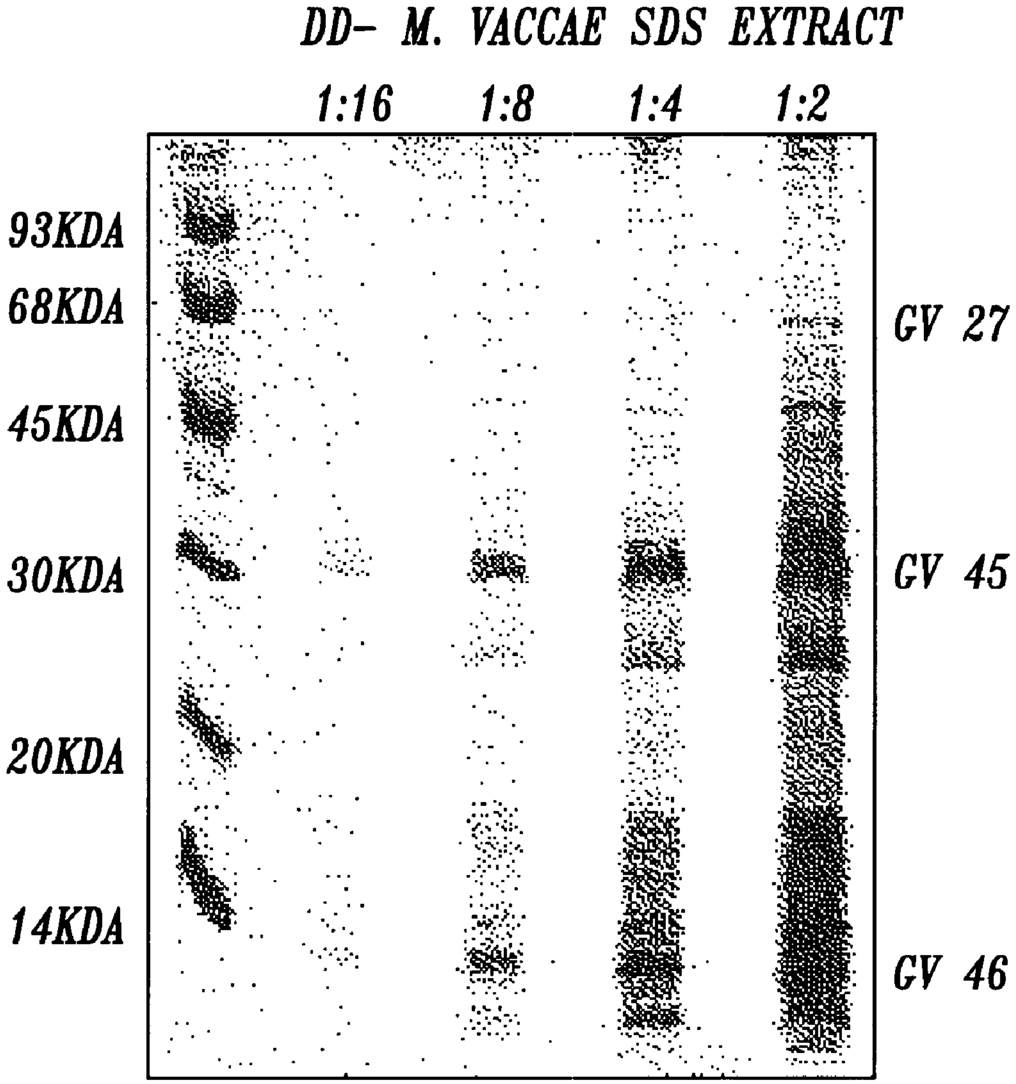
FIG. 5B shows the results of polyacrylamide gel electrophoresis analysis by Coomassie blue staining of larger amounts of SDS-extracted proteins derived from delipidated and deglycolipidated *M. vaccae*.

In subsequent experiments, larger amounts of SDS-extracted proteins from DD-*M.vaccae*, were analysed by polyacrylamide gel electrophoresis. As shown in FIG. 5B, the proteins on staining with Coomassie blue show several bands. A protein represented by a band of approximate molecular weight of 30 kDa was designated GV-45. The determined N-terminal sequence for GV-45 is provided in SEQ ID NO: 187. A protein of approximate molecular weight of 14 kDa was designated GV-46. The determined N-terminal amino acid sequence of GV-46 is provided in SEQ ID NO: 208.

Figure 6:
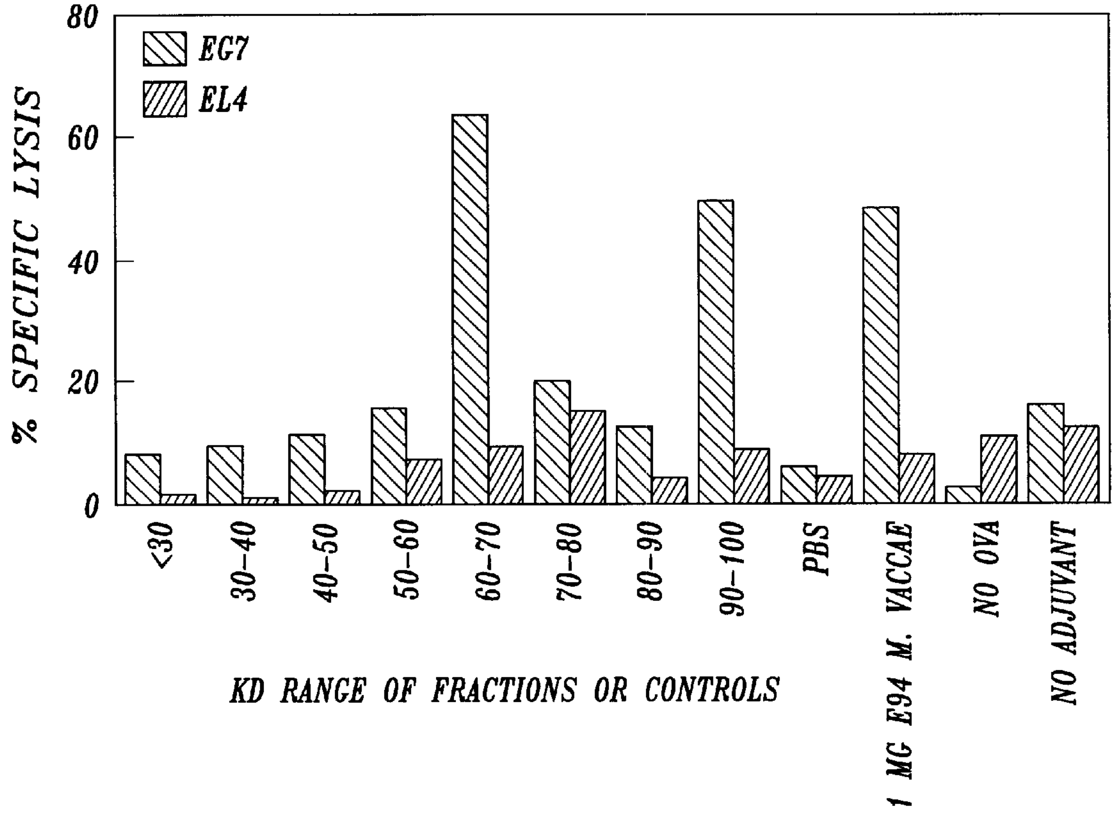
FIG. 6 illustrates the non-specific immune amplfying effects of different molecular weight fractions of SDS-extracted *M. vaccae* proteins.

In subsequent studies, more of the SDS-extracted proteins described above were prepared by preparative SDS-PAGE on a BioRad Prep Cell (Hercules, Calif.). Fractions corresponding to molecular weight ranges were precipitated by trichloroacetic acid to remove SDS before assaying for adjuvant activity in the anti-ovalbumin-specific cytotoxic response assay in C57BL/6 mice as described above. As seen in FIG. 6, the adjuvant activity was highest in the 60–70 kDa fraction. The most abundant protein in this size range was purified by SDS-PAGE blotted on to a polyvinylidene difluoride (PVDF) membrane and then sequenced. The sequence of the first ten amino acid residues is provided in SEQ ID NO:76. Comparison of this sequence with those in the gene bank as described above, revealed homology to the heat shock protein 65 (GroEL) gene from *M. tuberculosis*, indicating that this protein is an *M. vaccae* member of the GroEL family.

An expression library of *M. vaccae* genomic DNA in BamH1-lambda ZAP-Express (Stratagene) was screened using sera from cynomolgous monkeys immunized with *M. vaccae* secreted proteins prepared as described above. Positive plaques were identified using a colorimetric system. These plaques were re-screened until plaques were pure following standard procedures. pBK-CMV phagemid 2-1 containing an insert was excised from the lambda ZAP Express (Stratagene) vector in the presence of ExAssist helper phage following the manufacturer's protocol. The base sequence of the 5' end of the insert of this clone, hereinafter referred to as GV-27, was determined using Sanger sequencing with fluorescent primers on Perkin Elmer/Applied Biosystems Division automatic sequencer. The determined nucleotide sequence of the partial *M. vaccae* GroEL-homologue clone GV-27 is provided in SEQ ID NO: 77 and the predicted amino acid sequence in SEQ ID NO: 78. This clone was found to have homology to *M. tuberculosis* GroEL. A partial sequence of the 65 kDa heat shock protein of *M. vaccae* has been published by Kapur et al. (*Arch. Pathol. Lab. Med.* 119:131–138, 1995). The nucleotide sequence of the Kapur et al. fragment is shown in SEQ ID NO: 79 and the predicted amino acid sequence in SEQ ID NO: 80.

In subsequent studies, an extended (full-length except for the predicted 51 terminal nucleotides) DNA sequence for GV-27 was obtained (SEQ ID NO: 113). The corresponding predicted amino acid sequence is provided in SEQ ID NO: 114. Further studies led to the isolation of a full-length DNA sequence for GV-27 (SEQ ID NO: 159). The corresponding predicted amino acid sequence is provided in SEQ ID NO: 160. GV-27 was found to be 93.7% identical to the *M. tuberculosis* GroEL at the amino acid level.

Two peptide fragments, comprising the N-terminal sequence (hereinafter referred to as GV-27A) and the carboxy terminal sequence of GV-27 (hereinafter referred to as GV-27B) were prepared using techniques well known in the art. The nucleotide sequences for GV-27A and GV-27B are provided in SEQ ID NO: 115 and 116, respectively, with the corresponding amino acid sequences being provided in SEQ ID NO: 117 and 118. Subsequent studies led to the isolation of an extended DNA sequence for GV-27B. This sequence is provided in SEQ ID NO: 161, with the corresponding amino acid sequence being provided in SEQ ID NO: 162. The sequence of GV-27A is 95.8% identical to the *M. tuberculosis* GroEL sequence and contains the shorter *M. vaccae* sequence of Kapur et al. discussed above. The sequence for GV-27B shows about 92.2% identity to the corresponding region of *M. tuberculosis* HSP65.

Following the same protocol as for the isolation of GV-27, pBK-CMV phagemid 3-1 was isolated. The antigen encoded by this DNA was named GV-29. The determined nucleotide sequences of the 5' and 3' ends of the gene are provided in SEQ ID NOS: 163 and 164, respectively, with the predicted corresponding amino acid sequences being provided in SEQ ID NOS: 165 and 166 respectively. GV-29 showed homology to yeast urea amidolyase. The determined DNA sequence for the full-length gene encoding GV-29 is provided in SEQ ID NO: 198, with the corresponding predicted amino acid sequence in SEQ ID NO: 199. The DNA encoding GV-29 was sub-cloned into the vector pET16 (Novagen, Madison, Wisc.) for expression and purification according to standard protocols.

Figure 7:
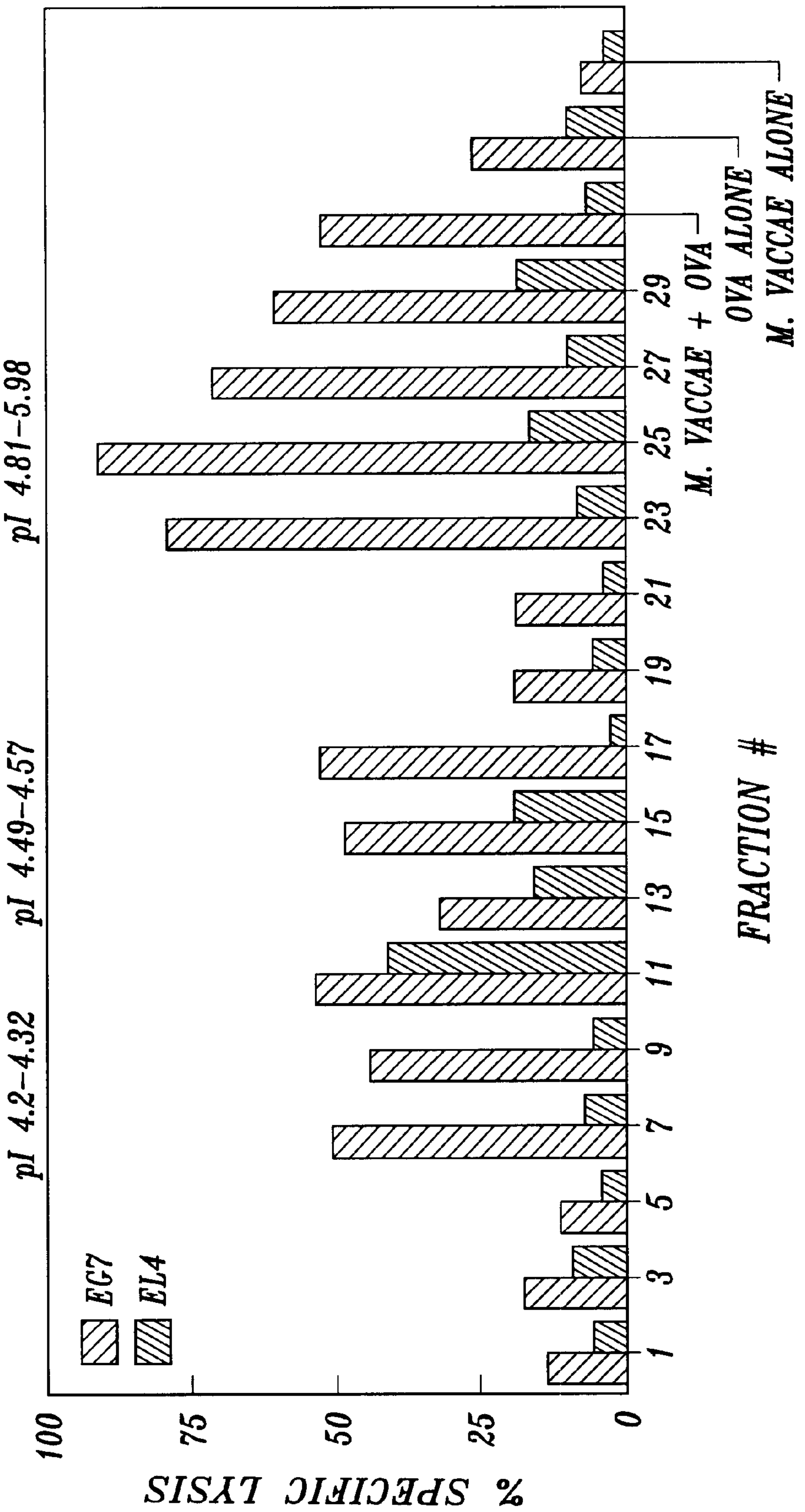
FIG. 7 illustrates the non-specific immune amplifying effects of different pI fractions of SDS-extracted *M. vaccae* proteins.

The *M. vaccae* culture filtrate described above was also fractionated by iso-electric focusing and the fractions assayed for adjuvant activity in the anti-ovalbumin-specific cytotoxic response assay in C57BL/6 mice as described above. As shown in FIG. 7, peak adjuvant activities were demonstrated in fractions corresponding to pI of 4.2–4.32 (fraction nos. 7–9), 4.49–4.57 (fraction nos. 13–17) and 4.81–5.98 (fraction nos. 23–27).

EXAMPLE 7

Autoclaved *M. vaccae* Generates Cytotoxic CD8 T Cells Against *M. TUBERCULOSIS* Infected Macrophages This example illustrates the ability of killed *M. vaccae* to stimulate cytotoxic CD8 T cells which preferentially kill macrophages that have been infected with *M. tuberculosis.*

Mice were immunized by the intraperitoneal injection of 500 μg of killed *M. vaccae* which was prepared as described in Example 1. Two weeks after immunization, the spleen cells of immunized mice were passed through a CD8 T cell enrichment column (R&D Systems, St. Paul, Minn., USA). The spleen cells recovered from the column have been shown to be enriched up to 90% CD8 T cells. These T cells, as well as CD8 T cells from spleens of non-immunized mice, were tested for their ability to kill uninfected macrophages or macrophages which have been infected with *M. tuberculosis.*

Macrophages were obtained from the peritoneal cavity of mice five days after they have been given 1 ml of 3% thioglycolate intraperitoneally. The macrophages were infected overnight with *M. tuberculosis* at the ratio of 2 mycobacteria per macrophage. All macrophage preparations were labelled with $^{51}$Chromium at 2 μCi per $10^4$ macrophages. The macrophages were then cultured with CD8 T cells overnight (16 hours) at killer to target ratios of 30:1. Specific killing was detected by the release of $^{51}$Chromium and expressed as % specific lysis, calculated as in Example 5.

The production of IFN-γ and its release into medium after 3 days of co-culture of CD8 T cells with macrophages was measured using an enzyme-linked immunosorbent assay (ELISA). ELISA plates were coated with a rat monoclonal antibody directed to mouse IFN-γ (Pharmigen, San Diego, Calif., USA) in PBS for 4 hours at 4° C. Wells were blocked with PBS containing 0.2% Tween 20 for 1 hour at room temperature. The plates were then washed four times in PBS containing 0.2% Tween 20, and samples diluted 1:2 in culture medium in the ELISA plates were incubated overnight at room temperature. The plates were again washed, and a biotinylated monoclonal rat anti-mouse IFN-γ antibody (Pharmigen), diluted to 1 μg/ml in PBS, was added to each well. The plates were then incubated for 1 hour at room temperature, washed, and horseradish peroxidase-coupled avidin D (Sigma A-3151) was added at a 1:4,000 dilution in PBS. After a further 1 hour incubation at room temperature, the plates were washed and OPD substrate added. The reaction was stopped after 10 min with 10% (v/v) HCl. The optical density was determined at 490 nm. Fractions that resulted in both replicates giving an OD two-fold greater than the mean OD from cells cultured in medium alone were considered positive.

As shown in Table 5, CD8 T cells from spleens of mice immunized with *M. vaccae* were cytotoxic for macrophages infected with *M. tuberculosis* and did not lyse uninfected macrophages. The CD8 T cells from non-immunized mice did not lyse macrophages. CD8 T cells from naive or non-immunized mice do produce IFN-γ when cocultured with infected macrophages. The amount of IFN-γ produced in coculture was greater with CD8 T cells derived from *M. vaccae* immunized mice.

TABLE 5

EFFECT WITH *M. TUBERCULOSIS* INFECTED AND UNINFECTED MACROPHAGES

| | % Specific Lysis of Macrophages | | IFN-γ (ng/ml) | |
|---|---|---|---|---|
| CD8 T cells | uninfected | infected | uninfected | infected |
| Control | 0 | 0 | 0.7 | 24.6 |
| *M. vaccae* Immunized | 0 | 95 | 2.2 | 43.8 |

EXAMPLE 8

DNA Cloning Strategy for the *M. vaccae* Antigens GV-23, GV-24, GV-25, GV-26, GV-38A AND GV-38B

*M. vaccae* (ATCC Number 15483) was grown in sterile Medium 90 at 37° C. for 4 days and harvested by centrifugation. Cells were resuspended in 1 ml Trizol (Gibco BRL, Life Technologies, Gaithersburg, Md.) and RNA extracted according to the standard manufacturer's protocol. *M. tuberculosis* strain H37Rv (ATCC Number 27294) was grown in sterile Middlebrook 7H9 medium with Tween 80™ and oleic acid/albumin/dextrose/catalase additive (Difco Laboratories, Detroit, Mich.) at 37° C. and harvested under appropriate laboratory safety conditions. Cells were resuspended in 1 ml Trizol (Gibco BRL) and RNA extracted according to the manufacturer's standard protocol.

Total *M. tuberculosis* and *M. vaccae* RNA was depleted of 16S and 23S ribosomal RNA (rRNA) by hybridisation of the total RNA fraction to oligonucleotides AD10 and AD11 (SEQ ID NO: 81 and 82) complementary to *M. tuberculosis* rRNA. These oligonucleotides were designed from mycobacterial 16S rRNA sequences published by Bottger (*FEMS Microbiol. Lett*. 65:171–176, 1989) and from sequences deposited in the databanks. Depletion was done by hybridisation of total RNA to oligonucleotides AD10 and AD11 immobilised on nylon membranes (Hybond N, Amersham International, United Kingdom). Hybridisation was repeated until rRNA bands were not visible on ethidium bromide-stained agarose gels. An oligonucleotide, AD12 (SEQ ID NO: 83), consisting of 20 dATP-residues, was ligated to the 3' ends of the enriched mRNA fraction using RNA ligase. First strand cDNA synthesis was performed following standard protocols, using oligonucleotide AD7 (SEQ ID NO:84) containing a poly(dT) sequence.

The *M. tuberculosis* and *M. vaccae* cDNA was used as template for single-sided-specific PCR (3S-PCR). For this protocol, a degenerate oligonucleotide AD1 (SEQ ID NO:85) was designed based on conserved leader sequences and membrane protein sequences. After 30 cycles of amplification using primer AD1 as 5'-primer and AD7 as 3'-primer, products were separated on a urea/polyacrylamide gel. DNA bands unique to *M. vaccae* were excised and re-amplified using primers AD1 and AD7. After gel purification, bands were cloned into pGEM-T (Promega) and the base sequence determined.

Searches with the determined nucleotide and predicted amino acid sequences of band 12B21 (SEQ ID NOS: 86 and 87, respectively) showed homology to the pota gene of *E.coli* encoding the ATP-binding protein of the spermidine/putrescine ABC transporter complex published by Furuchi et al. (*Jnl. Biol. Chem*. 266: 20928–20933, 1991). The spermidine/putrescine transporter complex of *E.coli* consists of four genes and is a member of the ABC transporter family. The ABC (ATP-binding Cassette) transporters typically consist of four genes: an ATP-binding gene, a periplasmic, or substrate binding, gene and two transmembrane genes. The transmembrane genes encode proteins each characteristically having six membrane-spanning regions. Homologues (by similarity) of this ABC transporter have been identified in the genomes of *Haemophilus influenza* (Fleischmann et al. *Science* 269 :496–512, 1995) and *Mycoplasma genitalium* (Fraser, et al. *Science*, 270:397–403, 1995).

An *M. vaccae* genomic DNA library constructed in BamH1-digested lambda ZAP Express (Stratagene) was probed with the radiolabelled 238 bp band 12B21 following standard protocols. A plaque was purified to purity by repetitive screening and a phagemid containing a 4.5 kb insert was identified by Southern blotting and hybridisation. The nucleotide sequence of the full-length *M. vaccae* homologue of pota (ATP-binding protein) was identified by subcloning of the 4.5 kb fragment and base sequencing. The gene consisted of 1449 bp including an untranslated 5' region of 320 bp containing putative −10 and −35 promoter elements. The nucleotide and predicted amino acid sequences of the *M. vaccae* pota homologue are provided in SEQ ID NO: 88 and 89, respectively.

The nucleotide sequence of the *M. vaccae* pota gene was used to design primers EV24 and EV25 (SEQ ID NO: 90 and 91) for expression cloning. The amplified DNA fragment was cloned into pProEX HT prokaryotic expression system (Gibco BRL) and expression in an appropriate *E.coli* host was induced by addition of 0.6 MM isopropylthio-p-galactoside (IPTG). The recombinant protein was named GV-23 and purified from inclusion bodies according to the manufacturer's protocol. In subsequent studies, GV-23 (SEQ ID NO: 88) was re-cloned into the alternative vector pET16 (Novagen). The amino acid sequence of SEQ ID NO: 89 contains an ATP binding site at residues 34 to 41. At residues 116 to 163 of SEQ ID NO: 89, there is a conserved region that is found in the ATP-transporter family of proteins. These findings suggest that GV-23 is an ATP binding protein.

A 322 bp Sal1-BamH1 subclone at the 3'-end of the 4.5 kb insert described above showed homology to the potd gene, (periplasmic protein), of the spermidine/putrescine ABC transporter complex of *E. coli*. The nucleotide sequence of this subclone is shown in SEQ ID NO:92. To identify the gene, the radiolabelled insert of this subclone was used to probe a *M. vaccae* genomic DNA library constructed in the Sal1-site of lambda Zap Express (Stratagene) following standard protocols. A clone was identified of which 1342 bp showed homology with the potd gene of *E. coli*. The potd homologue of *M. vaccae* was identified by sub-cloning and base sequencing. The determined nucleotide and predicted amino acid sequences are shown in SEQ ID NO: 93 and 94.

For expression cloning, primers EV-26 and EV-27 (SEQ ID NOS: 95–96) were designed from the determined *M. vaccae* potd homologue. The amplified fragment was cloned into pProEX HT Prokaryotic expression system (Gibco BRL). Expression in an appropriate *E. coli* host was induced by addition of 0.6 mM IPTG and the recombinant protein named GV-24. The recombinant antigen was purified from inclusion bodies according to the protocol of the supplier. In subsequent studies, GV-24 (SEQ ID NO: 93) was re-cloned into the alternative vector pET16 (Novagen).

To improve the solubility of the purified recombinant antigen, the gene encoding GV-24, but excluding the signal peptide, was re-cloned into the expression vector, employing. amplification primers EV101 and EV102 (SEQ ID NOS: 167 and 168). The construct was designated GV-24B. The nucleotide sequence of GV-24B is provided in SEQ ID NO: 169 and the predicted amino acid sequence in SEQ ID NO: 170. This fragment was cloned into pET16 for expression and purification of GV-24B according to the manufacturer's protocols.

The ability of purified recombinant protein GV-23 and GV-24 to stimulate proliferation of T cells and interferon-γ production in human PBL was determined as described in Example 2. The results of these assays are provided in Table 6, wherein (–) indicates a lack of activity, (+/–) indicates polypeptides having a result less than twice higher than background activity of control media, (+) indicates polypeptides having activity two to four times above background, (++) indicates polypeptides having activity greater than four times above background, and (ND) indicates not determined.

(Stratagene). The clone isolated from the library contained a novel open reading frame and the antigen encoded by this gene was named GV-38A. The determined nucleotide sequence and predicted amino acid sequence of GV-38A are shown in SEQ ID NO: 120 and 121, respectively. Subsequent studies led to the isolation of an extended DNA sequence for GV-38A, provided in SEQ ID NO: 171. The corresponding amino acid sequence is provided in SEQ ID NO: 172. Comparison of these sequences with those in the gene bank, revealed some homology to an unknown *M. tuberculosis* protein previously identified in cosmid MTCY428.12. (SPTREMBL:P71915).

Upstream of the GV-38A gene, a second novel open reading frame was identified and the antigen encoded by this gene was named GV-38B. The determined 5' and 3' nucleotide sequences for GV-38B are provided in SEQ ID NO: 122 and 123, respectively, with the corresponding predicted amino acid sequences being provided in SEQ ID NO: 124 and 125, respectively. Further studies led to the isolation of the full-length DNA sequence for GV-38B, provided in SEQ ID NO: 173. The corresponding amino acid sequence is provided in SEQ ID NO: 174. This protein was found to show homology to an unknown *M. tuberculosis* protein identified in cosmid MTCY428.11 (SPTREMBL: P71914).

Both the GV-38A and GV-38B antigens were amplified for expression cloning into pET16 (Novagen). GV-38A was amplified with primers KR11 and KR12 (SEQ ID NO: 126 and 127) and GV-38B with primers KR13 and KR14 (SEQ ID NO: 128 and 129). Protein expression in the host cells BL21(DE3) was induced with 1 mM IPTG, however no protein expression was obtained from these constructs.

TABLE 6

| | Donor G97005 | | Donor G97006 | | Donor G97007 | | Donor G97008 | | Donor G97009 | | Donor G97010 | |
|---|---|---|---|---|---|---|---|---|---|---|---|---|
| | Prolif | IFN-γ | Prolif | IFN-γ | Prolif | IFN-γ | Prolif | IFN-γ | Prolif | IFN-γ | Prolif | IFN-γ |
| GV-23 | ++ | ++ | ++ | ++ | + | + | ++ | ++ | + | – | + | ++ |
| GV-24 | ++ | + | ++ | + | ND | ND | + | +/– | + | +/– | +/– | ++ |

Base sequence adjacent to the *M. vaccae* potd gene-homologue was found to show homology to the potb gene of the spermidine/putrescine ABC transporter complex of *E.coli*, which is one of two transmembrane proteins in the ABC transporter complex. The *M. vaccae* potb homologue (referred to as GV-25) was identified through further subcloning and base sequencing. The determined nucleotide and predicted amino acid sequences for GV-25 are shown in SEQ ID NOS: 97 and 98, respectively.

Further subcloning and base sequence analysis of the adjacent 509 bp failed to reveal significant homology to PotC, the second transmembrane protein of *E.coli*, and suggests that a second transmembrane protein is absent in the *M. vaccae* homologue of the ABC transporter. An open reading frame with homology to *M. tuberculosis* acetyl-CoA acetyl transferase, however, was identified starting 530 bp downstream of the transmembrane protein and the translated protein was named GV-26. The determined partial nucleotide sequence and predicted amino acid sequence for GV-26 are shown in SEQ ID NO: 99 and 100, respectively.

Using a protocol similar to that described above for the isolation of GV-23, the 3S-PCR band 12B28 (SEQ ID NO: 119) was used to screen the *M. vaccae* genomic library constructed in the BamHI-site of lambda ZAP Express Hydrophobic regions were identified in the N-termini of antigens GV-38A and GV-38B which may inhibit expression of these constructs. The hydrophobic region present in GV-38A was identified as a possible transmembrane motif with six membrane spanning regions. To express the antigens without the hydrophobic regions, primers KR20 for GV-38A, (SEQ ID NO: 130) and KR21 for GV-38B (SEQ ID NO: 131) were designed. The truncated GV-38A gene was amplified with primers KR20 and KR12, and the truncated GV-38B gene with KR21 and KR14. The determined nucleotide sequences of truncated GV38A and GV-38B are shown in SEQ ID NO: 132 and 133, respectively, with the corresponding predicted amino acid sequences being shown in SEQ ID NO: 134 and 135, respectively. Extended DNA sequences for truncated GV-38A and GV-38B are provided in SEQ ID NO: 175 and 176, respectively, with the corresponding amino acid sequences being provided in SEQ ID NO: 177 and 178, respectively.

EXAMPLE 9

Purification and Characterisation of Polypeptides from *M. vaccae* Culture Filtrate by Preparative Isoelectric Focusing and Preparative Polyacrylamide Gel Electrophoresis

*M. vaccae* soluble proteins were isolated from culture filtrate using preparative isoelectric focusing and preparative polyacrylamide gel electrophoresis as described below. Unless otherwise noted, all percentages in the following example are weight per volume.

*M. vaccae* (ATCC Number 15483) was cultured in 250 l sterile Medium 90 which had been fractionated by ultrafiltration to remove all proteins of greater than 10 kDa molecular weight. The medium was centrifuged to remove the bacteria, and sterilised by filtration through a 0.45 $\mu$m filter. The sterile filtrate was concentrated by ultrafiltration over a 10 kDa molecular weight cut-off membrane.

Proteins were isolated from the concentrated culture filtrate by precipitation with 10% trichloroacetic acid. The precipitated proteins were re-dissolved in 100 mM Tris.HCl pH 8.0. and re-precipitated by the addition of an equal volume of acetone. The acetone precipitate was dissolved in water, and proteins were re-precipitated by the addition of an equal volume of chloroform:methanol 2:1 (v/v). The chloroform:methanol precipitate was dissolved in water, and the solution was freeze-dried.

The freeze-dried protein was dissolved in iso-electric focusing buffer, containing 8 M deionised urea, 2% Triton X-100, 10 mM dithiothreitol and 2% ampholytes (pH 2.5–5.0). The sample was fractionated by preparative iso-electric focusing on a horizontal bed of Ultrodex gel at 8 watts constant power for 16 hours. Proteins were eluted from the gel bed fractions with water and concentrated by precipitation with 10% trichloroacetic acid.

Pools of fractions containing proteins of interest were identified by analytical polyacrylamide gel electrophoresis and fractionated by preparative polyacrylamide gel electrophoresis. Samples were fractionated on 12.5% SDS-PAGE gels, and electroblotted onto nitrocellulose membranes. Proteins were located on the membranes by staining with Ponceau Red, destained with water and eluted from the membranes with 40% acetonitrile/0.1M ammonium bicarbonate pH 8.9 and then concentrated by lyophilisation.

Eluted proteins were assayed for their ability to induce proliferation and interferon-γ secretion from the peripheral blood lymphocytes of immune donors as detailed in Example 2. Proteins inducing a strong response in these assays were selected for further study.

Selected proteins were further purified by reversed-phase chromatography on a Vydac Protein C4 column, using a trifluoroacetic acid-acetonitrile system. Purified proteins were prepared for protein sequence determination by SDS-polyacrylamide gel electrophoresis, and electroblotted onto PVDF membranes. Protein sequences were determined as in Example 3. The proteins were named GV-40, GV-41, GV-42, GV-43 and GV-44. The determined N-terminal sequences for these polypeptides are shown in SEQ ID NOS: 101–105, respectively. Subsequent studies led to the isolation of a 5', middle fragment and 3' DNA sequence for GV-42 (SEQ ID NO: 136, 137 and 138, respectively). The corresponding predicted amino acid sequences are provided in SEQ ID NO: 139, 140 and 141, respectively.

Following standard DNA amplification and cloning procedures as described in Example 5, the genes encoding GV-41 and GV-42 were cloned. The determined nucleotide sequences are provided in SEQ ID NOS: 179 and 180, respectively, and the predicted amino acid sequences in SEQ ID NOS: 181 and 182. Further experiments lead to the cloning of the full-length gene encoding GV-41, which was named GV-41B. The determined nucleotide sequence and the predicted amino acid sequence of GV-41B are provided in SEQ ID NOS: 202 and 203, respectively. GV-41 had homology to the ribosome recycling factor of *M. tuberculosis* and *M. leprae*, and GV-42 had homogy to a *M. avium* fibronectin attachment protein FAP-A. Within the full-length sequence of GV-42, the amino acid sequence determined for GV-43 (SEQ ID NO: 104) was identified, indicating that the amino acid sequences for GV-42 and GV-43 were obtained from the same protein.

Murine polyclonal antisera were prepared against GV-40 and GV-44 following standard procedures. These antisera were used to screen a *M. vaccae* genomic DNA library consisting of randomly sheared DNA fragments. Clones encoding GV-40 and GV-44 were identified and sequenced. The determined nucleotide sequence of the partial gene encoding GV-40 is provided in SEQ ID NO: 183 and the predicted amino acid sequence in SEQ ID NO:184. The complete gene encoding GV-40 was not cloned, and the antigen encoded by this partial gene was named GV-40P. An extended DNA sequence for GV-40P is provided in SEQ ID NO: 206 with the corresponding predicted amino acid sequence being provided in SEQ ID NO 207. The determined nucleotide sequence of the gene encoding GV-44 is provided in SEQ ID NO: 185, and the predicted amino acid sequence in SEQ ID NO: 186. With further sequencing, the determined DNA sequence for the full-length gene encoding GV-44 was obtained and is provided in SEQ ID NO 204, with the corresponding predicted amino acid sequence being provided in SEQ ID NO: 205. Homology of GV-40 to *M. leprae* Elongation factor G was found and GV-44 had homology to *M. leprae* glyceraldehyde-3-phosphate dehydrogenase.

EXAMPLE 10

Immune Modulating Properties of Delipidated and Deglycolipidated *M. vaccae* and Recombinant Proteins from *M. vaccae*

This example illustrates the processing of different constituents of *M. vaccae* and their immune modulating properties.

Heat-killed *M. vaccae* and *M. vaccae* Culture Filtrate

*M. vaccae* (ATCC Number 15483) was cultured in sterile Medium 90 (yeast extract, 2.5 g/l; tryptone, 5 g/l; glucose 1 g/l) at 37° C. The cells were harvested by centrifugation, and transferred into sterile Middlebrook 7H9 medium (Difco Laboratories, Detroit, Mich., USA) with glucose at 37° C. for one day. The medium was then centrifuged to pellet the bacteria, and the culture filtrate removed. The bacterial pellet was resuspended in phosphate buffered saline at a concentration of 10 mg/ml, equivalent to $10^{10}$ *M. vaccae* organisms per ml. The cell suspension was then autoclaved for 15 min at 120° C. The culture filtrate was passaged through a 0.45 $\mu$m filter into sterile bottles.

Preparation of Delipidated and Deglycolipidated (DD-) *M.vaccae* and Compositional Analysis To prepare delipidated *M.vaccae*, the autoclaved *M.vaccae* was pelleted by centrifugation, the pellet washed with water and collected again by centrifugation and then freeze-dried. An aliquot of this freeze-dried *M.vaccae* was set aside and referred to as lyophilised *M.vaccae*. When used in experiments it was resuspended in PBS to the desired concentration. Freeze-dried *M. vaccae* was treated with chloroform/methanol (2:1) for 60 mins at room temperature to extract lipids, and the extraction was repeated once. The delipidated residue from chloroform/methanol extraction was further treated with 50% ethanol to remove glycolipids by refluxing for two hours. The 50% ethanol extraction was repeated two times. The pooled 50% ethanol extracts were used as a source of *M. vaccae* glycolipids (see below). The residue from the 50% ethanol extraction was freeze-dried and weighed. The amount of delipidated and deglycolipidated *M.vaccae* prepared was equivalent to 11.1% of the starting wet weight of *M.vaccae* used. For bioassay, the delipidated and deglycolipidated *M. vaccae* (DD-*M. vaccae*; referred to as delipidated *M. vaccae* in FIG. 9), was resuspended in phosphate-buffered saline by sonication, and sterilised by autoclaving.

The compositional analyses of heat-killed *M. vaccae* and DD-*M. vaccae* are presented in Table 7. Major changes are seen in the fatty acid composition and amino acid composition of DD-*M. vaccae* as compared to the insoluble fraction of heat-killed *M. vaccae*. The data presented in Table 7 show that the insoluble fraction of heat-killed *M.vaccae* contains 10% w/w of lipid, and the total amino acid content is 2750 nmoles/mg, or approximately 33% w/w. DD-*M. vaccae* contains 1.3% w/w of lipid and 4250 nmoles/mg amino acids, which is approximately 51% w/w.

TABLE 7

Compositional analyses of heat-killed *M. vaccae* and DD-*M. vaccae*

| | *M. vaccae* | DD-*M. vaccae* |
|---|---|---|
| MONOSACCHARIDE COMPOSITION | | |
| sugar alditol | | |
| Inositol | 3.2% | 1.7% |
| Ribitol* | 1.7% | 0.4% |
| Arabinitol | 22.7% | 27.0% |
| Mannitol | 8.3% | 3.3% |
| Galactitol | 11.5% | 12.6% |
| Glucitol | 52.7% | 55.2% |
| FATTY ACID COMPOSITION | | |
| Fatty acid | | |
| C14:0 | 3.9% | 10.0% |
| C16:0 | 21.1% | 7.3% |
| C16:1 | 14.0% | 3.3% |
| C18:0 | 4.0% | 1.5% |
| C18:1* | 1.2% | 2.7% |
| C18:1w9 | 20.6% | 3.1% |
| C18:1w7 | 12.5% | 5.9% |
| C22:0 | 12.1% | 43.0% |
| C24:1* | 6.5% | 22.9% |

The insoluble fraction of heat-killed *M. vaccae* contains 10% w/w of lipid, and DD-*M. vaccae* contains 1.3% w/w of lipid.

AMINO ACID COMPOSITION

| Nmoles/mg | *M. vaccae* | DD-*M. vaccae* |
|---|---|---|
| ASP | 231 | 361 |
| THR | 170 | 266 |
| SER | 131 | 199 |
| GLU | 319 | 505 |
| PRO | 216 | 262 |
| GLY | 263 | 404 |
| ALA | 416 | 621 |
| CYS* | 24 | 26 |
| VAL | 172 | 272 |

-continued

AMINO ACID COMPOSITION

| Nmoles/mg | *M. vaccae* | DD-*M. vaccae* |
|---|---|---|
| MET* | 72 | 94 |
| ILE | 104 | 171 |
| LEU | 209 | 340 |
| TYR | 39 | 75 |
| PHE | 76 | 132 |
| GlcNH2 | 5 | 6 |
| HIS | 44 | 77 |
| LYS | 108 | 167 |
| ARG | 147 | 272 |

The total amino acid content of the insoluble fraction of heat-killed *M. vaccae* is 2750 nmoles/mg, or approximately 33% w/w. The total amino acid content of DD-*M. vaccae* is 4250 nmoles/mg, or approximately 51% w/w.

Comparison of composition of DD-*M. vaccae* with Delipidated and Deglycolipidated Forms of *M. tuberculosis* and *M. smegmatis*

Delipidated and deglycolipidated *M. tuberculosis* and *M. smegmatis* were prepared using the procedure described above for delipidated and deglycolipidated *M. vaccae*. As indicated in Table 8, the profiles of the percentage composition of amino acids in DD-*M. vaccae*, DD-*M. tuberculosis* and DD-*M. smegmatis* showed no significant differences. However, the total amount of protein varied—the two batches of DD-*M. vaccae* contained 34% and 55% protein, whereas DD-*M. tuberculosis* and DD-*M. smegmatis* contained 79% and 72% protein, respectively.

TABLE 8

Amino Acid Composition of Delipidated and Deglycolipidated Mycobacteria

| Amino Acid | DD-*M. vaccae* Batch 1 | DD-*M. vaccae* Batch 2 | DD-*M. smegmatis* | DD-*M. tuberculosis* |
|---|---|---|---|---|
| Asp | 9.5 | 9.5 | 9.3 | 9.1 |
| Thr | 6.0 | 5.9 | 5.0 | 5.3 |
| Ser | 5.3 | 5.3 | 4.2 | 3.3 |
| Glu | 11.1 | 11.2 | 11.1 | 12.5 |
| Pro | 6.1 | 5.9 | 7.5 | 5.2 |
| Gly | 9.9 | 9.7 | 9.4 | 9.8 |
| Ala | 14.6 | 14.7 | 14.6 | 14.2 |
| Cys | 0.5 | 0.5 | 0.3 | 0.5 |
| Val | 6.3 | 6.4 | 7.2 | 7.8 |
| Met | 1.9 | 1.9 | 1.9 | 1.9 |
| Ile | 3.6 | 3.5 | 4.1 | 4.7 |
| Leu | 7.8 | 7.9 | 8.2 | 8.3 |
| Tyr | 1.4 | 1.7 | 1.8 | 1.8 |
| Phe | 4.2 | 4.0 | 3.2 | 3.0 |
| His | 1.9 | 1.8 | 2.0 | 1.9 |
| Lys | 4.1 | 4.0 | 4.1 | 4.2 |
| Arg | 5.8 | 5.9 | 6.2 | 6.4 |
| Total % Protein | 55.1 | 33.8 | 72.1 | 78.5 |

Analysis of the monosaccharide composition shows significant differences between DD-*M. vaccae*, and DD-*M. tuberculosis* and DD-*M. smegmatis*. The monosaccharide composition of two batches of DD-*M. vaccae* was the same and differed from that of DD-*M. tuberculosis* and *M. smegmatis*. Specifically, DD-*M. vaccae* was found to contain free glucose while both DD-*M. tuberculosis* and *M. smegmatis* contain glycerol, as shown in Table 9.

TABLE 9

| Alditol Acetate | wt % | mol % |
|---|---|---|
| DD-*M. vaccae* Batch 1 | | |
| Inositol | 0.0 | 0.0 |
| Arabinose | 54.7 | 59.1 |
| Mannose | 1.7 | 1.5 |
| Glucose | 31.1 | 28.1 |
| Galactose | 12.5 | 11.3 |
| | 100.0 | 100.0 |
| DD-*M. vaccae* Batch 2 | | |
| Inositol | 0.0 | 0.0 |
| Arabinose | 51.0 | 55.5 |
| Mannose | 2.0 | 1.8 |
| Glucose | 34.7 | 31.6 |
| Galactose | 12.2 | 11.1 |
| | 100.0 | 100.0 |
| DD-*M. smeg* | | |
| Inositol | 0.0 | 0.0 |
| Glycerol | 15.2 | 15.5 |
| Arabinose | 69.3 | 70.7 |
| Xylose | 3.9 | 4.0 |
| Mannose | 2.2 | 1.9 |
| Glucose | 0.0 | 0.0 |
| Galactose | 9.4 | 8.0 |
| | 100.0 | 100.0 |
| DD-Mtb | | |
| Inositol | 0.0 | 0.0 |
| Glycerol | 9.5 | 9.7 |
| Arabinose | 69.3 | 71.4 |
| Mannose | 3.5 | 3.0 |
| Glucose | 1.5 | 1.3 |
| Galactose | 12.4 | 10.7 |
| | 96.2 | 96.0 |

*M. vaccae* Glycolipids

The pooled 50% ethanol extracts described above were dried by rotary evaporation, redissolved in water, and freeze-dried. The amount of glycolipid recovered was 1.2% of the starting wet weight of *M. vaccae* used. For bioassay, the glycolipids were dissolved in phosphate-buffered saline.

Production of Interleukin-12 from Macrophages

Whole heat-killed *M. vaccae* and DD-*M. vaccae* were shown to have different cytokine stimulation properties. The stimulation of a Th1 immune response is enhanced by the production of interleukin-12 (IL-12) from macrophages. The ability of different *M. vaccae* preparations to stimulate IL-12 production was demonstrated as follows.

Figure 8:
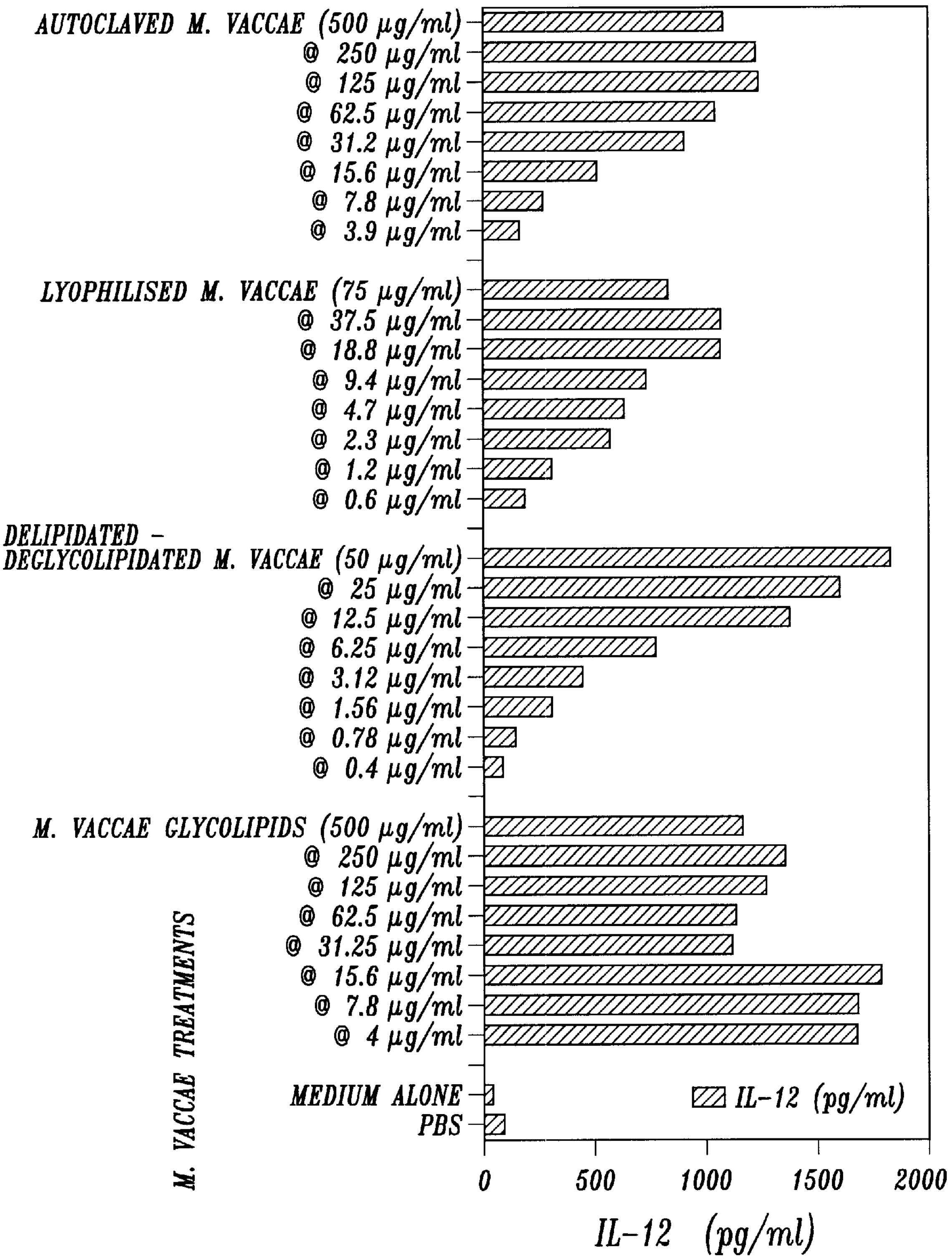
FIG. 8 illustrates the induction of IL-12 by autoclaved *M. vaccae*, lyophilized *M. vaccae*, delipidated and deglycolipidated *M. vaccae* and *M. vaccae* glycolipids.

A group of C57BL/6J mice were injected intraperitoneally with DIFCO thioglycolate and after three days, peritoneal macrophages were collected and placed in cell culture with interferon-gamma for three hours. The culture medium was replaced and various concentrations of whole heat-killed (autoclaved) *M. vaccae*, lyophilized *M. vaccae*, DD-*M. vaccae* (referred to as delipidated-deglycolipidated *M. vaccae* in FIG. 8) and *M. vaccae* glycolipids were added. After a further three days at 37° C., the culture supernatants were assayed for the presence of IL-12 produced by macrophages. As shown in FIG. 8, the *M. vaccae* preparations stimulated the production of IL-12 from macrophages.

Figure 10:
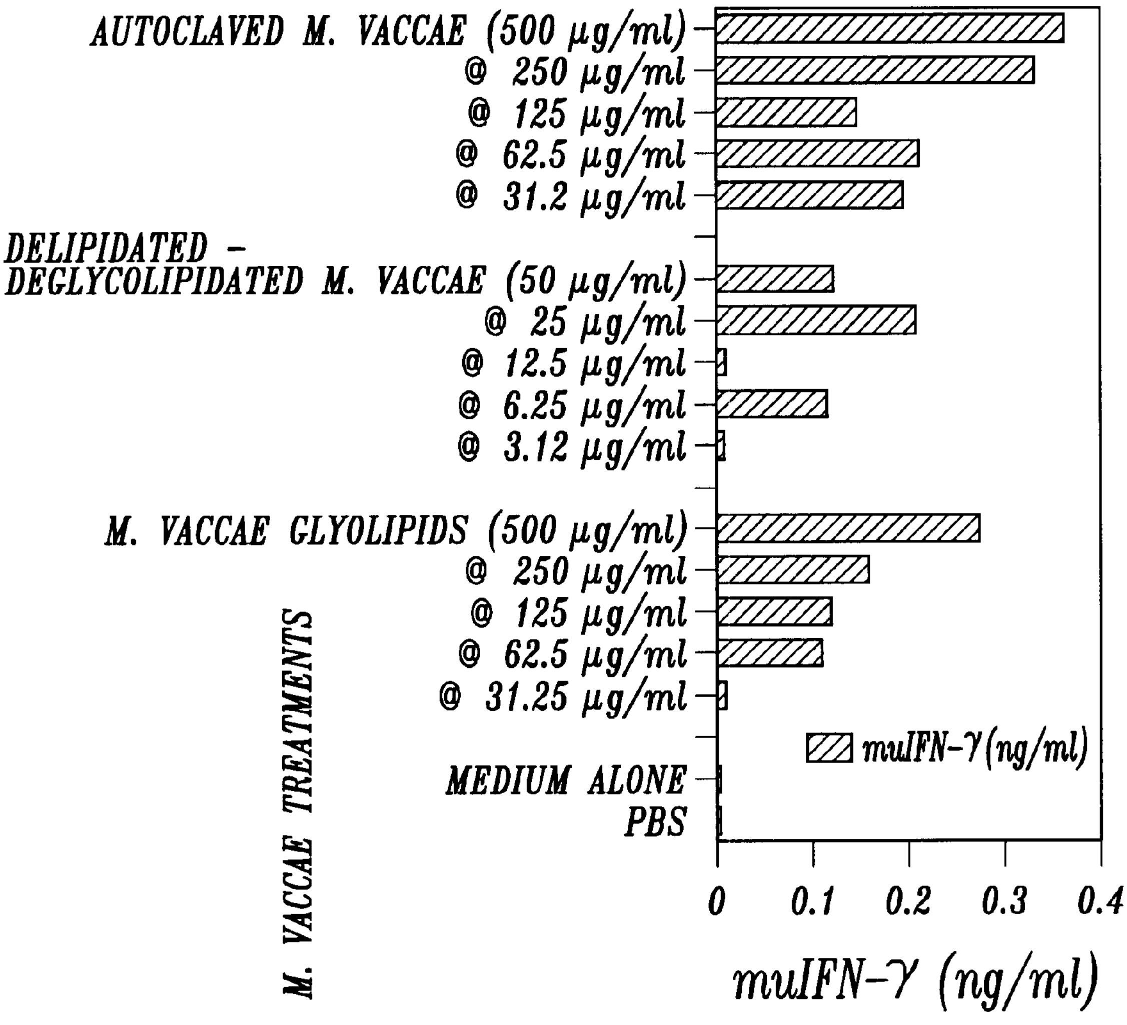
FIG. 10 compares the in vitro stimulation of interferon-gamma production in spleen cells from Severe Combined ImmunoDeficient (SCID) mice by different concentrations of heat-killed (autoclaved) *M. vaccae*, delipidated and deglycolipidated *M. vaccae*, and *M. vaccae* glycolipids.

By contrast, these same *M. vaccae* preparations were examined for the ability to stimulate interferon-gamma production from Natural Killer (NK) cells. Spleen cells were prepared from Severe Combined Immunodeficient (SCID) mice. These populations contain 75–80% NK cells. The spleen cells were incubated at 37° C. in culture with different concentrations of heat-killed *M. vaccae*, DD-*M. vaccae*, or *M. vaccae* glycolipids. The data shown in FIG. 10 demonstrates that, while heat-killed *M. vaccae* and *M. vaccae* glycolipids stimulate production of interferon-gamma, DD-*M. vaccae* stimulated relatively less interferon-gamma. The combined data from FIGS. 8 and 10 indicate that, compared with whole heat-killed *M. vaccae*, DD-*M. vaccae* is a better stimulator of IL-12 than interferon gamma.

Figure 9A:
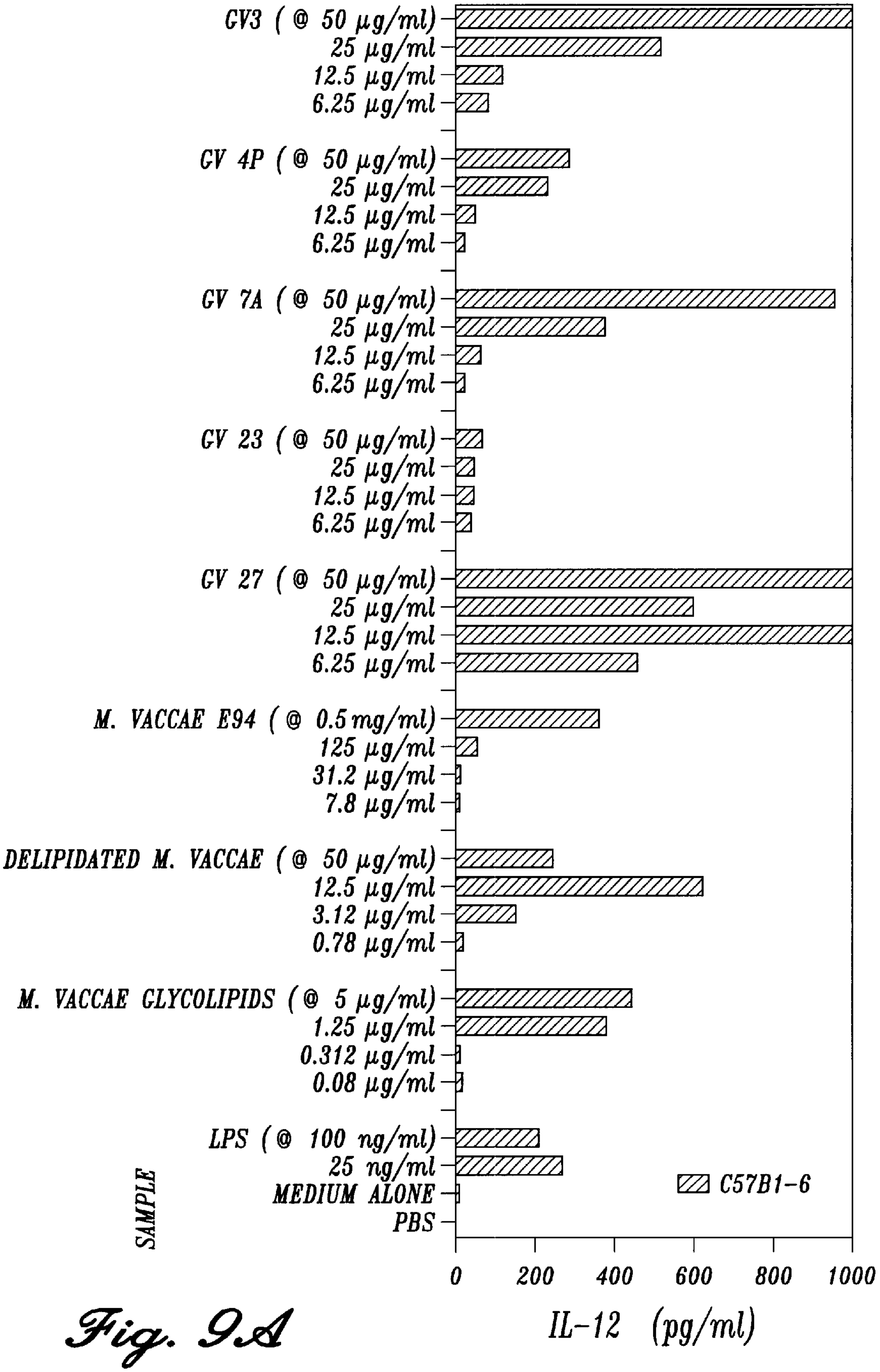
FIGS. 9A, B and C illustrate the stimulation of interferon-gamma production by different concentrations of *M. vaccae* recombinant proteins, heat-killed *M. vaccae*, delipidated and deglycolipidated *M. vaccae* (referred to in the figure as "delipidated *M. vaccae*"), *M. vaccae* glycolipids and lipopolysaccharide, in peritoneal macrophages from C57BL/6 mice (FIG. 9A), BALB/C mice (FIG. 9B) or C3H/HeJ mice (FIG. 9C).
Figure 9B:
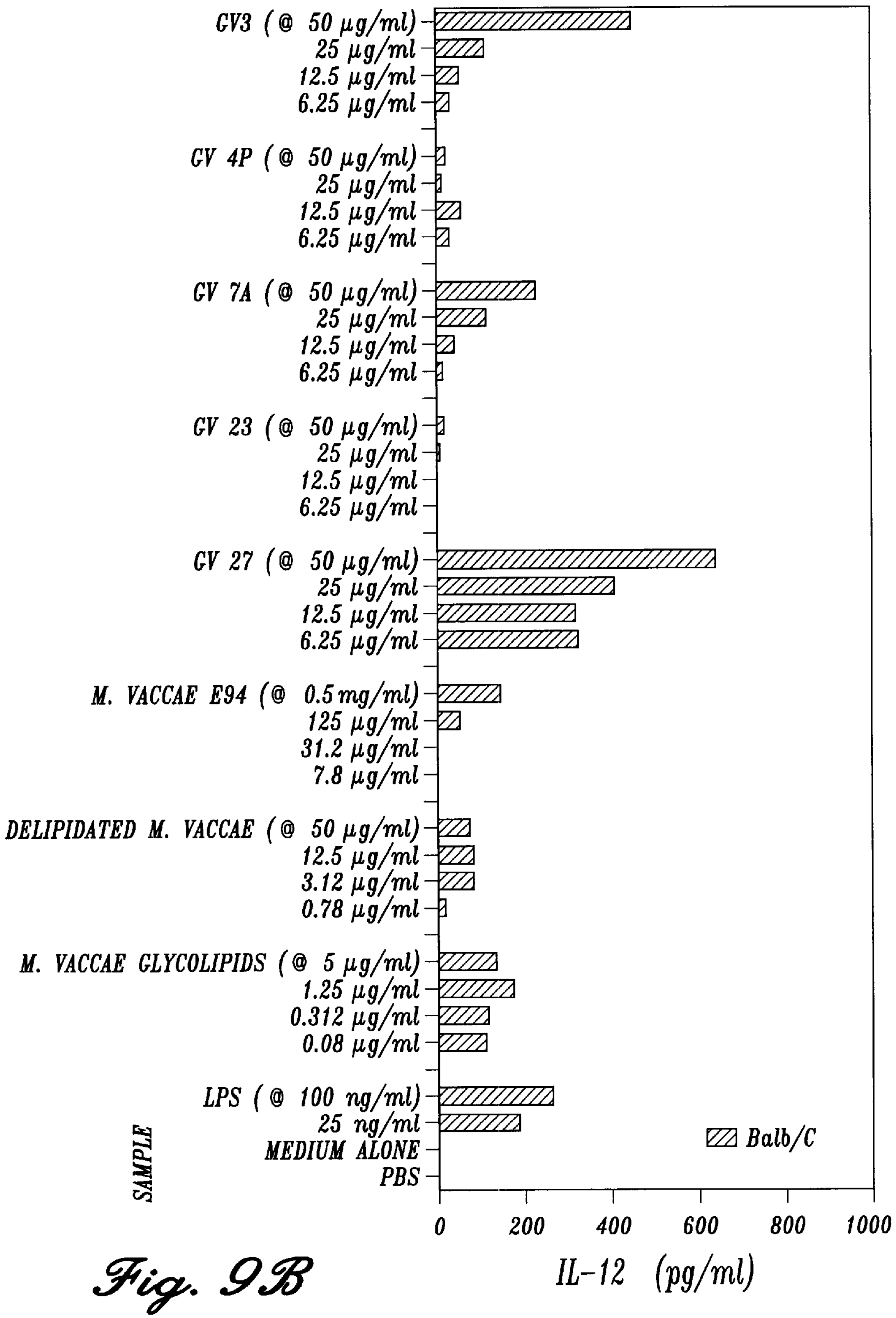
Figure 9C:
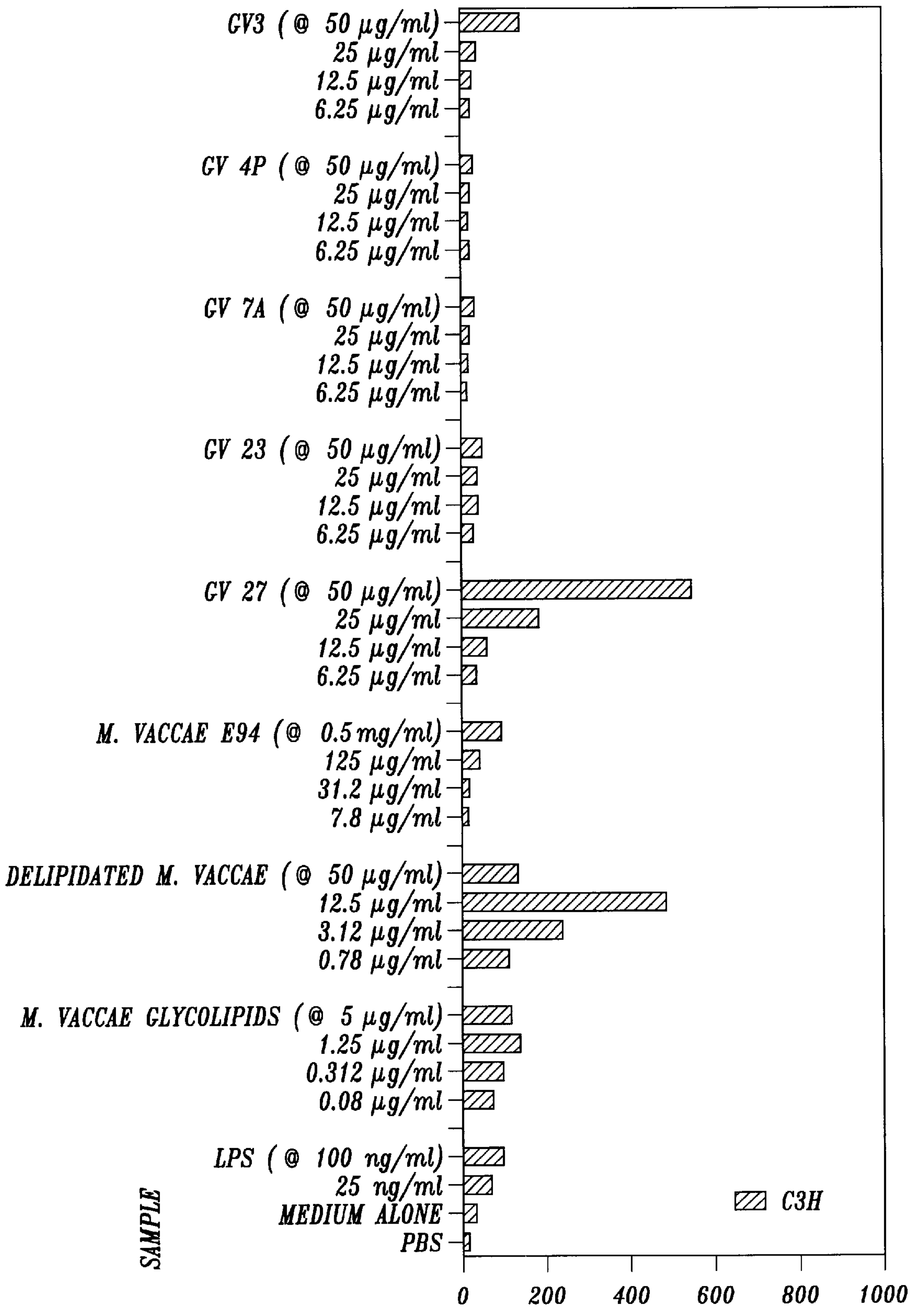

FIGS. 9A, B, and C show data from separate experiments in which groups of C57BL/6 mice (FIG. 9A), BALB/c mice (FIG. 9B) or C3H/HeJ mice (FIG. 9C) were given DIFCO thioglycolate intraperitoneally and, after three days, peritoneal macrophages were collected and placed in culture with interferon-gamma for three hours. The culture medium was replaced and various concentrations of *M. vaccae* recombinant proteins GVs-3 (GV-3), GV-4P (GV-4P), GVc-7 (GV-7), GV-23, GV-27, heat killed *M. vaccae*, DD-*M. vaccae* (referred to as delipidated *M. vaccae* in FIGS. 9A, B and C), *M. vaccae* glycolipids or lipopolysaccharide were added. After three days at 37° C., the culture supernatants were assayed for the presence of IL-12 produced by macrophages. As shown in FIGS. 9A, B and C, the recombinant proteins and *M. vaccae* preparations stimulated the production of IL-12 from macrophages.

Figure 11:
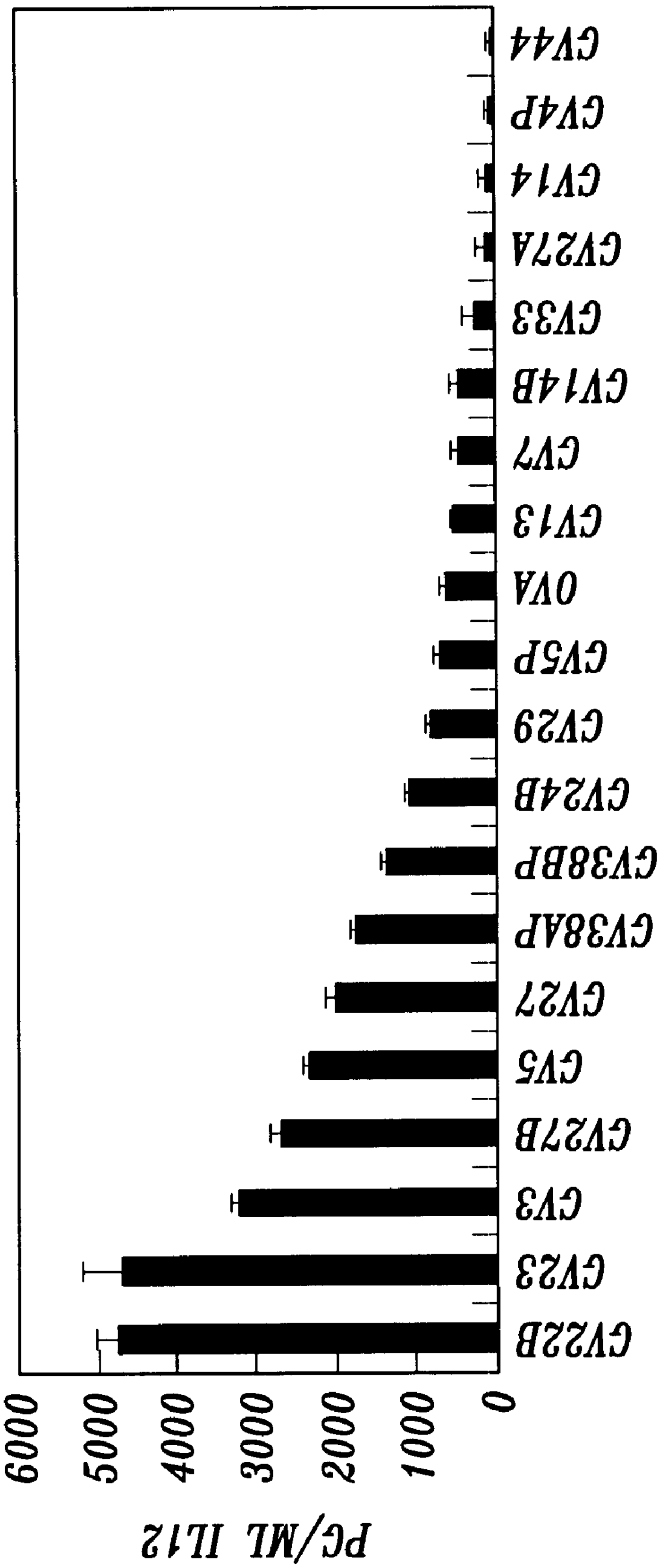
FIG. 11 illustrates the induction of IL-12 from peritoneal macrophages by recombinant proteins derived from *M. vaccae.*

In a subsequent experiment, IFNγ-primed peritoneal macrophages from BALB/c mice were stimulated with 40 ug/ml of *M. vaccae* recombinant proteins in culture for 3 days and the presence of IL-12 produced by macrophages was assayed. As shown in FIG. 11, in these experiments IFNγ-primed macrophages produced IL-12 when cultured with a control protein, ovalbumin (ova). However, the recombinant proteins GV 24B, 38BP, 38AP, 27, 5, 27B, 3 23, 22B stimulated more than twice the amount of IL-12 detected in control macrophage cultures.

Proteins in DD-*M. vaccae* Identified by Antibodies

BALB/c mice were immunized intra-peritoneally with 50 ug of DD-*M. vaccae* once a week for 5 weeks. At the $6^{th}$ week mice were sacrificed and their serum collected. The sera were tested for antibodies to recombinant *M. vaccae* derived GV proteins in standard enzyme-linked immunoassays.

The antisera did not react with several GV proteins nor with ovalbumin, which served as an irrelevant negative control protein in the enzyme-linked assays (data not shown). Antisera from DD-*M. vaccae* immunized mice reacted with 12 GV antigens and results are shown in the Table 10 below. The antisera have thus identified GV3, 5P, 5, 7, 9, 22B, 24, 27, 27A, 27B, 33 and 45 as being present in DD-*M. vaccae*.

TABLE 10

| | Reactivity of DD-*M. vaccae* antiserum with 12 GV antigens | | | | | | | | | | | |
|---|---|---|---|---|---|---|---|---|---|---|---|---|
| GV Antigen | 3 | 5P | 5 | 7 | 9 | 22B | 24 | 27 | 27A | 27B | 33 | 45 |
| Reactivity* | $10^3$ | $10^3$ | $10^3$ | $10^2$ | $10^4$ | $10^3$ | $10^4$ | $10^6$ | $10^5$ | $10^6$ | $10^4$ | $10^4$ |

*Expressed as highest dilution of serum from DD-*M. vaccae* immunized mice showing greater activity than serum from non-immunized mice.

Proteins in DD-*M.vaccae* Identified by T Cell Responses

BALB/c mice were injected in each footpad with 100 ug DD-*M.vaccae* in combination with incomplete Freund's adjuvant and 10 days later were sacrificed to obtain popliteal lymph node cells. The cells from immunized and non-immunized control mice were stimulated in vitro with recombinant *M. vaccae* derived GV proteins. After 3 days, cell proliferation and IFNγ production were assessed.

T Cell Proliferative Responses of Lymph Node Cells from DD-*M.vaccae* Immunized Mice to GV Proteins.

Lymph node cells from DD-*M. vaccae*-immunized mice did not proliferate in response to an irrelevant protein, ovalbumin, (data not shown). As shown in Table 11, lymph node cells from immunized mice showed proliferative responses to GV 3, 7, 9, 23, 27, 27B, and 33. The corresponding cells from non-immunized mice did not proliferate in response to these GV proteins suggesting that mice immunized with DD-*M. vaccae* have been immunized with these proteins. Thus, the *M.vaccae* derived proteins GV 3, 7, 9, 23, 27, 27B and 33 are likely to be present in DD-*M.vaccae*.

TABLE 11

Proliferative responses of lymph node cells from DD-*M. vaccae*-immunized mice and control mice to GV proteins in vitro

| | Stimulation index* observed in the presence of GV proteins at 50 μg/ml | |
|---|---|---|
| GV protein | DD-*M. vaccae immunized* mice | Control mice |
| GV3 | 4.63 | 1.52 |
| GV7 | 3.32 | 1.27 |
| GV9 | 6.48 | 2.64 |
| GV23 | 4.00 | 1.76 |
| GV27 | 5.13 | 1.40 |
| GV27B | 7.52 | 1.48 |
| GV33 | 3.31 | 1.45 |

*Stimulation index = cpm from tritiated Thymidine uptake in presence of GV protein/cpm in absence of GV protein IFNγ Production by Lymph Node Cells from DD-*M. vaccae* Immunized Mice Following in vitro Challenge with GV Proteins Lymph node cells from non-immunized mice did not produce IFNγ upon stimulation with GV proteins. As shown in Table 12 below, lymph node cells from DD-*M. vaccae* immunized mice secrete IFNγ in a dose dependent manner when stimulated with GV 3, 5, 23, 27A, 27B, 33, 45 and 46, suggesting that the mice have been immunized with these proteins. No IFNγ production was detectable when cells from immunized mice were stimulated with the irrelevant protein, ovalbumin (data not shown). The proteins GV 3, 5, 23, 27A, 27B, 33, 45 and 46 are thus likely to be present in DD-*M. vaccae*.

TABLE 12

Production of IFNγ by popliteal lymph node cells from DD-*M. vaccae* immunized mice following in vitro challenge with GV protein

| GV protein | IFNγ (ng/ml) Dose of GV protein used in vitro (μg/ml) | | |
|---|---|---|---|
| or control | 50 | 10 | 2 |
| GV-3 | 8.22 ± 3.73 | ND | ND |
| GV-4P | ND | ND | ND |
| GV-5 | 8.90 ± 4.54 | 0.57 ± 0.40 | ND |
| GV-5P | ND | ND | ND |
| GV-T | ND | ND | ND |
| GV-9 | ND | ND | ND |
| GV-13 | 1.64 ± 0.40 | ND | ND |
| GV-14 | ND | ND | ND |
| GV-14B | ND | ND | ND |
| GV-22B | 20.15 ± 1.96 | 4.34 ± 0.02 | ND |
| GV-23 | 41.38 ± 6.69 | 6.97 ± 2.78 | ND |
| GV-24B | ND | ND | ND |
| GV-27 | 46.86 ± 17.14 | 33.06 ± 17.61 | 10.14 ± 3.01 |
| GV-27A | 7.25 ± 4.36 | ND | ND |
| GV-27B | 100.36 ± 37.84' | 33.03 + 7.54 | 14.33 ± 1.01 |
| GV-29 | 5.93 ± 0.47 | ND | ND |
| GV-33 | 9.82 ± 4.64 | ND | ND |
| GV-38AP | 1.44 ± 1.20 | ND | ND |
| GV-38BP | 5.62 ± 0.70 | ND | ND |
| GV-42 | ND | ND | ND |
| GV-44 | ND | ND | ND |
| DD-*M. vaccae* | 109.59 ± 15.48 | 90.23 ± 6.48 | 65.16 ± 3.68 |
| *M. vaccae* | 68.89 ± 4.38 | 67.91 ± 7.92 | 48.92 ± 3.86 |

ND = Not Detectable

Proteins in DD-*M.vaccae* as Non-specific Immune Amplifiers

Figure 12:
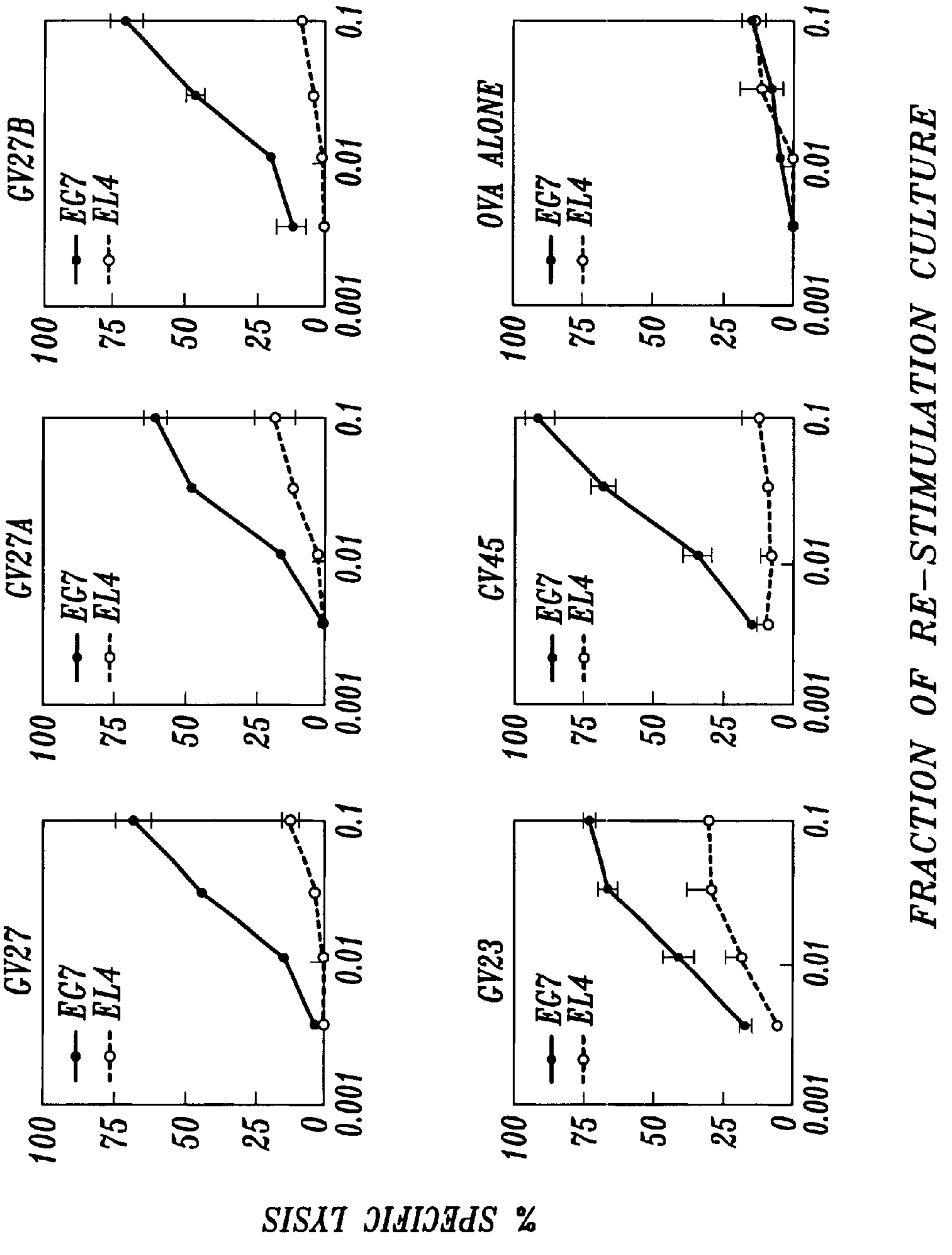
FIG. 12 illustrates the non-specific immune amplfying property of each of the recombinant proteins GV27, 27A, 27B, 23 and 45 in the generation of cytotoxic T cells to a structurally unrelated protein, ovalbumin.

In subsequent experiments, the five proteins GV27, 27A, 27B, 23 and 45 were used as non-specific immune amplifiers with ovalbumin antigen to immunize mice as described above in Example 6. As shown in FIG. 12, 50 ug of any one of the recombinant proteins GV27, 27A, 27B, 23 and 45, when injected with 50–100 ug of ovalbumin, demonstrated adjuvant properties in being able to generate cytotoxic cells to ovalbumin.

EXAMPLE 11

Effect of Intradermal Route of Immunization with *M. vaccae* on Tuberculosis in Cynomolgous Monkeys This example illustrates the effect of immunization with *M. vaccae* or *M. vaccae* culture filtrate intradermally in cynomolgous monkeys prior to challenge with live *M. tuberculosis*.

*M. vaccae* (ATCC Number 15483) was cultured in sterile Medium 90 (yeast extract, 2.5 g/l; tryptone, 5 g/l; glucose, 1 g/l) at 37° C. The cells were harvested by centrifugation, and transferred into sterile Middlebrook 7H9 medium (Difco Laboratories, Detroit, Mich., USA) with glucose at 37° C. for one day.- The medium was then centrifuged to pellet the bacteria, and the culture filtrate removed. The bacterial pellet was resuspended in phosphate buffered saline at a concentration of 10 mg/ml, equivalent to $10^{10}$ *M. vaccae* organisms per ml. The cell suspension was then autoclaved for 15 min at 120° C. The culture filtrate was passaged through a 0.45 $\mu$M filter into sterile bottles.

Three groups of cynomolgous monkeys were included in this study, with each group containing 2 monkeys. One group of monkeys were immunized with whole heat-killed *M. vaccae*; one group were immunized with *M. vaccae* culture filtrate and a control group received no immunizations. The composition employed for immunization; amount of immunogen and route of administration for each group of monkeys are provided in Table 13.

TABLE 13

COMPARISON OF INTRADERMAL ROUTE OF IMMUNIZATION

| Group Number | Identification Number of Monkey | Amount of Antigen | Route of Immunization |
|---|---|---|---|
| 1 | S3101-E | 0 | — |
| (Controls) | 3144-B | 0 | — |
| 2 | 4080-B | 500 $\mu$g | intradermal |
| (Immunized with heat-killed *M. vaccae*) | 3586-B | 500 $\mu$g | intradermal |
| 3 | 3564-B | 100 $\mu$g | intradermal |
| (Immunized with culture filtrate) | 3815-B | 100 $\mu$g | intradermal |

Prior to immunization, all monkeys were weighed (Wt kgs), body temperature measured (temp), and a blood sample taken for determination of eryffirocyte sedimentation rate (ESR mnm/hr) and lymphocyte proliferation (LPA) to an in vitro challenge with purified protein (PPD) prepared from *Mycobacterium bovis*. At day 33 post inmunization these measurements were repeated. At day 34, all monkeys received a second immunisation using the same amount of *M.vaccae*. On day 62, body weight, temperature, ESR and LPA to PPD were measured, then all monkeys were infected with 103 colony forming units of the Erdman strain of *M. tuberculosis*. Twenty eight days following infection, body weight, temperature, ESR and LPA to PPD were measured in all monkeys, and the lungs were X-rayed to determine whether infection with live *M. tuberculosis* had resulted in the onset of pneumonia.

As shown in Tables 14A, B and C, the monkeys in the control group showed radiologic evidence of pulmonary tuberculosis by 28 days after infection with *M. tuberculosis*. Clinical disease was not evident 84 days after infection in monkeys immunized intradermally with two doses of 500 $\mu$g of *M. vaccae*. The onset of clinical disease was delayed in both monkeys immunized intradermally with 100 $\mu$g of *M. vaccae* culture filtrate.

TABLE 14A

CONTROL MONKEYS

| ID # | Days | Wt. Kgs | Temp. | ESR Mm/hr | LPA PPD 10 $\mu$g | LPA PPD 1 $\mu$g | X-Ray |
|---|---|---|---|---|---|---|---|
| S3101E | 0 | 2.17 | 37.0 | 0 | 0.47 | 1.1 | Negative |
| | 34 | 1.88 | 37.3 | ND | 0.85 | 1.4 | ND |
| | 62 | 2.02 | 36.0 | ND | 1.3 | 1.5 | ND |
| → | Time of Infection | | | | | | |
| | 28 | 2.09 | 38.0 | 2 | 1.3 | 3.7 | Positive |
| | 56 | 1.92 | 37.2 | 20 | 5.6 | 9.1 | Positive |
| | 84 | 1.81 | 37.5 | 8 | 4.7 | 5.6 | Positive |
| 3144-B | 0 | 2.05 | 36.7 | 0 | 0.87 | 1.8 | Negative |
| | 34 | 1.86 | 37.6 | ND | 2.2 | 1.4 | ND |
| | 62 | 1.87 | 36.5 | ND | 1.6 | 1.6 | ND |
| → | Time of Infection | | | | | | |
| | 28 | 2.10 | 38.0 | 0 | 12 | 8.7 | Positive |
| | 56 | 1.96 | 37.6 | 0 | 29.6 | 21.1 | Positive |
| | 84 | 1.82 | 37.3 | 4 | 45.3 | 23.4 | Positive |

ND = Not Done

TABLE 14B

MONKEYS IMMUNIZED WITH WHOLE HEAT-KILLED *M. VACCAE* (500 $\mu$g) INTRADERMALLY

| ID # | Days | Wt. Kgs | Temp. | ESR Mm/hr | LPA PPD 10 $\mu$g | LPA PPD 1 $\mu$g | X-Ray |
|---|---|---|---|---|---|---|---|
| 4080-B | 0 | 2.05 | 37.1 | 1 | 1.1 | 0.77 | Negative |
| | 34 | 1.97 | 38.0 | ND | 1.7 | 1.4 | ND |
| | 62 | 2.09 | 36.7 | ND | 1.5 | 1.5 | ND |
| → | Time of Infection | | | | | | |
| | 28 | 2.15 | 37.6 | 0 | 2.6 | 2.1 | Negative |
| | 56 | 2.17 | 37.6 | 0 | 8.2 | 7.6 | Negative |
| | 84 | 2.25 | 37.3 | 0 | 3.8 | 2.8 | Negative |
| 3586-B | 0 | 2.29 | 37.0 | 0 | 1.1 | 1.4 | Negative |
| | 34 | 2.22 | 38.0 | ND | 1.9 | 1.6 | ND |
| | 62 | 2.39 | 36.0 | ND | 1.3 | 1.6 | ND |
| → | Time of Infection | | | | | | |
| | 28 | 2.31 | 38.2 | 0 | 3.2 | 2.6 | Negative |
| | 56 | 2.32 | 37.2 | 0 | 7.8 | 4.2 | Negative |
| | 84 | 2.81 | 37.4 | 0 | 3.4 | 1.8 | Negative |

ND = Not Done

TABLE 14C

MONKEYS IMMUNIZED WITH CULTURE FILTRATE (100 $\mu$g) INTRADERMALLY

| ID # | Days | Wt. Kgs | Temp. | ESR Mm/hr | LPA PPD 10 $\mu$g | LPA PPD 1 $\mu$g | X-Ray |
|---|---|---|---|---|---|---|---|
| 3564-B | 0 | 2.40 | 37.2 | 0 | 1.4 | 1.4 | Negative |
| | 34 | 2.42 | 38.1 | ND | 3.3 | 2.7 | ND |
| | 62 | 2.31 | 37.1 | ND | 3.1 | 3.4 | ND |
| → | Time of Infection | | | | | | |
| | 28 | 2.41 | 38.6 | 13 | 24 | 13.6 | Negative |
| | 56 | 2.38 | 38.6 | 0 | 12.7 | 12.0 | Negative |
| | 84 | 2.41 | 38.6 | 2 | 21.1 | 11.8 | Positive |
| 3815-B | 0 | 2.31 | 36.3 | 0 | 1.0 | 1.4 | Negative |
| | 34 | 2.36 | 38.2 | ND | 1.9 | 2.0 | ND |
| | 62 | 2.36 | 36.4 | ND | 3.7 | 2.8 | ND |

TABLE 14C-continued

| MONKEYS IMMUNIZED WITH CULTURE FILTRATE (100 μg) INTRADERMALLY | | | | | | | |
|---|---|---|---|---|---|---|---|
| ID # | Days | Wt. Kgs | Temp. | ESR Mm/hr | LPA PPD 10 μg | LPA PPD 1 μg | X-Ray |
| → | Time of Infection | | | | | | |
| | 28 | 2.45 | 37.8 | 0 | 2.1 | 3.3 | Negative |
| | 56 | 2.28 | 37.3 | 4 | 8.0 | 5.6 | Negative |
| | 84 | 2.32 | 37.4 | 0 | 1.9 | 2.2 | Positive |

ND = Not Done

EXAMPLE 12

Isolation of the DD-*M. vaccae* Antigens GV-45 AND GV-46

Proteins were extracted from DD-*M. vaccae* (500 mg; prepared as described in Example 10) by suspension in 10 ml 2% SDS/PBS and heating to 50° C. for 2 h. The insoluble residue was removed by centrifugation, and proteins precipitated from the supernatant by adding an equal volume of acetone and incubating at −20° C. for 1 hr. The precipitated proteins were collected by centrifugation, dissolved in reducing sample buffer, and fractionated by preparative SDS-polyacrylamide gel electrophoresis. The separated proteins were electroblotted onto PVDF membrane in 10 mM CAPS/0.01% SDS pH 11.0, and N-terminal sequences were determined in a gas-phase sequenator.

From these experiments, a protein represented by a band of approximate molecular weight of 30 kDa, designated GV-45, was isolated. The determined N-terminal sequence for GV-45 is provided in SEQ ID NO: 187. From the same experiments, a protein of approximate molecular weight of 14 kDa, designated GV-46, was obtained. The determined N-terminal amino acid sequence of GV-46 is provided in SEQ ID NO: 208. GV-46 is homologous to the highly conserved mycobacterial host integration factor of *M. tuberculosis* and *M. smegmatis.*

From the amino acid sequence of GV-45, degenerate oligonucleotides KR32 and KR33 (SEQ ID NOS: 188 and 189, respectively) were designed. A 100 bp fragment was amplified, cloned into plasmid pBluescript II SK$^+$ (Stratagene, La Jolla, Calif.) and sequenced (SEQ ID NO: 190) following standard procedures (Maniatis, Ibid). The cloned insert was used to screen a *M. vaccae* genomic DNA library constructed in the BamHI-site of lambda ZAP-Express (Stratagene). The isolated clone showed homology to a 35 kDa *M. tuberculosis* and a 22 kDa *M. leprae* protein containing bacterial histone-like motifs at the N-terminus and a unique C-terminus consisting of a five amino acid basic repeat. The determined nucleotide sequence for GV-45 is provided in SEQ ID NO: 191, with the corresponding predicted amino acid sequence being provided in SEQ ID NO: 192. With additional sequencing, the determined DNA sequence for the full-length gene encoding GV-45 was obtained and is provided in SEQ ID NO: 200, with the corresponding predicted amino acid sequence in SEQ ID NO: 201.

EXAMPLE 13

Immunogenicity and Immunodulating Properties of Recombinant Proteins Derived from *M. vaccae*

A. Induction of T Cell Proliferation and IFN-γ Production

The immunogenicity of *Mycobacterium vaccae* recombinant proteins (GV recombinant proteins) was tested by injecting female BALB/cByJ mice in each hind foot-pad with 10 ug of recombinant GV proteins emulsified in incomplete Freund's adjuvant (IFA). Control mice received phosphate buffered saline in IFA. The draining popliteal lymph nodes were excised 10 days later and the cells obtained therefrom were stimulated with the immunizing GV protein and assayed for proliferation by measuring the uptake of tritiated thymidine. The amount of interferon gamma (IFNγ) produced and secreted by these cells into the culture supernatants was assayed by standard enzyme-linked immunoassay.

As shown in Table 15 summarising proliferative responses, all GV proteins were found to induce a T cell proliferative response. The lymph node T cells from an immunized mouse proliferated in response to the specific GV protein used in the immunization. Lymph node cells from non-immunized mice did not proliferate in response to GV proteins.

The data in Table 16 showing IFNγ production, indicate that most of the GV proteins stimulated IFNγ production by lymph node cells from mice immunized with the corresponding GV protein. When lymph node cells from non-immunized mice were cultured with individual GV proteins, IFNγ production was not detectable.

The GV proteins are thus immunogenic in being able to stimulate T cell proliferation and/or IFNγ production when administered by subcutaneous injection. The antigen-specific stimulatory effects on T cell proliferation and IFNγ production are two advantageous properties of candidate vaccines for tuberculosis.

TABLE 15

| Immunogenic Properties of GV proteins: Proliferation | | | |
|---|---|---|---|
| | Proliferation (cpm) Dose of GV protein used in vitro (μg/ml) | | |
| GV protein | 50 | 2 | 0.08 |
| GV-1/70 | 31,550 ± 803 | 19,058 ± 2,449 | 5,596 ± 686 |
| GV-1/83 | 18,549 ± 2,716 | 23,932 ± 1,964 | 11,787 ± 1,128 |
| GV-3 | 34,751 ± 1,382 | 6,379 ± 319 | 4,590 ± 1,042 |
| GV-4P | 26,460 ± 1,877 | 10,370 ± 667 | 6,685 ± 673 |
| GV-5 | 42,418 ± 2,444 | 23,902 ± 2,312 | 13,973 ± 772 |
| GV-5P | 35,691 ± 159 | 14,457 ± 1,185 | 8,340 ± 725 |
| GV-7 | 38,686 ± 974 | 22,074 ± 3,698 | 15,906 ± 1,687 |
| GV-9 | 30,599 ± 2580 | 15,260 ± 2,764 | 4,531 ± 1,240 |
| GV-13 | 15,296 ± 2,006 | 7,163 ± 833 | 3,701 ± 243 |
| GV-14 | 27,754 ± 1,872 | 13,001 ± 3,273 | 9,897 ± 2,833 |
| GV-14B | 10,761 ± 485 | 5,075 ± 1,470 | 2,341 ± 289 |
| GV-22B | 3,199 ± 771 | 3,255 ± 386 | 1,841 ± 318 |
| GV-23 | 35,598 ± 1,330 | 15,423 ± 2,858 | 7,393 ± 2,188 |
| GV-24B | 43,678 ± 2,190 | 30,307 ± 1,533 | 15,375 ± 2,594 |
| GV-27 | 18,165 ± 3,300 | 16,329 ± 1,794 | 6,107 ± 1,773 |
| GV-27A | 23,723 ± 850 | 6,860 ± 746 | 4,295 ± 780 |
| GV-27B | 31,602 ± 1,939 | 29,468 ± 3,867 | 30,306 ± 1,912 |
| GV-29 | 20,034 ± 3,328 | 8,107 ± 488 | 2,982 ± 897 |
| GV-33 | 41,529 ± 1,919 | 27,529 ± 1,238 | 8,764 ± 256 |
| GV-35 | 29,163 ± 2,693 | 9,968 ± 314 | 1,626 ± 406 |
| GV-38AP | 28,971 ± 4,499 | 17,396 ± 878 | 8,060 ± 810 |
| GV-38BP | 19,746 ± 245 | 11,732 ± 3,207 | 6,264 ± 875 |
| GV-40P | 25,185 ± 2,877 | 19,292 ± 2,294 | 10,883 ± 893 |
| GV-41B | 24,646 ± 2,714 | 12,627 ± 3,622 | 5,772 ± 1,041 |
| GV-42 | 25,486 ± 3,029 | 20,591 ± 2,021 | 13,789 ± 775 |
| GV-44 | 2,684 ± 1,995 | 3,577 ± 1,725 | 1,499 ± 959 |
| GV-45 | 9,554 ± 482 | 3,683 ± 1,127 | 1,497 ± 199 |

TABLE 16

| Immunogenic properties of GV proteins: IFNγ production | | | |
|---|---|---|---|
| | IFNγ (ng/ml) Dose of GV protein used in vitro (μg/ml) | | |
| GV protein | 50 | 10 | 2 |
| GV-1/70 | 24.39 ± 6.66 | 6.19 ± 1.42 | 1.90 ± 0.53 |
| GV-1/83 | 11.34 ± 5.46 | 5.36 ± 1.34 | 2.73 ± 1.55 |
| GV-3 | 3.46 ± 0.30 | 1.57 ± 0.04 | not detectable |
| GV-4P | 6.48 ± 0.37 | 3.00 ± 0.52 | 1.38 ± 0.50 |
| GV-5 | 4.08 ± 1.41 | 6.10 ± 2.72 | 2.35 ± 0.40 |
| GV-5P | 34.98 ± 15.26 | 9.95 ± 3.42 | 5.68 ± 0.79 |
| GV-7 | 33.52 ± 3.08 | 25.47 ± 4.14 | 9.60 ± 1.74 |
| GV-9 | 92.27 ± 45.50 | 88.54 ± 16.48 | 30.46 ± 1.77 |
| GV-13 | 11.60 ± 2.89 | 2.04 ± 0.58 | 1.46 ± 0.62 |
| GV-14 | 8.28 ± 1.56 | 3.19 ± 0.56 | 0.94 ± 0.24 |
| GV-14B | not detectable | not detectable | not detectable |
| GV-22B | not detectable | not detectable | not detectable |
| GV-23 | 59.67 ± 14.88 | 30.70 ± 4.48 | 9.17 ± 1.51 |
| GV-24B | 6.76 ± 0.58 | 3.20 ± 0.50 | 1.97 ± 0.03 |
| GV-27 | 72.22 ± 11.14 | 30.86 ± 10.55 | 21.38 ± 3.12 |
| GV-27A | 4.25 ± 2.32 | 1.51 ± 0.73 | not detectable |
| GV-27B | 87.98 ± 15.78 | 44.43 ± 8.70 | 21.49 ± 5.60 |
| GV-29 | 7.56 ± 2.58 | 1.22 ± 0.56 | not detectable |
| GV-33 | 7.71 ± 0.26 | 8.44 ± 2.35 | 1.52 ± 0.24 |
| GV-38AP | 23.49 ± 5.89 | 8.87 ± 1.62 | 4.17 ± 1.72 |
| GV-38BP | 5.30 ± 0.95 | 3.10 ± 1.19 | 1.91 ± 1.01 |
| GV-40P | 15.65 ± 7.89 | 10.58 ± 1.31 | 3.57 ± 1.53 |
| GV-41B | 16.73 ± 1.61 | 5.08 ± 1.08 | 2.13 ± 1.10 |
| GV-42 | 95.97 ± 23.86 | 52.88 ± 5.79 | 30.06 ± 8.94 |
| GV-44 | not detectable | not detectable | not detectable |

B. Activation of Lymphocyte Subpopulations

The ability of recombinant *M. vaccae* proteins of the present invention, heat-killed *M. vaccae* and DD-*M. vaccae* to activate lymphocyte subpopulations was determined by examining upregulation of expression of CD69 (a surface protein expressed on activated cells).

PBMC from normal donors (5×10$^6$ cells/ml) were stimulated with 20 ug/ml of either heat-killed *M. vaccae* cells, DD-*M. vaccae* or recombinant GV-22B (SEQ ID NO: 145), GV-23 (SEQ ID NO: 89), GV-27 (SEQ ID NO: 160), GV27A (SEQ ID NO: 117), GV-27B (SEQ ID NO: 162) or GV-45 (SEQ ID NO: 201) for 24 hours. CD69 expression was determined by staining cultured cells with monoclonal antibody against CD56, αβT cells or γδT cells, in combination with monoclonal antibodies against CD69, followed by flow cytometry analysis.

Table 17 shows the percentage of αβT cells, γδT cells and NK cells expressing CD69 following stimulation with heat-killed *M. vaccae*, DD-*M. vaccae* or recombinant *M. vaccae* proteins. These results demonstrate that heat-killed *M. vaccae*, DD-*M. vaccae* and GV-23 stimulate the expression of CD69 in the lymphocyte subpopulations tested compared with control (non-stimulated cells), with particularly high levels of CD69 expression being seen in NK cells. GV-45 was found to upregulate CD69 expression in αβT cells.

TABLE 17

| Stimulation of CD69 Expression | | | |
|---|---|---|---|
| | αβT cells | γδT cells | NK cells |
| Control | 3.8 | 6.2 | 4.8 |
| Heat-killed *M. vaccae* | 8.3 | 10.2 | 40.3 |
| DD-*M. vaccae* | 10.1 | 17.5 | 49.9 |
| GV-22B | 5.6 | 3.9 | 8.6 |
| GV-23 | 5.8 | 10.0 | 46.8 |
| GV-27 | 5.5 | 4.4 | 13.3 |

TABLE 17-continued

| Stimulation of CD69 Expression | | | |
|---|---|---|---|
| | αβT cells | γδT cells | NK cells |
| GV-27A | 5.5 | 4.4 | 13.3 |
| GV-27B | 4.4 | 2.8 | 7.1 |
| GV-45 | 11.7 | 4.9 | 6.3 |

Figure 14:
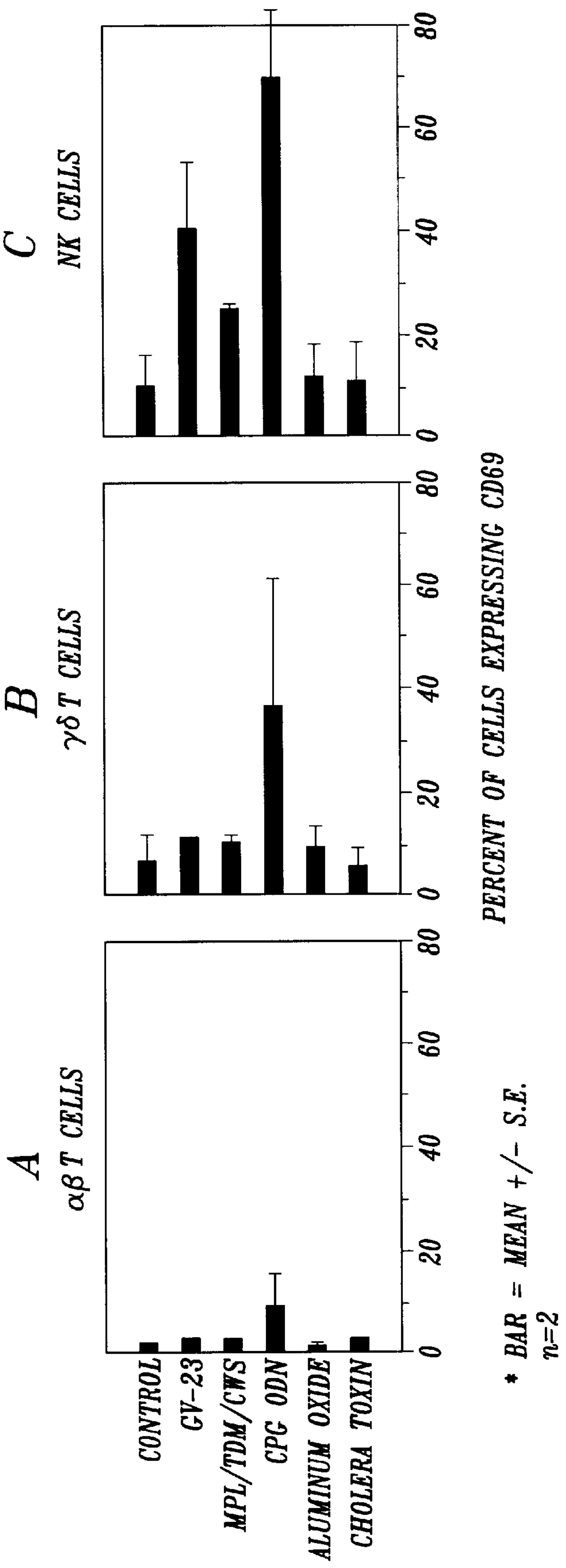
FIGS. 14A–C illustrate the stimulation of CD69 expression on αβT cells, γδT cells and NK cells, respectively, by the *M. vaccae* protein GV23, the Th1-inducing adjuvants MPL/TDM/CWS and CpG ODN, and the Th2-inducing adjuvants aluminium hydroxide and cholera toxin.
Figure 15:
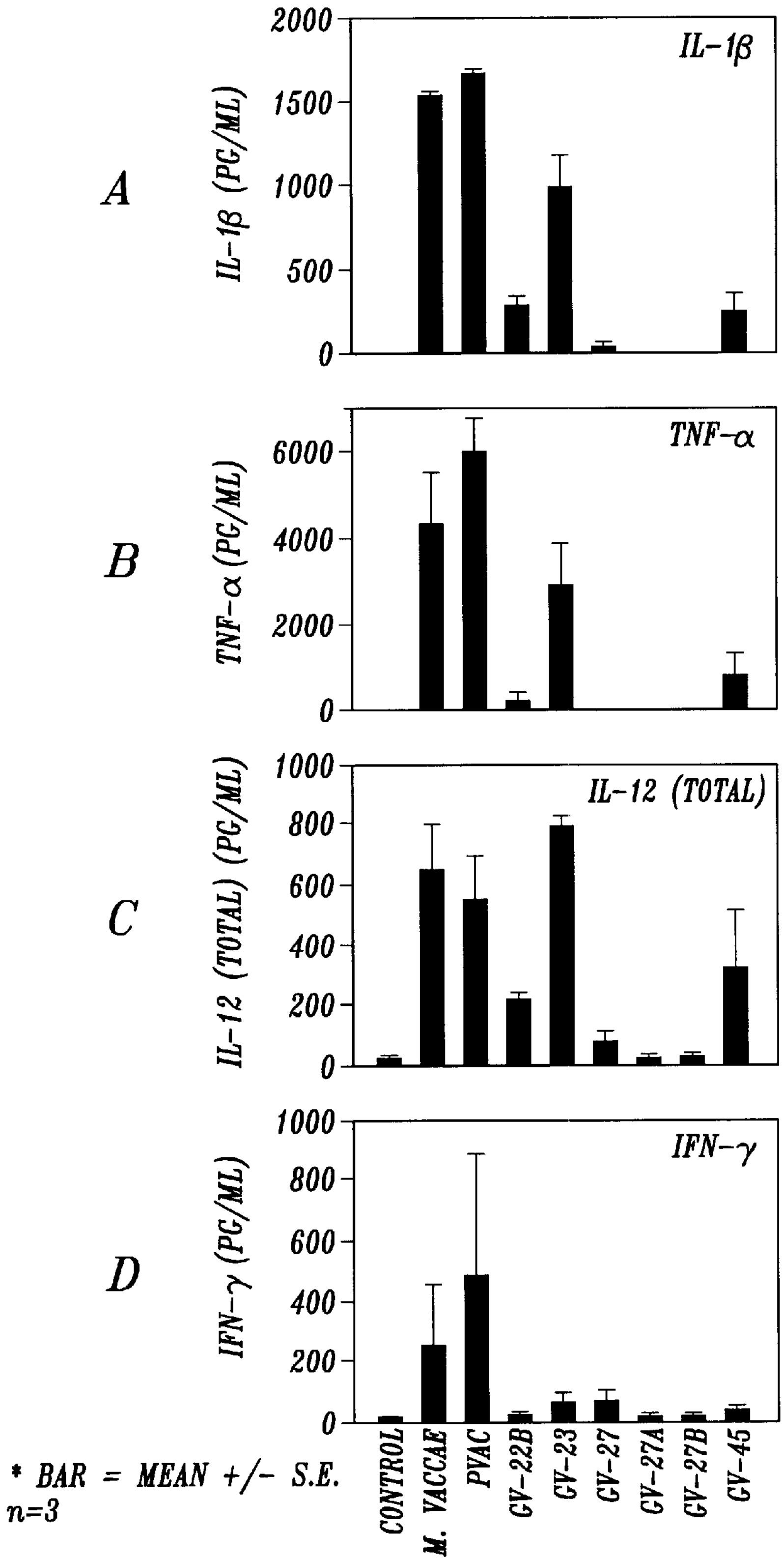
FIGS. 15A–D illustrate the effect of heat-killed *M. vaccae*, DD-*M. vaccae* and *M. vaccae* recombinant proteins on the production of IL-1β, TNF-α, IL-12 and IFN-γ, respectively, by human PBMC.

The ability of the recombinant protein GV-23 (20 ug/ml) to induce CD69 expression in lymphocyte subpopulations was compared with that of the known Th1-inducing adjuvants MPL/TDM/CWS (Monophosphoryl Lipid A/ Trehalose 6'6' dimycolate; Sigma, St. Louis, Mo.; at a final dilution of 1:20) and CpG ODN (Promega, Madison, Wisc.; 20 ug/ml), and the known Th2-inducing adjuvants aluminium hydroxide (Superfos Biosector, Kvistgard, Denmark; at a final dilution of 1:400) and cholera toxin (20 ug/ml), using the procedure described above. MPL/TDM/CWS and aluminium hydroxide were employed at the maximum concentration that does not cause cell cytotoxicity. FIGS. 14A–C show the stimulation of CD69 expression on αβT cells, γδT cells and NK cells, respectively. GV-23, MPL/TDM/CWS and CpG ODN induced CD69 expression on NK cells, whereas aluminium hydroxide and cholera toxin did not.

C. Stimulation of Cytokine Production

Figure 16:
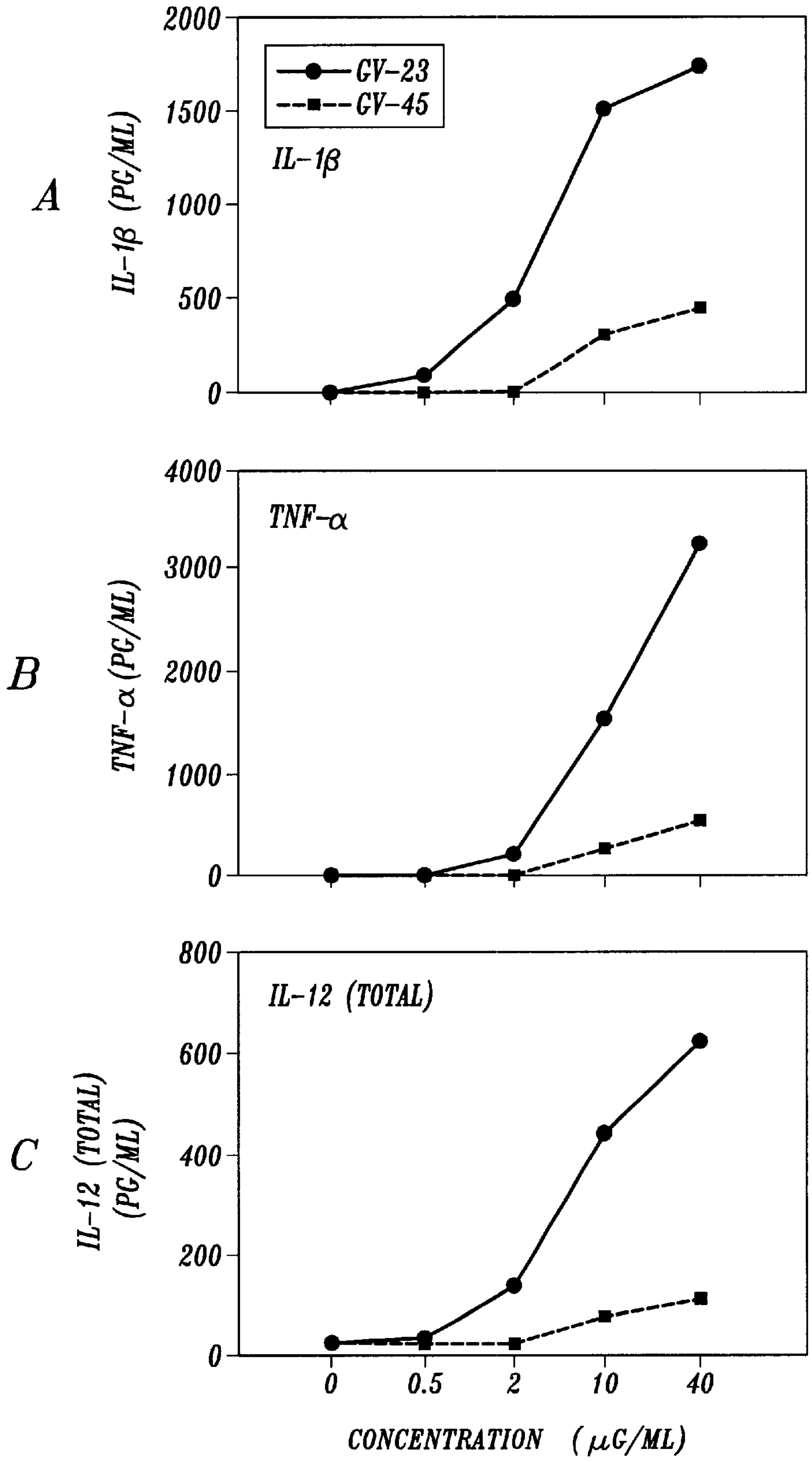
FIGS. 16A–C illustrate the effects of varying concentrations of the recombinant *M. vaccae* proteins GV-23 and GV-45 on the production of IL-1β, TNF-α and IL-12, respectively, by human PBMC.
Figure 17:
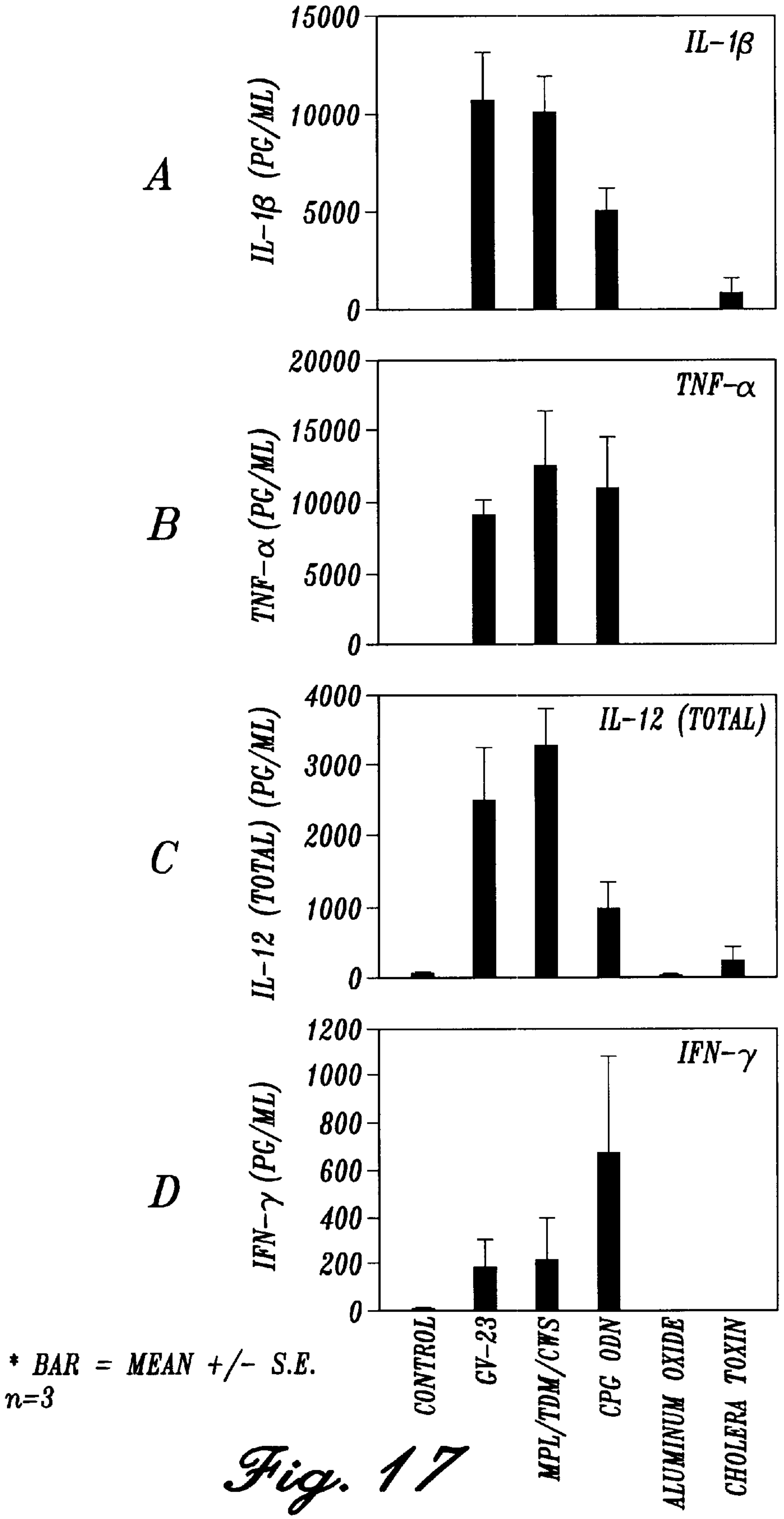
FIGS. 17A–D illustrate the stimulation of IL-1β, TNF-α, IL-12 and IFN-γ production, respectively, in human PBMC by the *M. vaccae* protein GV23, the Th1-inducing adjuvants MPL/TDM/CWS and CpG ODN, and the Th2-inducing adjuvants aluminium hydroxide and cholera toxin.

The ability of recombinant *M. vaccae* proteins of the present invention to stimulate cytokine production in PBMC was examined as follows. PBMC from normal donors (5×10$^6$ cells/ml) were stimulated with 20 ug/ml of either heat-killed *M. vaccae* cells, DD-*M. vaccae*, or recombinant GV-22B (SEQ ID NO: 145), GV-23 (SEQ ID NO: 89), GV-27 (SEQ ID NO: 160), GV27A (SEQ ID NO: 117), GV-27B (SEQ ID NO: 162) or GV-45 (SEQ ID NO: 201) for 24 hours. Culture supernatants were harvested and tested for the production of IL-1β, TNF-α, IL-12 and IFN-γ using standard ELISA kits (Genzyme, Cambridge, Mass.), following the manufacturer's instructions. FIGS. 15A–D show the stimulation of IL-1β, TNF-α, IL-12 and IFN-γ production, respectively. Heat-killed *M. vaccae* and DD-*M. vaccae* were found to stimulate the production of all four cytokines examined, while recombinant GV-23 and GV-45 were found to stimulate the production of IL-1β, TNF-α and IL-12. FIGS. 16A–C show the stimulation of IL-1β, TNF-α and IL-12 production, respectively, in human PBMC (determined as described above) by varying concentrations of GV-23 and GV-45.

FIGS. 17A–D show the stimulation of IL-1β, TNF-α, IL-12 and IFN-γ production, respectively, in PBMC by GV-23 as compared to that by the adjuvants MPL/TDM/CWS (at a final dilution of 1:20), CpG ODN (20 ug/ml), aluminium hydroxide (at a final dilution of 1:400) and cholera toxin (20 ug/ml). GV-23, MPL/TDM/CWS and CpG ODN induced significant levels of the four cytokines examined, with higher levels of IL-1β production being seen with GV-23 than with any of the known adjuvants. Aluminium hydroxide and cholera toxin induced only negligible amounts of the four cytokines.

D. Activation of Antigen Presenting Cells

The ability of heat-killed *M. vaccae*, DD-*M. vaccae* and recombinant *M. vaccae* proteins to enhance the expression of the co-stimulatory molecules CD40, CD80 and CD86 on B cells, monocytes and dendritic cells was examined as follows.

Peripheral blood mononuclear cells depleted of T cells and comprising mainly B cells, monocytes and dendritic cells were stimulated with 20 ug/ml of either heat-killed *M. vaccae* cells, DD-*M. vaccae*, or recombinant GV-22B (SEQ ID NO: 145), GV-23 (SEQ ID NO: 89), GV-27 (SEQ ID NO: 160), GV27A (SEQ ID NO: 117), GV-27B (SEQ ID NO: 162) or GV-45 (SEQ ID NO: 201) for 48 hours. Stimulated cells were harvested and analyzed for up-regulation of CD40, CD80 and CD86 using 3 color flow cytometric analysis. Tables 18, 19 and 20 show the fold increase in mean fluorescence intensity from control (non-stimulated cells) for dendritic cells, monocytes, and B cells, respectively.

TABLE 18

Stimulation of CD40, CD80 and CD86 Expression on Dendritic Cells

| | CD40 | CD80 | CD86 |
|---|---|---|---|
| Control | 0 | 0 | 0 |
| Heat-killed *M. vaccae* | 6.1 | 3.8 | 1.6 |
| DD-*M. vaccae* | 6.6 | 4.2 | 1.6 |
| GV-22B | 4.6 | 1.9 | 1.6 |
| GV-23 | 6.0 | 4.5 | 1.8 |
| GV-27 | 5.2 | 1.9 | 1.6 |
| GV-27A | 2.3 | 0.9 | 1.0 |
| GV-27B | 2.6 | 1.1 | 1.1 |
| GV-45 | 5.8 | 3.0 | 3.1 |

TABLE 19

Stimulation of CD40, CD80 and CD86 Expression on Monocytes

| | CD40 | CD80 | CD86 |
|---|---|---|---|
| Control | 0 | 0 | 0 |
| Heat-killed *M. vaccae* | 2.3 | 1.8 | 0.7 |
| DD-*M. vaccae* | 1.9 | 1.5 | 0.7 |
| GV-22B | 0.7 | 0.9 | 1.1 |
| GV-23 | 2.3 | 1.5 | 0.7 |
| GV-27 | 1.5 | 1.4 | 1.2 |
| GV-27A | 1.4 | 1.4 | 1.4 |
| GV-27B | 1.6 | 1.2 | 1.2 |
| GV-45 | 1.6 | 1.2 | 1.0 |

TABLE 20

Stimulation of CD40, CD80 and CD86 Expression on B Cells

| | CD40 | CD80 | CD86 |
|---|---|---|---|
| Control | 0 | 0 | 0 |
| Heat-killed *M. vaccae* | 1.6 | 1.0 | 1.7 |
| DD-*M. vaccae* | 1.5 | 0.9 | 1.7 |
| GV-22B | 1.1 | 0.9 | 1.2 |
| GV-23 | 1.2 | 1.1 | 1.4 |
| GV-27 | 1.1 | 0.9 | 1.1 |
| GV-27A | 1.0 | 1.1 | 0.9 |
| GV-27B | 1.0 | 0.9 | 0.9 |
| GV-45 | 1.2 | 1.1 | 1.3 |

Figure 18:
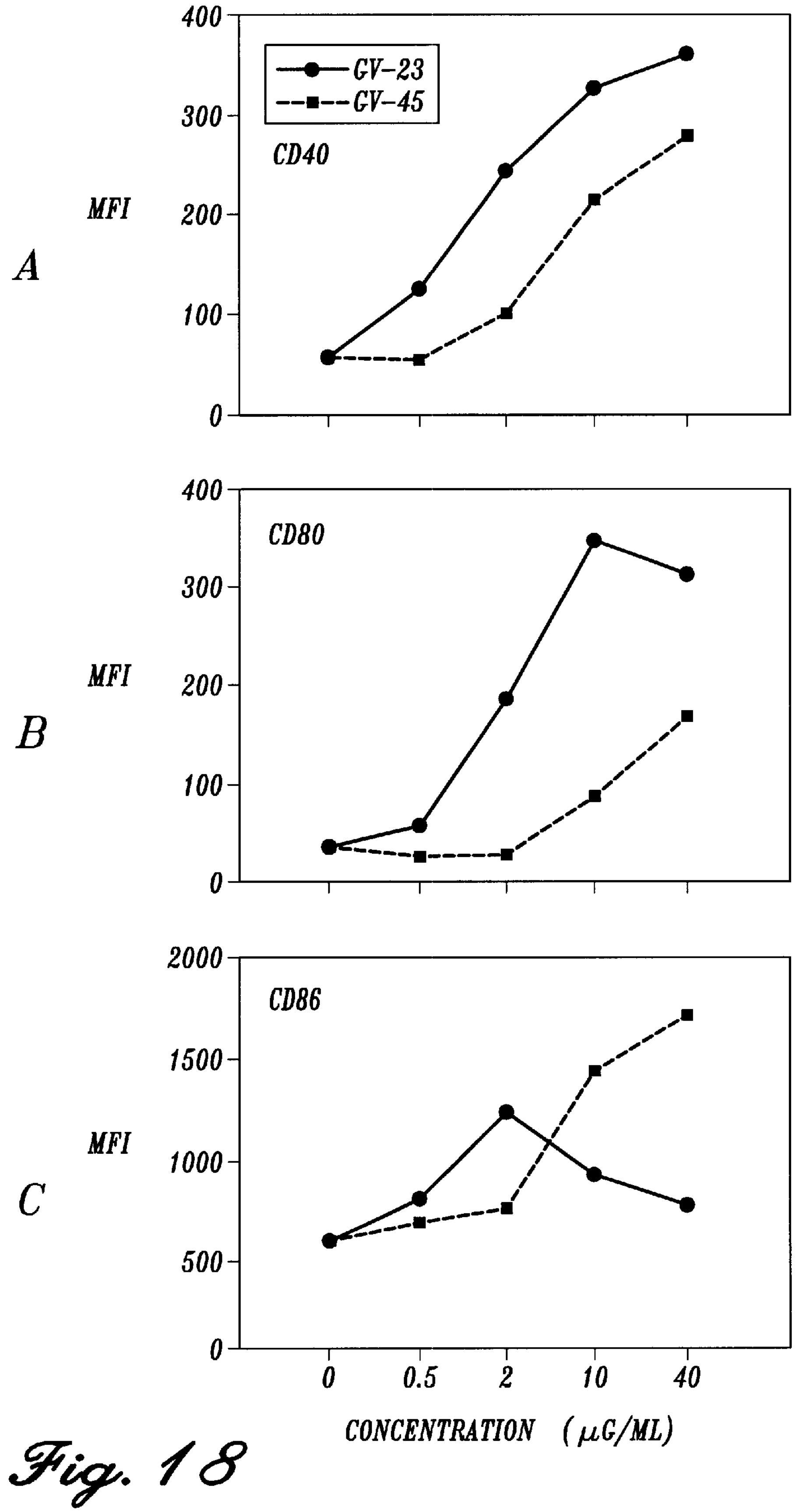
FIGS. 18A–C illustrate the effects of varying concentrations of the recombinant *M. vaccae* proteins GV-23 and GV-45 on the expression of CD40, CD80 and CD86, respectively, by dendritic cells.

As shown above, increased levels of CD40, CD80 and CD86 expression were seen in dendritic cells, monocytes and B cells with all the compositions tested. Expression levels were most increased in dendritic cells, with the highest levels of expression being obtained with heat-killed *M. vaccae*, DD-*M. vaccae*, GV-23 and GV-45. FIGS. 18A–C show the stimulation of expression of CD40, CD80 and CD86, respectively, in dendritic cells by varying concentrations of GV-23 and GV-45.

The ability of GV-23 to stimulate CD40, CD80 and CD86 expression in dendritic cells was compared to that of the Th1-inducing adjuvants MPL/TDM/CWS (at a final dilution of 1:20) and CpG ODN (20 ug/ml), and the known Th2-inducing adjuvants aluminium hydroxide (at a final dilution of 1:400) and cholera toxin (20 ug/ml). GV23, MPL/TDM/CWS and CpG ODN caused significant up-regulation of CD40, CD80 and CD86, whereas cholera toxin and aluminium hydroxide induced modest or negligible dendritic cell activation, respectively.

E. Dendritic Cell Maturation and Function

The effect of the recombinant *M. vaccae* protein GV-23 on the maturation and function of dendritic cells was examined as follows.

Purified dendritic cells ($5\times10^4$–$10^5$ cells/ml) were stimulated with GV-23 (20 ug/ml) or LPS (10 ug/ml) as a positive control. Cells were cultured for 20 hour and then analyzed for CD83 (a maturation marker) and CD80 expression by flow cytometry. Non-stimulated cells were used as a negative control. The results are shown below in Table 21.

TABLE 21

Stimulation of CD83 Expression in Dendritic Cells

| Treatments | % CD83-positive dendritic cells | % CD80-positive dendritic cells |
|---|---|---|
| Control | 15 ± 8 | 9 ± 6.6 |
| GV-23 | 35 ± 13.2 | 24.7 ± 14.2 |
| LPS | 36.3 ± 14.8 | 27.7 ± 13 |

Data=mean±SD (n=3)

Figure 19:
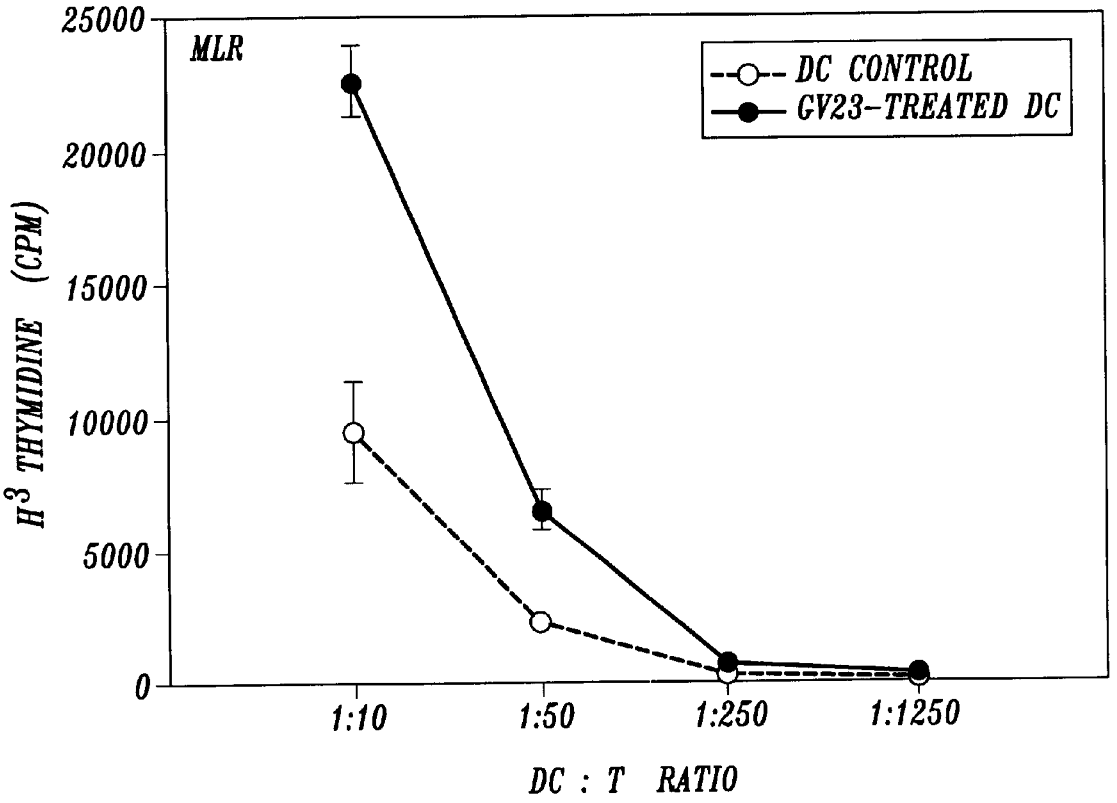
FIG. 19 illustrates the enhancement of dendritic cell mixed leukocyte reaction by the recombinant *M. vaccae* protein GV-23.

The ability of GV-23 to enhance dendritic cell function as antigen presenting cells was determined by mixed lymphocyte reaction (MLR) assay. Purified dendritic cells were culture in medium alone or with GV-23 (20 ug/ml) for 18–20 hours and then stimulated with allogeneic T cells ($2\times10^5$ cells/well). After 3 days of incubation, ($^3$H)-thymidine was added. Cells were harvested 1 day later and the uptake of radioactivity was measured. FIG. 19 shows the increase in uptake of ($^3$H)-thymidine with increase in the ratio of dendritic cells to T cells. Significantly higher levels of radioactivity uptake were seen in GV-23 stimulated dendritic cells compared to non-stimulated cells, showing that GV-23 enhances dendritic cell mixed leukocyte reaction.

EXAMPLE 14

Effect of Immunizing Mice with *M. vaccae*, Delipidated and Deglycolipidated *M. vaccae*, and Recombinant Proteins on Tuberculosis This example illustrates the effect of immunization with heat-killed *M. vaccae*, DD-*nM.vaccae*, recombinant *M. vaccae* proteins without additional adjuvants, or a combination of heat-killed *M.vaccae* with a pool of recombinant proteins derived from *M.vaccae.*

Mice were injected intraperitoneally with one of the following preparations on two occasions three weeks apart:

a) Phosphate buffered saline (PBS, control);
b) Heat-killed *M. vaccae* (500 ug);
c) DD-*M.vaccae* (50 ug);
d) A pool of recombinant proteins containing 15 ug of each of GV4P, 7, 9, 27B, 33 protein; and
e) Heat-killed *M.vaccae* plus the pool of recombinant proteins Three weeks after the last intraperitoneal immunization, the mice were infected with $5\times10^5$ live H37Rv *M. tuberculosis* organisms. After a further three weeks, the mice were sacrificed, and their spleens homogenized and assayed for colony forming units (CFU) of *M. tuberculosis* as an indicator of severity of infection.

Figure 13A:
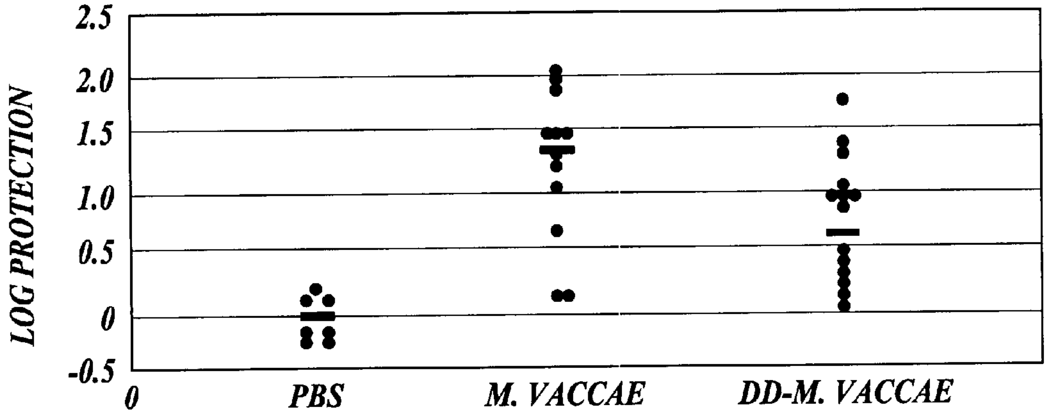
FIG. 13A illustrates the effect of immunizing mice with heat-killed *M. vaccae* or delipidated and deglycolipidated *M. vaccae* (DD-*M. vaccae*) prior to infection with tuberculosis.
Figure 13B:
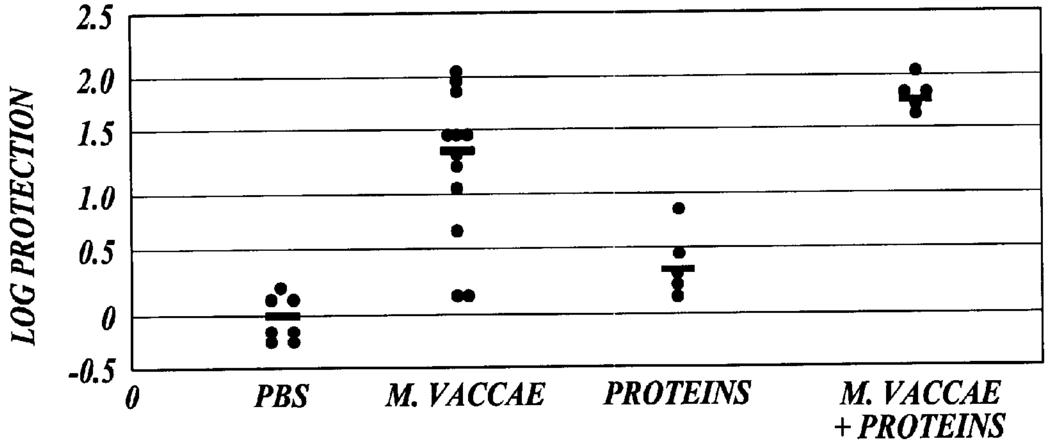
FIG. 13B illustrates the effect of immunizing mice with heat-killed *M. vaccae*, recombinant *M. vaccae* proteins, or a combination of heat-killed *M. vaccae* and *M. vaccae* recombinant proteins prior to infection with tuberculosis.

FIGS. 13A and 13B show data in which each point represents individual mice. The numbers of CFU recovered from control mice immunized with PBS alone were taken as the baseline. All data from experimental mice were expressed as number of logarithms of CFUs below the baseline for control mice (or log protection). As shown in FIG. 13A, mice immunized with heat-killed *M.vaccae* or DD-*M.vaccae* showed respectively a mean reduction of >1 or 0.5 logs CFU.

As shown in FIG. 13B, the spleens of mice immunized with the pool of recombinant proteins containing GV4P, 7, 9, 27B and 33, had CFUs slightly less than control mice. However, when GV4P, 7, 9, 27B and 33 were given in combination with heat-killed *M.vaccae*, the reduction in CFUs exceeded a mean of >1.5 logs.

The data indicates the effectiveness of immunization with *M.vaccae*, DD-*M.vaccae* or recombinant proteins derived from *M.vaccae* against subsequent infection with tuberculosis, and further indicates that Mvaccae, DD-*M.vaccae* and recombinant proteins may be developed as vaccines against tuberculosis.

Although the present invention has been described in some detail by way of illustration and example for purposes of clarity of understanding, changes and modifications can be carried out without departing from the scope of the invention which is intended to be limited only by the scope of the appended claims.

SEQUENCE LISTING

```
<160> NUMBER OF SEQ ID NOS: 208

<210> SEQ ID NO 1
<211> LENGTH: 25
<212> TYPE: PRT
<213> ORGANISM: Mycobacterium vaccae
<220> FEATURE:
<221> NAME/KEY: UNSURE
<222> LOCATION: (7)...(7)

<400> SEQUENCE: 1

Ala Pro Val Gly Pro Gly Xaa Ala Ala Tyr V al Gln Gln Val Pro Asp
 1               5                  10                  15

Gly Pro Gly Ser Val Gln Gly Met Ala
            20                  25


<210> SEQ ID NO 2
<211> LENGTH: 10
<212> TYPE: PRT
<213> ORGANISM: Mycobacterium vaccae
<220> FEATURE:
<221> NAME/KEY: UNSURE
<222> LOCATION: (2)...(2)

<400> SEQUENCE: 2

Met Xaa Asp Gln Leu Lys Val Asn Asp Asp
 1               5                  10


<210> SEQ ID NO 3
<211> LENGTH: 11
<212> TYPE: PRT
<213> ORGANISM: Mycobacterium vaccae
<220> FEATURE:
<221> NAME/KEY: UNSURE
<222> LOCATION: (2)...(2)

<400> SEQUENCE: 3

Met Xaa Pro Val Pro Val Ala Thr Ala Ala T yr
 1               5                  10


<210> SEQ ID NO 4
<211> LENGTH: 21
<212> TYPE: PRT
<213> ORGANISM: Mycobacterium vaccae

<400> SEQUENCE: 4

Thr Pro Ala Pro Ala Pro Pro Pro Tyr Val A sp His Val Glu Gln Ala
 1               5                  10                  15

Lys Phe Gly Asp Leu
            20
```

-continued

```
<210> SEQ ID NO 5
<211> LENGTH: 29
<212> TYPE: PRT
<213> ORGANISM: Mycobacterium vaccae
<220> FEATURE:
<221> NAME/KEY: UNSURE
<222> LOCATION: (25)...(25)

<400> SEQUENCE: 5

Met Gln Ala Phe Asn Ala Asp Ala Tyr Ala P he Ala Lys Arg Glu Lys
 1               5                  10                  15

Val Ser Leu Ala Pro Gly Val Pro Xaa Val P he Glu Thr
            20                  25


<210> SEQ ID NO 6
<211> LENGTH: 21
<212> TYPE: PRT
<213> ORGANISM: Mycobacterium vaccae
<220> FEATURE:
<221> NAME/KEY: UNSURE
<222> LOCATION: (6)...(6)

<400> SEQUENCE: 6

Met Ala Asp Pro Asn Xaa Ala Ile Leu Gln V al Ser Lys Thr Thr Arg
 1               5                  10                  15

Gly Gly Gln Ala Ala
            20


<210> SEQ ID NO 7
<211> LENGTH: 11
<212> TYPE: PRT
<213> ORGANISM: Mycobacterium vaccae

<400> SEQUENCE: 7

Met Pro Ile Leu Gln Val Ser Gln Thr Gly A rg
 1               5                  10


<210> SEQ ID NO 8
<211> LENGTH: 14
<212> TYPE: PRT
<213> ORGANISM: Mycobacterium vaccae
<220> FEATURE:
<221> NAME/KEY: UNSURE
<222> LOCATION: (2)...(2)
<221> NAME/KEY: UNSURE
<222> LOCATION: (6)...(6)

<400> SEQUENCE: 8

Met Xaa Asp Pro Ile Xaa Leu Gln Leu Gln V al Ser Ser Thr
 1               5                  10


<210> SEQ ID NO 9
<211> LENGTH: 16
<212> TYPE: PRT
<213> ORGANISM: Mycobacterium vaccae

<400> SEQUENCE: 9

Lys Ala Thr Tyr Val Gln Gly Gly Leu Gly A rg Ile Glu Ala Arg Val
 1               5                  10                  15


<210> SEQ ID NO 10
<211> LENGTH: 9
<212> TYPE: PRT
<213> ORGANISM: Mycobacterium vaccae
<220> FEATURE:
```

-continued

<221> NAME/KEY: UNSURE
<222> LOCATION: (2)...(2)

<400> SEQUENCE: 10

Lys Xaa Gly Leu Ala Asp Leu Ala Pro
1 5

<210> SEQ ID NO 11
<211> LENGTH: 14
<212> TYPE: PRT
<213> ORGANISM: Mycobacterium vaccae
<220> FEATURE:
<221> NAME/KEY: UNSURE
<222> LOCATION: (12)...(12)
<223> OTHER INFORMATION: Residue can be either Glu or Ile
<220> FEATURE:
<221> NAME/KEY: UNSURE
<222> LOCATION: (2)...(2)

<400> SEQUENCE: 11

Lys Xaa Tyr Ala Leu Ala Leu Met Ser Ala V al Xaa Ala Ala
1 5 10

<210> SEQ ID NO 12
<211> LENGTH: 11
<212> TYPE: PRT
<213> ORGANISM: Mycobacterium vaccae
<220> FEATURE:
<221> NAME/KEY: UNSURE
<222> LOCATION: (10)...(10)

<400> SEQUENCE: 12

Lys Asn Pro Gln Val Ser Asp Glu Leu Xaa T hr
1 5 10

<210> SEQ ID NO 13
<211> LENGTH: 21
<212> TYPE: PRT
<213> ORGANISM: Mycobacterium vaccae
<220> FEATURE:
<221> NAME/KEY: UNSURE
<222> LOCATION: (9)...(9)

<400> SEQUENCE: 13

Ala Pro Ala Pro Ala Ala Pro Ala Xaa Gly A sp Pro Ala Ala Val Val
1 5 10 15

Ala Ala Met Ser Thr
20

<210> SEQ ID NO 14
<211> LENGTH: 15
<212> TYPE: PRT
<213> ORGANISM: Mycobacterium vaccae
<220> FEATURE:
<221> NAME/KEY: UNSURE
<222> LOCATION: (5)...(5)

<400> SEQUENCE: 14

Glu Ala Glu Val Xaa Tyr Leu Gly Gln Pro G ly Glu Leu Val Asn
1 5 10 15

<210> SEQ ID NO 15
<211> LENGTH: 15
<212> TYPE: PRT
<213> ORGANISM: Mycobacterium vaccae
<220> FEATURE:
<221> NAME/KEY: UNSURE
<222> LOCATION: (2)...(2)

-continued

```
<223> OTHER INFORMATION: Residue can be either Gly or Ala
<220> FEATURE:
<221> NAME/KEY: UNSURE
<222> LOCATION: (15)...(15)
<223> OTHER INFORMATION: Residue can be either Pro or Ala
<220> FEATURE:
<221> NAME/KEY: UNSURE
<222> LOCATION: (7)...(7)

<400> SEQUENCE: 15

Ala Xaa Val Val Pro Pro Xaa Gly Pro Pro A la Pro Gly Ala Xaa
 1               5                   10                  15


<210> SEQ ID NO 16
<211> LENGTH: 15
<212> TYPE: PRT
<213> ORGANISM: Mycobacterium vaccae

<400> SEQUENCE: 16

Ala Pro Ala Pro Asp Leu Gln Gly Pro Leu V al Ser Thr Leu Ser
 1               5                   10                  15


<210> SEQ ID NO 17
<211> LENGTH: 25
<212> TYPE: PRT
<213> ORGANISM: Mycobacterium vaccae

<400> SEQUENCE: 17

Ala Thr Pro Asp Trp Ser Gly Arg Tyr Thr V al Val Thr Phe Ala Ser
 1               5                   10                  15

Asp Lys Leu Gly Thr Ser Val Ala Ala
            20                  25


<210> SEQ ID NO 18
<211> LENGTH: 25
<212> TYPE: PRT
<213> ORGANISM: Mycobacterium vaccae
<220> FEATURE:
<221> NAME/KEY: UNSURE
<222> LOCATION: (15)...(15)
<223> OTHER INFORMATION: Residue can be either Ala or Arg
<220> FEATURE:
<221> NAME/KEY: UNSURE
<222> LOCATION: (23)...(23)
<223> OTHER INFORMATION: Residue can be either Val or Leu
<220> FEATURE:
<221> NAME/KEY: UNSURE
<222> LOCATION: (16)...(16)

<400> SEQUENCE: 18

Ala Pro Pro Tyr Asp Asp Arg Gly Tyr Val A sp Ser Thr Ala Xaa Xaa
 1               5                   10                  15

Ala Ser Pro Pro Thr Leu Xaa Val Val
            20                  25


<210> SEQ ID NO 19
<211> LENGTH: 8
<212> TYPE: PRT
<213> ORGANISM: Mycobacterium vaccae

<400> SEQUENCE: 19

Glu Pro Glu Gly Val Ala Pro Pro
 1               5


<210> SEQ ID NO 20
<211> LENGTH: 25
<212> TYPE: PRT
```

-continued

```
<213> ORGANISM: Mycobacterium vaccae
<220> FEATURE:
<221> NAME/KEY: UNSURE
<222> LOCATION: (21)...(22)

<400> SEQUENCE: 20

Glu Pro Ala Gly Ile Pro Ala Gly Phe Pro A sp Val Ser Ala Tyr Ala
 1               5                  10                  15

Ala Val Asp Pro Xaa Xaa Tyr Val Val
            20                  25


<210> SEQ ID NO 21
<211> LENGTH: 15
<212> TYPE: PRT
<213> ORGANISM: Mycobacterium vaccae
<220> FEATURE:
<221> NAME/KEY: UNSURE
<222> LOCATION: (7)...(7)

<400> SEQUENCE: 21

Ala Pro Val Gly Pro Gly Xaa Ala Ala Tyr V al Gln Gln Val Pro
 1               5                  10                  15


<210> SEQ ID NO 22
<211> LENGTH: 15
<212> TYPE: PRT
<213> ORGANISM: Mycobacterium vaccae

<400> SEQUENCE: 22

Phe Ser Arg Pro Gly Leu Pro Val Glu Tyr L eu Met Val Pro Ser
 1               5                  10                  15


<210> SEQ ID NO 23
<211> LENGTH: 19
<212> TYPE: PRT
<213> ORGANISM: Mycobacterium vaccae

<400> SEQUENCE: 23

Phe Ser Arg Pro Gly Leu Pro Val Glu Tyr L eu Met Val Pro Ser Pro
 1               5                  10                  15

Ser Met Gly


<210> SEQ ID NO 24
<211> LENGTH: 15
<212> TYPE: PRT
<213> ORGANISM: Mycobacterium vaccae

<400> SEQUENCE: 24

Phe Ser Arg Pro Gly Leu Pro Val Glu Tyr L eu Asp Val Phe Ser
 1               5                  10                  15


<210> SEQ ID NO 25
<211> LENGTH: 14
<212> TYPE: PRT
<213> ORGANISM: Mycobacterium vaccae
<220> FEATURE:
<221> NAME/KEY: UNSURE
<222> LOCATION: (1)...(2)

<400> SEQUENCE: 25

Xaa Xaa Thr Gly Leu His Arg Leu Arg Met M et Val Pro Asn
 1               5                  10


<210> SEQ ID NO 26
<211> LENGTH: 20
```

-continued

<212> TYPE: PRT
<213> ORGANISM: Mycobacterium vaccae
<220> FEATURE:
<221> NAME/KEY: UNSURE
<222> LOCATION: (16)...(16)
<223> OTHER INFORMATION: Residue can be either Ser or Val
<220> FEATURE:
<221> NAME/KEY: UNSURE
<222> LOCATION: (17)...(17)
<223> OTHER INFORMATION: Residue can be either Gln or Val

<400> SEQUENCE: 26

Val Pro Ala Asp Pro Val Gly Ala Ala Ala G ln Ala Glu Pro Ala Xaa
 1               5                  10                  15

Xaa Arg Ile Asp
            20

<210> SEQ ID NO 27
<211> LENGTH: 14
<212> TYPE: PRT
<213> ORGANISM: Mycobacterium vaccae
<220> FEATURE:
<221> NAME/KEY: UNSURE
<222> LOCATION: (4)...(4)
<223> OTHER INFORMATION: Residue can be either Tyr or Pro
<220> FEATURE:
<221> NAME/KEY: UNSURE
<222> LOCATION: (8)...(8)
<223> OTHER INFORMATION: Residue can be either Val or Gly
<220> FEATURE:
<221> NAME/KEY: UNSURE
<222> LOCATION: (9)...(9)
<223> OTHER INFORMATION: Residue can be either Ile or Tyr
<220> FEATURE:
<221> NAME/KEY: UNSURE
<222> LOCATION: (3)...(3)

<400> SEQUENCE: 27

Asp Pro Xaa Xaa Asp Ile Glu Xaa Xaa Phe A la Arg Gly Thr
 1               5                  10

<210> SEQ ID NO 28
<211> LENGTH: 15
<212> TYPE: PRT
<213> ORGANISM: Mycobacterium vaccae

<400> SEQUENCE: 28

Ala Pro Ser Leu Ser Val Ser Asp Tyr Ala A rg Asp Ala Gly Phe
 1               5                  10                  15

<210> SEQ ID NO 29
<211> LENGTH: 16
<212> TYPE: PRT
<213> ORGANISM: Mycobacterium vaccae
<220> FEATURE:
<221> NAME/KEY: UNSURE
<222> LOCATION: (2)...(2)
<223> OTHER INFORMATION: Residue can be either Leu or Pro
<220> FEATURE:
<221> NAME/KEY: UNSURE
<222> LOCATION: (1)...(1)
<221> NAME/KEY: UNSURE
<222> LOCATION: (5)...(5)
<221> NAME/KEY: UNSURE
<222> LOCATION: (7)...(7)
<221> NAME/KEY: UNSURE
<222> LOCATION: (10)...(10)

<400> SEQUENCE: 29

Xaa Xaa Leu Ala Xaa Ala Xaa Leu Gly Xaa T hr Val Asp Ala Asp Gln
 1               5                  10                  15

-continued

<210> SEQ ID NO 30
<211> LENGTH: 330
<212> TYPE: PRT
<213> ORGANISM: Mycobacterium leprae

<400> SEQUENCE: 30

```
Met Lys Phe Val Asp Arg Phe Arg Gly Ala V al Ala Gly Met Leu Arg
 1               5                  10                  15

Arg Leu Val Val Glu Ala Met Gly Val Ala L eu Leu Ser Ala Leu Ile
            20                  25                  30

Gly Val Val Gly Ser Ala Pro Ala Glu Ala P he Ser Arg Pro Gly Leu
        35                  40                  45

Pro Val Glu Tyr Leu Gln Val Pro Ser Pro S er Met Gly Arg Asp Ile
    50                  55                  60

Lys Val Gln Phe Gln Asn Gly Gly Ala Asn S er Pro Ala Leu Tyr Leu
65                  70                  75                  80

Leu Asp Gly Leu Arg Ala Gln Asp Asp Phe S er Gly Trp Asp Ile Asn
                85                  90                  95

Thr Thr Ala Phe Glu Trp Tyr Tyr Gln Ser G ly Ile Ser Val Val Met
            100                 105                 110

Pro Val Gly Gly Gln Ser Ser Phe Tyr Ser A sp Trp Tyr Ser Pro Ala
        115                 120                 125

Cys Gly Lys Ala Gly Cys Gln Thr Tyr Lys T rp Glu Thr Phe Leu Thr
    130                 135                 140

Ser Glu Leu Pro Glu Tyr Leu Gln Ser Asn L ys Gln Ile Lys Pro Thr
145                 150                 155                 160

Gly Ser Ala Ala Val Gly Leu Ser Met Ala G ly Leu Ser Ala Leu Thr
                165                 170                 175

Leu Ala Ile Tyr His Pro Asp Gln Phe Ile T yr Val Gly Ser Met Ser
            180                 185                 190

Gly Leu Leu Asp Pro Ser Asn Ala Met Gly P ro Ser Leu Ile Gly Leu
        195                 200                 205

Ala Met Gly Asp Ala Gly Gly Tyr Lys Ala A la Asp Met Trp Gly Pro
    210                 215                 220

Ser Thr Asp Pro Ala Trp Lys Arg Asn Asp P ro Thr Val Asn Val Gly
225                 230                 235                 240

Thr Leu Ile Ala Asn Asn Thr Arg Ile Trp M et Tyr Cys Gly Asn Gly
                245                 250                 255

Lys Pro Thr Glu Leu Gly Gly Asn Asn Leu P ro Ala Lys Leu Leu Glu
            260                 265                 270

Gly Leu Val Arg Thr Ser Asn Ile Lys Phe G ln Asp Gly Tyr Asn Ala
        275                 280                 285

Gly Gly Gly His Asn Ala Val Phe Asn Phe P ro Asp Ser Gly Thr His
    290                 295                 300

Ser Trp Glu Tyr Trp Gly Glu Gln Leu Asn A sp Met Lys Pro Asp Leu
305                 310                 315                 320

Gln Gln Tyr Leu Gly Ala Thr Pro Gly Ala
                325                 330
```

<210> SEQ ID NO 31
<211> LENGTH: 327
<212> TYPE: PRT
<213> ORGANISM: Mycobacterium leprae

<400> SEQUENCE: 31

-continued

```
Met Ile Asp Val Ser Gly Lys Ile Arg Ala T rp Gly Arg Trp Leu Leu
 1               5                  10                  15

Val Gly Ala Ala Ala Thr Leu Pro Ser Leu I le Ser Leu Ala Gly Gly
            20                  25                  30

Ala Ala Thr Ala Ser Ala Phe Ser Arg Pro G ly Leu Pro Val Glu Tyr
        35                  40                  45

Leu Gln Val Pro Ser Glu Ala Met Gly Arg T hr Ile Lys Val Gln Phe
    50                  55                  60

Gln Asn Gly Gly Asn Gly Ser Pro Ala Val T yr Leu Leu Asp Gly Leu
65                  70                  75                  80

Arg Ala Gln Asp Asp Tyr Asn Gly Trp Asp I le Asn Thr Ser Ala Phe
                85                  90                  95

Glu Trp Tyr Tyr Gln Ser Gly Leu Ser Val V al Met Pro Val Gly Gly
            100                 105                 110

Gln Ser Ser Phe Tyr Ser Asp Trp Tyr Ser P ro Ala Cys Gly Lys Ala
        115                 120                 125

Gly Cys Thr Thr Tyr Lys Trp Glu Thr Phe L eu Thr Ser Glu Leu Pro
    130                 135                 140

Lys Trp Leu Ser Ala Asn Arg Ser Val Lys S er Thr Gly Ser Ala Val
145                 150                 155                 160

Val Gly Leu Ser Met Ala Gly Ser Ser Ala L eu Ile Leu Ala Ala Tyr
                165                 170                 175

His Pro Asp Gln Phe Ile Tyr Ala Gly Ser L eu Ser Ala Leu Met Asp
            180                 185                 190

Ser Ser Gln Gly Ile Glu Pro Gln Leu Ile G ly Leu Ala Met Gly Asp
        195                 200                 205

Ala Gly Gly Tyr Lys Ala Ala Asp Met Trp G ly Pro Pro Asn Asp Pro
    210                 215                 220

Ala Trp Gln Arg Asn Asp Pro Ile Leu Gln A la Gly Lys Leu Val Ala
225                 230                 235                 240

Asn Asn Thr His Leu Trp Val Tyr Cys Gly A sn Gly Thr Pro Ser Glu
                245                 250                 255

Leu Gly Gly Thr Asn Val Pro Ala Glu Phe L eu Glu Asn Phe Val His
            260                 265                 270

Gly Ser Asn Leu Lys Phe Gln Asp Ala Tyr A sn Gly Ala Gly Gly His
        275                 280                 285

Asn Ala Val Phe Asn Leu Asn Ala Asp Gly T hr His Ser Trp Glu Tyr
    290                 295                 300

Trp Gly Ala Gln Leu Asn Ala Met Lys Pro A sp Leu Gln Asn Thr Leu
305                 310                 315                 320

Met Ala Val Pro Arg Ser Gly
                325


<210> SEQ ID NO 32
<211> LENGTH: 338
<212> TYPE: PRT
<213> ORGANISM: Mycobacterium tuberculosis

<400> SEQUENCE: 32

Met Gln Leu Val Asp Arg Val Arg Gly Ala V al Thr Gly Met Ser Arg
 1               5                  10                  15

Arg Leu Val Val Gly Ala Val Gly Ala Ala L eu Val Ser Gly Leu Val
            20                  25                  30

Gly Ala Val Gly Gly Thr Ala Thr Ala Gly A la Phe Ser Arg Pro Gly
```

-continued

```
        35                  40                  45

Leu Pro Val Glu Tyr Leu Gln Val Pro Ser P ro Ser Met Gly Arg Asp
    50                  55                  60

Ile Lys Val Gln Phe Gln Ser Gly Gly Ala A sn Ser Pro Ala Leu Tyr
65                  70                  75                  80

Leu Leu Asp Gly Leu Arg Ala Gln Asp Asp P he Ser Gly Trp Asp Ile
                85                  90                  95

Asn Thr Pro Ala Phe Glu Trp Tyr Asp Gln S er Gly Leu Ser Val Val
            100                 105                 110

Met Pro Val Gly Gly Gln Ser Ser Phe Tyr S er Asp Trp Tyr Gln Pro
        115                 120                 125

Ala Cys Gly Lys Ala Gly Cys Gln Thr Tyr L ys Trp Glu Thr Phe Leu
    130                 135                 140

Thr Ser Glu Leu Pro Gly Trp Leu Gln Ala A sn Arg His Val Lys Pro
145                 150                 155                 160

Thr Gly Ser Ala Val Val Gly Leu Ser Met A la Ala Ser Ser Ala Leu
                165                 170                 175

Thr Leu Ala Ile Tyr His Pro Gln Gln Phe V al Tyr Ala Gly Ala Met
            180                 185                 190

Ser Gly Leu Leu Asp Pro Ser Gln Ala Met G ly Pro Thr Leu Ile Gly
        195                 200                 205

Leu Ala Met Gly Asp Ala Gly Gly Tyr Lys A la Ser Asp Met Trp Gly
    210                 215                 220

Pro Lys Glu Asp Pro Ala Trp Gln Arg Asn A sp Pro Leu Leu Asn Val
225                 230                 235                 240

Gly Lys Leu Ile Ala Asn Asn Thr Arg Val T rp Val Tyr Cys Gly Asn
                245                 250                 255

Gly Lys Pro Ser Asp Leu Gly Gly Asn Asn L eu Pro Ala Lys Phe Leu
            260                 265                 270

Glu Gly Phe Val Arg Thr Ser Asn Ile Lys P he Gln Asp Ala Tyr Asn
        275                 280                 285

Ala Gly Gly Gly His Asn Gly Val Phe Asp P he Pro Asp Ser Gly Thr
    290                 295                 300

His Ser Trp Glu Tyr Trp Gly Ala Gln Leu A sn Ala Met Lys Pro Asp
305                 310                 315                 320

Leu Gln Arg Ala Leu Gly Ala Thr Pro Asn T hr Gly Pro Ala Pro Gln
                325                 330                 335

Gly Ala


<210> SEQ ID NO 33
<211> LENGTH: 325
<212> TYPE: PRT
<213> ORGANISM: Mycobacterium tuberculosis

<400> SEQUENCE: 33

Met Thr Asp Val Ser Arg Lys Ile Arg Ala T rp Gly Arg Arg Leu Met
 1               5                  10                  15

Ile Gly Thr Ala Ala Ala Val Val Leu Pro G ly Leu Val Gly Leu Ala
            20                  25                  30

Gly Gly Ala Ala Thr Ala Gly Ala Phe Ser A rg Pro Gly Leu Pro Val
        35                  40                  45

Glu Tyr Leu Gln Val Pro Ser Pro Ser Met G ly Arg Asp Ile Lys Val
    50                  55                  60

Gln Phe Gln Ser Gly Gly Asn Asn Ser Pro A la Val Tyr Leu Leu Asp
```

-continued

```
65                  70                  75                  80

Gly Leu Arg Ala Gln Asp Asp Tyr Asn Gly T rp Asp Ile Asn Thr Pro
                85                  90                  95

Ala Phe Glu Trp Tyr Tyr Gln Ser Gly Leu S er Ile Val Met Pro Val
            100                 105                 110

Gly Gly Gln Ser Ser Phe Tyr Ser Asp Trp T yr Ser Pro Ala Cys Gly
        115                 120                 125

Lys Ala Gly Cys Gln Thr Tyr Lys Trp Glu T hr Phe Leu Thr Ser Glu
    130                 135                 140

Leu Pro Gln Trp Leu Ser Ala Asn Arg Ala V al Lys Pro Thr Gly Ser
145                 150                 155                 160

Ala Ala Ile Gly Leu Ser Met Ala Gly Ser S er Ala Met Ile Leu Ala
                165                 170                 175

Ala Tyr His Pro Gln Gln Phe Ile Tyr Ala G ly Ser Leu Ser Ala Leu
            180                 185                 190

Leu Asp Pro Ser Gln Gly Met Gly Pro Ser L eu Ile Gly Leu Ala Met
        195                 200                 205

Gly Asp Ala Gly Gly Tyr Lys Ala Ala Asp M et Trp Gly Pro Ser Ser
    210                 215                 220

Asp Pro Ala Trp Glu Arg Asn Asp Pro Thr G ln Gln Ile Pro Lys Leu
225                 230                 235                 240

Val Ala Asn Asn Thr Arg Leu Trp Val Tyr C ys Gly Asn Gly Thr Pro
                245                 250                 255

Asn Glu Leu Gly Gly Ala Asn Ile Pro Ala G lu Phe Leu Glu Asn Phe
            260                 265                 270

Val Arg Ser Ser Asn Leu Lys Phe Gln Asp A la Tyr Asn Ala Ala Gly
        275                 280                 285

Gly His Asn Ala Val Phe Asn Phe Pro Pro A sn Gly Thr His Ser Trp
    290                 295                 300

Glu Tyr Trp Gly Ala Gln Leu Asn Ala Met L ys Gly Asp Leu Gln Ser
305                 310                 315                 320

Ser Leu Gly Ala Gly
                325


<210> SEQ ID NO 34
<211> LENGTH: 338
<212> TYPE: PRT
<213> ORGANISM: Mycobacterium bovis

<400> SEQUENCE: 34

Met Gln Leu Val Asp Arg Val Arg Gly Ala V al Thr Gly Met Ser Arg
 1               5                  10                  15

Arg Leu Val Val Gly Ala Val Gly Ala Ala L eu Val Ser Gly Leu Val
            20                  25                  30

Gly Ala Val Gly Gly Thr Ala Thr Ala Gly A la Phe Ser Arg Pro Gly
        35                  40                  45

Leu Pro Val Glu Tyr Leu Gln Val Pro Ser P ro Ser Met Gly Arg Asp
    50                  55                  60

Ile Lys Val Gln Phe Gln Ser Gly Gly Ala A sn Ser Pro Ala Leu Tyr
65                  70                  75                  80

Leu Leu Asp Gly Leu Arg Ala Gln Asp Asp P he Ser Gly Trp Asp Ile
                85                  90                  95

Asn Thr Pro Ala Phe Glu Trp Tyr Asp Gln S er Gly Leu Ser Val Val
            100                 105                 110
```

-continued

```
Met Pro Val Gly Gly Gln Ser Ser Phe Tyr S er Asp Trp Tyr Gln Pro
        115                 120                 125

Ala Cys Gly Lys Ala Gly Cys Gln Thr Tyr L ys Trp Glu Thr Phe Leu
    130                 135                 140

Thr Ser Glu Leu Pro Gly Trp Leu Gln Ala A sn Arg His Val Lys Pro
145                 150                 155                 160

Thr Gly Ser Ala Val Val Gly Leu Ser Met A la Ala Ser Ser Ala Leu
                165                 170                 175

Thr Leu Ala Ile Tyr His Pro Gln Gln Phe V al Tyr Ala Gly Ala Met
            180                 185                 190

Ser Gly Leu Leu Asp Pro Ser Gln Ala Met G ly Pro Thr Leu Ile Gly
        195                 200                 205

Leu Ala Met Gly Asp Ala Gly Gly Tyr Lys A la Ser Asp Met Trp Gly
    210                 215                 220

Pro Lys Glu Asp Pro Ala Trp Gln Arg Asn A sp Pro Leu Leu Asn Val
225                 230                 235                 240

Gly Lys Leu Ile Ala Asn Asn Thr Arg Val T rp Val Tyr Cys Gly Asn
                245                 250                 255

Gly Lys Pro Ser Asp Leu Gly Gly Asn Asn L eu Pro Ala Lys Phe Leu
            260                 265                 270

Glu Gly Phe Val Arg Thr Ser Asn Ile Lys P he Gln Asp Ala Tyr Asn
        275                 280                 285

Ala Gly Gly Gly His Asn Gly Val Phe Asp P he Pro Asp Ser Gly Thr
    290                 295                 300

His Ser Trp Glu Tyr Trp Gly Ala Gln Leu A sn Ala Met Lys Pro Asp
305                 310                 315                 320

Leu Gln Arg Ala Leu Gly Ala Thr Pro Asn T hr Gly Pro Ala Pro Gln
                325                 330                 335

Gly Ala


<210> SEQ ID NO 35
<211> LENGTH: 323
<212> TYPE: PRT
<213> ORGANISM: Mycobacterium bovis

<400> SEQUENCE: 35

Met Thr Asp Val Ser Arg Lys Ile Arg Ala T rp Gly Arg Arg Leu Met
 1               5                  10                  15

Ile Gly Thr Ala Ala Ala Val Val Leu Pro G ly Leu Val Gly Leu Ala
            20                  25                  30

Gly Gly Ala Ala Thr Ala Gly Ala Phe Ser A rg Pro Gly Leu Pro Val
        35                  40                  45

Glu Tyr Leu Gln Val Pro Ser Pro Ser Met G ly Arg Asp Ile Lys Val
    50                  55                  60

Gln Phe Gln Ser Gly Gly Asn Asn Ser Pro A la Val Tyr Leu Leu Asp
65                  70                  75                  80

Gly Leu Arg Ala Gln Asp Asp Tyr Asn Gly T rp Asp Ile Asn Thr Pro
                85                  90                  95

Ala Phe Glu Trp Tyr Tyr Gln Ser Gly Leu S er Ile Val Met Pro Val
            100                 105                 110

Gly Gly Gln Ser Ser Phe Tyr Ser Asp Trp T yr Ser Pro Ala Cys Gly
        115                 120                 125

Lys Ala Gly Cys Gln Thr Tyr Lys Trp Glu T hr Leu Leu Thr Ser Glu
    130                 135                 140
```

-continued

Leu Pro Gln Trp Leu Ser Ala Asn Arg Ala V al Lys Pro Thr Gly Ser
145 150 155 160

Ala Ala Ile Gly Leu Ser Met Ala Gly Ser S er Ala Met Ile Leu Ala
165 170 175

Ala Tyr His Pro Gln Gln Phe Ile Tyr Ala G ly Ser Leu Ser Ala Leu
180 185 190

Leu Asp Pro Ser Gln Gly Met Gly Leu Ile G ly Leu Ala Met Gly Asp
195 200 205

Ala Gly Gly Tyr Lys Ala Ala Asp Met Trp G ly Pro Ser Ser Asp Pro
210 215 220

Ala Trp Glu Arg Asn Asp Pro Thr Gln Gln I le Pro Lys Leu Val Ala
225 230 235 240

Asn Asn Thr Arg Leu Trp Val Tyr Cys Gly A sn Gly Thr Pro Asn Glu
245 250 255

Leu Gly Gly Ala Asn Ile Pro Ala Glu Phe L eu Glu Asn Phe Val Arg
260 265 270

Ser Ser Asn Leu Lys Phe Gln Asp Ala Tyr L ys Pro Ala Gly Gly His
275 280 285

Asn Ala Val Phe Asn Phe Pro Pro Asn Gly T hr His Ser Trp Glu Tyr
290 295 300

Trp Gly Ala Gln Leu Asn Ala Met Lys Gly A sp Leu Gln Ser Ser Leu
305 310 315 320

Gly Ala Gly

<210> SEQ ID NO 36
<211> LENGTH: 333
<212> TYPE: PRT
<213> ORGANISM: Mycobacterium leprae

<400> SEQUENCE: 36

Met Lys Phe Leu Gln Gln Met Arg Lys Leu P he Gly Leu Ala Ala Lys
1 5 10 15

Phe Pro Ala Arg Leu Thr Ile Ala Val Ile G ly Thr Ala Leu Leu Ala
20 25 30

Gly Leu Val Gly Val Val Gly Asp Thr Ala I le Ala Val Ala Phe Ser
35 40 45

Lys Pro Gly Leu Pro Val Glu Tyr Leu Gln V al Pro Ser Pro Ser Met
50 55 60

Gly His Asp Ile Lys Ile Gln Phe Gln Gly G ly Gly Gln His Ala Val
65 70 75 80

Tyr Leu Leu Asp Gly Leu Arg Ala Gln Glu A sp Tyr Asn Gly Trp Asp
85 90 95

Ile Asn Thr Pro Ala Phe Glu Glu Tyr Tyr H is Ser Gly Leu Ser Val
100 105 110

Ile Met Pro Val Gly Gly Gln Ser Ser Phe T yr Ser Asn Trp Tyr Gln
115 120 125

Pro Ser Gln Gly Asn Gly Gln His Tyr Thr T yr Lys Trp Glu Thr Phe
130 135 140

Leu Thr Gln Glu Met Pro Ser Trp Leu Gln A la Asn Lys Asn Val Leu
145 150 155 160

Pro Thr Gly Asn Ala Ala Val Gly Leu Ser M et Ser Gly Ser Ser Ala
165 170 175

Leu Ile Leu Ala Ser Tyr Tyr Pro Gln Gln P he Pro Tyr Ala Ala Ser
180 185 190

-continued

```
Leu Ser Gly Phe Leu Asn Pro Ser Glu Gly T rp Trp Pro Thr Met Ile
        195                 200                 205

Gly Leu Ala Met Asn Asp Ser Gly Gly Tyr A sn Ala Asn Ser Met Trp
    210                 215                 220

Gly Pro Ser Thr Asp Pro Ala Trp Lys Arg A sn Asp Pro Met Val Gln
225                 230                 235                 240

Ile Pro Arg Leu Val Ala Asn Asn Thr Arg I le Trp Val Tyr Cys Gly
                245                 250                 255

Asn Gly Ala Pro Asn Glu Leu Gly Gly Asp A sn Ile Pro Ala Lys Phe
            260                 265                 270

Leu Glu Ser Leu Thr Leu Ser Thr Asn Glu I le Phe Gln Asn Thr Tyr
        275                 280                 285

Ala Ala Ser Gly Gly Arg Asn Gly Val Phe A sn Phe Pro Pro Asn Gly
    290                 295                 300

Thr His Ser Trp Pro Tyr Trp Asn Gln Gln L eu Val Ala Met Lys Pro
305                 310                 315                 320

Asp Ile Gln Gln Ile Leu Asn Gly Ser Asn A sn Asn Ala
                325                 330


<210> SEQ ID NO 37
<211> LENGTH: 340
<212> TYPE: PRT
<213> ORGANISM: Mycobacterium tuberculosis

<400> SEQUENCE: 37

Met Thr Phe Phe Glu Gln Val Arg Arg Leu A rg Ser Ala Ala Thr Thr
 1               5                  10                  15

Leu Pro Arg Arg Val Ala Ile Ala Ala Met G ly Ala Val Leu Val Tyr
            20                  25                  30

Gly Leu Val Gly Thr Phe Gly Gly Pro Ala T hr Ala Gly Ala Phe Ser
        35                  40                  45

Arg Pro Gly Leu Pro Val Glu Tyr Leu Gln V al Pro Ser Ala Ser Met
    50                  55                  60

Gly Arg Asp Ile Lys Val Gln Phe Gln Gly G ly Gly Pro His Ala Val
65                  70                  75                  80

Tyr Leu Leu Asp Gly Leu Arg Ala Gln Asp A sp Tyr Asn Gly Trp Asp
                85                  90                  95

Ile Asn Thr Pro Ala Phe Glu Glu Tyr Tyr G ln Ser Gly Leu Ser Val
            100                 105                 110

Ile Met Pro Val Gly Gly Gln Ser Ser Phe T yr Thr Asp Trp Tyr Gln
        115                 120                 125

Pro Ser Gln Ser Asn Gly Gln Asn Tyr Thr T yr Lys Trp Glu Thr Phe
    130                 135                 140

Leu Thr Arg Glu Met Pro Ala Trp Leu Gln A la Asn Lys Gly Val Ser
145                 150                 155                 160

Pro Thr Gly Asn Ala Ala Val Gly Leu Ser M et Ser Gly Gly Ser Ala
                165                 170                 175

Leu Ile Leu Ala Ala Tyr Tyr Pro Gln Gln P he Pro Tyr Ala Ala Ser
            180                 185                 190

Leu Ser Gly Phe Leu Asn Pro Ser Glu Gly T rp Trp Pro Thr Leu Ile
        195                 200                 205

Gly Leu Ala Met Asn Asp Ser Gly Gly Tyr A sn Ala Asn Ser Met Trp
    210                 215                 220

Gly Pro Ser Ser Asp Pro Ala Trp Lys Arg A sn Asp Pro Met Val Gln
225                 230                 235                 240
```

-continued

```
Ile Pro Arg Leu Val Ala Asn Asn Thr Arg I le Trp Val Tyr Cys Gly
                245                 250                 255

Asn Gly Thr Pro Ser Asp Leu Gly Gly Asp A sn Ile Pro Ala Lys Phe
            260                 265                 270

Leu Glu Gly Leu Thr Leu Arg Thr Asn Gln T hr Phe Arg Asp Thr Tyr
        275                 280                 285

Ala Ala Asp Gly Gly Arg Asn Gly Val Phe A sn Phe Pro Pro Asn Gly
    290                 295                 300

Thr His Ser Trp Pro Tyr Trp Asn Glu Gln L eu Val Ala Met Lys Ala
305                 310                 315                 320

Asp Ile Gln His Val Leu Asn Gly Ala Thr P ro Pro Ala Ala Pro Ala
                325                 330                 335

Ala Pro Ala Ala
            340


<210> SEQ ID NO 38
<211> LENGTH: 20
<212> TYPE: DNA
<213> ORGANISM: Artificial Sequence
<220> FEATURE:
<223> OTHER INFORMATION: Probe made in a lab

<400> SEQUENCE: 38

agcggctggg acatcaacac                                               20


<210> SEQ ID NO 39
<211> LENGTH: 20
<212> TYPE: DNA
<213> ORGANISM: Artificial Sequence
<220> FEATURE:
<223> OTHER INFORMATION: Probe made in a lab

<400> SEQUENCE: 39

cagacgcggg tgttgttggc                                               20


<210> SEQ ID NO 40
<211> LENGTH: 1211
<212> TYPE: DNA
<213> ORGANISM: Mycobacterium vaccae

<400> SEQUENCE: 40

ggtaccggaa gctggaggat tgacggtatg agacttcttg acaggattcg t gggccttgg     60

gcacgccgtt tcggcgtcgt ggctgtcgcg acagcgatga tgcctgcttt g gtgggcctg    120

gctggagggt cggcgaccgc cggagcattc tcccggccag gtctgccggt g gagtacctg    180

atggtgcctt cgccgtcgat ggggcgcgac atcaagatcc agttccagag c ggtggcgag    240

aactcgccgg ctctctacct gctcgacggc ctgcgtgcgc aggaggactt c aacggctgg    300

gacatcaaca ctcaggcttt cgagtggttc ctcgacagcg gcatctccgt g gtgatgccg    360

gtcggtggcc agtccagctt ctacaccgac tggtacgccc ccgcccgtaa c aagggcccg    420

accgtgacct acaagtggga gaccttcctg acccaggagc tcccgggctg g ctgcaggcc    480

aaccgcgcgg tcaagccgac cggcagcggc cctgtcggtc tgtcgatggc g ggttcggcc    540

gcgctgaacc tggcgacctg gcacccggag cagttcatct acgcgggctc g atgtccggc    600

ttcctgaacc cctccgaggg ctggtggccg ttcctgatca acatctcgat g ggtgacgcc    660

ggcggcttca aggccgacga catgtggggc aagaccgagg ggatcccaac a gcggttgga    720

cagcgcaacg atccgatgct gaacatcccg accctggtcg ccaacaacac c cgtatctgg    780
```

-continued gtctactgcg gtaacggcca gcccaccgag ctcggcggcg gcgacctgcc c gccacgttc 840 ctcgaaggtc tgaccatccg caccaacgag accttccgcg acaactacat c gccgcgggt 900 ggccacaacg gtgtgttcaa cttcccggcc aacggcacgc acaactgggc g tactggggt 960 cgcgagctgc aggcgatgaa gcctgacctg caggcgcacc ttctctgacg g ttgcacgaa 1020 acgaagcccc cggccgattg cggccgaggg tttcgtcgtc cggggctact g tggccgaca 1080 taaccgaaat caacgcgatg gtggctcatc aggaacgccg agggggtcat t gcgctacga 1140 cacgaggtgg gcgagcaatc cttcctgccc gacggagagg tcaacatcca c gtcgagtac 1200 tccagcgtga a 1211

<210> SEQ ID NO 41
<211> LENGTH: 485
<212> TYPE: DNA
<213> ORGANISM: Mycobacterium vaccae

<400> SEQUENCE: 41
agcggctggg acatcaacac cgccgccttc gagtggtacg tcgactcggg t ctcgcggtg 60 atcatgcccg tcggcgggca gtccagcttc tacagcgact ggtacagccc g gcctgcggt 120 aaggccggct gccagaccta caagtgggag acgttcctga cccaggagct g ccggcctac 180 ctcgccgcca acaagggggt cgacccgaac cgcaacgcgg ccgtcggtct g tccatggcc 240 ggttcggcgg cgctgacgct ggcgatctac cacccgcagc agttccagta c gccgggtcg 300 ctgtcgggct acctgaaccc gtccgagggg tggtggccga tgctgatcaa c atctcgatg 360 ggtgacgcgg gcggctacaa ggccaacgac atgtggggtc caccgaagga c ccgagcagc 420 gcctggaagc gcaacgaccc gatggtcaac atcggcaagc tggtggccaa c aacaccccc 480 ctctc 485

<210> SEQ ID NO 42
<211> LENGTH: 1052
<212> TYPE: DNA
<213> ORGANISM: Mycobacterium vaccae

<400> SEQUENCE: 42
gttgatgaga aaggtgggtt gtttgccgtt atgaagttca cagagaagtg g cggggctcc 60 gcaaaggcgg cgatgcaccg ggtgggcgtt gccgatatgg ccgccgttgc g ctgcccgga 120 ctgatcggct tcgccggggg ttcggcaacg gccggggcat tctcccggcc c ggtcttcct 180 gtcgagtacc tcgacgtgtt ctcgccgtcg atgggccgcg acatccgggt c cagttccag 240 ggtggcggta ctcatgcggt ctacctgctc gacggtctgc gtgcccagga c gactacaac 300 ggctgggaca tcaacacccc tgcgttcgag tggttctacg agtccggctt g tcgacgatc 360 atgccggtcg gcggacagtc cagcttctac agcgactggt accagccgtc t cggggcaac 420 gggcagaact acacctacaa gtgggagacg ttcctgaccc aggagctgcc g acgtggctg 480 gaggccaacc gcggagtgtc gcgcaccggc aacgcgttcg tcggcctgtc g atggcgggc 540 agcgcggcgc tgacctacgc gatccatcac ccgcagcagt tcatctacgc c tcgtcgctg 600 tcaggcttcc tgaacccgtc cgagggctgg tggccgatgc tgatcgggct g gcgatgaac 660 gacgcaggcg gcttcaacgc cgagagcatg tggggcccgt cctcggaccc g gcgtggaag 720 cgcaacgacc cgatggtcaa catcaaccag ctggtggcca acaacacccg g atctggatc 780 tactgcggca ccggcacccc gtcggagctg gacaccggga ccccgggcca g aacctgatg 840

-continued

```
gccgcgcagt tcctcgaagg attcacgttg cggaccaaca tcgccttccg t gacaactac    900

atcgcagccg gcggcaccaa cggtgtcttc aacttcccgg cctcgggcac c cacagctgg    960

gggtactggg ggcagcagct gcagcagatg aagcccgaca tccagcgggt t ctgggagct   1020

caggccaccg cctagccacc caccccacac cc                                 1052


<210> SEQ ID NO 43
<211> LENGTH: 326
<212> TYPE: PRT
<213> ORGANISM: Mycobacterium vaccae

<400> SEQUENCE: 43

Met Arg Leu Leu Asp Arg Ile Arg Gly Pro T rp Ala Arg Arg Phe Gly
 1               5                  10                  15

Val Val Ala Val Ala Thr Ala Met Met Pro A la Leu Val Gly Leu Ala
            20                  25                  30

Gly Gly Ser Ala Thr Ala Gly Ala Phe Ser A rg Pro Gly Leu Pro Val
        35                  40                  45

Glu Tyr Leu Met Val Pro Ser Pro Ser Met G ly Arg Asp Ile Lys Ile
    50                  55                  60

Gln Phe Gln Ser Gly Gly Glu Asn Ser Pro A la Leu Tyr Leu Leu Asp
65                  70                  75                  80

Gly Leu Arg Ala Gln Glu Asp Phe Asn Gly T rp Asp Ile Asn Thr Gln
                85                  90                  95

Ala Phe Glu Trp Phe Leu Asp Ser Gly Ile S er Val Val Met Pro Val
            100                 105                 110

Gly Gly Gln Ser Ser Phe Tyr Thr Asp Trp T yr Ala Pro Ala Arg Asn
        115                 120                 125

Lys Gly Pro Thr Val Thr Tyr Lys Trp Glu T hr Phe Leu Thr Gln Glu
    130                 135                 140

Leu Pro Gly Trp Leu Gln Ala Asn Arg Ala V al Lys Pro Thr Gly Ser
145                 150                 155                 160

Gly Pro Val Gly Leu Ser Met Ala Gly Ser A la Ala Leu Asn Leu Ala
                165                 170                 175

Thr Trp His Pro Glu Gln Phe Ile Tyr Ala G ly Ser Met Ser Gly Phe
            180                 185                 190

Leu Asn Pro Ser Glu Gly Trp Trp Pro Phe L eu Ile Asn Ile Ser Met
        195                 200                 205

Gly Asp Ala Gly Gly Phe Lys Ala Asp Asp M et Trp Gly Lys Thr Glu
    210                 215                 220

Gly Ile Pro Thr Ala Val Gly Gln Arg Asn A sp Pro Met Leu Asn Ile
225                 230                 235                 240

Pro Thr Leu Val Ala Asn Asn Thr Arg Ile T rp Val Tyr Cys Gly Asn
                245                 250                 255

Gly Gln Pro Thr Glu Leu Gly Gly Gly Asp L eu Pro Ala Thr Phe Leu
            260                 265                 270

Glu Gly Leu Thr Ile Arg Thr Asn Glu Thr P he Arg Asp Asn Tyr Ile
        275                 280                 285

Ala Ala Gly Gly His Asn Gly Val Phe Asn P he Pro Ala Asn Gly Thr
    290                 295                 300

His Asn Trp Ala Tyr Trp Gly Arg Glu Leu G ln Ala Met Lys Pro Asp
305                 310                 315                 320

Leu Gln Ala His Leu Leu
                325
```

-continued

<210> SEQ ID NO 44
<211> LENGTH: 161
<212> TYPE: PRT
<213> ORGANISM: Mycobacterium vaccae

<400> SEQUENCE: 44

Ser Gly Trp Asp Ile Asn Thr Ala Ala Phe G lu Trp Tyr Val Asp Ser
1 5 10 15

Gly Leu Ala Val Ile Met Pro Val Gly Gly G ln Ser Ser Phe Tyr Ser
20 25 30

Asp Trp Tyr Ser Pro Ala Cys Gly Lys Ala G ly Cys Gln Thr Tyr Lys
35 40 45

Trp Glu Thr Phe Leu Thr Gln Glu Leu Pro A la Tyr Leu Ala Ala Asn
50 55 60

Lys Gly Val Asp Pro Asn Arg Asn Ala Ala V al Gly Leu Ser Met Ala
65 70 75 80

Gly Ser Ala Ala Leu Thr Leu Ala Ile Tyr H is Pro Gln Gln Phe Gln
85 90 95

Tyr Ala Gly Ser Leu Ser Gly Tyr Leu Asn P ro Ser Glu Gly Trp Trp
100 105 110

Pro Met Leu Ile Asn Ile Ser Met Gly Asp A la Gly Gly Tyr Lys Ala
115 120 125

Asn Asp Met Trp Gly Pro Pro Lys Asp Pro S er Ser Ala Trp Lys Arg
130 135 140

Asn Asp Pro Met Val Asn Ile Gly Lys Leu V al Ala Asn Asn Thr Pro
145 150 155 160

Leu

<210> SEQ ID NO 45
<211> LENGTH: 334
<212> TYPE: PRT
<213> ORGANISM: Mycobacterium vaccae

<400> SEQUENCE: 45

Met Lys Phe Thr Glu Lys Trp Arg Gly Ser A la Lys Ala Ala Met His
1 5 10 15

Arg Val Gly Val Ala Asp Met Ala Ala Val A la Leu Pro Gly Leu Ile
20 25 30

Gly Phe Ala Gly Gly Ser Ala Thr Ala Gly A la Phe Ser Arg Pro Gly
35 40 45

Leu Pro Val Glu Tyr Leu Asp Val Phe Ser P ro Ser Met Gly Arg Asp
50 55 60

Ile Arg Val Gln Phe Gln Gly Gly Gly Thr H is Ala Val Tyr Leu Leu
65 70 75 80

Asp Gly Leu Arg Ala Gln Asp Asp Tyr Asn G ly Trp Asp Ile Asn Thr
85 90 95

Pro Ala Phe Glu Trp Phe Tyr Glu Ser Gly L eu Ser Thr Ile Met Pro
100 105 110

Val Gly Gly Gln Ser Ser Phe Tyr Ser Asp T rp Tyr Gln Pro Ser Arg
115 120 125

Gly Asn Gly Gln Asn Tyr Thr Tyr Lys Trp G lu Thr Phe Leu Thr Gln
130 135 140

Glu Leu Pro Thr Trp Leu Glu Ala Asn Arg G ly Val Ser Arg Thr Gly
145 150 155 160

Asn Ala Phe Val Gly Leu Ser Met Ala Gly S er Ala Ala Leu Thr Tyr

-continued

```
                165                 170                 175

Ala Ile His His Pro Gln Gln Phe Ile Tyr A la Ser Ser Leu Ser Gly
            180                 185                 190

Phe Leu Asn Pro Ser Glu Gly Trp Trp Pro M et Leu Ile Gly Leu Ala
        195                 200                 205

Met Asn Asp Ala Gly Gly Phe Asn Ala Glu S er Met Trp Gly Pro Ser
    210                 215                 220

Ser Asp Pro Ala Trp Lys Arg Asn Asp Pro M et Val Asn Ile Asn Gln
225                 230                 235                 240

Leu Val Ala Asn Asn Thr Arg Ile Trp Ile T yr Cys Gly Thr Gly Thr
                245                 250                 255

Pro Ser Glu Leu Asp Thr Gly Thr Pro Gly G ln Asn Leu Met Ala Ala
            260                 265                 270

Gln Phe Leu Glu Gly Phe Thr Leu Arg Thr A sn Ile Ala Phe Arg Asp
        275                 280                 285

Asn Tyr Ile Ala Ala Gly Gly Thr Asn Gly V al Phe Asn Phe Pro Ala
    290                 295                 300

Ser Gly Thr His Ser Trp Gly Tyr Trp Gly G ln Gln Leu Gln Gln Met
305                 310                 315                 320

Lys Pro Asp Ile Gln Arg Val Leu Gly Ala G ln Ala Thr Ala
                325                 330
```

<210> SEQ ID NO 46
<211> LENGTH: 795
<212> TYPE: DNA
<213> ORGANISM: Mycobacterium vaccae

<400> SEQUENCE: 46

```
ctgccgcggg tttgccatct cttgggtcct gggtcgggag gccatgttct g ggtaacgat     60

ccggtaccgt ccggcgatgt gaccaacatg cgaacagcga caacgaagct a ggagcggcg    120

ctcggcgcag cagcattggt ggccgccacg gggatggtca gcgcggcgac g gcgaacgcc    180

caggaagggc accaggtccg ttacacgctc acctcggccg gcgcttacga g ttcgacctg    240

ttctatctga cgacgcagcc gccgagcatg caggcgttca acgccgacgc g tatgcgttc    300

gccaagcggg agaaggtcag cctcgccccg ggtgtgccgt gggtcttcga a accacgatg    360

gccgacccga actgggcgat ccttcaggtc agcagcacca cccgcggtgg g caggccgcc    420

ccgaacgcgc actgcgacat cgccgtcgat ggccaggagg tgctcagcca g cacgacgac    480

ccctacaacg tgcggtgcca gctcggtcag tggtgagtca cctcgccgag a gtccggcca    540

gcgccggcgg cagcggctcg cggtgcagca ccccgaggcg ctgggtcgcg c gggtcagcg    600

cgacgtaaag atcgctggcc ccgcgcggcc cctcggcgag gatctgctcc g ggtagacca    660

ccagcacggc gtctaactcc agacccttgg tctgcgtggg tgccaccgcg c ccgggacac    720

cgggcgggcc gatcaccacg ctggtgccct cccggtccgc ctccgcacgc a cgaaatcgt    780

cgatggcacc ggcga                                                     795
```

<210> SEQ ID NO 47
<211> LENGTH: 142
<212> TYPE: PRT
<213> ORGANISM: Mycobacterium vaccae

<400> SEQUENCE: 47

```
Met Arg Thr Ala Thr Thr Lys Leu Gly Ala A la Leu Gly Ala Ala Ala
 1               5                  10                  15
```

-continued

```
Leu Val Ala Ala Thr Gly Met Val Ser Ala A la Thr Ala Asn Ala Gln
            20                  25                  30

Glu Gly His Gln Val Arg Tyr Thr Leu Thr S er Ala Gly Ala Tyr Glu
        35                  40                  45

Phe Asp Leu Phe Tyr Leu Thr Thr Gln Pro P ro Ser Met Gln Ala Phe
    50                  55                  60

Asn Ala Asp Ala Tyr Ala Phe Ala Lys Arg G lu Lys Val Ser Leu Ala
65                  70                  75                  80

Pro Gly Val Pro Trp Val Phe Glu Thr Thr M et Ala Asp Pro Asn Trp
                85                  90                  95

Ala Ile Leu Gln Val Ser Ser Thr Thr Arg G ly Gly Gln Ala Ala Pro
            100                 105                 110

Asn Ala His Cys Asp Ile Ala Val Asp Gly G ln Glu Val Leu Ser Gln
        115                 120                 125

His Asp Asp Pro Tyr Asn Val Arg Cys Gln L eu Gly Gln Trp
    130                 135                 140
```

<210> SEQ ID NO 48
<211> LENGTH: 300
<212> TYPE: DNA
<213> ORGANISM: Mycobacterium vaccae

<400> SEQUENCE: 48

```
gccagtgcgc caacggtttt catcgatgcc gcacacaacc ccggtgggcc c tgcgcttgc      60

cgaaggctgc gcgacgagtt cgacttccgg tatctcgtcg gcgtcgtctc g gtgatgggg     120

gacaaggacg tggacgggat ccgccaggac ccgggcgtgc cggacgggcg c ggtctcgca     180

ctgttcgtct cgggcgacaa ccttcgaaag ggtgcggcgc tcaacacgat c cagatcgcc     240

gagctgctgg ccgcccagtt gtaagtgttc cgccgaaatt gcattccacg c cgataatcg     300
```

<210> SEQ ID NO 49
<211> LENGTH: 563
<212> TYPE: DNA
<213> ORGANISM: Mycobacterium vaccae

<400> SEQUENCE: 49

```
ggatcctcgg ccggctcaag agtccgcgcc gaggtggatg tgacgctgga c ggctacgag      60

ttcagtcggg cctgcgaggc gctgtaccac ttcgcctggg acgagttctg c gactggtat     120

gtcgagcttg ccaaagtgca actgggtgaa ggtttctcgc acaccacggc c gtgttggcc     180

accgtgctcg atgtgctgct caagcttctg cacccggtca tgccgttcgt c accgaggtg     240

ctgtggaagg ccctgaccgg gcgggccggc gcgagcgaac gtctgggaaa t gtggagtca     300

ctggtcgtcg cggactggcc cacgcccacc ggatacgcgc tggatcaggc t gccgcacaa     360

cggatcgccg acacccagaa gttgatcacc gaggtgcgcc ggttccgcag c gatcagggt     420

ctggccgacc gccagcgggt gcctgcccgg ttgtccggca tcgacaccgc g ggtctggac     480

gcccatgtcc cggcggtgcg cgcgctggcc tggcttgacc gagggtgatg a gggcttcac     540

cgcgtccgaa tcggtcgagg tgc                                         563
```

<210> SEQ ID NO 50
<211> LENGTH: 434
<212> TYPE: DNA
<213> ORGANISM: Mycobacterium vaccae

<400> SEQUENCE: 50

```
gggccgggcc cgaggatgag caagttcgaa gtcgtcaccg ggatggcgtt c gcggctttc      60
```

-continued

```
gccgacgcgc ccatcgacgt cgccgtcgtc gaggtcgggc tcggtggtcg c tgggacgcg    120

acgaacgtgg tgaacgcacc ggtcgcggtc atcaccccga tcggggtgga c cacaccgac    180

tacctcggtg acacgatcgc cgagatcgcc ggggagaagg ccggaaatca t cacccgcca    240

gccgacgacc tggtgccgac cgacaccgtc gccgtgctgg cgcggcaggt t cccgaggcc    300

atggaggtgc tgctggccca ggcggtgcgc tcggatgcgg ctgtagcgcg c gaggattcg    360

gagtgcgcgg tgctgggccg tcaggtcgcc atcggcggca gctgctccgg t tgcaggggc    420

tcggtggcgt ctac                                                      434


<210> SEQ ID NO 51
<211> LENGTH: 438
<212> TYPE: DNA
<213> ORGANISM: Mycobacterium vaccae

<400> SEQUENCE: 51

ggatcccact cccgcgccgg cggcggccag ctggtacggc cattccagcg t gctgatcga     60

ggtcgacggc taccgcgtgc tggccgaccc ggtgtggagc aacagatgtt c gccctcacg    120

ggcggtcgga ccgcagcgca tgcacgacgt cccggtgccg ctggaggcgc t tcccgccgt    180

ggacgcggtg gtgatcgcca acgaccacta cgaccacctc gacatcgaca c catcgtcgc    240

gttggcgcac acccagcggg ccccgttcgt ggtgccgttg ggcatcggcg c acacctgcg    300

caagtggggc gtccccgagg cgcggatcgt cgagttggac tggcacgaag c ccaccgcat    360

cgacgacctg acgctggtct gcacccccgc ccggcacttc tccggccggt t gttctcccg    420

cgactcgacg ctgtgggc                                                  438


<210> SEQ ID NO 52
<211> LENGTH: 87
<212> TYPE: PRT
<213> ORGANISM: Mycobacterium vaccae

<400> SEQUENCE: 52

Ala Ser Ala Pro Thr Val Phe Ile Asp Ala A la His Asn Pro Gly Gly
 1              5                   10                  15

Pro Cys Ala Cys Arg Arg Leu Arg Asp Glu P he Asp Phe Arg Tyr Leu
            20                  25                  30

Val Gly Val Val Ser Val Met Gly Asp Lys A sp Val Asp Gly Ile Arg
        35                  40                  45

Gln Asp Pro Gly Val Pro Asp Gly Arg Gly L eu Ala Leu Phe Val Ser
    50                  55                  60

Gly Asp Asn Leu Arg Lys Gly Ala Ala Leu A sn Thr Ile Gln Ile Ala
65                  70                  75                  80

Glu Leu Leu Ala Ala Gln Leu
               85


<210> SEQ ID NO 53
<211> LENGTH: 175
<212> TYPE: PRT
<213> ORGANISM: Mycobacterium vaccae

<400> SEQUENCE: 53

Gly Ser Ser Ala Gly Ser Arg Val Arg Ala G lu Val Asp Val Thr Leu
 1              5                   10                  15

Asp Gly Tyr Glu Phe Ser Arg Ala Cys Glu A la Leu Tyr His Phe Ala
            20                  25                  30
```

-continued

Trp Asp Glu Phe Cys Asp Trp Tyr Val Glu L eu Ala Lys Val Gln Leu
35 40 45

Gly Glu Gly Phe Ser His Thr Thr Ala Val L eu Ala Thr Val Leu Asp
50 55 60

Val Leu Leu Lys Leu Leu His Pro Val Met P ro Phe Val Thr Glu Val
65 70 75 80

Leu Trp Lys Ala Leu Thr Gly Arg Ala Gly A la Ser Glu Arg Leu Gly
85 90 95

Asn Val Glu Ser Leu Val Val Ala Asp Trp P ro Thr Pro Thr Gly Tyr
100 105 110

Ala Leu Asp Gln Ala Ala Ala Gln Arg Ile A la Asp Thr Gln Lys Leu
115 120 125

Ile Thr Glu Val Arg Arg Phe Arg Ser Asp G ln Gly Leu Ala Asp Arg
130 135 140

Gln Arg Val Pro Ala Arg Leu Ser Gly Ile A sp Thr Ala Gly Leu Asp
145 150 155 160

Ala His Val Pro Ala Val Arg Ala Leu Ala T rp Leu Asp Arg Gly
165 170 175

<210> SEQ ID NO 54
<211> LENGTH: 144
<212> TYPE: PRT
<213> ORGANISM: Mycobacterium vaccae

<400> SEQUENCE: 54

Gly Pro Gly Pro Arg Asn Ser Lys Phe Glu V al Val Thr Gly Met Ala
1 5 10 15

Phe Ala Ala Phe Ala Asp Ala Pro Ile Asp V al Ala Val Val Glu Val
20 25 30

Gly Leu Gly Gly Arg Trp Asp Ala Thr Asn V al Val Asn Ala Pro Val
35 40 45

Ala Val Ile Thr Pro Ile Gly Val Asp His T hr Asp Tyr Leu Gly Asp
50 55 60

Thr Ile Ala Glu Ile Ala Gly Glu Lys Ala G ly Asn His His Pro Pro
65 70 75 80

Ala Asp Asp Leu Val Pro Thr Asp Thr Val A la Val Leu Ala Arg Gln
85 90 95

Val Pro Glu Ala Asn Glu Val Leu Leu Ala G ln Ala Val Arg Ser Asp
100 105 110

Ala Ala Val Ala Arg Glu Asp Ser Glu Cys A la Val Leu Gly Arg Gln
115 120 125

Val Ala Ile Gly Gly Ser Cys Ser Gly Cys A rg Gly Ser Val Ala Ser
130 135 140

<210> SEQ ID NO 55
<211> LENGTH: 145
<212> TYPE: PRT
<213> ORGANISM: Mycobacterium vaccae

<400> SEQUENCE: 55

Asp Pro Thr Pro Ala Pro Ala Ala Ala Ser T rp Tyr Gly His Ser Ser
1 5 10 15

Val Leu Ile Glu Val Asp Gly Tyr Arg Val L eu Ala Asp Pro Val Trp
20 25 30

Ser Asn Arg Cys Ser Pro Ser Arg Ala Val G ly Pro Gln Arg Met His
35 40 45

-continued

```
Asp Val Pro Val Pro Leu Glu Ala Leu Pro A la Val Asp Ala Val Val
    50                  55                  60

Ile Ser Asn Asp His Tyr Asp His Leu Asp I le Asp Thr Ile Val Ala
65                  70                  75                  80

Leu Ala His Thr Gln Arg Ala Pro Phe Val V al Pro Leu Gly Ile Gly
                85                  90                  95

Ala His Leu Arg Lys Trp Gly Val Pro Glu A la Arg Ile Val Glu Leu
            100                 105                 110

Asp Trp His Glu Ala His Arg Ile Asp Asp L eu Thr Leu Val Cys Thr
        115                 120                 125

Pro Ala Arg His Phe Ser Gly Arg Leu Phe S er Arg Asp Ser Thr Leu
    130                 135                 140

Trp
145


<210> SEQ ID NO 56
<211> LENGTH: 10
<212> TYPE: PRT
<213> ORGANISM: Mycobacterium vaccae
<220> FEATURE:
<221> NAME/KEY: UNSURE
<222> LOCATION: (1)...(1)
<223> OTHER INFORMATION: Residue can be either Gly, Ile, Leu or Val
<220> FEATURE:
<221> NAME/KEY: UNSURE
<222> LOCATION: (2)...(2)
<223> OTHER INFORMATION: Residue can be either Ile, Leu, Gly, or Ala
<220> FEATURE:
<221> NAME/KEY: UNSURE
<222> LOCATION: (5)...(5)
<221> NAME/KEY: UNSURE
<222> LOCATION: (9)...(9)

<400> SEQUENCE: 56

Xaa Xaa Ala Pro Xaa Gly Asp Ala Xaa Arg
 1               5                  10


<210> SEQ ID NO 57
<211> LENGTH: 8
<212> TYPE: PRT
<213> ORGANISM: Mycobacterium vaccae
<220> FEATURE:
<221> NAME/KEY: UNSURE
<222> LOCATION: (7)...(7)
<223> OTHER INFORMATION: Residue can be either Ile or Leu

<400> SEQUENCE: 57

Pro Glu Ala Glu Ala Asn Xaa Arg
 1               5


<210> SEQ ID NO 58
<211> LENGTH: 11
<212> TYPE: PRT
<213> ORGANISM: Mycobacterium vaccae
<220> FEATURE:
<221> NAME/KEY: UNSURE
<222> LOCATION: (4)...(4)
<223> OTHER INFORMATION: Residue can be either Gln or Gly
<220> FEATURE:
<221> NAME/KEY: UNSURE
<222> LOCATION: (5)...(5)
<223> OTHER INFORMATION: Residue can be either Gly or Gln

<400> SEQUENCE: 58

Thr Ala Asn Xaa Xaa Glu Tyr Tyr Asp Asn A rg
 1               5                  10
```

-continued

<210> SEQ ID NO 59
<211> LENGTH: 34
<212> TYPE: PRT
<213> ORGANISM: Mycobacterium vaccae

<400> SEQUENCE: 59

Asn Ser Pro Arg Ala Glu Ala Glu Ala Asn L eu Arg Gly Tyr Phe Thr
1 5 10 15

Ala Asn Pro Ala Glu Tyr Tyr Asp Leu Arg G ly Ile Leu Ala Pro Ile
20 25 30

Gly Asp

<210> SEQ ID NO 60
<211> LENGTH: 20
<212> TYPE: DNA
<213> ORGANISM: Artificial Sequence
<220> FEATURE:
<223> OTHER INFORMATION: Made in a lab

<400> SEQUENCE: 60
ccggtgggcc cgggctgcgc 20

<210> SEQ ID NO 61
<211> LENGTH: 20
<212> TYPE: DNA
<213> ORGANISM: Artificial Sequence
<220> FEATURE:
<223> OTHER INFORMATION: Made in a lab

<400> SEQUENCE: 61
tggccggcca ccacgtggta 20

<210> SEQ ID NO 62
<211> LENGTH: 313
<212> TYPE: DNA
<213> ORGANISM: Mycobacterium vaccae

<400> SEQUENCE: 62
gccggtgggc ccgggctgcg cggaatacgc ggcagccaat cccactgggc c ggcctcggt 60 gcagggaatg tcgcaggacc cggtcgcggt ggcggcctcg aacaatccgg a gttgacaac 120 gctgtacggc tgcactgtcg ggccagctca atccgcaagt aaacctggtg g acaccctca 180 acagcggtca gtacacggtg ttcgcaccga ccaacgcggc atttagcaag c tgccggcat 240 ccacgatcga cgagctcaag accaattcgt cactgctgac cagcatcctg a cctaccacg 300 tggtggccgg cca 313

<210> SEQ ID NO 63
<211> LENGTH: 18
<212> TYPE: PRT
<213> ORGANISM: Mycobacterium vaccae
<220> FEATURE:
<221> NAME/KEY: UNSURE
<222> LOCATION: (7)...(17)

<400> SEQUENCE: 63

Glu Pro Ala Gly Pro Leu Pro Xaa Tyr Asn G lu Arg Leu His Thr Leu
1 5 10 15

Xaa Gln

<210> SEQ ID NO 64
<211> LENGTH: 25

-continued

<212> TYPE: PRT
<213> ORGANISM: Mycobacterium vaccae
<220> FEATURE:
<221> NAME/KEY: UNSURE
<222> LOCATION: (21)...(21)

<400> SEQUENCE: 64

Gly Leu Asp Asn Glu Leu Ser Leu Val Asp G ly Gln Gly Arg Thr Leu
1 5 10 15

Thr Val Gln Gln Xaa Asp Thr Phe Leu
20 25

<210> SEQ ID NO 65
<211> LENGTH: 26
<212> TYPE: PRT
<213> ORGANISM: Mycobacterium vaccae
<220> FEATURE:
<221> NAME/KEY: UNSURE
<222> LOCATION: (3)...(3)
<221> NAME/KEY: UNSURE
<222> LOCATION: (21)...(22)
<221> NAME/KEY: UNSURE
<222> LOCATION: (24)...(24)

<400> SEQUENCE: 65

Asp Pro Xaa Pro Asp Ile Glu Val Glu Phe A la Arg Gly Thr Gly Ala
1 5 10 15

Glu Pro Gly Leu Xaa Xaa Val Xaa Asp Ala
20 25

<210> SEQ ID NO 66
<211> LENGTH: 32
<212> TYPE: DNA
<213> ORGANISM: Artificial Sequence
<220> FEATURE:
<223> OTHER INFORMATION: Made in a lab

<400> SEQUENCE: 66
accgccctcg agttctcccg gccaggtctg cc 32

<210> SEQ ID NO 67
<211> LENGTH: 32
<212> TYPE: DNA
<213> ORGANISM: Artificial Sequence
<220> FEATURE:
<223> OTHER INFORMATION: Made in a lab

<400> SEQUENCE: 67
aagcacgagc tcagtctctt ccacgcggac gt 32

<210> SEQ ID NO 68
<211> LENGTH: 30
<212> TYPE: DNA
<213> ORGANISM: Artificial Sequence
<220> FEATURE:
<223> OTHER INFORMATION: Made in a lab

<400> SEQUENCE: 68
catggatcca ttctcccggc ccggtcttcc 30

<210> SEQ ID NO 69
<211> LENGTH: 26
<212> TYPE: DNA
<213> ORGANISM: Artificial Sequence
<220> FEATURE:
<223> OTHER INFORMATION: Made in a lab -continued

<400> SEQUENCE: 69
tttgaattct aggcggtggc ctgagc 26

<210> SEQ ID NO 70
<211> LENGTH: 161
<212> TYPE: PRT
<213> ORGANISM: Mycobacterium vaccae

<400> SEQUENCE: 70

Ser Gly Trp Asp Ile Asn Thr Ala Ala Phe G lu Trp Tyr Val Asp Ser
1 5 10 15

Gly Leu Ala Val Ile Met Pro Val Gly Gly G ln Ser Ser Phe Tyr Ser
20 25 30

Asp Trp Tyr Ser Pro Ala Cys Gly Lys Ala G ly Cys Gln Thr Tyr Lys
35 40 45

Trp Glu Thr Phe Leu Thr Gln Glu Leu Pro A la Tyr Leu Ala Ala Asn
50 55 60

Lys Gly Val Asp Pro Asn Arg Asn Ala Ala V al Gly Leu Ser Met Ala
65 70 75 80

Gly Ser Ala Ala Leu Thr Leu Ala Ile Tyr H is Pro Gln Gln Phe Gln
85 90 95

Tyr Ala Gly Ser Leu Ser Gly Tyr Leu Asn P ro Ser Glu Gly Trp Trp
100 105 110

Pro Met Leu Ile Asn Ile Ser Met Gly Asp A la Gly Gly Tyr Lys Ala
115 120 125

Asn Asp Met Trp Gly Arg Thr Glu Asp Pro S er Ser Ala Trp Lys Arg
130 135 140

Asn Asp Pro Met Val Asn Ile Gly Lys Leu V al Ala Asn Asn Thr Pro
145 150 155 160

Leu

<210> SEQ ID NO 71
<211> LENGTH: 33
<212> TYPE: DNA
<213> ORGANISM: Artificial Sequence
<220> FEATURE:
<223> OTHER INFORMATION: Made in a lab

<400> SEQUENCE: 71
gagagactcg agaacgccca ggaagggcac cag 33

<210> SEQ ID NO 72
<211> LENGTH: 32
<212> TYPE: DNA
<213> ORGANISM: Artificial Sequence
<220> FEATURE:
<223> OTHER INFORMATION: Made in a lab

<400> SEQUENCE: 72
gagagactcg agtgactcac cactgaccga gc 32

<210> SEQ ID NO 73
<211> LENGTH: 20
<212> TYPE: DNA
<213> ORGANISM: Artificial Sequence
<220> FEATURE:
<223> OTHER INFORMATION: Made in a lab
<220> FEATURE:
<221> NAME/KEY: unsure
<222> LOCATION: (3)...(3)
<221> NAME/KEY: unsure -continued
<222> LOCATION: (6)...(6)
<221> NAME/KEY: unsure
<222> LOCATION: (9)...(9)
<221> NAME/KEY: unsure
<222> LOCATION: (15)...(15)

<400> SEQUENCE: 73
ggngcngcnc argcngarcc 20

<210> SEQ ID NO 74
<211> LENGTH: 825
<212> TYPE: DNA
<213> ORGANISM: Mycobacterium vaccae

<400> SEQUENCE: 74
ttggatccca ctcccgcgcc ggcggcggcc agctggtacg gccattccag c gtgctgatc 60 gaggtcgacg gctaccgcgt gctggccgac ccggtgtgga gcaacagatg t tcgccctca 120 cgggcggtcg gaccgcagcg catgcacgac gtcccggtgc cgctggaggc g cttcccgcc 180 gtggacgcgg tggtgatcag ccacgaccac tacgaccacc tcgacatcga c accatcgtc 240 gcgttggcgc acacccagcg ggccccgttc gtggtgccgt tgggcatcgg c gcacacctg 300 cgcaagtggg gcgtccccga ggcgcggatc gtcgagttgg actggcacga a gcccaccgc 360 atagacgacc tgacgctggt ctgcaccccc gcccggcact tctccggacg g ttgttctcc 420 cgcgactcga cgctgtgggc gtcgtgggtg gtcaccggct cgtcgcacaa g gcgttcttc 480 ggtggcgaca ccggatacac gaagagcttc gccgagatcg gcgacgagta c ggtccgttc 540 gatctgaccc tgctgccgat cggggcctac catcccgcgt tcgccgacat c cacatgaac 600 cccgaggagg cggtgcgcgc ccatctggac ctgaccgagg tggacaacag c ctgatggtg 660 cccatccact gggcgacatt ccgcctcgcc ccgcatccgt ggtccgagcc c gccgaacgc 720 ctgctgaccg ctgccgacgc cgagcgggta cgcctgaccg tgccgattcc c ggtcagcgg 780 gtggacccgg agtcgacgtt cgacccgtgg tggcggttct gaacc 825

<210> SEQ ID NO 75
<211> LENGTH: 273
<212> TYPE: PRT
<213> ORGANISM: Mycobacterium vaccae

<400> SEQUENCE: 75

Leu Asp Pro Thr Pro Ala Pro Ala Ala Ala S er Trp Tyr Gly His Ser
1 5 10 15

Ser Val Leu Ile Glu Val Asp Gly Tyr Arg V al Leu Ala Asp Pro Val
20 25 30

Trp Ser Asn Arg Cys Ser Pro Ser Arg Ala V al Gly Pro Gln Arg Met
35 40 45

His Asp Val Pro Val Pro Leu Glu Ala Leu P ro Ala Val Asp Ala Val
50 55 60

Val Ile Ser His Asp His Tyr Asp His Leu A sp Ile Asp Thr Ile Val
65 70 75 80

Ala Leu Ala His Thr Gln Arg Ala Pro Phe V al Val Pro Leu Gly Ile
85 90 95

Gly Ala His Leu Arg Lys Trp Gly Val Pro G lu Ala Arg Ile Val Glu
100 105 110

Leu Asp Trp His Glu Ala His Arg Ile Asp A sp Leu Thr Leu Val Cys
115 120 125

Thr Pro Ala Arg His Phe Ser Gly Arg Leu P he Ser Arg Asp Ser Thr

-continued

```
    130                 135                 140

Leu Trp Ala Ser Trp Val Val Thr Gly Ser S er His Lys Ala Phe Phe
145                 150                 155                 160

Gly Gly Asp Thr Gly Tyr Thr Lys Ser Phe A la Glu Ile Gly Asp Glu
                165                 170                 175

Tyr Gly Pro Phe Asp Leu Thr Leu Leu Pro I le Gly Ala Tyr His Pro
            180                 185                 190

Ala Phe Ala Asp Ile His Met Asn Pro Glu G lu Ala Val Arg Ala His
        195                 200                 205

Leu Asp Leu Thr Glu Val Asp Asn Ser Leu M et Val Pro Ile His Trp
    210                 215                 220

Ala Thr Phe Arg Leu Ala Pro His Pro Trp S er Glu Pro Ala Glu Arg
225                 230                 235                 240

Leu Leu Thr Ala Ala Asp Ala Glu Arg Val A rg Leu Thr Val Pro Ile
                245                 250                 255

Pro Gly Gln Arg Val Asp Pro Glu Ser Thr P he Asp Pro Trp Trp Arg
            260                 265                 270

Phe


<210> SEQ ID NO 76
<211> LENGTH: 10
<212> TYPE: PRT
<213> ORGANISM: Mycobacterium vaccae

<400> SEQUENCE: 76

Ala Lys Thr Ile Ala Tyr Asp Glu Glu Ala
 1               5                  10


<210> SEQ ID NO 77
<211> LENGTH: 337
<212> TYPE: DNA
<213> ORGANISM: Mycobacterium vaccae

<400> SEQUENCE: 77

gatccctaca tcctgctggt cagctccaag gtgtcgaccg tcaaggatct g ctcccgctg     60

ctggagaagg tcatccaggc cggcaagccg ctgctgatca tcgccgagga c gtcgagggc    120

gaggccctgt ccacgctggt ggtcaacaag atccgcggca ccttcaagtc c gtcgccgtc    180

aaggctccgg gcttcggtga ccgccgcaag gcgatgctgc aggacatggc c atcctcacc    240

ggtggtcagg tcgtcagcga aagagtcggg ctgtccctgg agaccgccga c gtctcgctg    300

ctgggccagg cccgcaaggt cgtcgtcacc aaggaca                             337


<210> SEQ ID NO 78
<211> LENGTH: 112
<212> TYPE: PRT
<213> ORGANISM: Mycobacterium vaccae

<400> SEQUENCE: 78

Asp Pro Tyr Ile Leu Leu Val Ser Ser Lys V al Ser Thr Val Lys Asp
 1               5                  10                  15

Leu Leu Pro Leu Leu Glu Lys Val Ile Gln A la Gly Lys Pro Leu Leu
            20                  25                  30

Ile Ile Ala Glu Asp Val Glu Gly Glu Ala L eu Ser Thr Leu Val Val
        35                  40                  45

Asn Lys Ile Arg Gly Thr Phe Lys Ser Val A la Val Lys Ala Pro Gly
    50                  55                  60
```

-continued

```
Phe Gly Asp Arg Arg Lys Ala Met Leu Gln A sp Met Ala Ile Leu Thr
65                  70                  75                  80

Gly Gly Gln Val Val Ser Glu Arg Val Gly L eu Ser Leu Glu Thr Ala
                85                  90                  95

Asp Val Ser Leu Leu Gly Gln Ala Arg Lys V al Val Val Thr Lys Asp
            100                 105                 110


<210> SEQ ID NO 79
<211> LENGTH: 360
<212> TYPE: DNA
<213> ORGANISM: Mycobacterium vaccae

<400> SEQUENCE: 79

ccgtacgaga agatcggcgc tgagctggtc aaagaggtcg ccaagaagac c gacgacgtc     60

gcgggcgacg gcaccaccac cgccaccgtg ctcgctcagg ctctggttcg c gaaggcctg    120

cgcaacgtcg cagccggcgc caacccgctc ggcctcaagc gtggcatcga g aaggctgtc    180

gaggctgtca cccagtcgct gctgaagtcg gccaaggagg tcgagaccaa g gagcagatt    240

tctgccaccg cggcgatctc cgccggcgac acccagatcg gcgagctcat c gccgaggcc    300

atggacaagg tcggcaacga gggtgtcatc accgtcgagg agtcgaacac c ttcggcctg    360


<210> SEQ ID NO 80
<211> LENGTH: 120
<212> TYPE: PRT
<213> ORGANISM: Mycobacterium vaccae

<400> SEQUENCE: 80

Pro Tyr Glu Lys Ile Gly Ala Glu Leu Val L ys Glu Val Ala Lys Lys
 1               5                  10                  15

Thr Asp Asp Val Ala Gly Asp Gly Thr Thr T hr Ala Thr Val Leu Ala
            20                  25                  30

Gln Ala Leu Val Arg Glu Gly Leu Arg Asn V al Ala Ala Gly Ala Asn
        35                  40                  45

Pro Leu Gly Leu Lys Arg Gly Ile Glu Lys A la Val Glu Ala Val Thr
    50                  55                  60

Gln Ser Leu Leu Lys Ser Ala Lys Glu Val G lu Thr Lys Glu Gln Ile
65                  70                  75                  80

Ser Ala Thr Ala Ala Ile Ser Ala Gly Asp T hr Gln Ile Gly Glu Leu
                85                  90                  95

Ile Ala Glu Ala Met Asp Lys Val Gly Asn G lu Gly Val Ile Thr Val
            100                 105                 110

Glu Glu Ser Asn Thr Phe Gly Leu
        115                 120


<210> SEQ ID NO 81
<211> LENGTH: 43
<212> TYPE: DNA
<213> ORGANISM: Artificial Sequence
<220> FEATURE:
<223> OTHER INFORMATION: Made in a lab

<400> SEQUENCE: 81

actgacgctg aggagcgaaa gcgtggggag cgaacaggat tag                        43


<210> SEQ ID NO 82
<211> LENGTH: 43
<212> TYPE: DNA
<213> ORGANISM: Artificial Sequence
<220> FEATURE:
```

-continued

<223> OTHER INFORMATION: Made in a lab

<400> SEQUENCE: 82
cgacaaggaa cttcgctacc ttaggaccgt catagttacg ggc 43

<210> SEQ ID NO 83
<211> LENGTH: 20
<212> TYPE: DNA
<213> ORGANISM: Artificial Sequence
<220> FEATURE:
<223> OTHER INFORMATION: Made in a lab

<400> SEQUENCE: 83
aaaaaaaaaa aaaaaaaaaa 20

<210> SEQ ID NO 84
<211> LENGTH: 31
<212> TYPE: DNA
<213> ORGANISM: Artificial Sequence
<220> FEATURE:
<223> OTHER INFORMATION: Made in a lab

<400> SEQUENCE: 84
ggaaggaagc ggccgctttt tttttttttt t 31

<210> SEQ ID NO 85
<211> LENGTH: 31
<212> TYPE: DNA
<213> ORGANISM: Artificial Sequence
<220> FEATURE:
<223> OTHER INFORMATION: Made in a lab

<400> SEQUENCE: 85
gagagagagc ccgggcatgc tsctsctsct s 31

<210> SEQ ID NO 86
<211> LENGTH: 238
<212> TYPE: DNA
<213> ORGANISM: Mycobacterium vaccae

<400> SEQUENCE: 86
ctcgatgaac cgctcggagc gctcgacctg aagctgcgcc acgtcatgca g ttcgagctc 60 aagcgcatcc agcgggaggt cgggatcacg ttcatctacg tgacccacga c caggaagag 120 gcgctcacga tgagtgaccg catcgcggtg atgaacgccg gcaacgtcga a cagatcggc 180 agcccgaccg agatctacga ccgtcccgcg acggtgttcg tcgccagctt c atcgaat 238

<210> SEQ ID NO 87
<211> LENGTH: 79
<212> TYPE: PRT
<213> ORGANISM: Mycobacterium vaccae

<400> SEQUENCE: 87

Leu Asp Glu Pro Leu Gly Ala Leu Asp Leu L ys Leu Arg His Val Met
1 5 10 15

Gln Phe Glu Leu Lys Arg Ile Gln Arg Glu V al Gly Ile Thr Phe Ile
20 25 30

Tyr Val Thr His Asp Gln Glu Glu Ala Leu T hr Met Ser Asp Arg Ile
35 40 45

Ala Val Met Asn Ala Gly Asn Val Glu Gln I le Gly Ser Pro Thr Glu
50 55 60

Ile Tyr Asp Arg Pro Ala Thr Val Phe Val A la Ser Phe Ile Glu

-continued 65 70 75

<210> SEQ ID NO 88
<211> LENGTH: 1518
<212> TYPE: DNA
<213> ORGANISM: Mycobacterium vaccae

<400> SEQUENCE: 88
cactcgccat gggtgttaca ataccccacc agttcctcga agtaaacgaa c agaaccgtg 60 acatccagct gagaaaatat tcacagcgac gaagcccggc cgatgcctga t ggggtccgg 120 catcagtaca gcgcgctttc ctgcgcggat tctattgtcg agtccggggt g tgacgaagg 180 aatccattgt cgaaatgtaa attcgttgcg gaatcacttg cataggtccg t cagatccgc 240 gaaggtttac cccacagcca cgacggctgt ccccgaggag gacctgccct g accggcaca 300 cacatcaccg ctgcagaacc tgcagaacag acggcggatt ccgcggcacc g cccaagggc 360 gcgccggtga tcgagatcga ccatgtcacg aagcgcttcg gcgactacct g gccgtcgcg 420 gacgcagact tctccatcgc gcccggggag ttcttctcca tgctcggccc g tccgggtgt 480 gggaagacga ccacgttgcg catgatcgcg ggattcgaga ccccgactga a ggggcgatc 540 cgcctcgaag gcgccgacgt gtcgaggacc ccacccaaca agcgcaacgt c aacacggtg 600 ttccagcact acgcgctgtt cccgcacatg acggtctggg acaacgtcgc g tacggcccg 660 cgcagcaaga aactcggcaa aggcgaggtc cgcaagcgcg tcgacgagct g ctggagatc 720 gtccggctga ccgaatttgc cgagcgcagg cccgcccagc tgtccggcgg g cagcagcag 780 cgggtggcgt tggcccgggc actggtgaac taccccagcg cgctgctgct c gatgaaccg 840 ctcggagcgc tcgacctgaa gctgcgccac gtcatgcagt tcgagctcaa g cgcatccag 900 cgggaggtcg ggatcacgtt catctacgtg acccacgacc aggaagaggc g ctcacgatg 960 agtgaccgca tcgcggtgat gaacgccggc aacgtcgaac agatcggcag c ccgaccgag 1020 atctacgacc gtcccgcgac ggtgttcgtc gccagcttca tcggacaggc c aacctctgg 1080 gcgggccggt gcaccggccg ctccaaccgc gattacgtcg agatcgacgt t ctcggctcg 1140 acgctgaagg cacgcccggg cgagaccacg atcgagcccg gcgggcacgc c accctgatg 1200 gtgcgtccgg aacgcatccg ggtcaccccg ggctcccagg acgcgccgac c ggtgacgtc 1260 gcctgcgtgc gtgccaccgt caccgacctg accttccaag gtccggtggt g cggctctcg 1320 ctggccgctc cggacgactc gaccgtgatc gcccacgtcg gccccgagca g gatctgccg 1380 ctgctgcgcc ccggcgacga cgtgtacgtc agctgggcac cggaagcctc c ctggtgctt 1440 cccggcgacg acatccccac caccgaggac ctcgaagaga tgctcgacga c tcctgagtc 1500 acgcttcccg attgccga 1518

<210> SEQ ID NO 89
<211> LENGTH: 376
<212> TYPE: PRT
<213> ORGANISM: Mycobacterium vaccae

<400> SEQUENCE: 89

Val Ile Glu Ile Asp His Val Thr Lys Arg P he Gly Asp Tyr Leu Ala
1 5 10 15

Val Ala Asp Ala Asp Phe Ser Ile Ala Pro G ly Glu Phe Phe Ser Met
20 25 30

Leu Gly Pro Ser Gly Cys Gly Lys Thr Thr T hr Leu Arg Met Ile Ala
35 40 45

-continued

Gly Phe Glu Thr Pro Thr Glu Gly Ala Ile A rg Leu Glu Gly Ala Asp
50 55 60

Val Ser Arg Thr Pro Pro Asn Lys Arg Asn V al Asn Thr Val Phe Gln
65 70 75 80

His Tyr Ala Leu Phe Pro His Met Thr Val T rp Asp Asn Val Ala Tyr
85 90 95

Gly Pro Arg Ser Lys Lys Leu Gly Lys Gly G lu Val Arg Lys Arg Val
100 105 110

Asp Glu Leu Leu Glu Ile Val Arg Leu Thr G lu Phe Ala Glu Arg Arg
115 120 125

Pro Ala Gln Leu Ser Gly Gly Gln Gln Gln A rg Val Ala Leu Ala Arg
130 135 140

Ala Leu Val Asn Tyr Pro Ser Ala Leu Leu L eu Asp Glu Pro Leu Gly
145 150 155 160

Ala Leu Asp Leu Lys Leu Arg His Val Met G ln Phe Glu Leu Lys Arg
165 170 175

Ile Gln Arg Glu Val Gly Ile Thr Phe Ile T yr Val Thr His Asp Gln
180 185 190

Glu Glu Ala Leu Thr Met Ser Asp Arg Ile A la Val Met Asn Ala Gly
195 200 205

Asn Val Glu Gln Ile Gly Ser Pro Thr Glu I le Tyr Asp Arg Pro Ala
210 215 220

Thr Val Phe Val Ala Ser Phe Ile Gly Gln A la Asn Leu Trp Ala Gly
225 230 235 240

Arg Cys Thr Gly Arg Ser Asn Arg Asp Tyr V al Glu Ile Asp Val Leu
245 250 255

Gly Ser Thr Leu Lys Ala Arg Pro Gly Glu T hr Thr Ile Glu Pro Gly
260 265 270

Gly His Ala Thr Leu Met Val Arg Pro Glu A rg Ile Arg Val Thr Pro
275 280 285

Gly Ser Gln Asp Ala Pro Thr Gly Asp Val A la Cys Val Arg Ala Thr
290 295 300

Val Thr Asp Leu Thr Phe Gln Gly Pro Val V al Arg Leu Ser Leu Ala
305 310 315 320

Ala Pro Asp Asp Ser Thr Val Ile Ala His V al Gly Pro Glu Gln Asp
325 330 335

Leu Pro Leu Leu Arg Pro Gly Asp Asp Val T yr Val Ser Trp Ala Pro
340 345 350

Glu Ala Ser Leu Val Leu Pro Gly Asp Asp I le Pro Thr Thr Glu Asp
355 360 365

Leu Glu Glu Met Leu Asp Asp Ser
370 375

<210> SEQ ID NO 90
<211> LENGTH: 33
<212> TYPE: DNA
<213> ORGANISM: Artificial Sequence
<220> FEATURE:
<223> OTHER INFORMATION: Made in a lab

<400> SEQUENCE: 90
gagagactcg aggtgatcga gatcgaccat gtc 33

<210> SEQ ID NO 91
<211> LENGTH: 31
<212> TYPE: DNA

-continued

<213> ORGANISM: Artificial Sequence
<220> FEATURE:
<223> OTHER INFORMATION: Made in a lab

<400> SEQUENCE: 91
agagactcga gcaatcggga agcgtgactc a 31

<210> SEQ ID NO 92
<211> LENGTH: 323
<212> TYPE: DNA
<213> ORGANISM: Mycobacterium vaccae

<400> SEQUENCE: 92
gtcgactaca aagaagactt caacgacaac gagcagtggt tcgccaaggt c aaggagccg 60 ttgtcgcgca agcaggacat aggcgccgac ctggtgatcc ccaccgagtt c atggccgcg 120 cgcgtcaagg gcctgggatg gctcaatgag atcagcgaag ccggcgtgcc c aatcgcaag 180 aatctgcgtc aggacctgtt ggactcgagc atcgacgagg gccgcaagtt c accgcgccg 240 tacatgaccg gcatggtcgg tctcgcctac aacaaggcag ccaccggacg c gatatccgc 300 accatcgacg acctctggga tcc 323

<210> SEQ ID NO 93
<211> LENGTH: 1341
<212> TYPE: DNA
<213> ORGANISM: Mycobacterium vaccae

<400> SEQUENCE: 93
ccccaccccc ttccctggag ccgacgaaag gcacccgcac atgtcccgtg a catcgatcc 60 ccacctgctg gcccgaatga ccgcacgccg caccttgcgt cgccgcttca t cggcggtgg 120 cgccgcggcc gccgcgggcc tgaccctcgg ttcgtcgttc ctggcggcgt g cgggtccga 180 cagtgggacc tcgagcacca cgtcacagga cagcggcccc gccagcggcg c cctgcgcgt 240 ctccaactgg ccgctctata tggccgacgg tttcatcgca gcgttccaga c cgcctcggg 300 catcacggtc gactacaaag aagacttcaa cgacaacgag cagtggttcg c caaggtcaa 360 ggagccgttg tcgcgcaagc aggacatagg cgccgacctg gtgatcccca c cgagttcat 420 ggccgcgcgc gtcaagggcc tgggatggct caatgagatc agcgaagccg g cgtgcccaa 480 tcgcaagaat ctgcgtcagg acctgttgga ctcgagcatc gacgagggcc g caagttcac 540 cgcgccgtac atgaccggca tggtcggtct cgcctacaac aaggcagcca c cggacgcga 600 tatccgcacc atcgacgacc tctgggatcc cgcgttcaag ggccgcgtca g tctgttctc 660 cgacgtccag gacggcctcg gcatgatcat gctctcgcag ggcaactcgc c ggagaatcc 720 gaccaccgag tccattcagc aggcggtcga tctggtccgc gaacagaacg a caggggtc 780 agatccgtcg cttcaccggc aacgactacg ccgacgacct ggccgcagaa a catcgccat 840 cgcgcaggcg tactccggtg acgtcgtgca gctgcaggcg gacaaccccg a tctgcagtt 900 catcgttccc gaatccggcg gcgactggtt cgtcgacacg atggtgatcc c gtacaccac 960 gcagaaccag aaggccgccg aggcgtggat cgactacatc tacgaccgag c caactacgc 1020 caagctggtc gcgttcaccc agttcgtgcc cgcactctcg gacatgaccg a cgaactcgc 1080 caaggtcgat cctgcatcgg cggagaaccc gctgatcaac ccgtcggccg a ggtgcaggc 1140 gaacctgaag tcgtgggcgg cactgaccga cgagcagacg caggagttca a cactgcgta 1200 cgccgccgtc accggcggct gacgcggtgg tagtgccgat gcgaggggca t aaatggccc 1260 tgcggacgcg aggagcataa atggccggtg tcgccaccag cagccgtcag c ggacaaggt 1320

-continued cgctccgtat ctgatggtcc t 1341

<210> SEQ ID NO 94
<211> LENGTH: 393
<212> TYPE: PRT
<213> ORGANISM: Mycobacterium vaccae

<400> SEQUENCE: 94

Met Ser Arg Asp Ile Asp Pro His Leu Leu A la Arg Met Thr Ala Arg
1 5 10 15

Arg Thr Leu Arg Arg Arg Phe Ile Gly Gly G ly Ala Ala Ala Ala Ala
20 25 30

Gly Leu Thr Leu Gly Ser Ser Phe Leu Ala A la Cys Gly Ser Asp Ser
35 40 45

Gly Thr Ser Ser Thr Thr Ser Gln Asp Ser G ly Pro Ala Ser Gly Ala
50 55 60

Leu Arg Val Ser Asn Trp Pro Leu Tyr Met A la Asp Gly Phe Ile Ala
65 70 75 80

Ala Phe Gln Thr Ala Ser Gly Ile Thr Val A sp Tyr Lys Glu Asp Phe
85 90 95

Asn Asp Asn Glu Gln Trp Phe Ala Lys Val L ys Glu Pro Leu Ser Arg
100 105 110

Lys Gln Asp Ile Gly Ala Asp Leu Val Ile P ro Thr Glu Phe Met Ala
115 120 125

Ala Arg Val Lys Gly Leu Gly Trp Leu Asn G lu Ile Ser Glu Ala Gly
130 135 140

Val Pro Asn Arg Lys Asn Leu Arg Gln Asp L eu Leu Asp Ser Ser Ile
145 150 155 160

Asp Glu Gly Arg Lys Phe Thr Ala Pro Tyr M et Thr Gly Met Val Gly
165 170 175

Leu Ala Tyr Asn Lys Ala Ala Thr Gly Arg A sp Ile Arg Thr Ile Asp
180 185 190

Asp Leu Trp Asp Pro Ala Phe Lys Gly Arg V al Ser Leu Phe Ser Asp
195 200 205

Val Gln Asp Gly Leu Gly Met Ile Met Leu S er Gln Gly Asn Ser Pro
210 215 220

Glu Asn Pro Thr Thr Glu Ser Ile Gln Gln A la Val Asp Leu Val Arg
225 230 235 240

Glu Gln Asn Asp Arg Gly Ser Asp Pro Ser L eu His Arg Gln Arg Leu
245 250 255

Arg Arg Arg Pro Gly Arg Arg Asn Ile Ala I le Ala Gln Ala Tyr Ser
260 265 270

Gly Asp Val Val Gln Leu Gln Ala Asp Asn P ro Asp Leu Gln Phe Ile
275 280 285

Val Pro Glu Ser Gly Gly Asp Trp Phe Val A sp Thr Met Val Ile Pro
290 295 300

Tyr Thr Thr Gln Asn Gln Lys Ala Ala Glu A la Trp Ile Asp Tyr Ile
305 310 315 320

Tyr Asp Arg Ala Asn Tyr Ala Lys Leu Val A la Phe Thr Gln Phe Val
325 330 335

Pro Ala Leu Ser Asp Met Thr Asp Glu Leu A la Lys Val Asp Pro Ala
340 345 350

Ser Ala Glu Asn Pro Leu Ile Asn Pro Ser A la Glu Val Gln Ala Asn
355 360 365

-continued

```
Leu Lys Ser Trp Ala Ala Leu Thr Asp Glu G ln Thr Gln Glu Phe Asn
    370                 375                 380

Thr Ala Tyr Ala Ala Val Thr Gly Gly
385                 390


<210> SEQ ID NO 95
<211> LENGTH: 22
<212> TYPE: DNA
<213> ORGANISM: Mycobacterium vaccae

<400> SEQUENCE: 95

atgtcccgtg acatcgatcc cc                                              22


<210> SEQ ID NO 96
<211> LENGTH: 21
<212> TYPE: DNA
<213> ORGANISM: Mycobacterium vaccae

<400> SEQUENCE: 96

atcggcacta ccaccgcgtc a                                               21


<210> SEQ ID NO 97
<211> LENGTH: 861
<212> TYPE: DNA
<213> ORGANISM: Mycobacterium vaccae

<400> SEQUENCE: 97

gccggcgctc gcatatctcg cgatcttctt ccgtggtgcc gttcttctcg c tggcacgca     60

cctcgttgtc ggagaccggc ggctcggtgt tcatgccgac gctgacgttc g cctgggact    120

tcggcaacta cgtcgacgcg ttcacgatgt accacgagca gatcttccgc t cgttcggct    180

acgcgttcgt cgccacggtg ctgtgcctgt tgctggcgtt cccgctggcc t acgtcatcg    240

cgttcaaggc cggccggttc aagaacctga tcctggggct ggtgatcctg c cgttcttcg    300

tcacgttcct gatccgcacc attgcgtgga agacgatcct ggccgacgaa g gctgggtgg    360

tcaccgcgct gggcgccatc gggctgctgc ctgacgaggg ccggctgctg t ccaccagct    420

gggcggtcat cggcggtctg acctacaact ggatcatctt catgatcctg c cgctgtacg    480

tcagcctgga gaagatcgac ccgcgtctgc tggaggcctc ccaggacctc t actcgtcgg    540

cgccgcgcag cttcggcaag gtgatcctgc cgatggcgat gcccggggtg c tggccggga    600

gcatgctggt gttcatcccg gccgtcggcg acttcatcaa cgccgactat c tcggcagta    660

cccagaccac catgatcggc aacgtgatcc agaagcagtt cctggtcgtc a aggactatc    720

cggcggcggc cgcgctgagt ctggggctga tgttgctgat cctgatcggc g tgctcctct    780

acacacgggc gctgggttcg gaggatctgg tatgaccacc caggcaggcg c cgcactggc    840

caccgccgcc cagcaggatc c                                              861


<210> SEQ ID NO 98
<211> LENGTH: 259
<212> TYPE: PRT
<213> ORGANISM: Mycobacterium vaccae

<400> SEQUENCE: 98

Val Val Pro Phe Phe Ser Leu Ala Arg Thr S er Leu Ser Glu Thr Gly
 1               5                  10                  15

Gly Ser Val Phe Met Pro Thr Leu Thr Phe A la Trp Asp Phe Gly Asn
            20                  25                  30
```

-continued

```
Tyr Val Asp Ala Phe Thr Met Tyr His Glu G ln Ile Phe Arg Ser Phe
        35                  40                  45

Gly Tyr Ala Phe Val Ala Thr Val Leu Cys L eu Leu Leu Ala Phe Pro
    50                  55                  60

Leu Ala Tyr Val Ile Ala Phe Lys Ala Gly A rg Phe Lys Asn Leu Ile
65                  70                  75                  80

Leu Gly Leu Val Ile Leu Pro Phe Phe Val T hr Phe Leu Ile Arg Thr
                85                  90                  95

Ile Ala Trp Thr Ile Leu Ala Asp Glu Gly T rp Val Val Thr Ala Leu
            100                 105                 110

Gly Ala Ile Gly Leu Leu Pro Asp Glu Gly A rg Leu Leu Ser Thr Ser
        115                 120                 125

Trp Ala Val Ile Gly Gly Leu Thr Tyr Asn T rp Ile Ile Phe Met Ile
    130                 135                 140

Leu Pro Leu Tyr Val Ser Leu Glu Lys Ile A sp Pro Arg Leu Leu Glu
145                 150                 155                 160

Ala Ser Gln Asp Leu Tyr Ser Ser Ala Pro A rg Ser Phe Gly Lys Val
                165                 170                 175

Ile Leu Pro Met Ala Met Pro Gly Val Leu A la Gly Ser Met Leu Val
            180                 185                 190

Phe Ile Pro Ala Val Gly Asp Phe Ile Asn A la Asp Tyr Leu Gly Ser
        195                 200                 205

Thr Gln Thr Thr Met Ile Gly Asn Val Ile G ln Lys Gln Phe Leu Val
    210                 215                 220

Val Lys Asp Tyr Pro Ala Ala Ala Ala Leu S er Leu Gly Leu Met Leu
225                 230                 235                 240

Leu Ile Leu Ile Gly Val Leu Leu Tyr Thr A rg Ala Leu Gly Ser Glu
                245                 250                 255

Asp Leu Val


<210> SEQ ID NO 99
<211> LENGTH: 277
<212> TYPE: DNA
<213> ORGANISM: Mycobacterium vaccae

<400> SEQUENCE: 99

gtaatctttg ctggagcccg tacgccggta ggcaaactca tgggttcgct c aaggacttc     60

aagggcagcg atctcggtgc cgtggcgatc aagggcgccc tggagaaagc c ttccccggc    120

gtcgacgacc ctgctcgtct cgtcgagtac gtgatcatgg gccaagtgct c tccgccggc    180

gccggccaga tgcccgcccg ccaggccgcc gtcgccgccg gcatcccgtg g gacgtcgcc    240

tcgctgacga tcaacaagat gtgcctgtcg ggcatcg                             277


<210> SEQ ID NO 100
<211> LENGTH: 92
<212> TYPE: PRT
<213> ORGANISM: Mycobacterium vaccae

<400> SEQUENCE: 100

Val Ile Phe Ala Gly Ala Arg Thr Pro Val G ly Lys Leu Met Gly Ser
 1               5                  10                  15

Leu Lys Asp Phe Lys Gly Ser Asp Leu Gly A la Val Ala Ile Lys Gly
            20                  25                  30

Ala Leu Glu Lys Ala Phe Pro Gly Val Asp A sp Pro Ala Arg Leu Val
        35                  40                  45
```

-continued

```
Glu Tyr Val Ile Met Gly Gln Val Leu Ser A la Gly Ala Gly Gln Met
    50                  55                  60

Pro Ala Arg Gln Ala Ala Val Ala Ala Gly I le Pro Trp Asp Val Ala
65                  70                  75                  80

Ser Leu Thr Ile Asn Lys Met Cys Leu Ser G ly Ile
                85                  90


<210> SEQ ID NO 101
<211> LENGTH: 12
<212> TYPE: PRT
<213> ORGANISM: Mycobacterium vaccae
<220> FEATURE:
<221> NAME/KEY: UNSURE
<222> LOCATION: (1)...(1)
<223> OTHER INFORMATION: Residue can be either Glu or Pro
<220> FEATURE:
<221> NAME/KEY: UNSURE
<222> LOCATION: (2)...(2)
<223> OTHER INFORMATION: Residue can be either Pro or Glu
<220> FEATURE:
<221> NAME/KEY: UNSURE
<222> LOCATION: (7)...(7)
<221> NAME/KEY: UNSURE
<222> LOCATION: (12)...(12)

<400> SEQUENCE: 101

Xaa Xaa Ala Asp Arg Gly Xaa Ser Lys Tyr A rg Xaa
1               5                   10


<210> SEQ ID NO 102
<211> LENGTH: 24
<212> TYPE: PRT
<213> ORGANISM: Mycobacterium vaccae
<220> FEATURE:
<221> NAME/KEY: UNSURE
<222> LOCATION: (1)...(1)

<400> SEQUENCE: 102

Xaa Ile Asp Glu Ser Leu Phe Asp Ala Glu G lu Lys Met Glu Lys Ala
 1               5                  10                  15

Val Ser Val Ala Arg Asp Ser Ala
            20


<210> SEQ ID NO 103
<211> LENGTH: 23
<212> TYPE: PRT
<213> ORGANISM: Mycobacterium vaccae
<220> FEATURE:
<221> NAME/KEY: UNSURE
<222> LOCATION: (1)...(2)
<221> NAME/KEY: UNSURE
<222> LOCATION: (15)...(15)
<221> NAME/KEY: UNSURE
<222> LOCATION: (17)...(17)

<400> SEQUENCE: 103

Xaa Xaa Ile Ala Pro Ala Thr Ser Gly Thr L eu Ser Glu Phe Xaa Ala
 1               5                  10                  15

Xaa Lys Gly Val Thr Met Glu
            20


<210> SEQ ID NO 104
<211> LENGTH: 15
<212> TYPE: PRT
<213> ORGANISM: Mycobacterium vaccae

<400> SEQUENCE: 104
```

-continued

```
Pro Asn Val Pro Asp Ala Phe Ala Val Leu A la Asp Arg Val Gly
 1               5                  10                  15


<210> SEQ ID NO 105
<211> LENGTH: 9
<212> TYPE: PRT
<213> ORGANISM: Mycobacterium vaccae
<220> FEATURE:
<221> NAME/KEY: UNSURE
<222> LOCATION: (1)...(1)

<400> SEQUENCE: 105

Xaa Ile Arg Val Gly Val Asn Gly Phe
 1               5


<210> SEQ ID NO 106
<211> LENGTH: 485
<212> TYPE: DNA
<213> ORGANISM: Mycobacterium vaccae

<400> SEQUENCE: 106

agcggctggg acatcaacac cgccgccttc gagtggtacg tcgactcggg t ctcgcggtg     60

atcatgcccg tcggcgggca gtccagcttc tacagcgact ggtacagccc g gcctgcggt    120

aaggccggct gccagaccta caagtgggag acgttcctga cccaggagct g ccggcctac    180

ctcgccgcca acaagggggt cgacccgaac cgcaacgcgg ccgtcggtct g tccatggcc    240

ggttcggcgg cgctgacgct ggcgatctac cacccgcagc agttccagta c gccgggtcg    300

ctgtcgggct acctgaaccc gtccgagggg tggtggccga tgctgatcaa c atctcgatg    360

ggtgacgcgg gcggctacaa ggccaacgac atgtggggtc gcaccgagga c ccgagcagc    420

gcctggaagc gcaacgaccc gatggtcaac atcggcaagc tggtcgccaa c aacaccccc    480

ctctc                                                                485


<210> SEQ ID NO 107
<211> LENGTH: 501
<212> TYPE: DNA
<213> ORGANISM: Mycobacterium vaccae
<220> FEATURE:
<221> NAME/KEY: unsure
<222> LOCATION: (441)...(441)
<221> NAME/KEY: unsure
<222> LOCATION: (450)...(450)

<400> SEQUENCE: 107

atgccggtgc gacgtgcgcg cagtgcgctt gcgtccgtga ccttcgtcgc g gccgcgtgc     60

gtgggcgctg agggcaccgc actggcggcg acgccggact ggagcgggcg c tacacggtg    120

gtgacgttcg cctccgacaa actcggcacg agtgtggccg cccgccagcc a gaacccgac    180

ttcagcggtc agtacacctt cagcacgtcc tgtgtgggca cctgcgtggc c accgcgtcc    240

gacggcccgg cgccgtcgaa cccgacgatt ccgcagcccg cgcgctacac c tgggacggc    300

aggcagtggg tgttcaacta caactggcag tgggagtgct tccgcggcgc c gacgtcccg    360

cgcgagtacg ccgccgcgcg ttcgctggtg ttctacgccc cgaccgccga c gggtcgatg    420

ttcggcacct ggcgcaccga natcctggan ggcctctgca agggcaccgt g atcatgccg    480

gtcgcggcct atccggcgta g                                              501


<210> SEQ ID NO 108
<211> LENGTH: 180
<212> TYPE: DNA
<213> ORGANISM: Mycobacterium vaccae
```

-continued

<400> SEQUENCE: 108
atgaaccagc cgcggcccga ggccgaggcg aacctgcggg gctacttcac c gccaacccg 60 gcggagtact acgacctgcg gggcatcctc gccccgatcg gtgacgcgca g cgcaactgc 120 aacatcaccg tgctgccggt agagctgcag acggcctacg acacgttcat g gccggctga 180

<210> SEQ ID NO 109
<211> LENGTH: 166
<212> TYPE: PRT
<213> ORGANISM: Mycobacterium vaccae

<400> SEQUENCE: 109

Met Pro Val Arg Arg Ala Arg Ser Ala Leu A la Ser Val Thr Phe Val
1 5 10 15

Ala Ala Ala Cys Val Gly Ala Glu Gly Thr A la Leu Ala Ala Thr Pro
20 25 30

Asp Trp Ser Gly Arg Tyr Thr Val Val Thr P he Ala Ser Asp Lys Leu
35 40 45

Gly Thr Ser Val Ala Ala Arg Gln Pro Glu P ro Asp Phe Ser Gly Gln
50 55 60

Tyr Thr Phe Ser Thr Ser Cys Val Gly Thr C ys Val Ala Thr Ala Ser
65 70 75 80

Asp Gly Pro Ala Pro Ser Asn Pro Thr Ile P ro Gln Pro Ala Arg Tyr
85 90 95

Thr Trp Asp Gly Arg Gln Trp Val Phe Asn T yr Asn Trp Gln Trp Glu
100 105 110

Cys Phe Arg Gly Ala Asp Val Pro Arg Glu T yr Ala Ala Ala Arg Ser
115 120 125

Leu Val Phe Tyr Ala Pro Thr Ala Asp Gly S er Met Phe Gly Thr Trp
130 135 140

Arg Thr Asp Ile Leu Asp Gly Leu Cys Lys G ly Thr Val Ile Met Pro
145 150 155 160

Val Ala Ala Tyr Pro Ala
165

<210> SEQ ID NO 110
<211> LENGTH: 74
<212> TYPE: PRT
<213> ORGANISM: Mycobacterium vaccae

<400> SEQUENCE: 110

Pro Arg Asp Thr His Pro Gly Ala Asn Gln A la Val Thr Ala Ala Met
1 5 10 15

Asn Gln Pro Arg Pro Glu Ala Glu Ala Asn L eu Arg Gly Tyr Phe Thr
20 25 30

Ala Asn Pro Ala Glu Tyr Tyr Asp Leu Arg G ly Ile Leu Ala Pro Ile
35 40 45

Gly Asp Ala Gln Arg Asn Cys Asn Ile Thr V al Leu Pro Val Glu Leu
50 55 60

Gln Thr Ala Tyr Asp Thr Phe Met Ala Gly
65 70

<210> SEQ ID NO 111
<211> LENGTH: 503
<212> TYPE: DNA
<213> ORGANISM: Mycobacterium vaccae
<220> FEATURE:

-continued

<221> NAME/KEY: unsure
<222> LOCATION: (358)...(358)

<400> SEQUENCE: 111

```
atgcaggtgc ggcgtgttct gggcagtgtc ggtgcagcag tcgcggtttc g gccgcgtta     60

tggcagacgg gggtttcgat accgaccgcc tcagcggatc cgtgtccgga c atcgaggtg    120

atcttcgcgc gcgggaccgg tgcggaaccc ggcctcgggt gggtcggtga t gcgttcgtc    180

aacgcgctgc ggcccaaggt cggtgagcag tcggtgggca cctacgcggt g aactacccg    240

gcaggattcg gacttcgaca aatcggcgcc catgggcgcg gccgacgcat c ggggcgggt    300

gcagtggatg gccgacaact gcccggacac caagcttgtc ctgggcggca t gtcgcangg    360

cgccggcgtc atcgacctga tcaccgtcga tccgcgaccg ctgggccggt t cacccccac    420

cccgatgccg ccccgcgtcg ccgaccacgt ggccgccgtt gtggtcttcg g aaatccgtt    480

gcgcgacatc cgtggtggcg gtc                                            503
```

<210> SEQ ID NO 112
<211> LENGTH: 167
<212> TYPE: PRT
<213> ORGANISM: Mycobacterium vaccae
<220> FEATURE:
<221> NAME/KEY: UNSURE
<222> LOCATION: (119)...(119)

<400> SEQUENCE: 112

```
Met Gln Val Arg Arg Val Leu Gly Ser Val G ly Ala Ala Val Ala Val
 1               5                  10                  15

Ser Ala Ala Leu Trp Gln Thr Gly Val Ser I le Pro Thr Ala Ser Ala
            20                  25                  30

Asp Pro Cys Pro Asp Ile Glu Val Ile Phe A la Arg Gly Thr Gly Ala
        35                  40                  45

Glu Pro Gly Leu Gly Trp Val Gly Asp Ala P he Val Asn Ala Leu Arg
    50                  55                  60

Pro Lys Val Gly Glu Gln Ser Val Gly Thr T yr Ala Val Asn Tyr Pro
65                  70                  75                  80

Ala Gly Phe Asp Phe Asp Lys Ser Ala Pro M et Gly Ala Ala Asp Ala
                85                  90                  95

Ser Gly Arg Val Gln Trp Met Ala Asp Asn C ys Pro Asp Thr Lys Leu
            100                 105                 110

Val Leu Gly Gly Met Ser Xaa Gly Ala Gly V al Ile Asp Leu Ile Thr
        115                 120                 125

Val Asp Pro Arg Pro Leu Gly Arg Phe Thr P ro Thr Pro Met Pro Pro
    130                 135                 140

Arg Val Ala Asp His Val Ala Ala Val Val V al Phe Gly Asn Pro Leu
145                 150                 155                 160

Arg Asp Ile Arg Gly Gly Gly
                165
```

<210> SEQ ID NO 113
<211> LENGTH: 1569
<212> TYPE: DNA
<213> ORGANISM: Mycobacterium vaccae

<400> SEQUENCE: 113

```
atggccaaga caattgcgta tgacgaagag gcccgccgtg gcctcgagcg g ggcctcaac     60

gccctcgcag acgccgtaaa ggtgacgttg ggcccgaagg gtcgcaacgt c gtgctggag    120
```

-continued

```
aagaagtggg gcgcccccac gatcaccaac gatggtgtgt ccatcgccaa g gagatcgag    180

ctggaggacc cgtacgagaa gatcggcgct gagctggtca aagaggtcgc c aagaagacc    240

gacgacgtcg cgggcgacgg caccaccacc gccaccgtgc tcgctcaggc t ctggttcgc    300

gaaggcctgc gcaacgtcgc agccggcgcc aacccgctcg gcctcaagcg t ggcatcgag    360

aaggctgtcg aggctgtcac ccagtcgctg ctgaagtcgg ccaaggaggt c gagaccaag    420

gagcagattt ctgccaccgc ggcgatttcc gccggcgaca cccagatcgg c gagctcatc    480

gccgaggcca tggacaaggt cggcaacgag ggtgtcatca ccgtcgagga g tcgaacacc    540

ttcggcctgc agctcgagct caccgagggt atgcgcttcg acaagggcta c atctcgggt    600

tacttcgtga ccgacgccga gcgccaggaa gccgtcctgg aggatcccta c atcctgctg    660

gtcagctcca aggtgtcgac cgtcaaggat ctgctcccgc tgctggagaa g gtcatccag    720

gccggcaagc cgctgctgat catcgccgag gacgtcgagg gcgaggccct g tccacgctg    780

gtggtcaaca agatccgcgg caccttcaag tccgtcgccg tcaaggctcc g ggcttcggt    840

gaccgccgca aggcgatgct gcaggacatg gccatcctca ccggtggtca g gtcgtcagc    900

gaaagagtcg ggctgtccct ggagaccgcc gacgtctcgc tgctgggcca g gcccgcaag    960

gtcgtcgtca ccaaggacga gaccaccatc gtcgagggct cgggcgattc c gatgccatc   1020

gccggccggg tggctcagat ccgcgccgag atcgagaaca gcgactccga c tacgaccgc   1080

gagaagctgc aggagcgcct ggccaagctg gccggcggtg ttgcggtgat c aaggccgga   1140

gctgccaccg aggtggagct caaggagcgc aagcaccgca tcgaggacgc c gtccgcaac   1200

gcgaaggctg ccgtcgaaga gggcatcgtc gccggtggcg gcgtggctct g ctgcagtcg   1260

gctcctgcgc tggacgacct cggcctgacg ggcgacgagg ccaccggtgc c aacatcgtc   1320

cgcgtggcgc tgtcggctcc gctcaagcag atcgccttca acggcggcct g gagcccggc   1380

gtcgttgccg agaaggtgtc caacctgccc gcgggtcacg gcctcaacgc c gcgaccggt   1440

gagtacgagg acctgctcaa ggccggcgtc gccgacccgg tgaaggtcac c cgctcggcg   1500

ctgcagaacg cggcgtccat cgcggctctg ttcctcacca ccgaggccgt c gtcgccgac   1560

aagccggag                                                          1569
```

```
<210> SEQ ID NO 114
<211> LENGTH: 523
<212> TYPE: PRT
<213> ORGANISM: Mycobacterium vaccae

<400> SEQUENCE: 114

Met Ala Lys Thr Ile Ala Tyr Asp Glu Glu A la Arg Arg Gly Leu Glu
 1               5                  10                  15

Arg Gly Leu Asn Ala Leu Ala Asp Ala Val L ys Val Thr Leu Gly Pro
            20                  25                  30

Lys Gly Arg Asn Val Val Leu Glu Lys Lys T rp Gly Ala Pro Thr Ile
        35                  40                  45

Thr Asn Asp Gly Val Ser Ile Ala Lys Glu I le Glu Leu Glu Asp Pro
    50                  55                  60

Tyr Glu Lys Ile Gly Ala Glu Leu Val Lys G lu Val Ala Lys Lys Thr
65                  70                  75                  80

Asp Asp Val Ala Gly Asp Gly Thr Thr Thr A la Thr Val Leu Ala Gln
                85                  90                  95

Ala Leu Val Arg Glu Gly Leu Arg Asn Val A la Ala Gly Ala Asn Pro
            100                 105                 110
```

-continued

```
Leu Gly Leu Lys Arg Gly Ile Glu Lys Ala V al Glu Ala Val Thr Gln
        115                 120                 125

Ser Leu Leu Lys Ser Ala Lys Glu Val Glu T hr Lys Glu Gln Ile Ser
    130                 135                 140

Ala Thr Ala Ala Ile Ser Ala Gly Asp Thr G ln Ile Gly Glu Leu Ile
145                 150                 155                 160

Ala Glu Ala Met Asp Lys Val Gly Asn Glu G ly Val Ile Thr Val Glu
                165                 170                 175

Glu Ser Asn Thr Phe Gly Leu Gln Leu Glu L eu Thr Glu Gly Met Arg
            180                 185                 190

Phe Asp Lys Gly Tyr Ile Ser Gly Tyr Phe V al Thr Asp Ala Glu Arg
        195                 200                 205

Gln Glu Ala Val Leu Glu Asp Pro Tyr Ile L eu Leu Val Ser Ser Lys
    210                 215                 220

Val Ser Thr Val Lys Asp Leu Leu Pro Leu L eu Glu Lys Val Ile Gln
225                 230                 235                 240

Ala Gly Lys Pro Leu Leu Ile Ile Ala Glu A sp Val Glu Gly Glu Ala
                245                 250                 255

Leu Ser Thr Leu Val Val Asn Lys Ile Arg G ly Thr Phe Lys Ser Val
            260                 265                 270

Ala Val Lys Ala Pro Gly Phe Gly Asp Arg A rg Lys Ala Met Leu Gln
        275                 280                 285

Asp Met Ala Ile Leu Thr Gly Gly Gln Val V al Ser Glu Arg Val Gly
    290                 295                 300

Leu Ser Leu Glu Thr Ala Asp Val Ser Leu L eu Gly Gln Ala Arg Lys
305                 310                 315                 320

Val Val Val Thr Lys Asp Glu Thr Thr Ile V al Glu Gly Ser Gly Asp
                325                 330                 335

Ser Asp Ala Ile Ala Gly Arg Val Ala Gln I le Arg Ala Glu Ile Glu
            340                 345                 350

Asn Ser Asp Ser Asp Tyr Asp Arg Glu Lys L eu Gln Glu Arg Leu Ala
        355                 360                 365

Lys Leu Ala Gly Gly Val Ala Val Ile Lys A la Gly Ala Ala Thr Glu
    370                 375                 380

Val Glu Leu Lys Glu Arg Lys His Arg Ile G lu Asp Ala Val Arg Asn
385                 390                 395                 400

Ala Lys Ala Ala Val Glu Glu Gly Ile Val A la Gly Gly Gly Val Ala
                405                 410                 415

Leu Leu Gln Ser Ala Pro Ala Leu Asp Asp L eu Gly Leu Thr Gly Asp
            420                 425                 430

Glu Ala Thr Gly Ala Asn Ile Val Arg Val A la Leu Ser Ala Pro Leu
        435                 440                 445

Lys Gln Ile Ala Phe Asn Gly Gly Leu Glu P ro Gly Val Val Ala Glu
    450                 455                 460

Lys Val Ser Asn Leu Pro Ala Gly His Gly L eu Asn Ala Ala Thr Gly
465                 470                 475                 480

Glu Tyr Glu Asp Leu Leu Lys Ala Gly Val A la Asp Pro Val Lys Val
                485                 490                 495

Thr Arg Ser Ala Leu Gln Asn Ala Ala Ser I le Ala Ala Leu Phe Leu
            500                 505                 510

Thr Thr Glu Ala Val Val Ala Asp Lys Pro G lu
        515                 520
```

-continued

```
<210> SEQ ID NO 115
<211> LENGTH: 647
<212> TYPE: DNA
<213> ORGANISM: Mycobacterium vaccae

<400> SEQUENCE: 115

atggccaaga caattgcgta tgacgaagag gcccgccgtg gcctcgagcg g ggcctcaac     60

gccctcgcag acgccgtaaa ggtgacgttg ggcccgaagg gtcgcaacgt c gtgctggag    120

aagaagtggg gcgcccccac gatcaccaac gatggtgtgt ccatcgccaa g gagatcgag    180

ctggaggacc cgtacgagaa gatcggcgct gagctggtca aagaggtcgc c aagaagacc    240

gacgacgtcg cgggcgacgg caccaccacc gccaccgtgc tcgctcaggc t ctggttcgc    300

gaaggcctgc gcaacgtcgc agccggcgcc aacccgctcg gcctcaagcg t ggcatcgag    360

aaggctgtcg aggctgtcac ccagtcgctg ctgaagtcgg ccaaggaggt c gagaccaag    420

gagcagattt ctgccaccgc ggcgatttcc gccggcgaca cccagatcgg c gagctcatc    480

gccgaggcca tggacaaggt cggcaacgag ggtgtcatca ccgtcgagga g tcgaacacc    540

ttcggcctgc agctcgagct caccgagggt atgcgcttcg acaagggcta c atctcgggt    600

tacttcgtga ccgacgccga gcgccaggaa gccgtcctgg aggatcc                 647


<210> SEQ ID NO 116
<211> LENGTH: 927
<212> TYPE: DNA
<213> ORGANISM: Mycobacterium vaccae

<400> SEQUENCE: 116

gatccctaca tcctgctggt cagctccaag gtgtcgaccg tcaaggatct g ctcccgctg     60

ctggagaagg tcatccaggc cggcaagccg ctgctgatca tcgccgagga c gtcgagggc    120

gaggccctgt ccacgctggt ggtcaacaag atccgcggca ccttcaagtc c gtcgccgtc    180

aaggctccgg gcttcggtga ccgccgcaag gcgatgctgc aggacatggc c atcctcacc    240

ggtggtcagg tcgtcagcga aagagtcggg ctgtccctgg agaccgccga c gtctcgctg    300

ctgggccagg cccgcaaggt cgtcgtcacc aaggacgaga ccaccatcgt c gagggctcg    360

ggcgattccg atgccatcgc cggccgggtg gctcagatcc gcgccgagat c gagaacagc    420

gactccgact acgaccgcga gaagctgcag gagcgcctgg ccaagctggc c ggcggtgtt    480

gcggtgatca aggccggagc tgccaccgag gtggagctca aggagcgcaa g caccgcatc    540

gaggacgccg tccgcaacgc gaaggctgcc gtcgaagagg gcatcgtcgc c ggtggcggc    600

gtggctctgc tgcagtcggc tcctgcgctg gacgacctcg gcctgacggg c gacgaggcc    660

accggtgcca acatcgtccg cgtggcgctg tcggctccgc tcaagcagat c gccttcaac    720

ggcggcctgg agcccggcgt cgttgccgag aaggtgtcca acctgcccgc g ggtcacggc    780

ctcaacgccg cgaccggtga gtacgaggac ctgctcaagg ccggcgtcgc c gacccggtg    840

aaggtcaccc gctcggcgct gcagaacgcg gcgtccatcg cggctctgtt c ctcaccacc    900

gaggccgtcg tcgccgacaa gccggag                                        927


<210> SEQ ID NO 117
<211> LENGTH: 215
<212> TYPE: PRT
<213> ORGANISM: Mycobacterium vaccae

<400> SEQUENCE: 117

Met Ala Lys Thr Ile Ala Tyr Asp Glu Glu A la Arg Arg Gly Leu Glu
 1               5                  10                  15
```

-continued

```
Arg Gly Leu Asn Ala Leu Ala Asp Ala Val L ys Val Thr Leu Gly Pro
            20                  25                  30

Lys Gly Arg Asn Val Val Leu Glu Lys Lys T rp Gly Ala Pro Thr Ile
        35                  40                  45

Thr Asn Asp Gly Val Ser Ile Ala Lys Glu I le Glu Leu Glu Asp Pro
    50                  55                  60

Tyr Glu Lys Ile Gly Ala Glu Leu Val Lys G lu Val Ala Lys Lys Thr
65                  70                  75                  80

Asp Asp Val Ala Gly Asp Gly Thr Thr Thr A la Thr Val Leu Ala Gln
                85                  90                  95

Ala Leu Val Arg Glu Gly Leu Arg Asn Val A la Ala Gly Ala Asn Pro
            100                 105                 110

Leu Gly Leu Lys Arg Gly Ile Glu Lys Ala V al Glu Ala Val Thr Gln
        115                 120                 125

Ser Leu Leu Lys Ser Ala Lys Glu Val Glu T hr Lys Glu Gln Ile Ser
    130                 135                 140

Ala Thr Ala Ala Ile Ser Ala Gly Asp Thr G ln Ile Gly Glu Leu Ile
145                 150                 155                 160

Ala Glu Ala Met Asp Lys Val Gly Asn Glu G ly Val Ile Thr Val Glu
                165                 170                 175

Glu Ser Asn Thr Phe Gly Leu Gln Leu Glu L eu Thr Glu Gly Met Arg
            180                 185                 190

Phe Asp Lys Gly Tyr Ile Ser Gly Tyr Phe V al Thr Asp Ala Glu Arg
        195                 200                 205

Gln Glu Ala Val Leu Glu Asp
    210                 215


<210> SEQ ID NO 118
<211> LENGTH: 309
<212> TYPE: PRT
<213> ORGANISM: Mycobacterium vaccae

<400> SEQUENCE: 118

Asp Pro Tyr Ile Leu Leu Val Ser Ser Lys V al Ser Thr Val Lys Asp
 1               5                  10                  15

Leu Leu Pro Leu Leu Glu Lys Val Ile Gln A la Gly Lys Pro Leu Leu
            20                  25                  30

Ile Ile Ala Glu Asp Val Glu Gly Glu Ala L eu Ser Thr Leu Val Val
        35                  40                  45

Asn Lys Ile Arg Gly Thr Phe Lys Ser Val A la Val Lys Ala Pro Gly
    50                  55                  60

Phe Gly Asp Arg Arg Lys Ala Met Leu Gln A sp Met Ala Ile Leu Thr
65                  70                  75                  80

Gly Gly Gln Val Val Ser Glu Arg Val Gly L eu Ser Leu Glu Thr Ala
                85                  90                  95

Asp Val Ser Leu Leu Gly Gln Ala Arg Lys V al Val Val Thr Lys Asp
            100                 105                 110

Glu Thr Thr Ile Val Glu Gly Ser Gly Asp S er Asp Ala Ile Ala Gly
        115                 120                 125

Arg Val Ala Gln Ile Arg Ala Glu Ile Glu A sn Ser Asp Ser Asp Tyr
    130                 135                 140

Asp Arg Glu Lys Leu Gln Glu Arg Leu Ala L ys Leu Ala Gly Gly Val
145                 150                 155                 160

Ala Val Ile Lys Ala Gly Ala Ala Thr Glu V al Glu Leu Lys Glu Arg
```

-continued 165 170 175

Lys His Arg Ile Glu Asp Ala Val Arg Asn A la Lys Ala Ala Val Glu
180 185 190

Glu Gly Ile Val Ala Gly Gly Gly Val Ala L eu Leu Gln Ser Ala Pro
195 200 205

Ala Leu Asp Asp Leu Gly Leu Thr Gly Asp G lu Ala Thr Gly Ala Asn
210 215 220

Ile Val Arg Val Ala Leu Ser Ala Pro Leu L ys Gln Ile Ala Phe Asn
225 230 235 240

Gly Gly Leu Glu Pro Gly Val Val Ala Glu L ys Val Ser Asn Leu Pro
245 250 255

Ala Gly His Gly Leu Asn Ala Ala Thr Gly G lu Tyr Glu Asp Leu Leu
260 265 270

Lys Ala Gly Val Ala Asp Pro Val Lys Val T hr Arg Ser Ala Leu Gln
275 280 285

Asn Ala Ala Ser Ile Ala Ala Leu Phe Leu T hr Thr Glu Ala Val Val
290 295 300

Ala Asp Lys Pro Glu
305

<210> SEQ ID NO 119
<211> LENGTH: 162
<212> TYPE: DNA
<213> ORGANISM: Mycobacterium vaccae

<400> SEQUENCE: 119
ctcgtacagg cgacggagat ctccgacgac gccacgtcgg tacggttggt c gccaccctg 60 ttcggcgtcg tgttgttgac gttggtgctg tccgggctca acgccaccct c atccagggc 120 gcaccagaag acagctggcg caggcggatt ccgtcgatct tc 162

<210> SEQ ID NO 120
<211> LENGTH: 1366
<212> TYPE: DNA
<213> ORGANISM: Mycobacterium vaccae
<220> FEATURE:
<221> NAME/KEY: unsure
<222> LOCATION: (955)...(955)
<221> NAME/KEY: unsure
<222> LOCATION: (973)...(973)

<400> SEQUENCE: 120
gatgagcagc gtgctgaact cgacctggtt ggcctgggcc gtcgcggtcg c ggtcgggtt 60 cccggtgctg ctggtcgtgc tgaccgaggt gcacaacgcg ttgcgtcggc g cggcagcgc 120 gctggcccgc ccggtgcaac tcctgcgtac ctacatcctg ccgctgggcg c gttgctgct 180 cctgctggta caggcgatgg agatctccga cgacgccacg tcggtacggt t ggtcgccac 240 cctgttcggc gtcgtgttgt tgacgttggt gctgtccggg ctcaacgcca c cctcatcca 300 gggcgcacca gaagacagct ggcgcaggcg gattccgtcg atcttcctcg a cgtcgcgcg 360 cttcgcgctg atcgcggtcg gtatcaccgt gatcatggcc tatgtctggg g cgcgaacgt 420 ggggggcctg ttcaccgcac tgggcgtcac ttccatcgtt cttggcctgg c tctgcagaa 480 ttcggtcggt cagatcatct cgggtctgct gctgctgttc gagcaaccgt t ccggctcgg 540 cgactggatc accgtcccca ccgcggcggg ccggccgtcc gcccacggcc g cgtggtgga 600 agtcaactgg cgtgcaacac atatcgacac cggcggcaac ctgctggtaa t gcccaacgc 660 cgaactcgcc ggcgcgtcgt tcaccaatta cagccggccc gtgggagagc a ccggctgac 720

-continued

```
cgtcgtcacc accttcaacg ccgcggacac ccccgatgat gtctgcgaga t gctgtcgtc    780

ggtcgcggcg tcgctgcccg aactgcgcac cgacggacag atcgccacgc t ctatctcgg    840

tgcggccgaa tacgagaagt cgatcccgtt gcacacaccc gcggtggacg a ctcggtcag    900

gagcacgtac ctgcgatggg tctggtacgc cgcgcgccgg caggaacttc g cctnaacgg    960

cgtcgccgac ganttcgaca cgccggaacg gatcgcctcg gccatgcggg c tgtggcgtc   1020

cacactgcgc ttggcagacg acgaacagca ggagatcgcc gacgtggtgc g tctggtccg   1080

ttacggcaac ggggaacgcc tccagcagcc gggtcaggta ccgaccggga t gaggttcat   1140

cgtagacggc agggtgagtc tgtccgtgat cgatcaggac ggcgacgtga t cccggcgcg   1200

ggtgctcgag cgtggcgact tcctggggca gaccacgctg acgcgggaac c ggtactggc   1260

gaccgcgcac gcgctggagg aagtcaccgt gctggagatg gcccgtgacg a gatcgagcg   1320

cctggtgcac cgaaagccga tcctgctgca cgtgatcggg gccgtg                 1366
```

```
<210> SEQ ID NO 121
<211> LENGTH: 455
<212> TYPE: PRT
<213> ORGANISM: Mycobacterium vaccae
<220> FEATURE:
<221> NAME/KEY: UNSURE
<222> LOCATION: (318)...(318)
<221> NAME/KEY: UNSURE
<222> LOCATION: (324)...(324)

<400> SEQUENCE: 121

Met Ser Ser Val Leu Asn Ser Thr Trp Leu A la Trp Ala Val Ala Val
 1               5                  10                  15

Ala Val Gly Phe Pro Val Leu Leu Val Val L eu Thr Glu Val His Asn
            20                  25                  30

Ala Leu Arg Arg Arg Gly Ser Ala Leu Ala A rg Pro Val Gln Leu Leu
        35                  40                  45

Arg Thr Tyr Ile Leu Pro Leu Gly Ala Leu L eu Leu Leu Leu Val Gln
    50                  55                  60

Ala Met Glu Ile Ser Asp Asp Ala Thr Ser V al Arg Leu Val Ala Thr
65                  70                  75                  80

Leu Phe Gly Val Val Leu Leu Thr Leu Val L eu Ser Gly Leu Asn Ala
                85                  90                  95

Thr Leu Ile Gln Gly Ala Pro Glu Asp Ser T rp Arg Arg Arg Ile Pro
            100                 105                 110

Ser Ile Phe Leu Asp Val Ala Arg Phe Ala L eu Ile Ala Val Gly Ile
        115                 120                 125

Thr Val Ile Met Ala Tyr Val Trp Gly Ala A sn Val Gly Gly Leu Phe
    130                 135                 140

Thr Ala Leu Gly Val Thr Ser Ile Val Leu G ly Leu Ala Leu Gln Asn
145                 150                 155                 160

Ser Val Gly Gln Ile Ile Ser Gly Leu Leu L eu Leu Phe Glu Gln Pro
                165                 170                 175

Phe Arg Leu Gly Asp Trp Ile Thr Val Pro T hr Ala Ala Gly Arg Pro
            180                 185                 190

Ser Ala His Gly Arg Val Val Glu Val Asn T rp Arg Ala Thr His Ile
        195                 200                 205

Asp Thr Gly Gly Asn Leu Leu Val Met Pro A sn Ala Glu Leu Ala Gly
    210                 215                 220

Ala Ser Phe Thr Asn Tyr Ser Arg Pro Val G ly Glu His Arg Leu Thr
```

-continued

```
225                 230                 235                 240

Val Val Thr Thr Phe Asn Ala Ala Asp Thr P ro Asp Asp Val Cys Glu
                245                 250                 255

Met Leu Ser Ser Val Ala Ala Ser Leu Pro G lu Leu Arg Thr Asp Gly
            260                 265                 270

Gln Ile Ala Thr Leu Tyr Leu Gly Ala Ala G lu Tyr Glu Lys Ser Ile
        275                 280                 285

Pro Leu His Thr Pro Ala Val Asp Asp Ser V al Arg Ser Thr Tyr Leu
    290                 295                 300

Arg Trp Val Trp Tyr Ala Ala Arg Arg Gln G lu Leu Arg Xaa Asn Gly
305                 310                 315                 320

Val Ala Asp Xaa Phe Asp Thr Pro Glu Arg I le Ala Ser Ala Met Arg
                325                 330                 335

Ala Val Ala Ser Thr Leu Arg Leu Ala Asp A sp Glu Gln Gln Glu Ile
            340                 345                 350

Ala Asp Val Val Arg Leu Val Arg Tyr Gly A sn Gly Glu Arg Leu Gln
        355                 360                 365

Gln Pro Gly Gln Val Pro Thr Gly Met Arg P he Ile Val Asp Gly Arg
    370                 375                 380

Val Ser Leu Ser Val Ile Asp Gln Asp Gly A sp Val Ile Pro Ala Arg
385                 390                 395                 400

Val Leu Glu Arg Gly Asp Phe Leu Gly Gln T hr Thr Leu Thr Arg Glu
                405                 410                 415

Pro Val Leu Ala Thr Ala His Ala Leu Glu G lu Val Thr Val Leu Glu
            420                 425                 430

Met Ala Arg Asp Glu Ile Glu Arg Leu Val H is Arg Lys Pro Ile Leu
        435                 440                 445

Leu His Val Ile Gly Ala Val
    450                 455


<210> SEQ ID NO 122
<211> LENGTH: 898
<212> TYPE: DNA
<213> ORGANISM: Mycobacterium vaccae

<400> SEQUENCE: 122

atgacaattc tgccctggaa tgcgcgaacg tctgaacacc cgacgcgaaa a agacgcggg     60

cgctaccacc tcctgtcgcg gatgagcatc cagtccaagt tgctgctgat g ctgcttctg    120

accagcattc tctcggctgc ggtggtcggt ttcatcggct atcagtccgg a cggtcctcg    180

ctgcgcgcat cggtgttcga ccgcctcacc gacatccgcg agtcgcagtc g cgcgggttg    240

gagaatcagt tcgcggacct gaagaactcg atggtgattt actcgcgcgg c agcactgcc    300

acggaggcga tcggcgcgtt cagcgacggt ttccgtcagc tcggcgatgc g acgatcaat    360

accgggcagg cggcgtcatt gcgccgttac tacgaccgga cgttcgccaa c accaccctc    420

gacgacagcg gaaaccgcgt cgacgtccgc gcgctcatcc cgaaatccaa c ccccagcgc    480

tatctgcagg cgctctatac ccgcccgttt cagaactggg agaaggcgat c gcgttcgac    540

gacgcgcgcg acggcagcgc ctggtcggcc gccaatgcca gattcaacga g ttcttccgc    600

gagatcgtgc accgcttcaa cttcgaggat ctgatgctgc tcgacctcga g ggcaacgtg    660

gtgtactccg cctacaaggg gccggatctc gggacaaaca tcgtcaacgg c ccctatcgc    720

aaccgggaac tgtcggaagc ctacgagaag gcggtcgcgt cgaactcgat c gactatgtc    780

ggtgtcaccg acttcgggtg gtacctgcct gccgaggaac cgaccgcctg g ttcctgtcc    840
```

-continued ccggtcgggt tgaaggaccg agtcgacggt gtgatggcgg tccagttccc c ggaattc 898

<210> SEQ ID NO 123
<211> LENGTH: 1259
<212> TYPE: DNA
<213> ORGANISM: Mycobacterium vaccae

<400> SEQUENCE: 123
cgcaattgat gacggcgcgg ggacagtggc gtgacaccgg gatgggagac a ccggtgaga 60 ccatcctggt cggaccggac aatctgatgc gctcggactc ccggctgttc c gcgagaacc 120 gggagaagtt cctggccgac gtcgtcgagg ggggaacccc gccggaggtc g ccgacgaat 180 cggttgaccg ccgcggcacc acgctggtgc agccggtgac cacccgctcc g tcgaggagg 240 cccaacgcgg caacaccggg acgacgatcg aggacgacta tctcggccac g aggcgttac 300 aggcgtactc accggtggac ctgccgggac tgcactgggt gatcgtggcc a agatcgaca 360 ccgacgaggc gttcgccccg gtggcgcagt tcaccaggac cctggtgctg t cgacggtga 420 tcatcatctt cggcgtgtcg ctggcggcca tgctgctggc gcggttgttc g tccgtccga 480 tccggcggtt gcaggccggc gcccagcaga tcagcggcgg tgactaccgc c tcgctctgc 540 cggtgttgtc tcgtgacgaa ttcggcgatc tgacaacagc tttcaacgac a tgagtcgca 600 atctgtcgat caaggacgag ctgctcggcg aggagcgcgc cgagaaccaa c ggctgatgc 660 tgtccctgat gcccgaaccg gtgatgcagc gctacctcga cggggaggag a cgatcgccc 720 aggaccacaa gaacgtcacg gtgatcttcg ccgacatgat gggcctcgac g agttgtcgc 780 gcatgttgac ctccgaggaa ctgatggtgg tggtcaacga cctgacccgc c agttcgacg 840 ccgccgccga gagtctcggg gtcgaccacg tgcggacgct gcacgacggg t acctggcca 900 gctgcgggtt aggcgtgccg cggctggaca acgtccggcg cacggtcaat t tcgcgatcg 960 aaatggaccg catcatcgac cggcacgccg ccgagtccgg gcacgacctg c ggctccgcg 1020 cgggcatcga caccgggtcg gcggccagcg ggctggtggg gcggtccacg t tggcgtacg 1080 acatgtgggg ttcggcggtc gatgtcgcct accaggtgca gcgcggctcc c cccagcccg 1140 gcatctacgt cacctcgcgg gtgcacgagg tcatgcagga aactctcgac t tcgtcgccg 1200 ccggggaggt cgtcggcgag cgcggcgtcg agacggtctg gcggttgcag g gccacccg 1259

<210> SEQ ID NO 124
<211> LENGTH: 299
<212> TYPE: PRT
<213> ORGANISM: Mycobacterium vaccae

<400> SEQUENCE: 124

Met Thr Ile Leu Pro Trp Asn Ala Arg Thr S er Glu His Pro Thr Arg
1 5 10 15

Lys Arg Arg Gly Arg Tyr His Leu Leu Ser A rg Met Ser Ile Gln Ser
20 25 30

Lys Leu Leu Leu Met Leu Leu Leu Thr Ser I le Leu Ser Ala Ala Val
35 40 45

Val Gly Phe Ile Gly Tyr Gln Ser Gly Arg S er Ser Leu Arg Ala Ser
50 55 60

Val Phe Asp Arg Leu Thr Asp Ile Arg Glu S er Gln Ser Arg Gly Leu
65 70 75 80

Glu Asn Gln Phe Ala Asp Leu Lys Asn Ser M et Val Ile Tyr Ser Arg
85 90 95

-continued

Gly Ser Thr Ala Thr Glu Ala Ile Gly Ala Phe Ser Asp Gly Phe Arg
100 105 110

Gln Leu Gly Asp Ala Thr Ile Asn Thr Gly Gln Ala Ala Ser Leu Arg
115 120 125

Arg Tyr Tyr Asp Arg Thr Phe Ala Asn Thr Thr Leu Asp Asp Ser Gly
130 135 140

Asn Arg Val Asp Val Arg Ala Leu Ile Pro Lys Ser Asn Pro Gln Arg
145 150 155 160

Tyr Leu Gln Ala Leu Tyr Thr Pro Pro Phe Gln Asn Trp Glu Lys Ala
165 170 175

Ile Ala Phe Asp Asp Ala Arg Asp Gly Ser Ala Trp Ser Ala Ala Asn
180 185 190

Ala Arg Phe Asn Glu Phe Phe Arg Glu Ile Val His Arg Phe Asn Phe
195 200 205

Glu Asp Leu Met Leu Leu Asp Leu Glu Gly Asn Val Val Tyr Ser Ala
210 215 220

Tyr Lys Gly Pro Asp Leu Gly Thr Asn Ile Val Asn Gly Pro Tyr Arg
225 230 235 240

Asn Arg Glu Leu Ser Glu Ala Tyr Glu Lys Ala Val Ala Ser Asn Ser
245 250 255

Ile Asp Tyr Val Gly Val Thr Asp Phe Gly Trp Tyr Leu Pro Ala Glu
260 265 270

Glu Pro Thr Ala Trp Phe Leu Ser Pro Val Gly Leu Lys Asp Arg Val
275 280 285

Asp Gly Val Met Ala Val Gln Phe Pro Gly Ile
290 295

<210> SEQ ID NO 125
<211> LENGTH: 419
<212> TYPE: PRT
<213> ORGANISM: Mycobacterium vaccae

<400> SEQUENCE: 125

Gln Leu Met Thr Ala Arg Gly Gln Trp Arg Asp Thr Gly Met Gly Asp
1 5 10 15

Thr Gly Glu Thr Ile Leu Val Gly Pro Asp Asn Leu Met Arg Ser Asp
20 25 30

Ser Arg Leu Phe Arg Glu Asn Arg Glu Lys Phe Leu Ala Asp Val Val
35 40 45

Glu Gly Gly Thr Pro Pro Glu Val Ala Asp Glu Ser Val Asp Arg Arg
50 55 60

Gly Thr Thr Leu Val Gln Pro Val Thr Thr Arg Ser Val Glu Glu Ala
65 70 75 80

Gln Arg Gly Asn Thr Gly Thr Thr Ile Glu Asp Asp Tyr Leu Gly His
85 90 95

Glu Ala Leu Gln Ala Tyr Ser Pro Val Asp Leu Pro Gly Leu His Trp
100 105 110

Val Ile Val Ala Lys Ile Asp Thr Asp Glu Ala Phe Ala Pro Val Ala
115 120 125

Gln Phe Thr Arg Thr Leu Val Leu Ser Thr Val Ile Ile Ile Phe Gly
130 135 140

Val Ser Leu Ala Ala Met Leu Leu Ala Arg Leu Phe Val Arg Pro Ile
145 150 155 160

Arg Arg Leu Gln Ala Gly Ala Gln Gln Ile Ser Gly Gly Asp Tyr Arg
165 170 175

-continued

```
Leu Ala Leu Pro Val Leu Ser Arg Asp Glu P he Gly Asp Leu Thr Thr
            180                 185                 190

Ala Phe Asn Asp Met Ser Arg Asn Leu Ser I le Lys Asp Glu Leu Leu
        195                 200                 205

Gly Glu Glu Arg Ala Glu Asn Gln Arg Leu M et Leu Ser Leu Met Pro
    210                 215                 220

Glu Pro Val Met Gln Arg Tyr Leu Asp Gly G lu Glu Thr Ile Ala Gln
225                 230                 235                 240

Asp His Lys Asn Val Thr Val Ile Phe Ala A sp Met Met Gly Leu Asp
                245                 250                 255

Glu Leu Ser Arg Met Leu Thr Ser Glu Glu L eu Met Val Val Val Asn
            260                 265                 270

Asp Leu Thr Arg Gln Phe Asp Ala Ala Ala G lu Ser Leu Gly Val Asp
        275                 280                 285

His Val Arg Thr Leu His Asp Gly Tyr Leu A la Ser Cys Gly Leu Gly
    290                 295                 300

Val Pro Arg Leu Asp Asn Val Arg Arg Thr V al Asn Phe Ala Ile Glu
305                 310                 315                 320

Met Asp Arg Ile Ile Asp Arg His Ala Ala G lu Ser Gly His Asp Leu
                325                 330                 335

Arg Leu Arg Ala Gly Ile Asp Thr Gly Ser A la Ala Ser Gly Leu Val
            340                 345                 350

Gly Arg Ser Thr Leu Ala Tyr Asp Met Trp G ly Ser Ala Val Asp Val
        355                 360                 365

Ala Tyr Gln Val Gln Arg Gly Ser Pro Gln P ro Gly Ile Tyr Val Thr
    370                 375                 380

Ser Arg Val His Glu Val Met Gln Glu Thr L eu Asp Phe Val Ala Ala
385                 390                 395                 400

Gly Glu Val Val Gly Glu Arg Gly Val Glu T hr Val Trp Arg Leu Gln
                405                 410                 415

Gly His Pro


<210> SEQ ID NO 126
<211> LENGTH: 27
<212> TYPE: DNA
<213> ORGANISM: Artificial Sequence
<220> FEATURE:
<223> OTHER INFORMATION: Made in a lab

<400> SEQUENCE: 126

ccggatccga tgagcagcgt gctgaac                                          27


<210> SEQ ID NO 127
<211> LENGTH: 26
<212> TYPE: DNA
<213> ORGANISM: Artificial Sequence
<220> FEATURE:
<223> OTHER INFORMATION: Made in a lab

<400> SEQUENCE: 127

gcggatccca cggccccgat cacgtg                                           26


<210> SEQ ID NO 128
<211> LENGTH: 33
<212> TYPE: DNA
<213> ORGANISM: Artificial Sequence
<220> FEATURE:
<223> OTHER INFORMATION: Made in a lab
```

-continued

<400> SEQUENCE: 128
ccggatccaa tgacatttct gccctggaat gcg 33

<210> SEQ ID NO 129
<211> LENGTH: 32
<212> TYPE: DNA
<213> ORGANISM: Artificial Sequence
<220> FEATURE:
<223> OTHER INFORMATION: Made in a lab

<400> SEQUENCE: 129
ccggatccat tcggtggccc tgcaaccgcc ag 32

<210> SEQ ID NO 130
<211> LENGTH: 27
<212> TYPE: DNA
<213> ORGANISM: Artificial Sequence
<220> FEATURE:
<223> OTHER INFORMATION: Made in a lab

<400> SEQUENCE: 130
ccggatccgg agcaaccgtt ccggctc 27

<210> SEQ ID NO 131
<211> LENGTH: 27
<212> TYPE: DNA
<213> ORGANISM: Artificial Sequence
<220> FEATURE:
<223> OTHER INFORMATION: Made in a lab

<400> SEQUENCE: 131
ccggatcccg gctatcagtc cggacgg 27

<210> SEQ ID NO 132
<211> LENGTH: 844
<212> TYPE: DNA
<213> ORGANISM: Mycobacterium vaccae

<400> SEQUENCE: 132
gagcaaccgt tccggctcgg cgactggatc accgtcccca ccgcggcggg c cggccgtcc 60 gcccacggcc gcgtggtgga agtcaactgg cgtgcaacac atatcgacac c ggcggcaac 120 ctgctggtaa tgcccaacgc cgaactcgcc ggcgcgtcgt tcaccaatta c agccggccc 180 gtgggagagc accggctgac cgtcgtcacc accttcaacg ccgcggacac c cccgatgat 240 gtctgcgaga tgctgtcgtc ggtcgcggcg tcgctgcccg aactgcgcac c gacggacag 300 atcgccacgc tctatctcgg tgcggccgaa tacgagaagt cgatcccgtt g cacacaccc 360 gcggtggacg actcggtcag gagcacgtac ctgcgatggg tctggtacgc c gcgcgccgg 420 caggaacttc gcctaacggc gtcgccgacg attcgacacg ccggaacgga t cgcctcggc 480 catgcgggct gtggcgtcca cactgcgctt ggcagacgac gaacagcagg a gatcgccga 540 cgtggtgcgt ctggtccgtt acggcaacgg ggaacgcctc cagcagccgg g tcaggtacc 600 gaccgggatg aggttcatcg tagacggcag ggtgagtctg tccgtgatcg a tcaggacgg 660 cgacgtgatc ccggcgcggg tgctcgagcg tggcgacttc ctggggcaga c cacgctgac 720 gcgggaaccg gtactggcga ccgcgcacgc gctggaggaa gtcaccgtgc t ggagatggc 780 ccgtgacgag atcgagcgcc tggtgcaccg aaagccgatc ctgctgcacg t gatcggggc 840 cgtg 844

-continued

<210> SEQ ID NO 133
<211> LENGTH: 742
<212> TYPE: DNA
<213> ORGANISM: Mycobacterium vaccae

<400> SEQUENCE: 133

```
ggctatcagt ccggacggtc ctcgctgcgc gcatcggtgt tcgaccgcct c accgacatc     60

cgcgagtcgc agtcgcgcgg gttggagaat cagttcgcgg acctgaagaa c tcgatggtg    120

atttactcgc gcggcagcac tgccacggag gcgatcggcg cgttcagcga c ggtttccgt    180

cagctcggcg atgcgacgat caataccggg caggcggcgt cattgcgccg t tactacgac    240

cggacgttcg ccaacaccac cctcgacgac agcggaaacc gcgtcgacgt c cgcgcgctc    300

atcccgaaat ccaaccccca gcgctatctg caggcgctct ataccccgcc g tttcagaac    360

tgggagaagg cgatcgcgtt cgacgacgcg cgcgacggca gcgcctggtc g gccgccaat    420

gccagattca acgagttctt ccgcgagatc gtgcaccgct tcaacttcga g gatctgatg    480

ctgctcgacc tcgagggcaa cgtggtgtac tccgcctaca aggggccgga t ctcgggaca    540

aacatcgtca acggccccta tcgcaaccgg gaactgtcgg aagcctacga g aaggcggtc    600

gcgtcgaact cgatcgacta tgtcggtgtc accgacttcg ggtggtacct g cctgccgag    660

gaaccgaccg cctggttcct gtccccggtc gggttgaagg accgagtcga c ggtgtgatg    720

gcggtccagt tccccggaat tc                                             742
```

<210> SEQ ID NO 134
<211> LENGTH: 282
<212> TYPE: PRT
<213> ORGANISM: Mycobacterium vaccae
<220> FEATURE:
<221> NAME/KEY: UNSURE
<222> LOCATION: (145)...(145)
<221> NAME/KEY: UNSURE
<222> LOCATION: (151)...(151)

<400> SEQUENCE: 134

```
Glu Gln Pro Phe Arg Leu Gly Asp Trp Ile T hr Val Pro Thr Ala Ala
 1               5                  10                  15

Gly Arg Pro Ser Ala His Gly Arg Val Val G lu Val Asn Trp Arg Ala
            20                  25                  30

Thr His Ile Asp Thr Gly Gly Asn Leu Leu V al Met Pro Asn Ala Glu
        35                  40                  45

Leu Ala Gly Ala Ser Phe Thr Asn Tyr Ser A rg Pro Val Gly Glu His
    50                  55                  60

Arg Leu Thr Val Val Thr Thr Phe Asn Ala A la Asp Thr Pro Asp Asp
65                  70                  75                  80

Val Cys Glu Met Leu Ser Ser Val Ala Ala S er Leu Pro Glu Leu Arg
                85                  90                  95

Thr Asp Gly Gln Ile Ala Thr Leu Tyr Leu G ly Ala Ala Glu Tyr Glu
            100                 105                 110

Lys Ser Ile Pro Leu His Thr Pro Ala Val A sp Asp Ser Val Arg Ser
        115                 120                 125

Thr Tyr Leu Arg Trp Val Trp Tyr Ala Ala A rg Arg Gln Glu Leu Arg
    130                 135                 140

Xaa Asn Gly Val Ala Asp Xaa Phe Asp Thr P ro Glu Arg Ile Ala Ser
145                 150                 155                 160

Ala Met Arg Ala Val Ala Ser Thr Leu Arg L eu Ala Asp Asp Glu Gln
                165                 170                 175
```

-continued

```
Gln Glu Ile Ala Asp Val Val Arg Leu Val A rg Tyr Gly Asn Gly Glu
            180                 185                 190

Arg Leu Gln Gln Pro Gly Gln Val Pro Thr G ly Met Arg Phe Ile Val
        195                 200                 205

Asp Gly Arg Val Ser Leu Ser Val Ile Asp G ln Asp Gly Asp Val Ile
    210                 215                 220

Pro Ala Arg Val Leu Glu Arg Gly Asp Phe L eu Gly Gln Thr Thr Leu
225                 230                 235                 240

Thr Arg Glu Pro Val Leu Ala Thr Ala His A la Leu Glu Glu Val Thr
                245                 250                 255

Val Leu Glu Met Ala Arg Asp Glu Ile Glu A rg Leu Val His Arg Lys
            260                 265                 270

Pro Ile Leu Leu His Val Ile Gly Ala Val
        275                 280


<210> SEQ ID NO 135
<211> LENGTH: 247
<212> TYPE: PRT
<213> ORGANISM: Mycobacterium vaccae

<400> SEQUENCE: 135

Gly Tyr Gln Ser Gly Arg Ser Ser Leu Arg A la Ser Val Phe Asp Arg
 1               5                  10                  15

Leu Thr Asp Ile Arg Glu Ser Gln Ser Arg G ly Leu Glu Asn Gln Phe
            20                  25                  30

Ala Asp Leu Lys Asn Ser Met Val Ile Tyr S er Arg Gly Ser Thr Ala
        35                  40                  45

Thr Glu Ala Ile Gly Ala Phe Ser Asp Gly P he Arg Gln Leu Gly Asp
    50                  55                  60

Ala Thr Ile Asn Thr Gly Gln Ala Ala Ser L eu Arg Arg Tyr Tyr Asp
65                  70                  75                  80

Arg Thr Phe Ala Asn Thr Thr Leu Asp Asp S er Gly Asn Arg Val Asp
                85                  90                  95

Val Arg Ala Leu Ile Pro Lys Ser Asn Pro G ln Arg Tyr Leu Gln Ala
            100                 105                 110

Leu Tyr Thr Pro Pro Phe Gln Asn Trp Glu L ys Ala Ile Ala Phe Asp
        115                 120                 125

Asp Ala Arg Asp Gly Ser Ala Trp Ser Ala A la Asn Ala Arg Phe Asn
    130                 135                 140

Glu Phe Phe Arg Glu Ile Val His Arg Phe A sn Phe Glu Asp Leu Met
145                 150                 155                 160

Leu Leu Asp Leu Glu Gly Asn Val Val Tyr S er Ala Tyr Lys Gly Pro
                165                 170                 175

Asp Leu Gly Thr Asn Ile Val Asn Gly Pro T yr Arg Asn Arg Glu Leu
            180                 185                 190

Ser Glu Ala Tyr Glu Lys Ala Val Ala Ser A sn Ser Ile Asp Tyr Val
        195                 200                 205

Gly Val Thr Asp Phe Gly Trp Tyr Leu Pro A la Glu Glu Pro Thr Ala
    210                 215                 220

Trp Phe Leu Ser Pro Val Gly Leu Lys Asp A rg Val Asp Gly Val Met
225                 230                 235                 240

Ala Val Gln Phe Pro Gly Ile
                245
```

-continued

<210> SEQ ID NO 136
<211> LENGTH: 45
<212> TYPE: DNA
<213> ORGANISM: Mycobacterium vaccae
<220> FEATURE:
<221> NAME/KEY: unsure
<222> LOCATION: (18)...(18)

<400> SEQUENCE: 136
atgagcgaaa tcgcccgncc ctggcgggtt ctggcatgtg gcatc 45

<210> SEQ ID NO 137
<211> LENGTH: 340
<212> TYPE: DNA
<213> ORGANISM: Mycobacterium vaccae
<220> FEATURE:
<221> NAME/KEY: unsure
<222> LOCATION: (273)...(273)
<221> NAME/KEY: unsure
<222> LOCATION: (286)...(286)

<400> SEQUENCE: 137
gccaccggcg gcgccgccgc ggtgcccgcc ggggtgagcg ccccggcggt c gcgccggcc 60 cccgcgatgc ccgcccgccc ggtgtccacg atcgcgccgg cgacctcggg c acgctcagc 120 gagtttttcg ccgccaaggg cgtcacgatg gagccgcagt ccagccgcga c ttccgcgcc 180 ctcaacatcg tgctgccgaa gccgcggggc tgggagcaca tcccggaccc g aacgtgccg 240 gacgcgttcg cggtgctggc cgaccgggtc agnggtaaag gtcagnagtc g acaaacgcc 300 cacgtggtgg tcgacaaaca cgtaggcgag ttcgacggca 340

<210> SEQ ID NO 138
<211> LENGTH: 235
<212> TYPE: DNA
<213> ORGANISM: Mycobacterium vaccae
<220> FEATURE:
<221> NAME/KEY: unsure
<222> LOCATION: (16)...(16)

<400> SEQUENCE: 138
ggtgaccacc agcgtngaac aggtcgttgc cgaagccgcg gaggccaccg a cgcgattgt 60 caacggcttc aaggtcagcg ttccgggtcc gggtccggcc gcaccgccac c tgcacccgg 120 tgcccccggt gtcccgcccg cccccggcgc cccggcgctg ccgctggccg t cgcaccacc 180 cccggctccc gctgttcccg ccgtggcgcc cgcgccacag ctgctgggac t gcag 235

<210> SEQ ID NO 139
<211> LENGTH: 15
<212> TYPE: PRT
<213> ORGANISM: Mycobacterium vaccae

<400> SEQUENCE: 139

Met Ser Glu Ile Ala Arg Pro Trp Arg Val L eu Ala Cys Gly Ile
1 5 10 15

<210> SEQ ID NO 140
<211> LENGTH: 113
<212> TYPE: PRT
<213> ORGANISM: Mycobacterium vaccae
<220> FEATURE:
<221> NAME/KEY: UNSURE
<222> LOCATION: (96)...(96)

<400> SEQUENCE: 140

Ala Thr Gly Gly Ala Ala Ala Val Pro Ala G ly Val Ser Ala Pro Ala

-continued

```
 1               5                  10                  15

Val Ala Pro Ala Pro Ala Met Pro Ala Arg P ro Val Ser Thr Ile Ala
            20                  25                  30

Pro Ala Thr Ser Gly Thr Leu Ser Glu Phe P he Ala Ala Lys Gly Val
        35                  40                  45

Thr Met Glu Pro Gln Ser Ser Arg Asp Phe A rg Ala Leu Asn Ile Val
    50                  55                  60

Leu Pro Lys Pro Arg Gly Trp Glu His Ile P ro Asp Pro Asn Val Pro
65                  70                  75                  80

Asp Ala Phe Ala Val Leu Ala Asp Arg Val G ly Gly Lys Gly Gln Xaa
                85                  90                  95

Ser Thr Asn Ala His Val Val Val Asp Lys H is Val Gly Glu Phe Asp
            100                 105                 110

Gly


<210> SEQ ID NO 141
<211> LENGTH: 73
<212> TYPE: PRT
<213> ORGANISM: Mycobacterium vaccae

<400> SEQUENCE: 141

Val Thr Thr Ser Val Glu Gln Val Val Ala A la Ala Asp Ala Thr Glu
 1               5                  10                  15

Ala Ile Val Asn Gly Phe Lys Val Ser Val P ro Gly Pro Gly Pro Ala
            20                  25                  30

Ala Pro Pro Pro Ala Pro Gly Ala Pro Gly V al Pro Pro Ala Pro Gly
        35                  40                  45

Ala Pro Ala Leu Pro Leu Ala Val Ala Pro P ro Pro Ala Pro Ala Val
    50                  55                  60

Pro Ala Val Ala Pro Ala Pro Gln Leu
65                  70


<210> SEQ ID NO 142
<211> LENGTH: 273
<212> TYPE: DNA
<213> ORGANISM: Mycobacterium vaccae

<400> SEQUENCE: 142

gcgacctacg tgcagggggg tctcggccgc atcgaggccc gggtggccga c agcggatac      60

agcaacgccg cggccaaggg ctacttcccg ctgagcttca ccgtcgccgg c atcgaccag     120

aacggtccga tcgtgaccgc caacgtcacc gcggcggccc cgacgggcgc c gtggccacc     180

cagccgctga cgttcatcgc cgggccgagc ccgaccggat ggcagctgtc c aagcagtcc     240

gcactggccc tgatgtccgc ggtcatcgcc gca                                   273


<210> SEQ ID NO 143
<211> LENGTH: 91
<212> TYPE: PRT
<213> ORGANISM: Mycobacterium vaccae

<400> SEQUENCE: 143

Ala Thr Tyr Val Gln Gly Gly Leu Gly Arg I le Glu Ala Arg Val Ala
 1               5                  10                  15

Asp Ser Gly Tyr Ser Asn Ala Ala Ala Lys G ly Tyr Phe Pro Leu Ser
            20                  25                  30

Phe Thr Val Ala Gly Ile Asp Gln Asn Gly P ro Ile Val Thr Ala Asn
        35                  40                  45
```

-continued

```
Val Thr Ala Ala Ala Pro Thr Gly Ala Val A la Thr Gln Pro Leu Thr
    50                  55                  60

Phe Ile Ala Gly Pro Ser Pro Thr Gly Trp G ln Leu Ser Lys Gln Ser
65                  70                  75                  80

Ala Leu Ala Leu Met Ser Ala Val Ile Ala A la
                85                  90


<210> SEQ ID NO 144
<211> LENGTH: 554
<212> TYPE: DNA
<213> ORGANISM: Mycobacterium vaccae

<400> SEQUENCE: 144

gatgtcacgc ccggagaatg taacgttcga ccggagaacg ccgtcggcac a acgagttac     60

gtttgagcac ttcagatctc ggttaccttg gatttcaggc gggggaagca g taaccgatc    120

caagattcga aggacccaaa caacatgaaa ttcactggaa tgaccgtgcg c gcaagccgc    180

gcgccctggc cggcgtcggg gcggcatgtc tgttcggcgg cgtggccgcg g caaccgtgg    240

cggcacagat ggcgggcgcc cagccggccg agtgcaacgc cagctcactc a ccggcaccg    300

tcagctcggt gaccggtcag gcgcgtcagt acctagacac ccacccgggc g ccaaccagg    360

ccgtcaccgc ggcgatgaac cagccgcggc ccgaggccga ggcgaacctg c ggggctact    420

tcaccgccaa cccggcggag tactacgacc tgcggggcat cctcgccccg a tcggtgacg    480

cgcagcgcaa ctgcaacatc accgtgctgc cggtagagct gcagacggcc t acgacacgt    540

tcatggccgg ctga                                                      554


<210> SEQ ID NO 145
<211> LENGTH: 136
<212> TYPE: PRT
<213> ORGANISM: Mycobacterium vaccae

<400> SEQUENCE: 145

Met Lys Phe Thr Gly Met Thr Val Arg Ala S er Arg Arg Ala Leu Ala
 1               5                  10                  15

Gly Val Gly Ala Ala Cys Leu Phe Gly Gly V al Ala Ala Ala Thr Val
            20                  25                  30

Ala Ala Gln Met Ala Gly Ala Gln Pro Ala G lu Cys Asn Ala Ser Ser
        35                  40                  45

Leu Thr Gly Thr Val Ser Ser Val Thr Gly G ln Ala Arg Gln Tyr Leu
    50                  55                  60

Asp Thr His Pro Gly Ala Asn Gln Ala Val T hr Ala Ala Met Asn Gln
65                  70                  75                  80

Pro Arg Pro Glu Ala Glu Ala Asn Leu Arg G ly Tyr Phe Thr Ala Asn
                85                  90                  95

Pro Ala Glu Tyr Tyr Asp Leu Arg Gly Ile L eu Ala Pro Ile Gly Asp
            100                 105                 110

Ala Gln Arg Asn Cys Asn Ile Thr Val Leu P ro Val Glu Leu Gln Thr
        115                 120                 125

Ala Tyr Asp Thr Phe Met Ala Gly
    130                 135


<210> SEQ ID NO 146
<211> LENGTH: 808
<212> TYPE: DNA
<213> ORGANISM: Mycobacterium vaccae
<220> FEATURE:
```

-continued

<221> NAME/KEY: unsure
<222> LOCATION: (15)...(15)

<400> SEQUENCE: 146
ccaagtgtga cgcgngtgtg acggtagacg ttccgaccaa tccaacgacg c cgcagctgg 60 gaatcacccg tgtgccaatt cagtgcgggc aacggtgtcc gtccacgaag g gattcagga 120 aatgatgaca actcgccgga agtcagccgc agtggcggga atcgctgcgg t ggccatcct 180 cggtgcggcc gcatgttcga gtgaggacgg tgggagcacg gcctcgtcgg c cagcagcac 240 ggcctcctcc gcgatggagt ccgcgaccga cgagatgacc acgtcgtcgg c ggccccttc 300 ggccgaccct gcggccaacc tgatcggctc cggctgcgcg gcctacgccg a gcaggtccc 360 cgaaggtccc gggtcggtgg ccgggatggc agccgatccg gtgacggtgg c ggcgtcgaa 420 caacccgatg ctgcagacgc tgtcccaggc gctgtccggc cagctcaatc c gcaggtcaa 480 tctcgtcgac accctcgacg gcggtgagtt caccgtgttc gcgccgaccg a cgacgcgtt 540 cgccaagatc gatccggcca cgctggagac cctcaagacg gactccgaca t gctgaccaa 600 catcctgacc taccacgtcg tgcccggcca ggccgcgccc gatcaggtgg t cggcgagca 660 tgtgacggtg gagggggcgc cggtcacggt gtccgggatg gccgaccagc t caaggtcaa 720 cgacgcgtcg gtggtgtgcg gtggggtgca gaccgccaac gcgacggtgt a tctgatcga 780 caccgtgctg atgccgccgg cagcgtag 808

<210> SEQ ID NO 147
<211> LENGTH: 228
<212> TYPE: PRT
<213> ORGANISM: Mycobacterium vaccae

<400> SEQUENCE: 147

Met Met Thr Thr Arg Arg Lys Ser Ala Ala V al Ala Gly Ile Ala Ala
1 5 10 15

Val Ala Ile Leu Gly Ala Ala Ala Cys Ser S er Glu Asp Gly Gly Ser
20 25 30

Thr Ala Ser Ser Ala Ser Ser Thr Ala Ser S er Ala Met Glu Ser Ala
35 40 45

Thr Asp Glu Met Thr Thr Ser Ser Ala Ala P ro Ser Ala Asp Pro Ala
50 55 60

Ala Asn Leu Ile Gly Ser Gly Cys Ala Ala T yr Ala Glu Gln Val Pro
65 70 75 80

Glu Gly Pro Gly Ser Val Ala Gly Met Ala A la Asp Pro Val Thr Val
85 90 95

Ala Ala Ser Asn Asn Pro Met Leu Gln Thr L eu Ser Gln Ala Leu Ser
100 105 110

Gly Gln Leu Asn Pro Gln Val Asn Leu Val A sp Thr Leu Asp Gly Gly
115 120 125

Glu Phe Thr Val Phe Ala Pro Thr Asp Asp A la Phe Ala Lys Ile Asp
130 135 140

Pro Ala Thr Leu Glu Thr Leu Lys Thr Asp S er Asp Met Leu Thr Asn
145 150 155 160

Ile Leu Thr Tyr His Val Val Pro Gly Gln A la Ala Pro Asp Gln Val
165 170 175

Val Gly Glu His Val Thr Val Glu Gly Ala P ro Val Thr Val Ser Gly
180 185 190

Met Ala Asp Gln Leu Lys Val Asn Asp Ala S er Val Val Cys Gly Gly
195 200 205

-continued

```
Val Gln Thr Ala Asn Ala Thr Val Tyr Leu I le Asp Thr Val Leu Met
    210                 215                 220

Pro Pro Ala Ala
225


<210> SEQ ID NO 148
<211> LENGTH: 22
<212> TYPE: DNA
<213> ORGANISM: Artificial Sequence
<220> FEATURE:
<223> OTHER INFORMATION: Made in a lab
<220> FEATURE:
<221> NAME/KEY: unsure
<222> LOCATION: (12)...(12)
<221> NAME/KEY: unsure
<222> LOCATION: (17)...(17)

<400> SEQUENCE: 148

gcsccsgtsg gnccggntgy gc                                              22


<210> SEQ ID NO 149
<211> LENGTH: 21
<212> TYPE: DNA
<213> ORGANISM: Artificial Sequence
<220> FEATURE:
<223> OTHER INFORMATION: Made in a lab
<220> FEATURE:
<221> NAME/KEY: unsure
<222> LOCATION: (10)...(10)
<221> NAME/KEY: unsure
<222> LOCATION: (13)...(13)
<221> NAME/KEY: unsure
<222> LOCATION: (16)...(16)
<221> NAME/KEY: unsure
<222> LOCATION: (20)...(20)

<400> SEQUENCE: 149

rtasgcsgcn gtngcnacng g                                               21


<210> SEQ ID NO 150
<211> LENGTH: 102
<212> TYPE: DNA
<213> ORGANISM: Artificial Sequence
<220> FEATURE:
<223> OTHER INFORMATION: Made in a lab

<400> SEQUENCE: 150

gcccccgtcg gccccggctg tgcggcctac gtgcaacagg tgccggacgg g ccgggatcg     60

gtgcagggca tggcgagctc gcccgtagcg accgccgcgt at                       102


<210> SEQ ID NO 151
<211> LENGTH: 683
<212> TYPE: DNA
<213> ORGANISM: Mycobacterium vaccae

<400> SEQUENCE: 151

gcccgccaac taaaaccgcc gatcatccac tgcaggaagg aatctcacga t catgaacat     60

cagcatgaaa actcttgccg gagcgggttt cgcgatgacc gccgccgtcg g tctgtcgct    120

gggtaccgca ggcagcgccg cagccgcgcc ggtcggaccg gggtgtgcgg c ctacgtgca    180

acaggtgccg gacgggccgg gatcggtgca gggcatggcg agctcgccgg t ggccaccgc    240

ggcggccgac aacccgctgc tcaccacgct ctcgcaggcg atctcgggtc a gctcaaccc    300

gaacgtcaat ctcgtcgaca cgttcaacgg cggccagttc accgtgttcg c gccgaccaa    360
```

-continued

```
tgacgccttc gccaagatcg atccggccac gctggagacc ctcaagaccg a ttccgacct    420

gctgaccaag atcctcacct accacgtcgt gcccggccag gccgcgcccg a tcaggtggt    480

cggcgagcat gtgacggtgg agggggcgcc ggtcacggtg tccgggatgg c cgaccagct    540

caaggtcaac gacgcgtcgg tggtgtgcgg tggggtgcag accgccaacg c gacggtgta    600

tctgatcgac accgtgctga tgccgccggc agcgtagccg ggcggcacca c agaagaggg    660

tcccccgcac ccggcctccc ccg                                             683
```

<210> SEQ ID NO 152
<211> LENGTH: 231
<212> TYPE: PRT
<213> ORGANISM: Mycobacterium vaccae

<400> SEQUENCE: 152

```
Asp Thr Val Leu Met Pro Pro Ala Asn Asn A rg Arg Ser Ser Thr Ala
 1               5                  10                  15

Gly Arg Asn Leu Thr Ile Met Asn Ile Ser M et Lys Thr Leu Ala Gly
            20                  25                  30

Ala Gly Phe Ala Met Thr Ala Ala Val Gly L eu Ser Leu Gly Thr Ala
        35                  40                  45

Gly Ser Ala Ala Ala Ala Pro Val Gly Pro G ly Cys Ala Ala Tyr Val
    50                  55                  60

Gln Gln Val Pro Asp Gly Pro Gly Ser Val G ln Gly Met Ala Ser Ser
65                  70                  75                  80

Pro Val Ala Thr Ala Ala Ala Asp Asn Pro L eu Leu Thr Thr Leu Ser
                85                  90                  95

Gln Ala Ile Ser Gly Gln Leu Asn Pro Asn V al Asn Leu Val Asp Thr
            100                 105                 110

Phe Asn Gly Gly Gln Phe Thr Val Phe Ala P ro Thr Asn Asp Ala Phe
        115                 120                 125

Ala Lys Ile Asp Pro Ala Thr Leu Glu Thr L eu Lys Thr Asp Ser Asp
    130                 135                 140

Leu Leu Thr Lys Ile Leu Thr Tyr His Val V al Pro Gly Gln Ala Ala
145                 150                 155                 160

Pro Asp Gln Val Val Gly Glu His Val Thr V al Glu Gly Ala Pro Val
                165                 170                 175

Thr Val Ser Gly Met Ala Asp Gln Leu Lys V al Asn Asp Ala Ser Val
            180                 185                 190

Val Cys Gly Gly Val Gln Thr Ala Asn Ala T hr Val Tyr Leu Ile Asp
        195                 200                 205

Thr Val Leu Met Pro Pro Ala Ala Pro Gly G ly Thr Thr Glu Glu Gly
    210                 215                 220

Pro Pro His Pro Ala Ser Pro
225                 230
```

<210> SEQ ID NO 153
<211> LENGTH: 1125
<212> TYPE: DNA
<213> ORGANISM: Mycobacterium vaccae
<220> FEATURE:
<221> NAME/KEY: unsure
<222> LOCATION: (358)...(358)

<400> SEQUENCE: 153

```
atgcaggtgc ggcgtgttct gggcagtgtc ggtgcagcag tcgcggtttc g gccgcgtta     60

tggcagacgg gggtttcgat accgaccgcc tcagcggatc cgtgtccgga c atcgaggtg    120
```

-continued atcttcgcgc gcgggaccgg tgcggaaccc ggcctcgggt gggtcggtga t gcgttcgtc 180 aacgcgctgc ggcccaaggt cggtgagcag tcggtgggca cctacgcggt g aactacccg 240 gcaggattcg gacttcgaca aatcggcgcc catgggcgcg gccgacgcat c ggggcgggt 300 gcagtggatg gccgacaact gcccggacac caagcttgtc ctgggcggca t gtcgcangg 360 cgccggcgtc atcgacctga tcaccgtcga tccgcgaccg ctgggccggt t cacccccac 420 cccgatgccg ccccgcgtcg ccgaccacgt ggccgccgtt gtggtcttcg g aaatccgtt 480 gcgcgacatc cgtggtggcg gtccgctgcc gcagatgagc ggcacctacg g gccgaagtc 540 gatcgatctg tgtgcgctcg acgatccgtt ctgctcgccc ggcttcaacc t gccggccca 600 cttcgcctac gccgacaacg gcatggtgga ggaagccgcg aacttcgccc g cctggaacc 660 gggccagagc gtcgagctgc ccgaggcgcc ctacctgcac ctgttcgtcc c gcggggcga 720 ggtaacgctg gaggacgccg gaccgctgcg cgaaggcgac gcagtgcgtt t caccgcatc 780 gggcggccag cgggtgaccg ccaccgcgcc cgcggagatc ctcgtctggg a gatgcatgc 840 gggactcggt gcggcataag cgaataggag tcctgctggc cggcgcagca c tgctcgccg 900 gatgcacatc cgaacctgga cccgggccgt cggcggcacc ggccccgacg a gcacaaccg 960 agagcgcacc cggtcccgga ctcgtcccgg tgaccgtcgc ggtcgacgaa c ctctggccg 1020 acgcgccgtt cgaccagccc cgggaggccc tggtgccgca gggttggacg c tgtcggtgt 1080 gggcgcggac cgcccggccg cggctggccg cgtgggcccc ggacg 1125

<210> SEQ ID NO 154
<211> LENGTH: 748
<212> TYPE: PRT
<213> ORGANISM: Mycobacterium vaccae
<220> FEATURE:
<221> NAME/KEY: UNSURE
<222> LOCATION: (119)...(119)

<400> SEQUENCE: 154

Met Gln Val Arg Arg Val Leu Gly Ser Val G ly Ala Ala Val Ala Val
1 5 10 15

Ser Ala Ala Leu Trp Gln Thr Gly Val Ser I le Pro Thr Ala Ser Ala
20 25 30

Asp Pro Cys Pro Asp Ile Glu Val Ile Phe A la Arg Gly Thr Gly Ala
35 40 45

Glu Pro Gly Leu Gly Trp Val Gly Asp Ala P he Val Asn Ala Leu Arg
50 55 60

Pro Lys Val Gly Glu Gln Ser Val Gly Thr T yr Ala Val Asn Tyr Pro
65 70 75 80

Ala Gly Phe Asp Phe Asp Lys Ser Ala Pro M et Gly Ala Ala Asp Ala
85 90 95

Ser Gly Arg Val Gln Trp Met Ala Asp Asn C ys Pro Asp Thr Lys Leu
100 105 110

Val Leu Gly Gly Met Ser Xaa Gly Ala Gly V al Ile Asp Leu Ile Thr
115 120 125

Val Asp Pro Arg Pro Leu Gly Arg Phe Thr P ro Thr Pro Met Pro Pro
130 135 140

Arg Val Ala Asp His Val Ala Ala Val Val V al Phe Gly Asn Pro Leu
145 150 155 160

Arg Asp Ile Arg Gly Gly Gly Pro Arg Leu G lu Pro Arg Gly Leu Asn
165 170 175

-continued

```
Met Glu Thr Ser Glu Arg Gly Leu Tyr Thr H is Arg Thr Tyr Arg Gly
            180                 185                 190

Leu Tyr Pro Arg Leu Tyr Ser Ser Glu Arg I le Leu Glu Ala Ser Pro
        195                 200                 205

Leu Glu Cys Tyr Ser Ala Leu Ala Leu Glu A la Ser Pro Ala Ser Pro
    210                 215                 220

Pro Arg Pro His Glu Cys Tyr Ser Ser Glu A rg Pro Arg Gly Leu Tyr
225                 230                 235                 240

Pro His Glu Ala Ser Asn Leu Glu Pro Arg A la Leu Ala His Ile Ser
                245                 250                 255

Pro His Glu Ala Leu Ala Thr Tyr Arg Ala L eu Ala Ala Ser Pro Ala
            260                 265                 270

Ser Asn Gly Leu Tyr Met Glu Thr Val Ala L eu Gly Leu Gly Leu Ala
        275                 280                 285

Leu Ala Ala Leu Ala Ala Ser Asn Pro His G lu Ala Leu Ala Ala Arg
    290                 295                 300

Gly Leu Glu Gly Leu Pro Arg Gly Leu Tyr G ly Leu Asn Ser Glu Arg
305                 310                 315                 320

Val Ala Leu Gly Leu Leu Glu Pro Arg Gly L eu Ala Leu Ala Pro Arg
                325                 330                 335

Thr Tyr Arg Leu Glu His Ile Ser Leu Glu P ro His Glu Val Ala Leu
            340                 345                 350

Pro Arg Ala Arg Gly Gly Leu Tyr Gly Leu V al Ala Leu Thr His Arg
        355                 360                 365

Leu Glu Gly Leu Ala Ser Pro Ala Leu Ala G ly Leu Tyr Pro Arg Leu
    370                 375                 380

Glu Ala Arg Gly Gly Leu Gly Leu Tyr Ala S er Pro Ala Leu Ala Val
385                 390                 395                 400

Ala Leu Ala Arg Gly Pro His Glu Thr His A rg Ala Leu Ala Ser Glu
                405                 410                 415

Arg Gly Leu Tyr Gly Leu Tyr Gly Leu Asn A la Arg Gly Val Ala Leu
            420                 425                 430

Thr His Arg Ala Leu Ala Thr His Arg Ala L eu Ala Pro Arg Ala Leu
        435                 440                 445

Ala Gly Leu Ile Leu Glu Leu Glu Val Ala L eu Thr Arg Pro Gly Leu
    450                 455                 460

Met Glu Thr His Ile Ser Ala Leu Ala Gly L eu Tyr Leu Glu Gly Leu
465                 470                 475                 480

Tyr Ala Leu Ala Ala Leu Ala Ala Leu Ala A la Ser Asn Ala Arg Gly
                485                 490                 495

Ser Glu Arg Pro Arg Ala Leu Ala Gly Leu T yr Ala Arg Gly Ala Arg
            500                 505                 510

Gly Ser Glu Arg Thr His Arg Ala Leu Ala A la Arg Gly Ala Arg Gly
        515                 520                 525

Met Glu Thr His Ile Ser Ile Leu Glu Ala A rg Gly Thr His Arg Thr
    530                 535                 540

Arg Pro Thr His Arg Ala Arg Gly Ala Leu A la Val Ala Leu Gly Leu
545                 550                 555                 560

Tyr Gly Leu Tyr Thr His Arg Gly Leu Tyr P ro Arg Ala Ser Pro Gly
                565                 570                 575

Leu His Ile Ser Ala Ser Asn Ala Arg Gly G ly Leu Ala Arg Gly Thr
            580                 585                 590

His Arg Ala Arg Gly Ser Glu Arg Ala Arg G ly Thr His Arg Ala Arg
```

-continued

```
        595                 600                 605

Gly Pro Arg Gly Leu Tyr Ala Ser Pro Ala A rg Gly Ala Arg Gly Gly
    610                 615                 620

Leu Tyr Ala Arg Gly Ala Arg Gly Thr His A rg Ser Glu Arg Gly Leu
625                 630                 635                 640

Tyr Ala Arg Gly Ala Arg Gly Ala Leu Ala V al Ala Leu Ala Arg Gly
                645                 650                 655

Pro Arg Ala Leu Ala Pro Arg Gly Leu Tyr G ly Leu Tyr Pro Arg Gly
            660                 665                 670

Leu Tyr Ala Leu Ala Ala Leu Ala Gly Leu T yr Leu Glu Ala Ser Pro
        675                 680                 685

Ala Leu Ala Val Ala Leu Gly Leu Tyr Val A la Leu Gly Leu Tyr Ala
    690                 695                 700

Leu Ala Ala Ser Pro Ala Arg Gly Pro Arg A la Leu Ala Ala Leu Ala
705                 710                 715                 720

Ala Leu Ala Gly Leu Tyr Ala Arg Gly Val A la Leu Gly Leu Tyr Pro
                725                 730                 735

Arg Gly Leu Tyr Ala Arg Gly Pro Arg Gly L eu Tyr
            740                 745


<210> SEQ ID NO 155
<211> LENGTH: 666
<212> TYPE: DNA
<213> ORGANISM: Mycobacterium vaccae

<400> SEQUENCE: 155

atgaaggcaa atcattcggg atgctacaaa tccgccggcc cgatatggtc g catccatcg     60

ccgctttgtt cgcccgcact ggcaccatct catgcaggtc tggacaatga g ctgagcctg    120

ggcatccacg gccagggccc ggaacgactg accattcagc agtgggacac c ttcctcaac    180

ggcgtcttcc cgttggaccg caaccggttg acccgggagt ggttccactc g ggcaaggcg    240

acctacgtcg tggccggtga aggtgccgac gagttcgagg gcacgctgga g ctgggctac    300

caggtgggct ttccgtggtc gctgggcgtg ggcatcaact tcagctacac c accccgaac    360

atcacgtacg acggttacgg cctcaacttc gccgacccgc tgctgggctt c ggtgattcc    420

atcgtgaccc cgccgctgtt cccgggtgtc tcgatcacgg cggacctggg c aacggcccc    480

ggcatccagg aggtcgcgac cttctccgtg gacgtggccg gccccggtgg t tccgtggtg    540

gtgtccaacg cgcacggcac ggtcaccggt gctgccggtg gtgtgctgct g cgtccgttc    600

gcccgcctga tctcgtcgac cggcgacagc gtcaccacct acggcgcacc c tggaacatg    660

aactga                                                               666


<210> SEQ ID NO 156
<211> LENGTH: 221
<212> TYPE: PRT
<213> ORGANISM: Mycobacterium vaccae

<400> SEQUENCE: 156

Met Lys Ala Asn His Ser Gly Cys Tyr Lys S er Ala Gly Pro Ile Trp
 1               5                  10                  15

Ser His Pro Ser Pro Leu Cys Ser Pro Ala L eu Ala Pro Ser His Ala
            20                  25                  30

Gly Leu Asp Asn Glu Leu Ser Leu Gly Val H is Gly Gln Gly Pro Glu
        35                  40                  45

His Leu Thr Ile Gln Gln Trp Asp Thr Phe L eu Asn Gly Val Phe Pro
```

-continued

```
    50                  55                  60

Leu Asp Arg Asn Arg Leu Thr Arg Glu Trp P he His Ser Gly Lys Ala
65                  70                  75                  80

Thr Tyr Val Val Ala Gly Glu Gly Ala Asp G lu Phe Glu Gly Thr Leu
                85                  90                  95

Glu Leu Gly Tyr His Val Gly Phe Pro Trp S er Leu Gly Val Gly Ile
            100                 105                 110

Asn Phe Ser Tyr Thr Thr Pro Asn Ile Thr T yr Asp Gly Tyr Gly Leu
        115                 120                 125

Asn Phe Ala Asp Pro Leu Leu Gly Phe Gly A sp Ser Ile Val Thr Pro
    130                 135                 140

Pro Leu Phe Pro Gly Val Ser Ile Thr Ala A sp Leu Gly Asn Gly Pro
145                 150                 155                 160

Gly Ile Gln Glu Val Ala Thr Phe Ser Val A sp Val Ala Gly Pro Gly
                165                 170                 175

Gly Ser Val Val Val Ser Asn Ala His Gly T hr Val Thr Gly Ala Ala
            180                 185                 190

Gly Gly Val Leu Leu Arg Pro Phe Ala Arg L eu Ile Ser Ser Thr Gly
        195                 200                 205

Asp Ser Val Thr Thr Tyr Gly Ala Pro Trp A sn Met Asn
    210                 215                 220


<210> SEQ ID NO 157
<211> LENGTH: 480
<212> TYPE: DNA
<213> ORGANISM: Mycobacterium vaccae

<400> SEQUENCE: 157

aacggctggg acatcaacac ccctgcgttc gagtggttct acgagtccgg c ttgtcgacg     60

atcatgccgg tcggcggaca gtccagcttc tacagcgact ggtaccagcc g tctcggggc    120

aacgggcaga actacaccta caagtgggag acgttcctga cccaggagct g ccgacgtgg    180

ctggaggcca accgcggagt gtcgcgcacc ggcaacgcgt tcgtcggcct g tcgatggcg    240

ggcagcgcgg cgctgaccta cgcgatccat cacccgcagc agttcatcta c gcctcgtcg    300

ctgtcaggct tcctgaaccc gtccgagggc tggtggccga tgctgatcgg g ctggcgatg    360

aacgacgcag gcggcttcaa cgccgagagc atgtggggcc cgtcctcgga c ccggcgtgg    420

aagcgcaacg acccgatggt caacatcaac cagctggtgg ccaacaacac c cggatctgg    480


<210> SEQ ID NO 158
<211> LENGTH: 161
<212> TYPE: PRT
<213> ORGANISM: Mycobacterium vaccae

<400> SEQUENCE: 158

Asn Gly Trp Asp Ile Asn Thr Pro Ala Phe G lu Trp Phe Tyr Glu Ser
 1               5                  10                  15

Gly Leu Ser Thr Ile Met Pro Val Gly Gly G ln Ser Ser Phe Tyr Ser
            20                  25                  30

Asp Trp Tyr Gln Pro Ser Arg Gly Asn Gly G ln Asn Tyr Thr Tyr Lys
        35                  40                  45

Trp Glu Thr Phe Leu Thr Gln Glu Leu Pro T hr Trp Leu Glu Ala Asn
    50                  55                  60

Arg Gly Val Ser Arg Thr Gly Asn Ala Phe V al Gly Leu Ser Met Ala
65                  70                  75                  80
```

-continued

```
Gly Ser Ala Ala Leu Thr Tyr Ala Ile His H is Pro Gln Gln Phe Ile
                85                  90                  95

Tyr Ala Ser Ser Leu Ser Gly Phe Leu Asn P ro Ser Glu Gly Trp Trp
            100                 105                 110

Pro Met Leu Ile Gly Leu Ala Met Asn Asp A la Gly Gly Phe Asn Ala
        115                 120                 125

Glu Ser Met Trp Gly Pro Ser Ser Asp Pro A la Trp Lys Arg Asn Asp
    130                 135                 140

Pro Met Val Asn Ile Asn Gln Leu Val Ala A sn Asn Thr Arg Ile Trp
145                 150                 155                 160

Ile


<210> SEQ ID NO 159
<211> LENGTH: 1626
<212> TYPE: DNA
<213> ORGANISM: Mycobacterium vaccae

<400> SEQUENCE: 159

atggccaaga caattgcgta tgacgaagag gcccgccgtg gcctcgagcg g ggcctcaac     60

gccctcgcag acgccgtaaa ggtgacgttg ggcccgaagg gtcgcaacgt c gtgctggag    120

aagaagtggg gcgcccccac gatcaccaac gatggtgtgt ccatcgccaa g gagatcgag    180

ctggaggacc cgtacgagaa gatcggcgct gagctggtca aagaggtcgc c aagaagacc    240

gacgacgtcg cgggcgacgg caccaccacc gccaccgtgc tcgctcaggc t ctggttcgc    300

gaaggcctgc gcaacgtcgc agccggcgcc aacccgctcg gcctcaagcg t ggcatcgag    360

aaggctgtcg aggctgtcac ccagtcgctg ctgaagtcgg ccaaggaggt c gagaccaag    420

gagcagattt ctgccaccgc ggcgatttcc gccggcgaca cccagatcgg c gagctcatc    480

gccgaggcca tggacaaggt cggcaacgag ggtgtcatca ccgtcgagga g tcgaacacc    540

ttcggcctgc agctcgagct caccgagggt atgcgcttcg acaagggcta c atctcgggt    600

tacttcgtga ccgacgccga gcgccaggaa gccgtcctgg aggatcccta c atcctgctg    660

gtcagctcca aggtgtcgac cgtcaaggat ctgctcccgc tgctggagaa g gtcatccag    720

gccggcaagc cgctgctgat catcgccgag gacgtcgagg gcgaggccct g tccacgctg    780

gtggtcaaca agatccgcgg caccttcaag tccgtcgccg tcaaggctcc g ggcttcggt    840

gaccgccgca aggcgatgct gcaggacatg gccatcctca ccggtggtca g gtcgtcagc    900

gaaagagtcg ggctgtccct ggagaccgcc gacgtctcgc tgctgggcca g gcccgcaag    960

gtcgtcgtca ccaaggacga gaccaccatc gtcgagggct cgggcgattc c gatgccatc   1020

gccggccggg tggctcagat ccgcgccgag atcgagaaca gcgactccga c tacgaccgc   1080

gagaagctgc aggagcgcct ggccaagctg gccggcggtg ttgcggtgat c aaggccgga   1140

gctgccaccg aggtggagct caaggagcgc aagcaccgca tcgaggacgc c gtccgcaac   1200

gcgaaggctg ccgtcgaaga gggcatcgtc gccggtggcg gcgtggctct g ctgcagtcg   1260

gctcctgcgc tggacgacct cggcctgacg ggcgacgagg ccaccggtgc c aacatcgtc   1320

cgcgtggcgc tgtcggctcc gctcaagcag atcgccttca acggcggcct g gagcccggc   1380

gtcgttgccg agaaggtgtc caacctgccc gcgggtcacg gcctcaacgc c gcgaccggt   1440

gagtacgagg acctgctcaa ggccggcgtc gccgacccgg tgaaggtcac c cgctcggcg   1500

ctgcagaacg cggcgtccat cgcggctctg ttcctcacca ccgaggccgt c gtcgccgac   1560

aagccggaga aggcgtccgc acccgcgggc gacccgaccg gtggcatggg c ggtatggac   1620
```

-continued ttctaa 1626

<210> SEQ ID NO 160
<211> LENGTH: 541
<212> TYPE: PRT
<213> ORGANISM: Mycobacterium vaccae

<400> SEQUENCE: 160

Met Ala Lys Thr Ile Ala Tyr Asp Glu Glu A la Arg Arg Gly Leu Glu
1 5 10 15

Arg Gly Leu Asn Ala Leu Ala Asp Ala Val L ys Val Thr Leu Gly Pro
20 25 30

Lys Gly Arg Asn Val Val Leu Glu Lys Lys T rp Gly Ala Pro Thr Ile
35 40 45

Thr Asn Asp Gly Val Ser Ile Ala Lys Glu I le Glu Leu Glu Asp Pro
50 55 60

Tyr Glu Lys Ile Gly Ala Glu Leu Val Lys G lu Val Ala Lys Lys Thr
65 70 75 80

Asp Asp Val Ala Gly Asp Gly Thr Thr Thr A la Thr Val Leu Ala Gln
85 90 95

Ala Leu Val Arg Glu Gly Leu Arg Asn Val A la Ala Gly Ala Asn Pro
100 105 110

Leu Gly Leu Lys Arg Gly Ile Glu Lys Ala V al Glu Ala Val Thr Gln
115 120 125

Ser Leu Leu Lys Ser Ala Lys Glu Val Glu T hr Lys Glu Gln Ile Ser
130 135 140

Ala Thr Ala Ala Ile Ser Ala Gly Asp Thr G ln Ile Gly Glu Leu Ile
145 150 155 160

Ala Glu Ala Met Asp Lys Val Gly Asn Glu G ly Val Ile Thr Val Glu
165 170 175

Glu Ser Asn Thr Phe Gly Leu Gln Leu Glu L eu Thr Glu Gly Met Arg
180 185 190

Phe Asp Lys Gly Tyr Ile Ser Gly Tyr Phe V al Thr Asp Ala Glu Arg
195 200 205

Gln Glu Ala Val Leu Glu Asp Pro Tyr Ile L eu Leu Val Ser Ser Lys
210 215 220

Val Ser Thr Val Lys Asp Leu Leu Pro Leu L eu Glu Lys Val Ile Gln
225 230 235 240

Ala Gly Lys Pro Leu Leu Ile Ile Ala Glu A sp Val Glu Gly Glu Ala
245 250 255

Leu Ser Thr Leu Val Val Asn Lys Ile Arg G ly Thr Phe Lys Ser Val
260 265 270

Ala Val Lys Ala Pro Gly Phe Gly Asp Arg A rg Lys Ala Met Leu Gln
275 280 285

Asp Met Ala Ile Leu Thr Gly Gly Gln Val V al Ser Glu Arg Val Gly
290 295 300

Leu Ser Leu Glu Thr Ala Asp Val Ser Leu L eu Gly Gln Ala Arg Lys
305 310 315 320

Val Val Val Thr Lys Asp Glu Thr Thr Ile V al Glu Gly Ser Gly Asp
325 330 335

Ser Asp Ala Ile Ala Gly Arg Val Ala Gln I le Arg Ala Glu Ile Glu
340 345 350

Asn Ser Asp Ser Asp Tyr Asp Arg Glu Lys L eu Gln Glu Arg Leu Ala
355 360 365

-continued

```
Lys Leu Ala Gly Gly Val Ala Val Ile Lys A la Gly Ala Ala Thr Glu
    370                 375                 380

Val Glu Leu Lys Glu Arg Lys His Arg Ile G lu Asp Ala Val Arg Asn
385                 390                 395                 400

Ala Lys Ala Ala Val Glu Glu Gly Ile Val A la Gly Gly Gly Val Ala
                405                 410                 415

Leu Leu Gln Ser Ala Pro Ala Leu Asp Asp L eu Gly Leu Thr Gly Asp
            420                 425                 430

Glu Ala Thr Gly Ala Asn Ile Val Arg Val A la Leu Ser Ala Pro Leu
        435                 440                 445

Lys Gln Ile Ala Phe Asn Gly Gly Leu Glu P ro Gly Val Val Ala Glu
    450                 455                 460

Lys Val Ser Asn Leu Pro Ala Gly His Gly L eu Asn Ala Ala Thr Gly
465                 470                 475                 480

Glu Tyr Glu Asp Leu Leu Lys Ala Gly Val A la Asp Pro Val Lys Val
                485                 490                 495

Thr Arg Ser Ala Leu Gln Asn Ala Ala Ser I le Ala Ala Leu Phe Leu
            500                 505                 510

Thr Thr Glu Ala Val Val Ala Asp Lys Pro G lu Lys Ala Ser Ala Pro
        515                 520                 525

Ala Gly Asp Pro Thr Gly Gly Met Gly Gly M et Asp Phe
    530                 535                 540
```

<210> SEQ ID NO 161
<211> LENGTH: 985
<212> TYPE: DNA
<213> ORGANISM: Mycobacterium vaccae

<400> SEQUENCE: 161

```
ggatccctac atcctgctgg tcagctccaa ggtgtcgacc gtcaaggatc t gctcccgct     60

gctggagaag gtcatccagg ccggcaagcc gctgctgatc atcgccgagg a cgtcgaggg    120

cgaggccctg tccacgctgg tggtcaacaa gatccgcggc accttcaagt c cgtcgccgt    180

caaggctccg ggcttcggtg accgccgcaa ggcgatgctg caggacatgg c catcctcac    240

cggtggtcag gtcgtcagcg aaagagtcgg gctgtccctg gagaccgccg a cgtctcgct    300

gctgggccag gcccgcaagg tcgtcgtcac caaggacgag accaccatcg t cgagggctc    360

gggcgattcc gatgccatcg ccggccgggt ggctcagatc cgcgccgaga t cgagaacag    420

cgactccgac tacgaccgcg agaagctgca ggagcgcctg gccaagctgg c cggcggtgt    480

tgcggtgatc aaggccggag ctgccaccga ggtggagctc aaggagcgca a gcaccgcat    540

cgaggacgcc gtccgcaacg cgaaggctgc cgtcgaagag ggcatcgtcg c cggtggcgg    600

cgtggctctg ctgcagtcgg ctcctgcgct ggacgacctc ggcctgacgg g cgacgaggc    660

caccggtgcc aacatcgtcc gcgtggcgct gtcggctccg ctcaagcaga t cgccttcaa    720

cggcggcctg gagcccggcg tcgttgccga gaaggtgtcc aacctgcccg c gggtcacgg    780

cctcaacgcc gcgaccggtg agtacgagga cctgctcaag gccggcgtcg c cgacccggt    840

gaaggtcacc cgctcggcgc tgcagaacgc ggcgtccatc gcggctctgt t cctcaccac    900

cgaggccgtc gtcgccgaca agccggagaa ggcgtccgca cccgcgggcg a cccgaccgg    960

tggcatgggc ggtatggact tctaa                                          985
```

<210> SEQ ID NO 162
<211> LENGTH: 327
<212> TYPE: PRT

-continued

<213> ORGANISM: Mycobacterium vaccae

<400> SEQUENCE: 162

Asp Pro Tyr Ile Leu Leu Val Ser Ser Lys V al Ser Thr Val Lys Asp
1 5 10 15

Leu Leu Pro Leu Leu Glu Lys Val Ile Gln A la Gly Lys Pro Leu Leu
20 25 30

Ile Ile Ala Glu Asp Val Glu Gly Glu Ala L eu Ser Thr Leu Val Val
35 40 45

Asn Lys Ile Arg Gly Thr Phe Lys Ser Val A la Val Lys Ala Pro Gly
50 55 60

Phe Gly Asp Arg Arg Lys Ala Met Leu Gln A sp Met Ala Ile Leu Thr
65 70 75 80

Gly Gly Gln Val Val Ser Glu Arg Val Gly L eu Ser Leu Glu Thr Ala
85 90 95

Asp Val Ser Leu Leu Gly Gln Ala Arg Lys V al Val Val Thr Lys Asp
100 105 110

Glu Thr Thr Ile Val Glu Gly Ser Gly Asp S er Asp Ala Ile Ala Gly
115 120 125

Arg Val Ala Gln Ile Arg Ala Glu Ile Glu A sn Ser Asp Ser Asp Tyr
130 135 140

Asp Arg Glu Lys Leu Gln Glu Arg Leu Ala L ys Leu Ala Gly Gly Val
145 150 155 160

Ala Val Ile Lys Ala Gly Ala Ala Thr Glu V al Glu Leu Lys Glu Arg
165 170 175

Lys His Arg Ile Glu Asp Ala Val Arg Asn A la Lys Ala Ala Val Glu
180 185 190

Glu Gly Ile Val Ala Gly Gly Gly Val Ala L eu Leu Gln Ser Ala Pro
195 200 205

Ala Leu Asp Asp Leu Gly Leu Thr Gly Asp G lu Ala Thr Gly Ala Asn
210 215 220

Ile Val Arg Val Ala Leu Ser Ala Pro Leu L ys Gln Ile Ala Phe Asn
225 230 235 240

Gly Gly Leu Glu Pro Gly Val Val Ala Glu L ys Val Ser Asn Leu Pro
245 250 255

Ala Gly His Gly Leu Asn Ala Ala Thr Gly G lu Tyr Glu Asp Leu Leu
260 265 270

Lys Ala Gly Val Ala Asp Pro Val Lys Val T hr Arg Ser Ala Leu Gln
275 280 285

Asn Ala Ala Ser Ile Ala Ala Leu Phe Leu T hr Thr Glu Ala Val Val
290 295 300

Ala Asp Lys Pro Glu Lys Ala Ser Ala Pro A la Gly Asp Pro Thr Gly
305 310 315 320

Gly Met Gly Gly Met Asp Phe
325

<210> SEQ ID NO 163
<211> LENGTH: 403
<212> TYPE: DNA
<213> ORGANISM: Mycobacterium vaccae

<400> SEQUENCE: 163
ggatccgcgg caccggctgg tgacgaccaa gtacaacccg gcccgcacct g gacggccga 60 gaactccgtc ggcatcggcg gcgcgtacct gtgcatctac gggatggagg g ccccggcgg 120

-continued

```
ctatcagttc gtcggccgca ccacccaggt gtggagtcgt taccgccaca c ggcgccgtt    180

cgaacccgga agtccctggc tgctgcggtt tttcgaccga atttcgtggt a tccggtgtc    240

ggccgaggag ctgctggaat tgcgagccga catggccgca ggccggggct c ggtcgacat    300

caccgacggc gtgttctccc tcgccgagca cgaacggttc ctggccgaca a cgccgacga    360

catcgccgcg ttccgttccc ggcaggcggc cgcgttctcc gcc                      403
```

<210> SEQ ID NO 164
<211> LENGTH: 336
<212> TYPE: DNA
<213> ORGANISM: Mycobacterium vaccae

<400> SEQUENCE: 164

```
cggaccgcgt gggcggccgc cggcgagttc gaccgcgccg agaaagccgc g tcgaaggcc     60

accgacgccg ataccgggga cctggtgctc tacgacggtg cgagcgggtc g acgctccgt    120

tcgcgtcgag cgtgtggaag gtcgacgtcg ccgtcggtga ccgggtggtg g ccggacagc    180

cgttgctggc gctggaggcg atgaagatgg agaccgtgct gcgcgccccg g ccgacgggg    240

tggtcaccca gatcctggtc tccgctgggc atctcgtcga tcccggcacc c cactggtcg    300

tggtcggcac cggagtgcgc gcatgagcgc cgtcga                              336
```

<210> SEQ ID NO 165
<211> LENGTH: 134
<212> TYPE: PRT
<213> ORGANISM: Mycobacterium vaccae

<400> SEQUENCE: 165

```
Asp Pro Arg His Arg Leu Val Thr Thr Lys T yr Asn Pro Ala Arg Thr
 1               5                  10                  15

Trp Thr Ala Glu Asn Ser Val Gly Ile Gly G ly Ala Tyr Leu Cys Ile
            20                  25                  30

Tyr Gly Met Glu Gly Pro Gly Gly Tyr Gln P he Val Gly Arg Thr Thr
        35                  40                  45

Gln Val Trp Ser Arg Tyr Arg His Thr Ala P ro Phe Glu Pro Gly Ser
    50                  55                  60

Pro Trp Leu Leu Arg Phe Phe Asp Arg Ile S er Trp Tyr Pro Val Ser
65                  70                  75                  80

Ala Glu Glu Leu Leu Glu Leu Arg Ala Asp M et Ala Ala Gly Arg Gly
                85                  90                  95

Ser Val Asp Ile Thr Asp Gly Val Phe Ser L eu Ala Glu His Glu Arg
            100                 105                 110

Phe Leu Ala Asp Asn Ala Asp Asp Ile Ala A la Phe Arg Ser Arg Gln
        115                 120                 125

Ala Ala Ala Phe Ser Ala
    130
```

<210> SEQ ID NO 166
<211> LENGTH: 108
<212> TYPE: PRT
<213> ORGANISM: Mycobacterium vaccae

<400> SEQUENCE: 166

```
Arg Thr Ala Trp Ala Ala Ala Gly Glu Phe A sp Arg Ala Glu Lys Ala
 1               5                  10                  15

Ala Ser Lys Ala Thr Asp Ala Asp Thr Gly A sp Leu Val Leu Tyr Asp
            20                  25                  30
```

-continued

```
Gly Asp Glu Arg Val Asp Ala Pro Phe Ala S er Ser Val Trp Lys Val
        35                  40                  45

Asp Val Ala Val Gly Asp Arg Val Val Ala G ly Gln Pro Leu Leu Ala
    50                  55                  60

Leu Glu Ala Met Lys Met Glu Thr Val Leu A rg Ala Pro Ala Asp Gly
65                  70                  75                  80

Val Val Thr Gln Ile Leu Val Ser Ala Gly H is Leu Val Asp Pro Gly
                85                  90                  95

Thr Pro Leu Val Val Val Gly Thr Gly Val A rg Ala
            100                 105


<210> SEQ ID NO 167
<211> LENGTH: 31
<212> TYPE: DNA
<213> ORGANISM: Artificial Sequence
<220> FEATURE:
<223> OTHER INFORMATION: Made in a lab

<400> SEQUENCE: 167

atagaattcg tccgacagtg ggacctcgag c                                    31


<210> SEQ ID NO 168
<211> LENGTH: 27
<212> TYPE: DNA
<213> ORGANISM: Artificial Sequence
<220> FEATURE:
<223> OTHER INFORMATION: Made in a lab

<400> SEQUENCE: 168

atagaattcc caccgcgtca gccgccg                                         27


<210> SEQ ID NO 169
<211> LENGTH: 1111
<212> TYPE: DNA
<213> ORGANISM: Mycobacterium vaccae

<400> SEQUENCE: 169

gtccgacagt gggacctcga gcaccacgtc acaggacagc ggccccgcca g cggcgccct     60

gcgcgtctcc aactggccgc tctatatggc cgacggtttc atcgcagcgt t ccagaccgc    120

ctcgggcatc acggtcgact acaaagaaga cttcaacgac aacgagcagt g gttcgccaa    180

ggtcaaggag ccgttgtcgc gcaagcagga cataggcgcc gacctggtga t ccccaccga    240

gttcatggcc gcgcgcgtca agggcctggg atggctcaat gagatcagcg a agccggcgt    300

gcccaatcgc aagaatctgc gtcaggacct gttggactcg agcatcgacg a gggccgcaa    360

gttcaccgcg ccgtacatga ccggcatggt cggtctcgcc tacaacaagg c agccaccgg    420

acgcgatatc cgcaccatcg acgacctctg ggatcccgcg ttcaagggcc g cgtcagtct    480

gttctccgac gtccaggacg gcctcggcat gatcatgctc tcgcagggca a ctcgccgga    540

gaatccgacc accgagtcca ttcagcaggc ggtcgatctg gtccgcgaac a gaacgacag    600

ggggtcagat ccgtcgcttc accggcaacg actacgccga cgacctggcc g cagaaacat    660

cgccatcgcg caggcgtact ccggtgacgt cgtgcagctg caggcggaca a ccccgatct    720

gcagttcatc gttcccgaat ccggcggcga ctggttcgtc gacacgatgg t gatcccgta    780

caccacgcag aaccagaagg ccgccgaggc gtggatcgac tacatctacg a ccgagccaa    840

ctacgccaag ctggtcgcgt tcacccagtt cgtgcccgca ctctcggaca t gaccgacga    900

actcgccaag gtcgatcctg catcggcgga gaacccgctg atcaacccgt c ggccgaggt    960
```

-continued

```
gcaggcgaac ctgaagtcgt gggcggcact gaccgacgag cagacgcagg a gttcaacac   1020

tgcgtacgcc gccgtcaccg gcggctgacg cggtggtagt gccgatgcga g gggcataaa   1080

tggccctgcg gacgcgagga gcataaatgg c                                  1111


<210> SEQ ID NO 170
<211> LENGTH: 348
<212> TYPE: PRT
<213> ORGANISM: Mycobacterium vaccae

<400> SEQUENCE: 170

Ser Asp Ser Gly Thr Ser Ser Thr Thr Ser G ln Asp Ser Gly Pro Ala
 1               5                  10                  15

Ser Gly Ala Leu Arg Val Ser Asn Trp Pro L eu Tyr Met Ala Asp Gly
            20                  25                  30

Phe Ile Ala Ala Phe Gln Thr Ala Ser Gly I le Thr Val Asp Tyr Lys
        35                  40                  45

Glu Asp Phe Asn Asp Asn Glu Gln Trp Phe A la Lys Val Lys Glu Pro
    50                  55                  60

Leu Ser Arg Lys Gln Asp Ile Gly Ala Asp L eu Val Ile Pro Thr Glu
65                  70                  75                  80

Phe Met Ala Ala Arg Val Lys Gly Leu Gly T rp Leu Asn Glu Ile Ser
                85                  90                  95

Glu Ala Gly Val Pro Asn Arg Lys Asn Leu A rg Gln Asp Leu Leu Asp
            100                 105                 110

Ser Ser Ile Asp Glu Gly Arg Lys Phe Thr A la Pro Tyr Met Thr Gly
        115                 120                 125

Met Val Gly Leu Ala Tyr Asn Lys Ala Ala T hr Gly Arg Asp Ile Arg
    130                 135                 140

Thr Ile Asp Asp Leu Trp Asp Pro Ala Phe L ys Gly Arg Val Ser Leu
145                 150                 155                 160

Phe Ser Asp Val Gln Asp Gly Leu Gly Met I le Met Leu Ser Gln Gly
                165                 170                 175

Asn Ser Pro Glu Asn Pro Thr Thr Glu Ser I le Gln Gln Ala Val Asp
            180                 185                 190

Leu Val Arg Glu Gln Asn Asp Arg Gly Gln I le Arg Arg Phe Thr Gly
        195                 200                 205

Asn Asp Tyr Ala Asp Asp Leu Ala Ala Gly A sn Ile Ala Ile Ala Gln
    210                 215                 220

Ala Tyr Ser Gly Asp Val Val Gln Leu Gln A la Asp Asn Pro Asp Leu
225                 230                 235                 240

Gln Phe Ile Val Pro Glu Ser Gly Gly Asp T rp Phe Val Asp Thr Met
                245                 250                 255

Val Ile Pro Tyr Thr Thr Gln Asn Gln Lys A la Ala Glu Ala Trp Ile
            260                 265                 270

Asp Tyr Ile Tyr Asp Arg Ala Asn Tyr Ala L ys Leu Val Ala Phe Thr
        275                 280                 285

Gln Phe Val Pro Ala Leu Ser Asp Met Thr A sp Glu Leu Ala Lys Val
    290                 295                 300

Asp Pro Ala Ser Ala Glu Asn Pro Leu Ile A sn Pro Ser Ala Glu Val
305                 310                 315                 320

Gln Ala Asn Leu Lys Ser Trp Ala Ala Leu T hr Asp Glu Gln Thr Gln
                325                 330                 335

Glu Phe Asn Thr Ala Tyr Ala Ala Val Thr G ly Gly
            340                 345
```

-continued

<210> SEQ ID NO 171
<211> LENGTH: 1420
<212> TYPE: DNA
<213> ORGANISM: Mycobacterium vaccae
<220> FEATURE:
<221> NAME/KEY: unsure
<222> LOCATION: (955)...(955)
<221> NAME/KEY: unsure
<222> LOCATION: (973)...(973)

<400> SEQUENCE: 171
gatgagcagc gtgctgaact cgacctggtt ggcctgggcc gtcgcggtcg c ggtcgggtt 60 cccggtgctg ctggtcgtgc tgaccgaggt gcacaacgcg ttgcgtcggc g cggcagcgc 120 gctggcccgc ccggtgcaac tcctgcgtac ctacatcctg ccgctgggcg c gttgctgct 180 cctgctggta caggcgatgg agatctccga cgacgccacg tcggtacggt t ggtcgccac 240 cctgttcggc gtcgtgttgt tgacgttggt gctgtccggg ctcaacgcca c cctcatcca 300 gggcgcacca gaagacagct ggcgcaggcg gattccgtcg atcttcctcg a cgtcgcgcg 360 cttcgcgctg atcgcggtcg gtatcaccgt gatcatggcc tatgtctggg g cgcgaacgt 420 ggggggcctg ttcaccgcac tgggcgtcac ttccatcgtt cttggcctgg c tctgcagaa 480 ttcggtcggt cagatcatct cgggtctgct gctgctgttc gagcaaccgt t ccggctcgg 540 cgactggatc accgtcccca ccgcggcggg ccggccgtcc gcccacggcc g cgtggtgga 600 agtcaactgg cgtgcaacac atatcgacac cggcggcaac ctgctggtaa t gcccaacgc 660 cgaactcgcc ggcgcgtcgt tcaccaatta cagccggccc gtgggagagc a ccggctgac 720 cgtcgtcacc accttcaacg ccgcggacac ccccgatgat gtctgcgaga t gctgtcgtc 780 ggtcgcggcg tcgctgcccg aactgcgcac cgacggacag atcgccacgc t ctatctcgg 840 tgcggccgaa tacgagaagt cgatcccgtt gcacacaccc gcggtggacg a ctcggtcag 900 gagcacgtac ctgcgatggg tctggtacgc cgcgcgccgg caggaacttc g cctnaacgg 960 cgtcgccgac ganttcgaca cgccggaacg gatcgcctcg gccatgcggg c tgtggcgtc 1020 cacactgcgc ttggcagacg acgaacagca ggagatcgcc gacgtggtgc g tctggtccg 1080 ttacggcaac ggggaacgcc tccagcagcc gggtcaggta ccgaccggga t gaggttcat 1140 cgtagacggc agggtgagtc tgtccgtgat cgatcaggac ggcgacgtga t cccggcgcg 1200 ggtgctcgag cgtggcgact tcctggggca gaccacgctg acgcgggaac c ggtactggc 1260 gaccgcgcac gcgctggagg aagtcaccgt gctggagatg gcccgtgacg a gatcgagcg 1320 cctggtgcac cgaaagccga tcctgctgca cgtgatcggg gccgtgatcg c cgaccggcg 1380 cgcgcacgaa cttcggttga tggcggactc gcaggactga 1420

<210> SEQ ID NO 172
<211> LENGTH: 471
<212> TYPE: PRT
<213> ORGANISM: Mycobacterium vaccae
<220> FEATURE:
<221> NAME/KEY: UNSURE
<222> LOCATION: (318)...(318)
<221> NAME/KEY: UNSURE
<222> LOCATION: (324)...(324)

<400> SEQUENCE: 172

Met Ser Ser Val Leu Asn Ser Thr Trp Leu A la Trp Ala Val Ala Val
1 5 10 15

Ala Val Gly Phe Pro Val Leu Leu Val Val L eu Thr Glu Val His Asn

-continued

```
            20                  25                  30

Ala Leu Arg Arg Arg Gly Ser Ala Leu Ala A rg Pro Val Gln Leu Leu
        35                  40                  45

Arg Thr Tyr Ile Leu Pro Leu Gly Ala Leu L eu Leu Leu Leu Val Gln
    50                  55                  60

Ala Met Glu Ile Ser Asp Asp Ala Thr Ser V al Arg Leu Val Ala Thr
65                  70                  75                  80

Leu Phe Gly Val Val Leu Leu Thr Leu Val L eu Ser Gly Leu Asn Ala
                85                  90                  95

Thr Leu Ile Gln Gly Ala Pro Glu Asp Ser T rp Arg Arg Arg Ile Pro
            100                 105                 110

Ser Ile Phe Leu Asp Val Ala Arg Phe Ala L eu Ile Ala Val Gly Ile
        115                 120                 125

Thr Val Ile Met Ala Tyr Val Trp Gly Ala A sn Val Gly Gly Leu Phe
    130                 135                 140

Thr Ala Leu Gly Val Thr Ser Ile Val Leu G ly Leu Ala Leu Gln Asn
145                 150                 155                 160

Ser Val Gly Gln Ile Ile Ser Gly Leu Leu L eu Leu Phe Glu Gln Pro
                165                 170                 175

Phe Arg Leu Gly Asp Trp Ile Thr Val Pro T hr Ala Ala Gly Arg Pro
            180                 185                 190

Ser Ala His Gly Arg Val Val Glu Val Asn T rp Arg Ala Thr His Ile
        195                 200                 205

Asp Thr Gly Gly Asn Leu Leu Val Met Pro A sn Ala Glu Leu Ala Gly
    210                 215                 220

Ala Ser Phe Thr Asn Tyr Ser Arg Pro Val G ly Glu His Arg Leu Thr
225                 230                 235                 240

Val Val Thr Thr Phe Asn Ala Ala Asp Thr P ro Asp Asp Val Cys Glu
                245                 250                 255

Met Leu Ser Ser Val Ala Ala Ser Leu Pro G lu Leu Arg Thr Asp Gly
            260                 265                 270

Gln Ile Ala Thr Leu Tyr Leu Gly Ala Ala G lu Tyr Glu Lys Ser Ile
        275                 280                 285

Pro Leu His Thr Pro Ala Val Asp Asp Ser V al Arg Ser Thr Tyr Leu
    290                 295                 300

Arg Trp Val Trp Tyr Ala Ala Arg Arg Gln G lu Leu Arg Xaa Asn Gly
305                 310                 315                 320

Val Ala Asp Xaa Phe Asp Thr Pro Glu Arg I le Ala Ser Ala Met Arg
                325                 330                 335

Ala Val Ala Ser Thr Leu Arg Leu Ala Asp A sp Glu Gln Gln Glu Ile
            340                 345                 350

Ala Asp Val Val Arg Leu Val Arg Tyr Gly A sn Gly Glu Arg Leu Gln
        355                 360                 365

Gln Pro Gly Gln Val Pro Thr Gly Met Arg P he Ile Val Asp Gly Arg
    370                 375                 380

Val Ser Leu Ser Val Ile Asp Gln Asp Gly A sp Val Ile Pro Ala Arg
385                 390                 395                 400

Val Leu Glu Arg Gly Asp Phe Leu Gly Gln T hr Thr Leu Thr Arg Glu
                405                 410                 415

Pro Val Leu Ala Thr Ala His Ala Leu Glu G lu Val Thr Val Leu Glu
            420                 425                 430

Met Ala Arg Asp Glu Ile Glu Arg Leu Val H is Arg Lys Pro Ile Leu
        435                 440                 445
```

-continued

Leu His Val Ile Gly Ala Val Ile Ala Asp A rg Arg Ala His Glu Leu
450 455 460

Arg Leu Met Asp Ser Gln Asp
465 470

<210> SEQ ID NO 173
<211> LENGTH: 2172
<212> TYPE: DNA
<213> ORGANISM: Mycobacterium vaccae

<400> SEQUENCE: 173
tagatgacaa ttctgccctg gaatgcgcga acgtctgaac acccgacgcg a aaaagacgc 60 gggcgctacc acctcctgtc gcggatgagc atccagtcca agttgctgct g atgctgctt 120 ctgaccagca ttctctcggc tgcggtggtc ggtttcatcg gctatcagtc c ggacggtcc 180 tcgctgcgcg catcggtgtt cgaccgcctc accgacatcc gcgagtcgca g tcgcgcggg 240 ttggagaatc agttcgcgga cctgaagaac tcgatggtga tttactcgcg c ggcagcact 300 gccacggagg cgatcggcgc gttcagcgac ggtttccgtc agctcggcga t gcgacgatc 360 aataccgggc aggcggcgtc attgcgccgt tactacgacc ggacgttcgc c aacaccacc 420 ctcgacgaca gcggaaaccg cgtcgacgtc cgcgcgctca tcccgaaatc c aacccccag 480 cgctatctgc aggcgctcta taccccgccg tttcagaact gggagaaggc g atcgcgttc 540 gacgacgcgc gcgacggcag cgcctggtcg gccgccaatg ccagattcaa c gagttcttc 600 cgcgagatcg tgcaccgctt caacttcgag gatctgatgc tgctcgacct c gagggcaac 660 gtggtgtact ccgcctacaa ggggccggat ctcgggacaa acatcgtcaa c ggcccctat 720 cgcaaccggg aactgtcgga agcctacgag aaggcggtcg cgtcgaactc g atcgactat 780 gtcggtgtca ccgacttcgg gtggtacctg cctgccgagg aaccgaccgc c tggttcctg 840 tccccggtcg ggttgaagga ccgagtcgac ggtgtgatgg cggtccagtt c ccgatcgcg 900 cggatcaacg aattgatgac ggcgcgggga cagtggcgtg acaccgggat g ggagacacc 960 ggtgagacca tcctggtcgg accggacaat ctgatgcgct cggactcccg g ctgttccgc 1020 gagaaccggg agaagttcct ggccgacgtc gtcgaggggg gaaccccgcc g gaggtcgcc 1080 gacgaatcgg ttgaccgccg cggcaccacg ctggtgcagc cggtgaccac c cgctccgtc 1140 gaggaggccc aacgcggcaa caccgggacg acgatcgagg acgactatct c ggccacgag 1200 gcgttacagg cgtactcacc ggtggacctg ccgggactgc actgggtgat c gtggccaag 1260 atcgacaccg acgaggcgtt cgccccggtg gcgcagttca ccaggaccct g gtgctgtcg 1320 acggtgatca tcatcttcgg cgtgtcgctg gcggccatgc tgctggcgcg g ttgttcgtc 1380 cgtccgatcc ggcggttgca ggccggcgcc cagcagatca gcggcggtga c taccgcctc 1440 gctctgccgg tgttgtctcg tgacgaattc ggcgatctga caacagcttt c aacgacatg 1500 agtcgcaatc tgtcgatcaa ggacgagctg ctcggcgagg agcgcgccga g aaccaacgg 1560 ctgatgctgt ccctgatgcc cgaaccggtg atgcagcgct acctcgacgg g gaggagacg 1620 atcgcccagg accacaagaa cgtcacggtg atcttcgccg acatgatggg c ctcgacgag 1680 ttgtcgcgca tgttgacctc cgaggaactg atggtggtgg tcaacgacct g acccgccag 1740 ttcgacgccg ccgccgagag tctcggggtc gaccacgtgc ggacgctgca c gacgggtac 1800 ctggccagct gcgggttagg cgtgccgcgg ctggacaacg tccggcgcac g gtcaatttc 1860 gcgatcgaaa tggaccgcat catcgaccgg cacgccgccg agtccgggca c gacctgcgg 1920

-continued ctccgcgcgg gcatcgacac cgggtcggcg gccagcgggc tggtggggcg g tccacgttg 1980 gcgtacgaca tgtggggttc ggcggtcgat gtcgctaacc aggtgcagcg c ggctccccc 2040 cagcccggca tctacgtcac ctcgcgggtg cacgaggtca tgcaggaaac t ctcgacttc 2100 gtcgccgccg gggaggtcgt cggcgagcgc ggcgtcgaga cggtctggcg g ttgcagggc 2160 caccggcgat ga 2172

<210> SEQ ID NO 174
<211> LENGTH: 722
<212> TYPE: PRT
<213> ORGANISM: Mycobacterium vaccae

<400> SEQUENCE: 174

Met Thr Ile Leu Pro Trp Asn Ala Arg Thr S er Glu His Pro Thr Arg
1 5 10 15

Lys Arg Arg Gly Arg Tyr His Leu Leu Ser A rg Met Ser Ile Gln Ser
20 25 30

Lys Leu Leu Leu Met Leu Leu Leu Thr Ser I le Leu Ser Ala Ala Val
35 40 45

Val Gly Phe Ile Gly Tyr Gln Ser Gly Arg S er Ser Leu Arg Ala Ser
50 55 60

Val Phe Asp Arg Leu Thr Asp Ile Arg Glu S er Gln Ser Arg Gly Leu
65 70 75 80

Glu Asn Gln Phe Ala Asp Leu Lys Asn Ser M et Val Ile Tyr Ser Arg
85 90 95

Gly Ser Thr Ala Thr Glu Ala Ile Gly Ala P he Ser Asp Gly Phe Arg
100 105 110

Gln Leu Gly Asp Ala Thr Ile Asn Thr Gly G ln Ala Ala Ser Leu Arg
115 120 125

Arg Tyr Tyr Asp Arg Thr Phe Ala Asn Thr T hr Leu Asp Asp Ser Gly
130 135 140

Asn Arg Val Asp Val Arg Ala Leu Ile Pro L ys Ser Asn Pro Gln Arg
145 150 155 160

Tyr Leu Gln Ala Leu Tyr Thr Pro Pro Phe G ln Asn Trp Glu Lys Ala
165 170 175

Ile Ala Phe Asp Asp Ala Arg Asp Gly Ser A la Trp Ser Ala Ala Asn
180 185 190

Ala Arg Phe Asn Glu Phe Phe Arg Glu Ile V al His Arg Phe Asn Phe
195 200 205

Glu Asp Leu Met Leu Leu Asp Leu Glu Gly A sn Val Val Tyr Ser Ala
210 215 220

Tyr Lys Gly Pro Asp Leu Gly Thr Asn Ile V al Asn Gly Pro Tyr Arg
225 230 235 240

Asn Arg Glu Leu Ser Glu Ala Tyr Glu Lys A la Val Ala Ser Asn Ser
245 250 255

Ile Asp Tyr Val Gly Val Thr Asp Phe Gly T rp Tyr Leu Pro Ala Glu
260 265 270

Glu Pro Thr Ala Trp Phe Leu Ser Pro Val G ly Leu Lys Asp Arg Val
275 280 285

Asp Gly Val Met Ala Val Gln Phe Pro Ile A la Arg Ile Asn Glu Leu
290 295 300

Met Thr Ala Arg Gly Gln Trp Arg Asp Thr G ly Met Gly Asp Thr Gly
305 310 315 320

Glu Thr Ile Leu Val Gly Pro Asp Asn Leu M et Arg Ser Asp Ser Arg

-continued

```
                325                 330                 335

Leu Phe Arg Glu Asn Arg Glu Lys Phe Leu Ala Asp Val Val Glu Gly
            340                 345                 350

Gly Thr Pro Pro Glu Val Ala Asp Glu Ser Val Asp Arg Arg Gly Thr
        355                 360                 365

Thr Leu Val Gln Pro Val Thr Thr Arg Ser Val Glu Glu Ala Gln Arg
    370                 375                 380

Gly Asn Thr Gly Thr Thr Ile Glu Asp Asp Tyr Leu Gly His Glu Ala
385                 390                 395                 400

Leu Gln Ala Tyr Ser Pro Val Asp Leu Pro Gly Leu His Trp Val Ile
                405                 410                 415

Val Ala Lys Ile Asp Thr Asp Glu Ala Phe Ala Pro Val Ala Gln Phe
            420                 425                 430

Thr Arg Thr Leu Val Leu Ser Thr Val Ile Ile Ile Phe Gly Val Ser
        435                 440                 445

Leu Ala Ala Met Leu Leu Ala Arg Leu Phe Val Arg Pro Ile Arg Arg
    450                 455                 460

Leu Gln Ala Gly Ala Gln Gln Ile Ser Gly Gly Asp Tyr Arg Leu Ala
465                 470                 475                 480

Leu Pro Val Leu Ser Arg Asp Glu Phe Gly Asp Leu Thr Thr Ala Phe
                485                 490                 495

Asn Asp Met Ser Arg Asn Leu Ser Ile Lys Asp Glu Leu Leu Gly Glu
            500                 505                 510

Glu Arg Ala Glu Asn Gln Arg Leu Met Leu Ser Leu Met Pro Glu Pro
        515                 520                 525

Val Met Gln Arg Tyr Leu Asp Gly Glu Glu Thr Ile Ala Gln Asp His
    530                 535                 540

Lys Asn Val Thr Val Ile Phe Ala Asp Met Met Gly Leu Asp Glu Leu
545                 550                 555                 560

Ser Arg Met Leu Thr Ser Glu Glu Leu Met Val Val Val Asn Asp Leu
                565                 570                 575

Thr Arg Gln Phe Asp Ala Ala Ala Glu Ser Leu Gly Val Asp His Val
            580                 585                 590

Arg Thr Leu His Asp Gly Tyr Leu Ala Ser Cys Gly Leu Gly Val Pro
        595                 600                 605

Arg Leu Asp Asn Val Arg Arg Thr Val Asn Phe Ala Ile Glu Met Asp
    610                 615                 620

Arg Ile Ile Asp Arg His Ala Ala Glu Ser Gly His Asp Leu Arg Leu
625                 630                 635                 640

Arg Ala Gly Ile Asp Thr Gly Ser Ala Ala Ser Gly Leu Val Gly Arg
                645                 650                 655

Ser Thr Leu Ala Tyr Asp Met Trp Gly Ser Ala Val Asp Val Ala Asn
            660                 665                 670

Gln Val Gln Arg Gly Ser Pro Gln Pro Gly Ile Tyr Val Thr Ser Arg
        675                 680                 685

Val His Glu Val Met Gln Glu Thr Leu Asp Phe Val Ala Ala Gly Glu
    690                 695                 700

Val Val Gly Glu Arg Gly Val Glu Thr Val Trp Arg Leu Gln Gly His
705                 710                 715                 720

Arg Arg
```

<210> SEQ ID NO 175
<211> LENGTH: 898

-continued

<212> TYPE: DNA
<213> ORGANISM: Mycobacterium vaccae

<400> SEQUENCE: 175
gagcaaccgt tccggctcgg cgactggatc accgtcccca ccgcggcggg c cggccgtcc 60 gcccacggcc gcgtggtgga agtcaactgg cgtgcaacac atatcgacac c ggcggcaac 120 ctgctggtaa tgcccaacgc cgaactcgcc ggcgcgtcgt tcaccaatta c agccggccc 180 gtgggagagc accggctgac cgtcgtcacc accttcaacg ccgcggacac c cccgatgat 240 gtctgcgaga tgctgtcgtc ggtcgcggcg tcgctgcccg aactgcgcac c gacggacag 300 atcgccacgc tctatctcgg tgcggccgaa tacgagaagt cgatcccgtt g cacacaccc 360 gcggtggacg actcggtcag gagcacgtac ctgcgatggg tctggtacgc c gcgcgccgg 420 caggaacttc gcctaacggc gtcgccgacg attcgacacg ccggaacgga t cgcctcggc 480 catgcgggct gtggcgtcca cactgcgctt ggcagacgac gaacagcagg a gatcgccga 540 cgtggtgcgt ctggtccgtt acggcaacgg ggaacgcctc cagcagccgg g tcaggtacc 600 gaccgggatg aggttcatcg tagacggcag ggtgagtctg tccgtgatcg a tcaggacgg 660 cgacgtgatc ccggcgcggg tgctcgagcg tggcgacttc ctggggcaga c cacgctgac 720 gcgggaaccg gtactggcga ccgcgcacgc gctggaggaa gtcaccgtgc t ggagatggc 780 ccgtgacgag atcgagcgcc tggtgcaccg aaagccgatc ctgctgcacg t gatcggggc 840 cgtgatcgcc gaccggcgcg cgcacgaact tcggttgatg gcggactcgc a ggactga 898

<210> SEQ ID NO 176
<211> LENGTH: 2013
<212> TYPE: DNA
<213> ORGANISM: Mycobacterium vaccae

<400> SEQUENCE: 176
ggctatcagt ccggacggtc ctcgctgcgc gcatcggtgt tcgaccgcct c accgacatc 60 cgcgagtcgc agtcgcgcgg gttggagaat cagttcgcgg acctgaagaa c tcgatggtg 120 atttactcgc gcggcagcac tgccacggag gcgatcggcg cgttcagcga c ggtttccgt 180 cagctcggcg atgcgacgat caataccggg caggcggcgt cattgcgccg t tactacgac 240 cggacgttcg ccaacaccac cctcgacgac agcggaaacc gcgtcgacgt c cgcgcgctc 300 atcccgaaat ccaaccccca gcgctatctg caggcgctct ataccccgcc g tttcagaac 360 tgggagaagg cgatcgcgtt cgacgacgcg cgcgacggca gcgcctggtc g gccgccaat 420 gccagattca acgagttctt ccgcgagatc gtgcaccgct tcaacttcga g gatctgatg 480 ctgctcgacc tcgagggcaa cgtggtgtac tccgcctaca aggggccgga t ctcgggaca 540 aacatcgtca acggccccta tcgcaaccgg gaactgtcgg aagcctacga g aaggcggtc 600 gcgtcgaact cgatcgacta tgtcggtgtc accgacttcg ggtggtacct g cctgccgag 660 gaaccgaccg cctggttcct gtccccggtc gggttgaagg accgagtcga c ggtgtgatg 720 gcggtccagt tcccgatcgc gcggatcaac gaattgatga cggcgcgggg a cagtggcgt 780 gacaccggga tgggagacac cggtgagacc atcctggtcg gaccggacaa t ctgatgcgc 840 tcggactccc ggctgttccg cgagaaccgg gagaagttcc tggccgacgt c gtcgagggg 900 ggaaccccgc cggaggtcgc cgacgaatcg gttgaccgcc gcggcaccac g ctggtgcag 960 ccggtgacca cccgctccgt cgaggaggcc caacgcggca acaccgggac g acgatcgag 1020 gacgactatc tcggccacga ggcgttacag gcgtactcac cggtggacct g ccgggactg 1080

-continued

```
cactgggtga tcgtggccaa gatcgacacc gacgaggcgt tcgccccggt g gcgcagttc   1140

accaggaccc tggtgctgtc gacggtgatc atcatcttcg gcgtgtcgct g gcggccatg   1200

ctgctggcgc ggttgttcgt ccgtccgatc cggcggttgc aggccggcgc c cagcagatc   1260

agcggcggtg actaccgcct cgctctgccg gtgttgtctc gtgacgaatt c ggcgatctg   1320

acaacagctt tcaacgacat gagtcgcaat ctgtcgatca aggacgagct g ctcggcgag   1380

gagcgcgccg agaaccaacg gctgatgctg tccctgatgc ccgaaccggt g atgcagcgc   1440

tacctcgacg gggaggagac gatcgcccag gaccacaaga acgtcacggt g atcttcgcc   1500

gacatgatgg gcctcgacga gttgtcgcgc atgttgacct ccgaggaact g atggtggtg   1560

gtcaacgacc tgacccgcca gttcgacgcc gccgccgaga gtctcggggt c gaccacgtg   1620

cggacgctgc acgacgggta cctggccagc tgcgggttag gcgtgccgcg g ctggacaac   1680

gtccggcgca cggtcaattt cgcgatcgaa atggaccgca tcatcgaccg g cacgccgcc   1740

gagtccgggc acgacctgcg gctccgcgcg ggcatcgaca ccgggtcggc g gccagcggg   1800

ctggtggggc ggtccacgtt ggcgtacgac atgtggggtt cggcggtcga t gtcgctaac   1860

caggtgcagc gcggctcccc ccagcccggc atctacgtca cctcgcgggt g cacgaggtc   1920

atgcaggaaa ctctcgactt cgtcgccgcc ggggaggtcg tcggcgagcg c ggcgtcgag   1980

acggtctggc ggttgcaggg ccaccggcga tga                             2013
```

```
<210> SEQ ID NO 177
<211> LENGTH: 297
<212> TYPE: PRT
<213> ORGANISM: Mycobacterium vaccae
<220> FEATURE:
<221> NAME/KEY: UNSURE
<222> LOCATION: (145)...(145)
<221> NAME/KEY: UNSURE
<222> LOCATION: (151)...(151)

<400> SEQUENCE: 177

Glu Gln Pro Phe Arg Leu Gly Asp Trp Ile T hr Val Pro Thr Ala Ala
 1               5                   10                  15

Gly Arg Pro Ser Ala His Gly Arg Val Val G lu Val Asn Trp Arg Ala
            20                  25                  30

Thr His Ile Asp Thr Gly Gly Asn Leu Leu V al Met Pro Asn Ala Glu
        35                  40                  45

Leu Ala Gly Ala Ser Phe Thr Asn Tyr Ser A rg Pro Val Gly Glu His
    50                  55                  60

Arg Leu Thr Val Val Thr Thr Phe Asn Ala A la Asp Thr Pro Asp Asp
65                  70                  75                  80

Val Cys Glu Met Leu Ser Ser Val Ala Ala S er Leu Pro Glu Leu Arg
                85                  90                  95

Thr Asp Gly Gln Ile Ala Thr Leu Tyr Leu G ly Ala Ala Glu Tyr Glu
            100                 105                 110

Lys Ser Ile Pro Leu His Thr Pro Ala Val A sp Asp Ser Val Arg Ser
        115                 120                 125

Thr Tyr Leu Arg Trp Val Trp Tyr Ala Ala A rg Arg Gln Glu Leu Arg
    130                 135                 140

Xaa Asn Gly Val Ala Asp Xaa Phe Asp Thr P ro Glu Arg Ile Ala Ser
145                 150                 155                 160

Ala Met Arg Ala Val Ala Ser Thr Leu Arg L eu Ala Asp Asp Glu Gln
                165                 170                 175

Gln Glu Ile Ala Asp Val Val Arg Leu Val A rg Tyr Gly Asn Gly Glu
```

-continued

```
            180                 185                 190

Arg Leu Gln Gln Pro Gly Gln Val Pro Thr G ly Met Arg Phe Ile Val
        195                 200                 205

Asp Gly Arg Val Ser Leu Ser Val Ile Asp G ln Asp Gly Asp Val Ile
    210                 215                 220

Pro Ala Arg Val Leu Glu Arg Gly Asp Phe L eu Gly Gln Thr Thr Leu
225                 230                 235                 240

Thr Arg Glu Pro Val Leu Ala Thr Ala His A la Leu Glu Glu Val Thr
                245                 250                 255

Val Leu Glu Met Ala Arg Asp Glu Ile Glu A rg Leu Val His Arg Lys
            260                 265                 270

Pro Ile Leu Leu His Val Ile Gly Ala Val A la Asp Arg Arg Ala His
        275                 280                 285

Glu Leu Arg Leu Met Asp Ser Gln Asp
    290                 295


<210> SEQ ID NO 178
<211> LENGTH: 670
<212> TYPE: PRT
<213> ORGANISM: Mycobacterium vaccae

<400> SEQUENCE: 178

Gly Tyr Gln Ser Gly Arg Ser Ser Leu Arg A la Ser Val Phe Asp Arg
 1               5                  10                  15

Leu Thr Asp Ile Arg Glu Ser Gln Ser Arg G ly Leu Glu Asn Gln Phe
            20                  25                  30

Ala Asp Leu Lys Asn Ser Met Val Ile Tyr S er Arg Gly Ser Thr Ala
        35                  40                  45

Thr Glu Ala Ile Gly Ala Phe Ser Asp Gly P he Arg Gln Leu Gly Asp
    50                  55                  60

Ala Thr Ile Asn Thr Gly Gln Ala Ala Ser L eu Arg Arg Tyr Tyr Asp
65                  70                  75                  80

Arg Thr Phe Ala Asn Thr Thr Leu Asp Asp S er Gly Asn Arg Val Asp
                85                  90                  95

Val Arg Ala Leu Ile Pro Lys Ser Asn Pro G ln Arg Tyr Leu Gln Ala
            100                 105                 110

Leu Tyr Thr Pro Pro Phe Gln Asn Trp Glu L ys Ala Ile Ala Phe Asp
        115                 120                 125

Asp Ala Arg Asp Gly Ser Ala Trp Ser Ala A la Asn Ala Arg Phe Asn
    130                 135                 140

Glu Phe Phe Arg Glu Ile Val His Arg Phe A sn Phe Glu Asp Leu Met
145                 150                 155                 160

Leu Leu Asp Leu Glu Gly Asn Val Val Tyr S er Ala Tyr Lys Gly Pro
                165                 170                 175

Asp Leu Gly Thr Asn Ile Val Asn Gly Pro T yr Arg Asn Arg Glu Leu
            180                 185                 190

Ser Glu Ala Tyr Glu Lys Ala Val Ala Ser A sn Ser Ile Asp Tyr Val
        195                 200                 205

Gly Val Thr Asp Phe Gly Trp Tyr Leu Pro A la Glu Glu Pro Thr Ala
    210                 215                 220

Trp Phe Leu Ser Pro Val Gly Leu Lys Asp A rg Val Asp Gly Val Met
225                 230                 235                 240

Ala Val Gln Phe Pro Ile Ala Arg Ile Asn G lu Leu Met Thr Ala Arg
                245                 250                 255
```

-continued

```
Gly Gln Trp Arg Asp Thr Gly Met Gly Asp T hr Gly Glu Thr Ile Leu
            260                 265                 270

Val Gly Pro Asp Asn Leu Met Arg Ser Asp S er Arg Leu Phe Arg Glu
        275                 280                 285

Asn Arg Glu Lys Phe Leu Ala Asp Val Val G lu Gly Gly Thr Pro Pro
    290                 295                 300

Glu Val Ala Asp Glu Ser Val Asp Arg Arg G ly Thr Thr Leu Val Gln
305                 310                 315                 320

Pro Val Thr Thr Arg Ser Val Glu Glu Ala G ln Arg Gly Asn Thr Gly
                325                 330                 335

Thr Thr Ile Glu Asp Asp Tyr Leu Gly His G lu Ala Leu Gln Ala Tyr
            340                 345                 350

Ser Pro Val Asp Leu Pro Gly Leu His Trp V al Ile Val Ala Lys Ile
        355                 360                 365

Asp Thr Asp Glu Ala Phe Ala Pro Val Ala G ln Phe Thr Arg Thr Leu
    370                 375                 380

Val Leu Ser Thr Val Ile Ile Ile Phe Gly V al Ser Leu Ala Ala Met
385                 390                 395                 400

Leu Leu Ala Arg Leu Phe Val Arg Pro Ile A rg Arg Leu Gln Ala Gly
                405                 410                 415

Ala Gln Gln Ile Ser Gly Gly Asp Tyr Arg L eu Ala Leu Pro Val Leu
            420                 425                 430

Ser Arg Asp Glu Phe Gly Asp Leu Thr Thr A la Phe Asn Asp Met Ser
        435                 440                 445

Arg Asn Leu Ser Ile Lys Asp Glu Leu Leu G ly Glu Glu Arg Ala Glu
    450                 455                 460

Asn Gln Arg Leu Met Leu Ser Leu Met Pro G lu Pro Val Met Gln Arg
465                 470                 475                 480

Tyr Leu Asp Gly Glu Glu Thr Ile Ala Gln A sp His Lys Asn Val Thr
                485                 490                 495

Val Ile Phe Ala Asp Met Met Gly Leu Asp G lu Leu Ser Arg Met Leu
            500                 505                 510

Thr Ser Glu Glu Leu Met Val Val Val Asn A sp Leu Thr Arg Gln Phe
        515                 520                 525

Asp Ala Ala Ala Glu Ser Leu Gly Val Asp H is Val Arg Thr Leu His
    530                 535                 540

Asp Gly Tyr Leu Ala Ser Cys Gly Leu Gly V al Pro Arg Leu Asp Asn
545                 550                 555                 560

Val Arg Arg Thr Val Asn Phe Ala Ile Glu M et Asp Arg Ile Ile Asp
                565                 570                 575

Arg His Ala Ala Glu Ser Gly His Asp Leu A rg Leu Arg Ala Gly Ile
            580                 585                 590

Asp Thr Gly Ser Ala Ala Ser Gly Leu Val G ly Arg Ser Thr Leu Ala
        595                 600                 605

Tyr Asp Met Trp Gly Ser Ala Val Asp Val A la Asn Gln Val Gln Arg
    610                 615                 620

Gly Ser Pro Gln Pro Gly Ile Tyr Val Thr S er Arg Val His Glu Val
625                 630                 635                 640

Met Gln Glu Thr Leu Asp Phe Val Ala Ala G ly Glu Val Val Gly Glu
                645                 650                 655

Arg Gly Val Glu Thr Val Trp Arg Leu Gln G ly His Arg Arg
            660                 665                 670
```

-continued

<210> SEQ ID NO 179
<211> LENGTH: 520
<212> TYPE: DNA
<213> ORGANISM: Mycobacterium vaccae

<400> SEQUENCE: 179

```
gtgatcgacg aaaccctctt ccatgccgag gagaagatgg agaaggccgt c tcggtggca     60
cccgacgacc tggcgtcgat tcgtaccggc cgcgcgaacc ccggcatgtt c aaccggatc    120
aacatcgact actacggcgc ctccaccccg atcacgcagc tgtccagcat c aacgtgccc    180
gaggcgcgca tggtggtgat caagccctac gaggcgagcc agctgcgcct c atcgaggat    240
gcgatccgca actccgacct cggcgtcaat ccgaccaacg acggcaacat c atccgggtg    300
tcgatcccgc agctcaccga ggagcgccgc cgcgacctgg tcaagcaggc c aaggccaag    360
ggcgaggacg ccaaggtgtc ggtgcgcaac atccgtcgca acgatatgaa c acctttcgc    420
atcgcaccgg tacggctgcc gacgccaccg ccgtcgtaga agcgacagag g atcgcaggt    480
aacggtattg gccacgcctt ctgtggcggg ccgacaccac                          520
```

<210> SEQ ID NO 180
<211> LENGTH: 1071
<212> TYPE: DNA
<213> ORGANISM: Mycobacterium vaccae

<400> SEQUENCE: 180

```
cgtggggaag gattgcactc tatgagcgaa atcgcccgtc cctggcgggt t ctggcaggt     60
ggcatcggtg cctgcgccgc gggtatcgcc ggggtgctga gcatcgcggt c accacggcg    120
tcggcccagc cgggcctccc gcagcccccg ctgcccgccc ctgccacagt g acgcaaacc    180
gtcacggttg cgcccaacgc cgcgccacaa ctcatcccgc gccccggtgt g acgcctgcc    240
accggcggcg ccgccgcggt gcccgccggg gtgagcgccc cggcggtcgc g ccggccccc    300
gcgctgcccg cccgcccggt gtccacgatc gccccggcca cctcgggcac g ctcagcgag    360
ttcttcgccg ccaagggcgt cacgatggag ccgcagtcca gccgcgactt c cgcgccctc    420
aacatcgtgc tgccgaagcc gcggggctgg gagcacatcc cggacccgaa c gtgccggac    480
gcgttcgcgg tgctggccga ccgggtcggc ggcaacggcc tgtactcgtc g aacgcccag    540
gtggtggtct acaaactcgt cggcgagttc gaccccaagg aagcgatcag c cacggcttc    600
gtcgacagcc agaagctgcc ggcgtggcgt tccaccgacg cgtcgctggc c gacttcggc    660
ggaatgccgt cctcgctgat cgagggcacc taccgcgaga acaacatgaa g ctgaacacg    720
tcccggcgcc acgtcattgc caccgcgggg cccgaccact acctggtgtc g ctgtcggtg    780
accaccagcg tcgaacaggc cgtggccgaa gccgcggagg ccaccgacgc g attgtcaac    840
ggcttcaagg tcagcgttcc gggtccgggt ccggccgcac cgccacctgc a cccggtgcc    900
cccggtgtcc cgcccgcccc cggcgccccg gcgctgccgc tggccgtcgc a ccacccccg    960
gctcccgctg ttcccgccgt ggcgcccgcg ccacagctgc tgggactgca g ggatagacg   1020
tcgtcgtccc ccgggcgaag cctggcgccc gggggacgac ggcccctttc t             1071
```

<210> SEQ ID NO 181
<211> LENGTH: 152
<212> TYPE: PRT
<213> ORGANISM: Mycobacterium vaccae

<400> SEQUENCE: 181

```
Val Ile Asp Glu Thr Leu Phe His Ala Glu G lu Lys Met Glu Lys Ala
 1               5                  10                  15
```

-continued

```
Val Ser Val Ala Pro Asp Asp Leu Ala Ser I le Arg Thr Gly Arg Ala
            20                  25                  30

Asn Pro Gly Met Phe Asn Arg Ile Asn Ile A sp Tyr Tyr Gly Ala Ser
        35                  40                  45

Thr Pro Ile Thr Gln Leu Ser Ser Ile Asn V al Pro Glu Ala Arg Met
    50                  55                  60

Val Val Ile Lys Pro Tyr Glu Ala Ser Gln L eu Arg Leu Ile Glu Asp
65                  70                  75                  80

Ala Ile Arg Asn Ser Asp Leu Gly Val Asn P ro Thr Asn Asp Gly Asn
                85                  90                  95

Ile Ile Arg Val Ser Ile Pro Gln Leu Thr G lu Glu Arg Arg Arg Asp
            100                 105                 110

Leu Val Lys Gln Ala Lys Ala Lys Gly Glu A sp Ala Lys Val Ser Val
        115                 120                 125

Arg Asn Ile Arg Arg Asn Asp Met Asn Thr P he Arg Ile Ala Pro Val
    130                 135                 140

Arg Leu Pro Thr Pro Pro Pro Ser
145                 150


<210> SEQ ID NO 182
<211> LENGTH: 331
<212> TYPE: PRT
<213> ORGANISM: Mycobacterium vaccae

<400> SEQUENCE: 182

Met Ser Glu Ile Ala Arg Pro Trp Arg Val L eu Ala Gly Gly Ile Gly
 1               5                  10                  15

Ala Cys Ala Ala Gly Ile Ala Gly Val Leu S er Ile Ala Val Thr Thr
            20                  25                  30

Ala Ser Ala Gln Pro Gly Leu Pro Gln Pro P ro Leu Pro Ala Pro Ala
        35                  40                  45

Thr Val Thr Gln Thr Val Thr Val Ala Pro A sn Ala Ala Pro Gln Leu
    50                  55                  60

Ile Pro Arg Pro Gly Val Thr Pro Ala Thr G ly Gly Ala Ala Ala Val
65                  70                  75                  80

Pro Ala Gly Val Ser Ala Pro Ala Val Ala P ro Ala Pro Ala Leu Pro
                85                  90                  95

Ala Arg Pro Val Ser Thr Ile Ala Pro Ala T hr Ser Gly Thr Leu Ser
            100                 105                 110

Glu Phe Phe Ala Ala Lys Gly Val Thr Met G lu Pro Gln Ser Ser Arg
        115                 120                 125

Asp Phe Arg Ala Leu Asn Ile Val Leu Pro L ys Pro Arg Gly Trp Glu
    130                 135                 140

His Ile Pro Asp Pro Asn Val Pro Asp Ala P he Ala Val Leu Ala Asp
145                 150                 155                 160

Arg Val Gly Gly Asn Gly Leu Tyr Ser Ser A sn Ala Gln Val Val Val
                165                 170                 175

Tyr Lys Leu Val Gly Glu Phe Asp Pro Lys G lu Ala Ile Ser His Gly
            180                 185                 190

Phe Val Asp Ser Gln Lys Leu Pro Ala Trp A rg Ser Thr Asp Ala Ser
        195                 200                 205

Leu Ala Asp Phe Gly Gly Met Pro Ser Ser L eu Ile Glu Gly Thr Tyr
    210                 215                 220

Arg Glu Asn Asn Met Lys Leu Asn Thr Ser A rg Arg His Val Ile Ala
```

-continued

```
225                 230                 235                 240

Thr Ala Gly Pro Asp His Tyr Leu Val Ser L eu Ser Val Thr Thr Ser
                245                 250                 255

Val Glu Gln Ala Val Ala Glu Ala Ala Glu A la Thr Asp Ala Ile Val
            260                 265                 270

Asn Gly Phe Lys Val Ser Val Pro Gly Pro G ly Pro Ala Ala Pro Pro
        275                 280                 285

Pro Ala Pro Gly Ala Pro Gly Val Pro Pro A la Pro Gly Ala Pro Ala
    290                 295                 300

Leu Pro Leu Ala Val Ala Pro Pro Pro Ala P ro Ala Val Pro Ala Val
305                 310                 315                 320

Ala Pro Ala Pro Gln Leu Leu Gly Leu Gln G ly
                325                 330


<210> SEQ ID NO 183
<211> LENGTH: 207
<212> TYPE: DNA
<213> ORGANISM: Mycobacterium vaccae

<400> SEQUENCE: 183

acctacgagt tcgagaacaa ggtcacgggc ggccgcatcc cgcgcgagta c atcccgtcg     60

gtggatgccg gcgcgcagga cgccatgcag tacggcgtgc tggccggcta c ccgctggtt    120

aacgtcaagc tgacgctgct cgacggtgcc taccacgaag tcgactcgtc g gaaatggca    180

ttcaaggttg ccggctccca ggtcata                                        207


<210> SEQ ID NO 184
<211> LENGTH: 69
<212> TYPE: PRT
<213> ORGANISM: Mycobacterium vaccae

<400> SEQUENCE: 184

Thr Tyr Glu Phe Glu Asn Lys Val Thr Gly G ly Arg Ile Pro Arg Glu
 1               5                  10                  15

Tyr Ile Pro Ser Val Asp Ala Gly Ala Gln A sp Ala Met Gln Tyr Gly
            20                  25                  30

Val Leu Ala Gly Tyr Pro Leu Val Asn Val L ys Leu Thr Leu Leu Asp
        35                  40                  45

Gly Ala Tyr His Glu Val Asp Ser Ser Glu M et Ala Phe Lys Val Ala
    50                  55                  60

Gly Ser Gln Val Ile
65


<210> SEQ ID NO 185
<211> LENGTH: 898
<212> TYPE: DNA
<213> ORGANISM: Mycobacterium vaccae
<220> FEATURE:
<221> NAME/KEY: unsure
<222> LOCATION: (637)...(637)
<221> NAME/KEY: unsure
<222> LOCATION: (662)...(662)

<400> SEQUENCE: 185

cgacctccac ccgggcgtga ggccaaccac taggctggtc accagtagtc g acggcacac     60

ttcaccgaaa aaatgaggac agaggagaca cccgtgacga tccgtgttgg t gtgaacggc    120

ttcggccgta tcggacgcaa cttcttccgc gcgctggacg cgcagaaggc c gaaggcaag    180

aacaaggaca tcgagatcgt cgcggtcaac gacctcaccg acaacgccac g ctggcgcac    240
```

-continued

```
ctgctgaagt tcgactcgat cctgggccgg ctgccctacg acgtgagcct c gaaggcgag    300

gacaccatcg tcgtcggcag caccaagatc aaggcgctcg aggtcaagga a ggcccggcg    360

gcgctgccct ggggcgacct gggcgtcgac gtcgtcgtcg agtccaccgg c atcttcacc    420

aagcgcgaca aggcccaggg ccacctcgac gcgggcgcca agaaggtcat c atctccgcg    480

ccggccaccg atgaggacat caccatcgtg ctcggcgtca acgacgacaa g tacgacggc    540

agccagaaca tcatctccaa cgcgtcgtgc accacgaact gcctcggccc g ctggcgaag    600

gtcatcaacg acgagttcgg catcgtcaag ggcctgntga ccaccatcca c gcctacacc    660

cnggtccaga acctgcagga cggcccgcac aaggatctgc gccgggcccg c gccgccgcg    720

ctgaacatcg tgccgacctc caccggtgcc gccaaggcca tcggactggt g ctgcccgag    780

ctgaagggca agctcgacgg ctacgcgctg cgggtgccga tccccaccgg c tcggtcacc    840

gacctgaccg ccgagctggg caagtcggcc accgtggacg agatcaacgc c gcgatga      898


<210> SEQ ID NO 186
<211> LENGTH: 268
<212> TYPE: PRT
<213> ORGANISM: Mycobacterium vaccae
<220> FEATURE:
<221> NAME/KEY: UNSURE
<222> LOCATION: (182)...(182)
<221> NAME/KEY: UNSURE
<222> LOCATION: (190)...(190)

<400> SEQUENCE: 186

Val Thr Ile Arg Val Gly Val Asn Gly Phe G ly Arg Ile Gly Arg Asn
 1               5                   10                  15

Phe Phe Arg Ala Leu Asp Ala Gln Lys Ala G lu Gly Lys Asn Lys Asp
            20                  25                  30

Ile Glu Ile Val Ala Val Asn Asp Leu Thr A sp Asn Ala Thr Leu Ala
        35                  40                  45

His Leu Leu Lys Phe Asp Ser Ile Leu Gly A rg Leu Pro Tyr Asp Val
    50                  55                  60

Ser Leu Glu Gly Glu Asp Thr Ile Val Val G ly Ser Thr Lys Ile Lys
65                  70                  75                  80

Ala Leu Glu Val Lys Glu Gly Pro Ala Ala L eu Pro Trp Gly Asp Leu
                85                  90                  95

Gly Val Asp Val Val Val Glu Ser Thr Gly I le Phe Thr Lys Arg Asp
            100                 105                 110

Lys Ala Gln Gly His Leu Asp Ala Gly Ala L ys Lys Val Ile Ile Ser
        115                 120                 125

Ala Pro Ala Thr Asp Glu Asp Ile Thr Ile V al Leu Gly Val Asn Asp
    130                 135                 140

Asp Lys Tyr Asp Gly Ser Gln Asn Ile Ile S er Asn Ala Ser Cys Thr
145                 150                 155                 160

Thr Asn Cys Leu Gly Pro Leu Ala Lys Val I le Asn Asp Glu Phe Gly
                165                 170                 175

Ile Val Lys Gly Leu Xaa Thr Thr Ile His A la Tyr Thr Xaa Val Gln
            180                 185                 190

Asn Leu Gln Asp Gly Pro His Lys Asp Leu A rg Arg Ala Arg Ala Ala
        195                 200                 205

Ala Leu Asn Ile Val Pro Thr Ser Thr Gly A la Ala Lys Ala Ile Gly
    210                 215                 220

Leu Val Leu Pro Glu Leu Lys Gly Lys Leu A sp Gly Tyr Ala Leu Arg
```

-continued

```
225                 230                 235                 240

Val Pro Ile Pro Thr Gly Ser Val Thr Asp L eu Thr Ala Glu Leu Gly
               245                 250                 255

Lys Ser Ala Thr Val Asp Glu Ile Asn Ala A la Met
            260                 265


<210> SEQ ID NO 187
<211> LENGTH: 41
<212> TYPE: PRT
<213> ORGANISM: Mycobacterium vaccae
<220> FEATURE:
<221> NAME/KEY: UNSURE
<222> LOCATION: (39)...(39)

<400> SEQUENCE: 187

Met Asn Lys Ala Glu Leu Ile Asp Val Leu T hr Glu Lys Leu Gly Ser
 1               5                  10                  15

Asp Arg Arg Gln Ala Thr Ala Ala Val Glu A sn Val Val Asp Thr Ile
            20                  25                  30

Val Ala Ala Val Pro Lys Xaa Val Val
        35                  40


<210> SEQ ID NO 188
<211> LENGTH: 26
<212> TYPE: DNA
<213> ORGANISM: Artificial Sequence
<220> FEATURE:
<223> OTHER INFORMATION: Made in a lab
<220> FEATURE:
<221> NAME/KEY: unsure
<222> LOCATION: (12)...(12)

<400> SEQUENCE: 188

atgaayaarg cngarctsat ygaygt                                           26


<210> SEQ ID NO 189
<211> LENGTH: 20
<212> TYPE: DNA
<213> ORGANISM: Artificial Sequence
<220> FEATURE:
<223> OTHER INFORMATION: Made in a lab

<400> SEQUENCE: 189

atsgtrtgva cvacgttytc                                                  20


<210> SEQ ID NO 190
<211> LENGTH: 84
<212> TYPE: DNA
<213> ORGANISM: Artificial Sequence
<220> FEATURE:
<223> OTHER INFORMATION: Made in a lab
<220> FEATURE:
<221> NAME/KEY: unsure
<222> LOCATION: (2)...(2)

<400> SEQUENCE: 190

gnactcattg acgtactcac tgagaagctg ggctcggatt gtcggcaagc g actgcggca     60

atggagaacg tggtccacac cata                                             84


<210> SEQ ID NO 191
<211> LENGTH: 337
<212> TYPE: DNA
<213> ORGANISM: Mycobacterium vaccae
<220> FEATURE:
<221> NAME/KEY: unsure
```

-continued

<222> LOCATION: (2)...(2)

<400> SEQUENCE: 191
gnactcattg acgtactcac tgagaagctg ggctcggatt gtcggcaagc g actgcggcg 60 gtggagaatg ttgtcgacac catcgtgcgc gccgtgcaca agggtgagag c gtcaccatc 120 acgggcttcg gtgttttcga gcagcgtcgt cgcgcagcac gcgtggcacg c aatccgcgc 180 accggcgaga ccgtgaaggt caagcccacc tcagtcccgg cattccgtcc c ggcgctcag 240 ttcaaggctg ttgtctctgg cgcacagaag cttccggccg agggtccggc g gtcaagcgc 300 ggtgtgaccg cgacgagcac cgcccgcaag gcagcca 337

<210> SEQ ID NO 192
<211> LENGTH: 111
<212> TYPE: PRT
<213> ORGANISM: Mycobacterium vaccae
<220> FEATURE:
<221> NAME/KEY: UNSURE
<222> LOCATION: (1)...(1)

<400> SEQUENCE: 192

Xaa Leu Ile Asp Val Leu Thr Glu Lys Leu G ly Ser Asp Arg Gln Ala
1 5 10 15

Thr Ala Ala Val Glu Asn Val Val Asp Thr I le Val Arg Ala Val His
20 25 30

Lys Gly Glu Ser Val Thr Ile Thr Gly Phe G ly Val Phe Glu Gln Arg
35 40 45

Arg Arg Ala Ala Arg Val Ala Arg Asn Pro A rg Thr Gly Glu Thr Val
50 55 60

Lys Val Lys Pro Thr Ser Val Pro Ala Phe A rg Pro Gly Ala Gln Phe
65 70 75 80

Lys Ala Val Val Ser Gly Ala Gln Lys Leu P ro Ala Glu Gly Pro Ala
85 90 95

Val Lys Arg Gly Val Thr Ala Thr Ser Thr A la Arg Lys Ala Ala
100 105 110

<210> SEQ ID NO 193
<211> LENGTH: 1164
<212> TYPE: DNA
<213> ORGANISM: Mycobacterium vaccae

<400> SEQUENCE: 193
ggtggcgcgc atcgagaagc gcccgccccg gttcacgggc gcctgatcat g gtgcgggcg 60 gcgctgcgct acggcttcgg gacggcctca ctgctggccg gcgggttcgt g ctgcgcgcc 120 ctgcagggca cgcctgccgc cctcggcgcg actccgggcg aggtcgcgcc g gtggcgcgc 180 cgctcgccga actaccgcga cggcaagttc gtcaacctgg agcccccgtc g ggcatcacg 240 atggatcgcg acctgcagcg gatgctgttg cgcgatctgg ccaacgccgc a tcccagggc 300 aagccgcccg gaccgatccc gctggccgag ccgccgaagg gggatcccac t cccgcgccg 360 gcggcggcca gctggtacgg ccattccagc gtgctgatcg aggtcgacgg c taccgcgtg 420 ctggccgacc cggtgtggag caacagatgt tcgccctcac gggcggtcgg a ccgcagcgc 480 atgcacgacg tcccggtgcc gctggaggcg cttcccgccg tggacgcggt g gtgatcagc 540 cacgaccact acgaccacct cgacatcgac accatcgtcg cgttggcgca c acccagcgg 600 gccccgttcg tggtgccgtt gggcatcggc gcacacctgc gcaagtgggg c gtccccgag 660 gcgcggatcg tcgagttgga ctggcacgaa gcccaccgca tagacgacct g acgctggtc 720

-continued tgcacccccg cccggcactt ctccggacgg ttgttctccc gcgactcgac g ctgtgggcg 780 tcgtgggtgg tcaccggctc gtcgcacaag gcgttcttcg gtggcgacac c ggatacacg 840 aagagcttcg ccgagatcgg cgacgagtac ggtccgttcg atctgaccct g ctgccgatc 900 ggggcctacc atcccgcgtt cgccgacatc cacatgaacc ccgaggaggc g gtgcgcgcc 960 catctggacc tgaccgaggt ggacaacagc ctgatggtgc ccatccactg g gcgacattc 1020 cgcctcgccc cgcatccgtg gtccgagccc gccgaacgcc tgctgaccgc t gccgacgcc 1080 gagcgggtac gcctgaccgt gccgattccc ggtcagcggg tggacccgga g tcgacgttc 1140 gacccgtggt ggcggttctg aacc 1164

<210> SEQ ID NO 194
<211> LENGTH: 370
<212> TYPE: PRT
<213> ORGANISM: Mycobacterium vaccae

<400> SEQUENCE: 194

Met Val Arg Ala Ala Leu Arg Tyr Gly Phe G ly Thr Ala Ser Leu Leu
1 5 10 15

Ala Gly Gly Phe Val Leu Arg Ala Leu Gln G ly Thr Pro Ala Ala Leu
20 25 30

Gly Ala Thr Pro Gly Glu Val Ala Pro Val A la Arg Arg Ser Pro Asn
35 40 45

Tyr Arg Asp Gly Lys Phe Val Asn Leu Glu P ro Pro Ser Gly Ile Thr
50 55 60

Met Asp Arg Asp Leu Gln Arg Met Leu Leu A rg Asp Leu Ala Asn Ala
65 70 75 80

Ala Ser Gln Gly Lys Pro Pro Gly Pro Ile P ro Leu Ala Glu Pro Pro
85 90 95

Lys Gly Asp Pro Thr Pro Ala Pro Ala Ala A la Ser Trp Tyr Gly His
100 105 110

Ser Ser Val Leu Ile Glu Val Asp Gly Tyr A rg Val Leu Ala Asp Pro
115 120 125

Val Trp Ser Asn Arg Cys Ser Pro Ser Arg A la Val Gly Pro Gln Arg
130 135 140

Met His Asp Val Pro Val Pro Leu Glu Ala L eu Pro Ala Val Asp Ala
145 150 155 160

Val Val Ile Ser His Asp His Tyr Asp His L eu Asp Ile Asp Thr Ile
165 170 175

Val Ala Leu Ala His Thr Gln Arg Ala Pro P he Val Val Pro Leu Gly
180 185 190

Ile Gly Ala His Leu Arg Lys Trp Gly Val P ro Glu Ala Arg Ile Val
195 200 205

Glu Leu Asp Trp His Glu Ala His Arg Ile A sp Asp Leu Thr Leu Val
210 215 220

Cys Thr Pro Ala Arg His Phe Ser Gly Arg L eu Phe Ser Arg Asp Ser
225 230 235 240

Thr Leu Trp Ala Ser Trp Val Val Thr Gly S er Ser His Lys Ala Phe
245 250 255

Phe Gly Gly Asp Thr Gly Tyr Thr Lys Ser P he Ala Glu Ile Gly Asp
260 265 270

Glu Tyr Gly Pro Phe Asp Leu Thr Leu Leu P ro Ile Gly Ala Tyr His
275 280 285

-continued

```
Pro Ala Phe Ala Asp Ile His Met Asn Pro G lu Glu Ala Val Arg Ala
    290                 295                 300

His Leu Asp Leu Thr Glu Val Asp Asn Ser L eu Met Val Pro Ile His
305                 310                 315                 320

Trp Ala Thr Phe Arg Leu Ala Pro His Pro T rp Ser Glu Pro Ala Glu
                325                 330                 335

Arg Leu Leu Thr Ala Ala Asp Ala Glu Arg V al Arg Leu Thr Val Pro
            340                 345                 350

Ile Pro Gly Gln Arg Val Asp Pro Glu Ser T hr Phe Asp Pro Trp Trp
        355                 360                 365

Arg Phe
    370


<210> SEQ ID NO 195
<211> LENGTH: 650
<212> TYPE: DNA
<213> ORGANISM: Mycobacterium vaccae

<400> SEQUENCE: 195

gacacaccag caccactgtt aacctcgcta gatcagtcgg ccgaacggaa g gacagccgt     60

gaccctgaaa accctagtca ccagcatgac cgctggggca gcagcagccg c aacactcgg    120

cgctgccgcc gtgggtgtga cctcgattgc cgtcggtgcg ggtgtcgccg g cgcgtcgcc    180

cgcggtgctg aacgcaccgc tgctttccgc ccctgccccc gatctgcagg g accgctggt    240

ctccaccttg agcgcgctgt cgggcccggg ctccttcgcc ggcgccaagg c cacctacgt    300

ccagggcggt ctcggccgca tcgaggcccg ggtggccgac agcggataca g caacgccgc    360

ggccaagggc tacttcccgc tgagcttcac cgtcgccggc atcgaccaga a cggtccgat    420

cgtgaccgcc aacgtcaccg cggcggcccc gacgggcgcc gtggccaccc a gccgctgac    480

gttcatcgcc gggccgagcc cgaccggatg gcagctgtcc aagcagtccg c actggccct    540

gatgtccgcg gtgggtgatc tcccgcacga ttctggtccg cagcgccgtc a catgtgtgg    600

cggcgctcgg gctgggtggg tgcctgggcg gctgcgcgca agatgaacat               650


<210> SEQ ID NO 196
<211> LENGTH: 159
<212> TYPE: PRT
<213> ORGANISM: Mycobacterium vaccae

<400> SEQUENCE: 196

Met Thr Ala Gly Ala Ala Ala Ala Ala Thr L eu Gly Ala Ala Ala Val
 1               5                  10                  15

Gly Val Thr Ser Ile Ala Val Gly Ala Gly V al Ala Gly Ala Ser Pro
            20                  25                  30

Ala Val Leu Asn Ala Pro Leu Leu Ser Ala P ro Ala Pro Asp Leu Gln
        35                  40                  45

Gly Pro Leu Val Ser Thr Leu Ser Ala Leu S er Gly Pro Gly Ser Phe
    50                  55                  60

Ala Gly Ala Lys Ala Thr Tyr Val Gln Gly G ly Leu Gly Arg Ile Glu
65                  70                  75                  80

Ala Arg Val Ala Asp Ser Gly Tyr Ser Asn A la Ala Ala Lys Gly Tyr
                85                  90                  95

Phe Pro Leu Ser Phe Thr Val Ala Gly Ile A sp Gln Asn Gly Pro Ile
            100                 105                 110

Val Thr Ala Asn Val Thr Ala Ala Ala Pro T hr Gly Ala Val Ala Thr
        115                 120                 125
```

-continued

```
Gln Pro Leu Thr Phe Ile Ala Gly Pro Ser P ro Thr Gly Trp Gln Leu
    130                 135                 140

Ser Lys Gln Ser Ala Leu Ala Leu Met Ser A la Val Ile Ala Ala
145                 150                 155


<210> SEQ ID NO 197
<211> LENGTH: 285
<212> TYPE: PRT
<213> ORGANISM: Mycobacterium vaccae

<400> SEQUENCE: 197

Met Gln Val Arg Arg Val Leu Gly Ser Val G ly Ala Ala Val Ala Val
 1               5                  10                  15

Ser Ala Ala Leu Trp Gln Thr Gly Val Ser I le Pro Thr Ala Ser Ala
            20                  25                  30

Asp Pro Cys Pro Asp Ile Glu Val Ile Phe A la Arg Gly Thr Gly Ala
        35                  40                  45

Glu Pro Gly Leu Gly Trp Val Gly Asp Ala P he Val Asn Ala Leu Arg
    50                  55                  60

Pro Lys Val Gly Glu Gln Ser Val Gly Thr T yr Ala Val Asn Tyr Pro
65                  70                  75                  80

Ala Gly Phe Asp Phe Asp Lys Ser Ala Pro M et Gly Ala Ala Asp Ala
                85                  90                  95

Ser Gly Arg Val Gln Trp Met Ala Asp Asn C ys Pro Asp Thr Lys Leu
            100                 105                 110

Val Leu Gly Gly Met Ser Gln Gly Ala Gly V al Ile Asp Leu Ile Thr
        115                 120                 125

Val Asp Pro Arg Pro Leu Gly Arg Phe Thr P ro Thr Pro Met Pro Pro
    130                 135                 140

Arg Val Ala Asp His Val Ala Ala Val Val V al Phe Gly Asn Pro Leu
145                 150                 155                 160

Arg Asp Ile Arg Gly Gly Gly Pro Leu Pro G ln Met Ser Gly Thr Tyr
                165                 170                 175

Gly Pro Lys Ser Ile Asp Leu Cys Ala Leu A sp Asp Pro Phe Cys Ser
            180                 185                 190

Pro Gly Phe Asn Leu Pro Ala His Phe Ala T yr Ala Asp Asn Gly Met
        195                 200                 205

Val Glu Glu Ala Ala Asn Phe Ala Arg Leu G lu Pro Gly Gln Ser Val
    210                 215                 220

Glu Leu Pro Glu Ala Pro Tyr Leu His Leu P he Val Pro Arg Gly Glu
225                 230                 235                 240

Val Thr Leu Glu Asp Ala Gly Pro Leu Arg G lu Gly Asp Ala Val Arg
                245                 250                 255

Phe Thr Ala Ser Gly Gly Gln Arg Val Thr A la Thr Ala Pro Ala Glu
            260                 265                 270

Ile Leu Val Trp Glu Met His Ala Gly Leu G ly Ala Ala
        275                 280                 285


<210> SEQ ID NO 198
<211> LENGTH: 743
<212> TYPE: DNA
<213> ORGANISM: Mycobacterium vaccae

<400> SEQUENCE: 198

ggatccgcgg caccggctgg tgacgaccaa gtacaacccg gcccgcacct g gacggccga     60
```

-continued gaactccgtc ggcatcggcg gcgcgtacct gtgcatctac gggatggagg g ccccggcgg 120 ctatcagttc gtcggccgca ccacccaggt gtggagtcgt taccgccaca c ggcgccgtt 180 cgaacccgga agtccctggc tgctgcggtt tttcgaccga atttcgtggt a tccggtgtc 240 ggccgaggag ctgctggaat tgcgagccga catggccgca ggccggggct c ggtcgacat 300 caccgacggc gtgttctccc tcgccgagca cgaacggttc ctggccgaca a cgccgacga 360 catcgccgcg ttccgttccc ggcaggcggc cgcgttctcc gccgagcgga c cgcgtgggc 420 ggccgccggc gagttcgacc gcgccgagaa agccgcgtcg aaggccaccg a cgccgatac 480 cggggacctg gtgctctacg acggtgacga gcgggtcgac gctccgttcg c gtcgagcgt 540 gtggaaggtc gacgtcgccg tcggtgaccg ggtggtggcc ggacagccgt t gctggcgct 600 ggaggcgatg aagatggaga ccgtgctgcg cgccccggcc gacggggtgg t cacccagat 660 cctggtctcc gctgggcatc tcgtcgatcc cggcacccca ctggtcgtgg t cggcaccgg 720 agtgcgcgca tgagcgccgt cga 743

<210> SEQ ID NO 199
<211> LENGTH: 243
<212> TYPE: PRT
<213> ORGANISM: Mycobacterium vaccae

<400> SEQUENCE: 199

Asp Pro Arg His Arg Leu Val Thr Thr Lys T yr Asn Pro Ala Arg Thr
1 5 10 15

Trp Thr Ala Glu Asn Ser Val Gly Ile Gly G ly Ala Tyr Leu Cys Ile
20 25 30

Tyr Gly Met Glu Gly Pro Gly Gly Tyr Gln P he Val Gly Arg Thr Thr
35 40 45

Gln Val Trp Ser Arg Tyr Arg His Thr Ala P ro Phe Glu Pro Gly Ser
50 55 60

Pro Trp Leu Leu Arg Phe Phe Asp Arg Ile S er Trp Tyr Pro Val Ser
65 70 75 80

Ala Glu Glu Leu Leu Glu Leu Arg Ala Asp M et Ala Ala Gly Arg Gly
85 90 95

Ser Val Asp Ile Thr Asp Gly Val Phe Ser L eu Ala Glu His Glu Arg
100 105 110

Phe Leu Ala Asp Asn Ala Asp Asp Ile Ala A la Phe Arg Ser Arg Gln
115 120 125

Ala Ala Ala Phe Ser Ala Glu Arg Thr Ala T rp Ala Ala Ala Gly Glu
130 135 140

Phe Asp Arg Ala Glu Lys Ala Ala Ser Lys A la Thr Asp Ala Asp Thr
145 150 155 160

Gly Asp Leu Val Leu Tyr Asp Gly Asp Glu A rg Val Asp Ala Pro Phe
165 170 175

Ala Ser Ser Val Trp Lys Val Asp Val Ala V al Gly Asp Arg Val Val
180 185 190

Ala Gly Gln Pro Leu Leu Ala Leu Glu Ala M et Lys Met Glu Thr Val
195 200 205

Leu Arg Ala Pro Ala Asp Gly Val Val Thr G ln Ile Leu Val Ser Ala
210 215 220

Gly His Leu Val Asp Pro Gly Thr Pro Leu V al Val Val Gly Thr Gly
225 230 235 240

Val Arg Ala

-continued

<210> SEQ ID NO 200
<211> LENGTH: 858
<212> TYPE: DNA
<213> ORGANISM: Mycobacterium vaccae

<400> SEQUENCE: 200
gaaatcccgc gtctgaaacc ctcttttcgc ggcgcccctc aggacggtaa g ggggccaag 60 cggattgaaa aatgttcgct gaatgagcct gaaattgcgc gtggctcttg g aaatcagca 120 gcgatgggtt taccgtgtcc actagtcggt ccaaagagga ccactggttt t cggaggttt 180 tgcatgaaca aagcagagct catcgacgta ctcactgaga agctgggctc g gatcgtcgg 240 caagcgactg cggcggtgga gaacgttgtc gacaccatcg tgcgcgccgt g cacaagggt 300 gagagcgtca ccatcacggg cttcggtgtt ttcgagcagc gtcgtcgcgc a gcacgcgtg 360 gcacgcaatc cgcgcaccgg cgagaccgtg aaggtcaagc ccacctcagt c ccggcattc 420 cgtcccggcg ctcagttcaa ggctgttgtc tctggcgcac agaagcttcc g gccgagggt 480 ccggcggtca agcgcggtgt gaccgcgacg agcaccgccc gcaaggcagc c aagaaggct 540 ccggccaaga aggctgccgc gaagaaggcc gcgccggcca agaaggctcc g gcgaagaag 600 gctgcgacca aggctgcacc ggccaagaag gccactgccg ccaagaaggc c gcgccggcc 660 aagaaggcca ctgccgccaa gaaggctgca ccggccaaga aggctccggc c aagaaggct 720 gcgaccaagg ctgcaccggc caagaaggct ccggccaaga aggccgcgac c aaggctgca 780 ccggccaaga aggctccggc cgccaagaag gcgcccgcca agaaggctcc g gccaagcgc 840 ggcggacgca agtaagtc 858

<210> SEQ ID NO 201
<211> LENGTH: 223
<212> TYPE: PRT
<213> ORGANISM: Mycobacterium vaccae

<400> SEQUENCE: 201

Met Asn Lys Ala Glu Leu Ile Asp Val Leu T hr Glu Lys Leu Gly Ser
1 5 10 15

Asp Arg Arg Gln Ala Thr Ala Ala Val Glu A sn Val Val Asp Thr Ile
20 25 30

Val Arg Ala Val His Lys Gly Glu Ser Val T hr Ile Thr Gly Phe Gly
35 40 45

Val Phe Glu Gln Arg Arg Arg Ala Ala Arg V al Ala Arg Asn Pro Arg
50 55 60

Thr Gly Glu Thr Val Lys Val Lys Pro Thr S er Val Pro Ala Phe Arg
65 70 75 80

Pro Gly Ala Gln Phe Lys Ala Val Val Ser G ly Ala Gln Lys Leu Pro
85 90 95

Ala Glu Gly Pro Ala Val Lys Arg Gly Val T hr Ala Thr Ser Thr Ala
100 105 110

Arg Lys Ala Ala Lys Lys Ala Pro Ala Lys L ys Ala Ala Ala Lys Lys
115 120 125

Ala Ala Pro Ala Lys Lys Ala Pro Ala Lys L ys Ala Ala Thr Lys Ala
130 135 140

Ala Pro Ala Lys Lys Ala Thr Ala Ala Lys L ys Ala Ala Pro Ala Lys
145 150 155 160

Lys Ala Thr Ala Ala Lys Lys Ala Ala Pro A la Lys Lys Ala Pro Ala
165 170 175

-continued

```
Lys Lys Ala Ala Thr Lys Ala Ala Pro Ala L ys Lys Ala Pro Ala Lys
            180                 185                 190

Lys Ala Ala Thr Lys Ala Ala Pro Ala Lys L ys Ala Pro Ala Ala Lys
        195                 200                 205

Lys Ala Pro Ala Lys Lys Ala Pro Ala Lys A rg Gly Gly Arg Lys
    210                 215                 220


<210> SEQ ID NO 202
<211> LENGTH: 570
<212> TYPE: DNA
<213> ORGANISM: Mycobacterium vaccae

<400> SEQUENCE: 202

agacagacag tgatcgacga aaccctcttc catgccgagg agaagatgga g aaggccgtc     60

tcggtggcac ccgacgacct ggcgtcgatt cgtaccggcc gcgcgaaccc c ggcatgttc    120

aaccggatca acatcgacta ctacggcgcc tccaccccga tcacgcagct g tccagcatc    180

aacgtgcccg aggcgcgcat ggtggtgatc aagccctacg aggcgagcca g ctgcgcctc    240

atcgaggatg cgatccgcaa ctccgacctc ggcgtcaatc cgaccaacga c ggcaacatc    300

atccgggtgt cgatcccgca gctcaccgag gagcgccgcc gcgacctggt c aagcaggcc    360

aaggccaagg gcgaggacgc caaggtgtcg gtgcgcaaca tccgtcgcaa g gcgatggag    420

gaactctccc ggatcaagaa ggacggcgac gccggcgaag accaagtgac c cgcgccgag    480

aaggatctcg acaagagcac ccaccagtac acgaatcaga tcgacgaact g gtcaagcac    540

aaggaaggcg agttgctgga ggtctgacca                                     570


<210> SEQ ID NO 203
<211> LENGTH: 187
<212> TYPE: PRT
<213> ORGANISM: Mycobacterium vaccae
<220> FEATURE:
<221> NAME/KEY: UNSURE
<222> LOCATION: (186)...(186)

<400> SEQUENCE: 203

Val Ile Asp Glu Thr Leu Phe His Ala Glu G lu Lys Met Glu Lys Ala
 1               5                  10                  15

Val Ser Val Ala Pro Asp Asp Leu Ala Ser I le Arg Thr Gly Arg Ala
            20                  25                  30

Asn Pro Gly Met Phe Asn Arg Ile Asn Ile A sp Tyr Tyr Gly Ala Ser
        35                  40                  45

Thr Pro Ile Thr Gln Leu Ser Ser Ile Asn V al Pro Glu Ala Arg Met
    50                  55                  60

Val Val Ile Lys Pro Tyr Glu Ala Ser Gln L eu Arg Leu Ile Glu Asp
65                  70                  75                  80

Ala Ile Arg Asn Ser Asp Leu Gly Val Asn P ro Thr Asn Asp Gly Asn
                85                  90                  95

Ile Ile Arg Val Ser Ile Pro Gln Leu Thr G lu Glu Arg Arg Arg Asp
            100                 105                 110

Leu Val Lys Gln Ala Lys Ala Lys Gly Glu A sp Ala Lys Val Ser Val
        115                 120                 125

Arg Asn Ile Arg Arg Lys Ala Met Glu Glu L eu Ser Arg Ile Lys Lys
    130                 135                 140

Asp Gly Asp Ala Gly Glu Asp Glu Val Thr A rg Ala Glu Lys Asp Leu
145                 150                 155                 160

Asp Lys Ser Thr His Gln Tyr Thr Asn Gln I le Asp Glu Leu Val Lys
```

-continued

```
              165                 170                 175

His Lys Glu Gly Glu Leu Leu Glu Val Xaa P ro
            180                 185
```

<210> SEQ ID NO 204
<211> LENGTH: 1364
<212> TYPE: DNA
<213> ORGANISM: Mycobacterium vaccae

<400> SEQUENCE: 204

```
cgacctccac ccgggcgtga ggccaaccac taggctggtc accagtagtc g acggcacac     60

ttcaccgaaa aaatgaggac agaggagaca cccgtgacga tccgtgttgg t gtgaacggc    120

ttcggccgta tcggacgcaa cttcttccgc gcgctggacg cgcagaaggc c gaaggcaag    180

aacaaggaca tcgagatcgt cgcggtcaac gacctcaccg acaacgccac g ctggcgcac    240

ctgctgaagt tcgactcgat cctgggccgg ctgccctacg acgtgagcct c gaaggcgag    300

gacaccatcg tcgtcggcag caccaagatc aaggcgctcg aggtcaagga a ggcccggcg    360

gcgctgccct ggggcgacct gggcgtcgac gtcgtcgtcg agtccaccgg c atcttcacc    420

aagcgcgaca aggcccaggg ccacctcgac gcgggcgcca agaaggtcat c atctccgcg    480

ccggccaccg atgaggacat caccatcgtg ctcggcgtca acgacgacaa g tacgacggc    540

agccagaaca tcatctccaa cgcgtcgtgc accacgaact gcctcggccc g ctggcgaag    600

gtcatcaacg acgagttcgg catcgtcaag ggcctgatga ccaccatcca c gcctacacc    660

caggtccaga acctgcagga cggcccgcac aaggatctgc gccgggcccg c gccgccgcg    720

ctgaacatcg tgccgacctc caccggtgcc gccaaggcca tcggactggt g ctgcccgag    780

ctgaagggca agctcgacgg ctacgcgctg cgggtgccga tccccaccgg c tcggtcacc    840

gacctgaccg ccgagctggg caagtcggcc accgtggacg agatcaacgc c gcgatgaag    900

gctgcggccg agggcccgct caagggcatc ctcaagtact acgacgcccc g atcgtgtcc    960

agcgacatcg tcaccgatcc gcacagctcg atcttcgact cgggtctgac c aaggtcatc   1020

gacaaccagg ccaaggtcgt gtcctggtac gacaacgagt ggggctactc c aaccgcctc   1080

gtcgacctgg tcgccctggt cggcaagtcg ctgtaggggc gagcgaagcg a cgggagaac   1140

agaggcgcca tggcgatcaa gtcactcgac gaccttctgt ccgaaggggt g acggggcgg   1200

ggcgtactcg tgcgctccga cctgaacgtc cccctcgacg gcgacacgat c accgacccg   1260

gggcgcatca tcgcctcggt gccgacgttg aaggcgttga gtgacgccgg c gccaaggtg   1320

gtcgtcaccg cgcatctggg caggcccaag ggtgagccgg atcc                  136 4
```

<210> SEQ ID NO 205
<211> LENGTH: 340
<212> TYPE: PRT
<213> ORGANISM: Mycobacterium vaccae

<400> SEQUENCE: 205

```
Val Thr Ile Arg Val Gly Val Asn Gly Phe G ly Arg Ile Gly Arg Asn
 1               5                  10                  15

Phe Phe Arg Ala Leu Asp Ala Gln Lys Ala G lu Gly Lys Asn Lys Asp
            20                  25                  30

Ile Glu Ile Val Ala Val Asn Asp Leu Thr A sp Asn Ala Thr Leu Ala
        35                  40                  45

His Leu Leu Lys Phe Asp Ser Ile Leu Gly A rg Leu Pro Tyr Asp Val
    50                  55                  60
```

-continued

```
Ser Leu Glu Gly Glu Asp Thr Ile Val Val G ly Ser Thr Lys Ile Lys
65                  70                  75                  80

Ala Leu Glu Val Lys Glu Gly Pro Ala Ala L eu Pro Trp Gly Asp Leu
                85                  90                  95

Gly Val Asp Val Val Val Glu Ser Thr Gly I le Phe Thr Lys Arg Asp
            100                 105                 110

Lys Ala Gln Gly His Leu Asp Ala Gly Ala L ys Lys Val Ile Ile Ser
        115                 120                 125

Ala Pro Ala Thr Asp Glu Asp Ile Thr Ile V al Leu Gly Val Asn Asp
    130                 135                 140

Asp Lys Tyr Asp Gly Ser Gln Asn Ile Ile S er Asn Ala Ser Cys Thr
145                 150                 155                 160

Thr Asn Cys Leu Gly Pro Leu Ala Lys Val I le Asn Asp Glu Phe Gly
                165                 170                 175

Ile Val Lys Gly Leu Met Thr Thr Ile His A la Tyr Thr Gln Val Gln
            180                 185                 190

Asn Leu Gln Asp Gly Pro His Lys Asp Leu A rg Arg Ala Arg Ala Ala
        195                 200                 205

Ala Leu Asn Ile Val Pro Thr Ser Thr Gly A la Ala Lys Ala Ile Gly
    210                 215                 220

Leu Val Leu Pro Glu Leu Lys Gly Lys Leu A sp Gly Tyr Ala Leu Arg
225                 230                 235                 240

Val Pro Ile Pro Thr Gly Ser Val Thr Asp L eu Thr Ala Glu Leu Gly
                245                 250                 255

Lys Ser Ala Thr Val Asp Glu Ile Asn Ala A la Met Lys Ala Ala Ala
            260                 265                 270

Glu Gly Pro Leu Lys Gly Ile Leu Lys Tyr T yr Asp Ala Pro Ile Val
        275                 280                 285

Ser Ser Asp Ile Val Thr Asp Pro His Ser S er Ile Phe Asp Ser Gly
    290                 295                 300

Leu Thr Lys Val Ile Asp Asn Gln Ala Lys V al Val Ser Trp Tyr Asp
305                 310                 315                 320

Asn Glu Trp Gly Tyr Ser Asn Arg Leu Val A sp Leu Val Ala Leu Val
                325                 330                 335

Gly Lys Ser Leu
            340
```

<210> SEQ ID NO 206
<211> LENGTH: 522
<212> TYPE: DNA
<213> ORGANISM: Mycobacterium vaccae

<400> SEQUENCE: 206

```
acctacgagt tcgagaacaa ggtcacgggc ggccgcatcc cgcgcgagta c atcccgtcg     60

gtggatgccg gcgcgcagga cgccatgcag tacggcgtgc tggccggcta c ccgctggtt    120

aacgtcaagc tgacgctgct cgacggtgcc taccacgaag tcgactcgtc g gaaatggca    180

ttcaaggttg ccggctccca ggtcatgaag aaggctgccg cccaggcgca g ccggtgatc    240

ctggagccag tgatggcggt cgaggtcacg acgcccgagg attacatggg t gaagtgagc    300

ggcgacctga actcccgccg tggtcagatc caggccatgg aggagcggag c ggtgctcgt    360

gtcgtgaagg cgcaggttcc gctgtcggag atgttcggct acgtcggaga c cttcggtcg    420

aagacccagg gccgggccaa ctactccatg gtgttcgact cgtacgccga a gttccggcg    480

aacgtgtcga aggagatcat cgcgaaggcg acgggccagt aa                        522
```

-continued

```
<210> SEQ ID NO 207
<211> LENGTH: 173
<212> TYPE: PRT
<213> ORGANISM: Mycobacterium vaccae

<400> SEQUENCE: 207

Thr Tyr Glu Phe Glu Asn Lys Val Thr Gly G ly Arg Ile Pro Arg Glu
 1               5                  10                  15

Tyr Ile Pro Ser Val Asp Ala Gly Ala Gln A sp Ala Met Gln Tyr Gly
            20                  25                  30

Val Leu Ala Gly Tyr Pro Leu Val Asn Val L ys Leu Thr Leu Leu Asp
        35                  40                  45

Gly Ala Tyr His Glu Val Asp Ser Ser Glu M et Ala Phe Lys Val Ala
    50                  55                  60

Gly Ser Gln Val Met Lys Lys Ala Ala Ala G ln Ala Gln Pro Val Ile
65                  70                  75                  80

Leu Glu Pro Val Met Ala Val Glu Val Thr T hr Pro Glu Asp Tyr Met
                85                  90                  95

Gly Glu Val Ile Gly Asp Leu Asn Ser Arg A rg Gly Gln Ile Gln Ala
            100                 105                 110

Met Glu Glu Arg Ser Gly Ala Arg Val Val L ys Ala Gln Val Pro Leu
        115                 120                 125

Ser Glu Met Phe Gly Tyr Val Gly Asp Leu A rg Ser Lys Thr Gln Gly
    130                 135                 140

Arg Ala Asn Tyr Ser Met Val Phe Asp Ser T yr Ala Glu Val Pro Ala
145                 150                 155                 160

Asn Val Ser Lys Glu Ile Ile Ala Lys Ala T hr Gly Gln
                165                 170


<210> SEQ ID NO 208
<211> LENGTH: 12
<212> TYPE: PRT
<213> ORGANISM: Mycobacterium vaccae

<400> SEQUENCE: 208

Ala Leu Pro Gln Leu Thr Asp Glu Gln Arg A la Ala
 1               5                  10
```

We claim:

1. An isolated polypeptide comprising SEQ ID NO: 201.

2. An immunogenic composition comprising at least one polypeptide according to claim 1 and a physiologically acceptable carrier.

3. An immunogenic composition comprising at least one polypeptide according to claim 1 and a non-specific immune response enhancer.

4. A fusion protein comprising at least one polypeptide according to claim 1.

5. An immunogenic composition comprising at least one fusion protein according to claim 4 and a physiologically acceptable carrier.

6. An immunogenic composition comprising at least one fusion protein according to claim 4 and a non-specific immune response enhancer.

7. An isolated polypeptide comprising an immunogenic portion of SEQ ID NO: 201.

8. An immunogenic composition comprising at least one polypeptide according to claim 7 and a physiologically acceptable carrier.

9. An immunogenic composition comprising at least one polypeptide according to claim 7 and a non-specific immune response enhancer.

10. A fusion protein comprising at least one polypeptide according to claim 7.

11. An immunogenic composition comprising at least one fusion protein according to claim 10 and a non-specific immune response enhancer.

12. An isolated polypeptide comprising an amino acid sequence selected from the group consisting of sequences having at least 75% identical residues to SEQ ID NO: 201, wherein the polypeptide exhibits the same immunological characteristics as a polypeptide of SEQ ID NO: 201.

13. An immunogenic composition comprising at least one polypeptide according to claim 12 and a physiologically acceptable carrier.

14. An immunogenic composition comprising at least one polypeptide according to claim 12 and a non-specific immune response enhancer.

15. A fusion protein comprising at least one polypeptide according to claim 12.

16. An immunogenic composition comprising at least one fusion protein according to claim 15 and a non-specific immune response enhancer.

17. An isolated polypeptide comprising an amino acid sequence selected from the group consisting of sequences having at least 90% identical residues to SEQ ID NO: 201, wherein the polypeptide exhibits the same immunological characteristics as a polypeptide of SEQ ID NO: 201.

18. An immunogenic composition comprising at least one polypeptide according to claim 17 and a physiologically acceptable carrier.

19. An immunogenic composition comprising at least one polypeptide according to claim 17 and a non-specific immune response enhancer.

20. A fusion protein comprising at least one polypeptide according to claim 17.

21. An immunogenic composition comprising at least one fusion protein according to claim 20 and a non-specific immune response enhancer.

* * * * *